US011999748B2

(12) United States Patent
Qin et al.

(10) Patent No.: US 11,999,748 B2
(45) Date of Patent: *Jun. 4, 2024

(54) EXATECAN DERIVATIVES, LINKER-PAYLOADS, AND CONJUGATES AND THEREOF

(71) Applicant: GENEQUANTUM HEALTHCARE (SUZHOU) CO., LTD., Suzhou (CN)

(72) Inventors: Gang Qin, Suzhou (CN); Tony Yantao Zhang, Shanghai (CN); Guangming Chen, Shanghai (CN); Paul H. Song, Suzhou (CN); Boyu Zhong, Shanghai (CN); Mingyu Hu, Suzhou (CN)

(73) Assignee: GENEQUANTUM HEALTHCARE (SUZHOU) CO., LTD., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/453,748

(22) Filed: Aug. 22, 2023

(65) Prior Publication Data

US 2024/0018159 A1 Jan. 18, 2024

Related U.S. Application Data

(63) Continuation of application No. 18/053,459, filed on Nov. 8, 2022, now Pat. No. 11,814,394.

(30) Foreign Application Priority Data

Nov. 16, 2021 (WO) ................ PCT/CN2021/130896

(51) Int. Cl.
C07D 491/22 (2006.01)
(52) U.S. Cl.
CPC ................ *C07D 491/22* (2013.01)
(58) Field of Classification Search
None
See application file for complete search history.

(56) References Cited

U.S. PATENT DOCUMENTS

| 11,040,084 | B2 | 6/2021 | Qin et al. |
|---|---|---|---|
| 11,453,870 | B2 | 9/2022 | Qin et al. |
| 11,578,297 | B2 | 2/2023 | Qin et al. |
| 2011/0321183 | A1 | 12/2011 | Ploegh et al. |
| 2015/0297748 | A1 | 10/2015 | Masuda et al. |
| 2016/0193355 | A1 | 7/2016 | Qin et al. |
| 2016/0333112 | A1 | 11/2016 | Naito et al. |
| 2017/0035906 | A1 | 2/2017 | Naito et al. |
| 2017/0112944 | A1 | 4/2017 | Qin et al. |
| 2021/0177929 | A1 | 6/2021 | Qin et al. |
| 2021/0187114 | A1 | 6/2021 | Qin et al. |
| 2021/0221907 | A1 | 7/2021 | Hou et al. |
| 2021/0347894 | A1 | 11/2021 | Ying et al. |
| 2021/0353764 | A1 | 11/2021 | Xu et al. |
| 2021/0401924 | A1 | 12/2021 | Qin et al. |
| 2022/0251494 | A1 | 8/2022 | Qin et al. |
| 2022/0251530 | A1 | 8/2022 | Qin et al. |
| 2022/0378928 | A1 | 12/2022 | Zhu et al. |
| 2022/0378930 | A1 | 12/2022 | Song et al. |
| 2022/0395581 | A1 | 12/2022 | Qin et al. |
| 2022/0403360 | A1 | 12/2022 | Qin et al. |
| 2022/0411436 | A1 | 12/2022 | Zhu et al. |
| 2023/0054458 | A1 | 2/2023 | Yang et al. |
| 2023/0086097 | A1 | 3/2023 | Zhang et al. |
| 2023/0097252 | A1 | 3/2023 | Qin et al. |
| 2023/0101266 | A1 | 3/2023 | Qin et al. |
| 2023/0159875 | A1 | 5/2023 | Qin et al. |

FOREIGN PATENT DOCUMENTS

| AU | 2021289927 A1 | 1/2023 |
|---|---|---|
| AU | 2021359457 A1 | 5/2023 |
| CN | 104755494 A | 7/2015 |
| CN | 110167355 A | 8/2019 |
| CN | 111689980 A | 9/2020 |
| CN | 113816969 A | 12/2021 |
| CN | 113827736 A | 12/2021 |
| CN | 113943310 A | 1/2022 |
| CN | 114569739 A | 6/2022 |
| CN | 115103691 A | 9/2022 |
| EP | 0 495 432 A1 | 7/1992 |
| EP | 0 700 914 A1 | 3/1996 |
| EP | 4095148 A1 | 11/2022 |
| EP | 4129345 A1 | 2/2023 |
| EP | 4130006 A1 | 2/2023 |
| EP | 4130045 A1 | 2/2023 |
| WO | WO 2014/057687 A1 | 4/2014 |
| WO | WO 2014/177042 A1 | 11/2014 |
| WO | WO 2015/115091 A1 | 8/2015 |
| WO | WO 2015/165413 A1 | 11/2015 |
| WO | WO 2018/112253 A1 | 6/2018 |
| WO | WO 2020/016662 A2 | 1/2020 |
| WO | WO 2020/063673 A1 | 4/2020 |

(Continued)

OTHER PUBLICATIONS

Certified Chinese Patent Application No. 202110159956.6, Filing date listed as: Feb. 5, 2021, 71 pages, retrieved from WIPO in International Application No. PCT/CN2022/074328 (WO 2022/166762).

Certified Chinese Patent Application No. 202110533304.4, Filing date listed as: May 17, 2021, 113 pages, retrieved from WIPO in International Application No. PCT/CN2022/074328 (WO 2022/166762).

Certified Chinese Patent Application No. 202110718245.8, Filing date listed as: Jun. 28, 2021, 159 pages, retrieved from WIPO in International Application No. PCT/CN2022/074328 (WO 2022/166762).

Certified Chinese Patent Application No. 202110936768.X, Filing date listed as: Aug. 16, 2021, 181 pages, retrieved from WIPO in International Application No. PCT/CN2022/074328 (WO 2022/166762).

(Continued)

*Primary Examiner* — Samantha L Shterengarts
(74) *Attorney, Agent, or Firm* — Hoxie & Associates LLC

(57) ABSTRACT

The present disclosure relates to the biopharmaceutical field, in particular, Exatecan derivatives, linker-payloads, and conjugates and thereof antibody-drug conjugates, and the corresponding preparing process and use thereof.

17 Claims, 7 Drawing Sheets

Specification includes a Sequence Listing.

(56) References Cited

FOREIGN PATENT DOCUMENTS

| WO | WO 2020/063676 A1 | 4/2020 |
|---|---|---|
| WO | WO 2021/115426 A1 | 6/2021 |
| WO | WO 2021/136475 A1 | 7/2021 |
| WO | WO 2021/136483 A1 | 7/2021 |
| WO | WO 2021/147993 A1 | 7/2021 |
| WO | WO 2021/190581 A1 | 9/2021 |
| WO | WO 2021/190583 A1 | 9/2021 |
| WO | WO 2021/190586 A1 | 9/2021 |
| WO | WO 2021/190602 A1 | 9/2021 |
| WO | WO 2021/249228 A1 | 12/2021 |
| WO | WO 2022/056696 A1 | 3/2022 |
| WO | WO 2022/068878 A1 | 4/2022 |
| WO | WO 2022/078259 A1 | 4/2022 |
| WO | WO 2022/078260 A1 | 4/2022 |
| WO | WO 2022/078279 A1 | 4/2022 |
| WO | WO 2022/133722 A1 | 6/2022 |
| WO | WO 2022/160156 A1 | 8/2022 |
| WO | WO 2022/166762 A1 | 8/2022 |
| WO | WO 2022/170676 A1 | 8/2022 |
| WO | WO 2022/188740 A1 | 9/2022 |
| WO | WO 2022/188743 A1 | 9/2022 |
| WO | WO 2022/218331 A1 | 10/2022 |
| WO | WO 2022/236136 A1 | 11/2022 |
| WO | WO 2022/253284 A1 | 12/2022 |

OTHER PUBLICATIONS

Certified Chinese Patent Application No. 202111355330.9, Filing date listed as: Nov. 16, 2021, 127 pages, retrieved from WIPO in International Application No. PCT/CN2022/074328 (WO 2022/166762).
English language machine translation for CN 111689980 A, retrieved from EPO on Mar. 31, 2023, 19 pages.
English language machine translation for CN 111689980 A (description and claims), retrieved from EPO on Jul. 31, 2023, 19 pages.
English language machine translation for CN 113816969 A (description and claims), retrieved from EPO on Jul. 31, 2023, 37 pages.
English language machine translation for CN 113943310 A, retrieved from EPO on Mar. 31, 2023, 190 pages.
English language machine translation for CN 113943310 A (description and claims), retrieved from EPO on Jul. 31, 2023, 53 pages.
English language machine translation for CN 114569739 A (description and claims), retrieved from EPO on Jul. 31, 2023, 137 pages.
English language machine translation for WO 2021/190586 A1, retrieved from WIPO on Mar. 30, 2023, 36 pages.
English language machine translation for WO 2022/078259 A1, retrieved from WIPO on Mar. 30, 2023, 45 pages.
English language machine translation for WO 2022/078260 A1, retrieved from WIPO on Mar. 30, 2023, 40 pages.
English language machine translation for WO 2022/078279 A1, retrieved from WIPO on Apr. 11, 2023, 97 pages.
English language machine translation for WO 2022/253284 A1, retrieved from WIPO on Aug. 7, 2023, 104 pages.
English language machine translation for International Publication No. WO 2022/166762 A1, retrieved from WIPO, 84 pages.
Sugimori, M., et al. "Synthesis and Antitumor Activity of Ring A- and F-Modified Hexacyclic Camptothecin Analogues," Journal of Medical Chemistry, vol. 41, No. 13, pp. 2308-2318, (1998).
Tamura, A., et al. "Re-evaluation and functional classification of non-synonymous Single nucleotide polymorphisms of the human ATP-binding cassette transporter ABCG2," Cancer Science, vol. 98, No. 2, pp. 231-239, (2007).
Wani, M.C., et al. "Plant Antitumor Agents. 23.1 Synthesis and Antileukemic Activity of Camptothecin Analogues," *Journal of Medical Chemistry*, vol. 29, No. 11, pp. 2358-2363, (1986).
Yaegashi, T., et al. "Synthesis and Antitumor Activity of 20(S)-"Camptothecin Derivative. A-Ring-Substituted 7-Ethylcamptothecins and Their E-Ring Modified Water-Soluble Derivatives, Chemical and Pharmaceutical Bulletin, vol. 42, No. 12, pp. 2518-2525, (1994).

EXATECAN DERIVATIVES, LINKER-PAYLOADS, AND CONJUGATES AND THEREOF

CROSS-REFERENCE TO RELATED APPLICATIONS

This application is a continuation of U.S. patent application Ser. No. 18/053,459 filed Nov. 8, 2022, which is a U.S. Non-Provisional application under 35 U.S.C. § 111(a), which claims priority to and the benefit of International Application No. PCT/CN2021/130896 filed Nov. 16, 2021, the contents of each of which are hereby incorporated by reference in their entireties.

REFERENCE TO A SEQUENCE LISTING

This application contains a Sequence Listing as a separate part of the disclosure. The contents of the Sequence Listing (GQH-14-USC_SequenceListing.xml; Size: 14,566 bytes; and Date of Creation: Aug. 18, 2023) are incorporated herein by reference.

TECHNICAL FIELD

The present disclosure relates to the biopharmaceutical field, in particular, Exatecan derivatives, linker-payloads, and conjugates and thereof antibody-drug conjugates, and the corresponding preparing process and use thereof.

BACKGROUND

In traditional tumor treatment, chemotherapy is one of the main treatment strategies. However, the off-target toxicity from non-specific accumulation in normal tissues, narrow therapeutic window and low tolerance limit the chemotherapy drug development. In recent decades, targeted therapies using monoclonal antibodies and polypeptides which bind to specific markers on the tumor cell's surface has demonstrated less toxicity than chemotherapy. However, they both lack potency in killing tumor cells.

The treatment strategy of antibodies armed with toxins to selectively kill target cells was first proposed in 1970. The tumor-targeting drug conjugates mainly compose of ADCs that generally couple antibodies which specifically recognize the surface antigens of tumor cells with chemical toxins which effectively kill tumor tissues through linkers.

Until 2021, more than 120 ADCs have been in the process of clinical development.

Most of cytotoxic payloads developed belong to two major families: tubulin inhibitors (maytansinoids or auristatins) and DNA-damaging agents (mainly calicheamicins). All of them are extremely potent cytotoxic drugs characterized by an $IC_{50}$ (the inhibitory concentrations that inhibited 50% of cells) in the nanomolar and picomolar range, and an unfavorable toxicity profile if administered systemically. Conjugation into ADC hides the cytotoxic drug in the bloodstream to convey it directly into tumor cells, thus significantly reducing toxicity of these potent agents. In general, drugs with a more favorable therapeutic index are considered unsuitable for development as warheads, with the IC50 too low to be effective when released in the amount delivered into tumor cells.

Researches on ADCs with an increased DAR or exhibiting the bystander effect propose a promising new approach to exploit the less cytotoxic drugs as warheads.

So far, anti-microtubules agents such as Auristatins (e.g., monomethyl auristatin E (MMAE) and F (MMAF)) represent the large majority of warheads developed. Brentuximab vedotin, polatuzumab vedotin and enfortumab vedotin are all approved ADCs carrying the MMAE payload.

Topoisomerase I (TOP1) inhibitors are used as warheads in several ADCs. Sacituzumab govitecan bears SN-38, the active metabolite of irinotecan, as the warhead. Enhertu (fam-trastuzumab deruxtecan (DS8201a), also known as T-Dxd) bears deruxtecan (Dxd) as the warhead (WO2014057687A), and was recently approved for treating breast cancer. On this basis, novel small molecule topoisomerase I inhibitors, either used alone or as a component of ADCs, with greater activity, stability, physiochemical properties are required in the field.

However, on one hand, Enhertu, as well as the other commercially available ADCs and most of the ADCs in clinical trials, are prepared by chemical conjugation, using a thiosuccinimide structure (thiosuccinimide linkage) to conjugate the small molecule drug with the targeting antibody or protein. The thiosuccinimide structure is formed by the reaction of a thiol group and a maleimide. The thiosuccinimide linkage is not stable. In organisms, reverse Michael addition or exchange with other thiol groups leads to the fall-off of the cytotoxin from the ADC and off-target toxicity, which reduces the safety and limits the clinical application. For example, albeit the great efficacy, Enhertu caused more than 10% of interstitial lung disease, which limited its usage in part of patients. On another hand, chemical coupling reaction is not site specific, and the resulting ADCs show high heterogeneity.

New ADCs with higher efficacy and less toxicity are still in urgent need.

SUMMARY

In a first aspect, provided is a compound of formula (I):

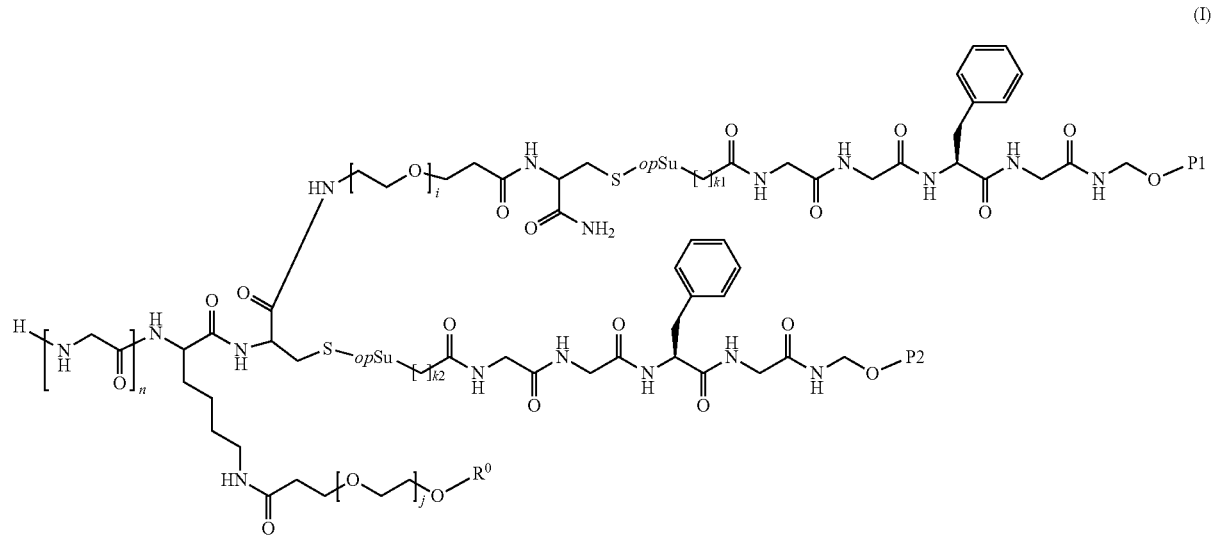

(I)

wherein,
opSu is

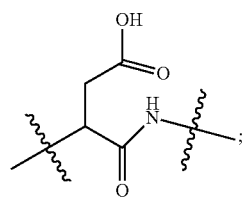

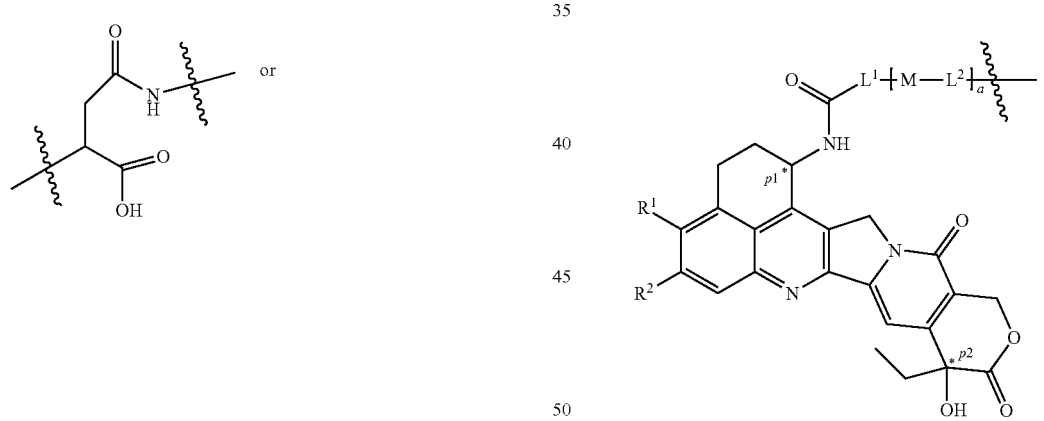

$R^0$ is $C_{1-10}$ alkyl;
n is any integer of 2 to 20;
k1 and k2 are independently an integer of 1 to 7;
i is an integer of 1-100;
j is an integer of 1-100;

P1 and P2 are independently a payload having the structure of formula (i'):

(i')

wherein,
a is 0 or 1;
the carbon atoms marked with p1* and p2* each is asymmetric center, and the asymmetric center is S configured, R configured or racemic;
$L^1$ is selected from $C_{1-6}$ alkylene, which is unsubstituted or substituted with one substituent selected from halogen, —OH and —NH$_2$;
M is —CH$_2$—, —NH— or —O—;
$L^2$ is $C_{1-3}$ alkylene;
$R^1$ and $R^2$ are each independently selected from hydrogen, $C_{1-6}$ alkyl, halogen and $C_{1-6}$ alkoxy.

In a second aspect, provided is a conjugate having the structure of formula (II):

(II)

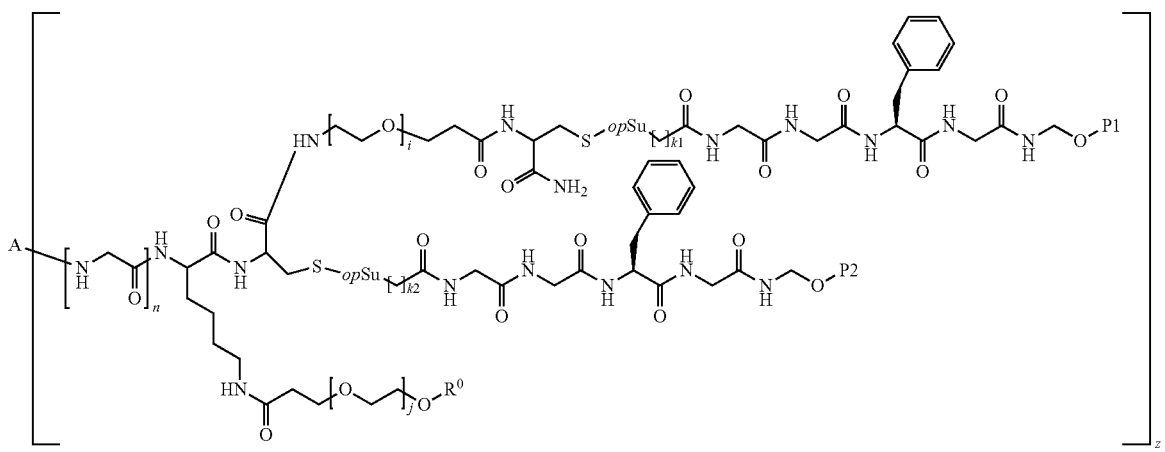

wherein,

A is an antibody or an antigen binding fragment thereof, the antibody or antigen binding fragment is preferably modified to connect with the (Gly)$_n$ moiety in the compound of formula (I);

z is an integer of 1 to 20; preferably 1 to 4; particularly 2;

P1, P2, R$^0$, opSu, n, k1, k2, i and j are as defined in formula (I).

In a third aspect, provided is a pharmaceutical composition comprising the conjugate of the present disclosure, and at least one pharmaceutically acceptable carrier.

In a fourth aspect, provided is use of the conjugate of the present disclosure or the pharmaceutical composition of the present disclosure in the manufacture of a medicament for treating a disease; wherein the disease is a tumor or an autoimmune disease; preferably a tumor comprising HER2-positive tumor cells.

In a fifth aspect, provided is a compound, having the structure of formula (i):

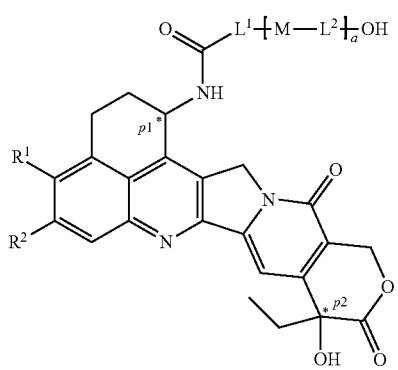

wherein, a, the carbon atoms marked with p1* and p2*, L$^1$, M, L$^2$, R$^1$ and R$^2$ are as defined in formula (I).

In a sixth aspect, provided is a compound of formula (1):

(1)

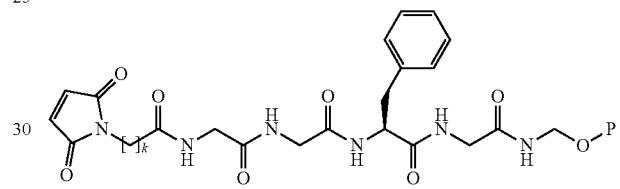

wherein, k is an integer of 1 to 7; preferably 1, or 3 or 5, particularly 5

P is a payload having the structure of formula (i'), wherein the structure of formula (i') is as defined in formula (I).

BRIEF DESCRIPTION OF THE DRAWINGS

FIG. 4a shows result detected by GFP fluorescence. FIG. 4b shows result detected by luciferase substrate chemiluminescence.

DETAILED DESCRIPTION

Figure 1:
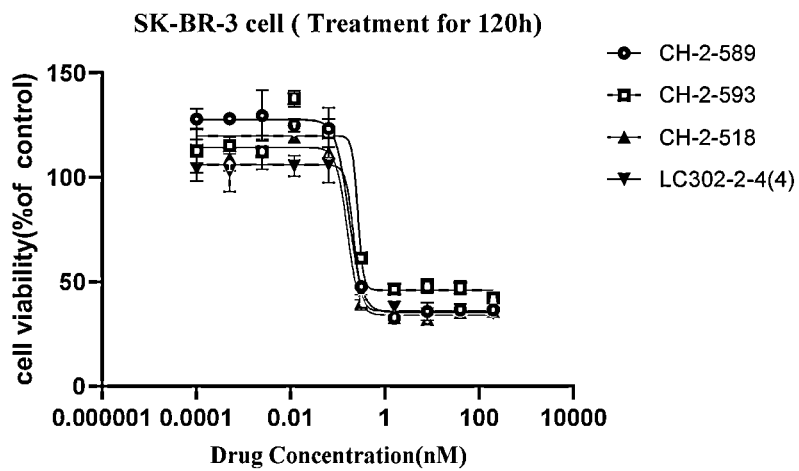
FIG. 1 shows the efficacy of conjugates in the SK-BR-3 HER2-high cell line.

The specific embodiments are provided below to illustrate technical contents of the present disclosure. Those skilled in the art can easily understand other advantages and effects of the present disclosure through the contents disclosed in the specification. The present disclosure can also be implemented or applied through other different specific embodiments. Various modifications and variations can be made by those skilled in the art without departing from the spirit of the present disclosure.

Definitions

Unless otherwise defined hereinafter, all technical and scientific terms used herein have the same meaning as commonly understood by those skilled in the art. The techniques used herein refer to those that are generally understood in the art, including the variants and equivalent substitutions that are obvious to those skilled in the art. While the following terms are believed to be readily comprehensible by those skilled in the art, the following definitions are set forth to better illustrate the present disclosure. When a trade name is present herein, it refers to the corresponding commodity or the active ingredient thereof. All patents, published patent applications and publications cited herein are hereby incorporated by reference.

When a certain amount, concentration, or other value or parameter is set forth in the form of a range, a preferred range, or a preferred upper limit or a preferred lower limit, it should be understood that it is equivalent to specifically revealing any range formed by combining any upper limit or preferred value with any lower limit or preferred value, regardless of whether the said range is explicitly recited. Unless otherwise stated, the numerical ranges listed herein are intended to include the endpoints of the range and all integers and fractions (decimals) within the range. For example, the expression "i is an integer of 1 to 20" means that i is any integer of 1 to 20, for example, i can be 1, 2, 3, 4, 5, 6, 7, 8, 9, 10, 11, 12, 13, 14, 15, 16, 17, 18, 19 or 20. Other similar expressions such as j, k and g should also be understood in a similar manner.

Unless the context clearly dictates otherwise, singular forms like "a" and "the" include the plural forms. The expression "one or more" or "at least one" may mean 1, 2, 3, 4, 5, 6, 7, 8, 9 or more.

The terms "about" and "approximately", when used in connection with a numerical variable, generally mean that the value of the variable and all values of the variable are within experimental error (for example, within a 95% confidence interval for the mean) or within ±10% of a specified value, or a wider range.

The term "optional" or "optionally" means the event described subsequent thereto may, but not necessarily happen, and the description includes the cases wherein said event or circumstance happens or does not happen.

The expressions "comprising", "including", "containing" and "having" are open-ended, and do not exclude additional unrecited elements, steps, or ingredients. The expression "consisting of" excludes any element, step, or ingredient not designated. The expression "consisting essentially of" means that the scope is limited to the designated elements, steps or ingredients, plus elements, steps or ingredients that are optionally present that do not substantially affect the essential and novel characteristics of the claimed subject matter. It should be understood that the expression "comprising" encompasses the expressions "consisting essentially of" and "consisting of".

As used herein, the term "antibody" is used in a broad way and particularly includes intact monoclonal antibodies, polyclonal antibodies, monospecific antibodies, multispecific antibodies (e.g., bispecific antibodies), and antibody fragments, as long as they have the desired biological activity. The antibody may be of any subtype (such as IgG, IgE, IgM, IgD, and IgA) or subclass, and may be derived from any suitable species. In some embodiments, the antibody is of human or murine origin. The antibody may also be a fully human antibody, humanized antibody or chimeric antibody prepared by recombinant methods.

Monoclonal antibodies are used herein to refer to antibodies obtained from a substantially homogeneous population of antibodies, i.e., the individual antibodies constituting the population are identical except for a small number of possible natural mutations. Monoclonal antibodies are highly specific for a single antigenic site. The word "monoclonal" refers to that the characteristics of the antibody are derived from a substantially homogeneous population of antibodies and are not to be construed as requiring some particular methods to produce the antibody.

An intact antibody or full-length antibody essentially comprises the antigen-binding variable region(s) as well as the light chain constant region(s) (CL) and heavy chain constant region(s) (CH), which could include CH1, CH2, CH3 and CH4, depending on the subtype of the antibody. An antigen-biding variable region (also known as a fragment variable region, Fv fragment) typically comprises a light chain variable region (VL) and a heavy chain variable region (VH). A constant region can be a constant region with a native sequence (such as a constant region with a human native sequence) or an amino acid sequence variant thereof. The variable region recognizes and interacts with the target antigen. The constant region can be recognized by and interacts with the immune system.

An antibody fragment may comprise a portion of an intact antibody, preferably its antigen binding region or variable region. Examples of antibody fragments include Fab, Fab', F(ab')2, Fd fragment consisting of VH and CH1 domains, Fv fragment, single-domain antibody (dAb) fragment, and isolated complementarity determining region (CDR). The Fab fragment is an antibody fragment obtained by papain digestion of a full-length immunoglobulin, or a fragment having the same structure produced by, for example, recombinant expression. A Fab fragment comprises a light chain (comprising a VL and a CL) and another chain, wherein the said other chain comprises a variable domain of the heavy chain (VH) and a constant region domain of the heavy chain (CH1). The F(ab')2 fragment is an antibody fragment obtained by pepsin digestion of an immunoglobulin at pH 4.0-4.5, or a fragment having the same structure produced by, for example, recombinant expression. The F(ab')2 fragment essentially comprises two Fab fragments, wherein each heavy chain portion comprises a few additional amino acids, including the cysteines that form disulfide bonds connecting the two fragments. A Fab' fragment is a fragment comprising one half of a F(ab')2 fragment (one heavy chain and one light chain). The antibody fragment may comprise a plurality of chains joined together, for example, via a disulfide bond and/or via a peptide linker. Examples of antibody fragments also include single-chain Fv (scFv), Fv, dsFv, diabody, Fd and Fd' fragments, and other fragments, including modified fragments. An antibody fragment typically comprises at least or about 50 amino acids, and typically at least or about 200 amino acids. An antigen-binding fragment can include any antibody fragment that, when inserted into an antibody framework (e.g., by substitution of the corresponding region), can result in an antibody that immunospecifically binds to the antigen.

Antibodies according to the present disclosure can be prepared using techniques well known in the art, such as the following techniques or a combination thereof: recombinant techniques, phage display techniques, synthetic techniques, or other techniques known in the art. For example, a genetically engineered recombinant antibody (or antibody mimic) can be expressed by a suitable culture system (e.g., *E. coli* or mammalian cells). The engineering can refer to, for example, the introduction of a ligase-specific recognition sequence at its terminals.

HER2 refers to human epidermal growth factor receptor-2, which belongs to the epidermal growth factor (EGFR) receptor tyrosine kinase family. In the present application, the terms ErbB2 and HER2 have the same meaning and can be used interchangeably.

As used herein, the term "antibody-drug conjugate" is referred to as "conjugate".

A small molecule compound refers to a molecule with a size comparable to that of an organic molecule commonly used in medicine. The term does not encompass biological macromolecules (e.g., proteins, nucleic acids, etc.), but encompasses low molecular weight peptides or derivatives thereof, such as dipeptides, tripeptides, tetrapeptides, pentapeptides, and the like. Typically, the molecular weight of the small molecule compound can be, for example, about 100 to about 2000 Da, about 200 to about 1000 Da, about 200 to about 900 Da, about 200 to about 800 Da, about 200 to about 700 Da, about 200 to about 600 Da, about 200 to about 500 Da.

A spacer is a structure that is located between different structural modules and can spatially separate the structural modules. The definition of spacer is not limited by whether it has a certain function or whether it can be cleaved or degraded in vivo. Examples of spacers include but are not limited to amino acids and non-amino acid structures, wherein non-amino acid structures can be, but are not limited to, amino acid derivatives or analogues. "Spacer sequence" refers to an amino acid sequence serving as a spacer, and examples thereof include but are not limited to a single amino acid, a sequence containing a plurality of amino acids, for example, a sequence containing two amino acids such as GA, etc., or, for example, GGGGS (SEQ ID NO: 3), GGGGSGGGGS(SEQ ID NO: 4), GGGGSGGGGSGGGGS (SEQ ID NO: 5), etc. Self-immolative spacers are covalent assemblies tailored to correlate the cleavage of two chemical bonds after activation of a protective part in a precursor: Upon stimulation, the protective moiety (such as a cleavable sequence) is removed, which generates a cascade of disassembling reactions leading to the temporally sequential release of smaller molecules. Examples of self-immolative spacers include but not limited to PABC (p-benzyloxycarbonyl), acetal, heteroacetal and the combination thereof.

The term "alkyl" refers to a saturated aliphatic hydrocarbon group consisting of carbon atoms and hydrogen atoms, which is connected to the rest of the molecule through a single bond. Alkyl groups comprise straight alkyl, branched alkyl or cyclic alkyl (cycloalkyl) or partially cyclic alkyl (e.g., cycloalkyl-linear alkyl and cycloalkyl-branched alkyl). The alkyl group may contain 1 to 10 carbon atoms, referring to $C_{1-10}$ alkyl group, for example, $C_{1-6}$ alkyl group, $C_{1-4}$ alkyl group, $C_{1-3}$ alkyl group, $C_{1-2}$ alkyl, $C_3$ alkyl, $C_4$ alkyl, $C_{3-6}$ alkyl. Non-limiting examples of linear alkyl groups include but are not limited to methyl, ethyl, n-propyl, n-butyl, n-pentyl, n-hexyl, etc. Non-limiting examples of branched alkyl groups include but are not limited to isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethyl butyl, 1,1-dimethylbutyl, 2,3-dimethylbutyl, 1,3-dimethylbutyl or 1,2-dimethylbutyl, etc.

The terms "cyclic alkyl" and "cycloalkyl" have the same meaning and are used herein interchangeably. Cyclic alkyl groups can include mono- or polycyclic (e.g., having 2 or more than 2 fused rings) groups. In a multicyclic cycloalkyl, two or more rings can be fused or bridged or spiro together. Ring-forming carbon atoms of a cyclic alkyl group can be optionally substituted by oxo (i.e., C(O)). Cyclic alkyl groups can have 3, 4, 5, 6, 7, 8, 9, or 10 ring-forming carbon atoms ($C_{3-10}$). Examples of cyclic alkyl groups include but are not limited to cyclopropyl, cyclobutyl, cyclopentyl, cyclohexyl, bicyclo[1.1.1]pentyl and bicyclo[2.1.1]hexyl. In some embodiments, the cyclic alkyl is a $C_{3-6}$ monocyclic or bicyclic cyclic alkyl, preferably $C_{3-6}$ monocyclic cyclic alkyl, especially cyclopropyl.

The term "partially cyclic" refers to that the group contains one or more cyclic moieties and one or more acyclic (i.e. linear or branched) moieties. Partially cyclic alkyl groups can include cyclic alkyl-linear alkyl groups and cyclic alkyl-branched alkyl groups. Partially cyclic alkyl groups can have 4, 5, 6, 7, 8, 9, or 10 carbon atoms ($C_{3-10}$), including ring-forming carbon atoms and non-ring-forming carbon atoms. Examples of partially cyclic alkyl groups include but are not limited to $C_{3-9}$ cyclic alkyl-C1 alkyl groups, $C_{3-8}$ cyclic alkyl-$C_2$ alkyl groups, $C_{3-7}$ cyclic alkyl-$C_3$ linear alkyl groups, $C_{3-6}$ cyclic alkyl-$C_4$ linear alkyl groups, $C_{3-5}$ cyclic alkyl-$C_5$ linear alkyl groups, $C_{3-4}$ cyclic alkyl-$C_6$ linear alkyl groups, $C_3$ cyclic alkyl-$C_7$ linear alkyl groups, $C_{3-7}$ cyclic alkyl-$C_3$ branched alkyl groups, $C_{3-6}$ cyclic alkyl-$C_4$ branched alkyl groups, $C_{3-5}$ cyclic alkyl-$C_5$ branched alkyl groups, $C_{3-4}$ cyclic alkyl-$C_6$ branched alkyl groups, and $C_3$ cyclic alkyl-$C_7$ branched alkyl groups. In some embodiments, the partially cyclic alkyl is a $C_{3-9}$ cyclic alkyl-$C_1$ alkyl group, preferably a $C_{3-6}$ cyclic alkyl-$C_{1-2}$ alkyl group, $C_{3-6}$ cyclic alkyl-$C_1$ alkyl group, more preferably $C_{3-4}$ cyclic alkyl-$C_{1-2}$ alkyl group, particularly $C_{3-4}$ cyclic alkyl-$C_1$ alkyl group, especially cyclopropyl-methyl.

A bivalent radical refers to a group obtained from the corresponding monovalent radical by removing one hydrogen atom from a carbon atom with free valence electron(s). A bivalent radical have two connecting sites which are connected to the rest of the molecule, wherein the two connecting sites may be on the same atom or on two different atoms of the bivalent radical.

An "alkylene" or an "alkylidene" refers to a saturated divalent hydrocarbon group. Alkylene groups comprise linear, branched, cyclic or partially cyclic groups. Examples of linear alkylene groups include but are not limited to methylene (—CH$_2$—), —(CH$_2$)$_2$—, —(CH$_2$)$_3$—, —(CH$_2$)$_4$—, —(CH$_2$)$_5$—, —(CH$_2$)$_6$—, etc. Examples of branched alkylene groups include but are not limited to —CH(CH$_3$)—, —CH(C$_2$H$_5$)—, —CH(CH$_3$)—CH$_2$—, —CH(C$_3$H$_7$)—, —CH(C$_2$H$_5$)—CH$_2$—, —C(CH$_3$)$_2$—CH$_2$—, —(CH(CH$_3$))$_2$—, —CH(CH$_3$)—(CH$_2$)$_2$—, —CH$_2$—CH —(CH₃)—CH₂—, —CH(C₄H₉)—, —C(CH₃)(C₃H₇)—, —C(C₂H₅)₂—, —CH(C₃H₇)—CH₂—, —CH(C₂H₅)—CH(CH₃)—, —CH(C₂H₅)—(CH₂)₂—, —CH₂—CH(C₂H₅)—CH₂—, —C(CH₃)₂—(CH₂)₂—, —CH₂—C(CH₃)₂—CH₂—, —CH(CH₃)—(CH₂)₃—, —CH₂—CH(CH₃)—(CH₂)₂—, —CH(C₅H₁₁)—, —C(C₂H₅)(C₃H₇)—, —C(CH₃)(C₄H₉)—, —CH(C₄H₉)—CH₂—, —C(C₂H₅)₂—CH₂—, —C(CH₃)(C₃H₇)—CH₂—, —CH(C₂H₅)—CH(C₂H₅)—, —CH(CH₃)—CH(C₃H₇)—, —C(CH₃)₂—C(CH₃)₂—, —CH(C₃H₇)—(CH₂)₂—, —CH₂—CH(C₃H₇)—CH₂—, —CH(C₂H₅)—C(CH₃)₂—, —C(CH₃)₂—CH(CH₃)—CH₂—, —CH(CH₃)—C(CH₃)₂—CH₂—, —CH(C₂H₅)—CH(CH₃)—CH₂—, —CH(CH₃)—CH(C₂H₅)—CH₂—, —CH(CH₃)—CH₂—CH(C₂H₅)—, —CH(CH₃)—C(CH₃)₂—CH₂—, —(CH(CH₃))₃—, —C(CH₃)₂—(CH₂)₃—, —CH(C₂H₅)—(CH₂)₃—, —CH₂—CH(C₂H₅)—(CH₂)₂—, —CH₂—CH(CH₃)—CH(CH₃)—CH₂—, —(CH(CH₃))₂ —(CH₂)₂—, —CH(CH₃)—(CH₂)₂—CH(CH₃)—, —(CH₂)₂—CH(CH₃)—(CH₂)₂—, —CH₂—CH(CH₃)—(CH₂)₃—, —CH(CH₃)—(CH₂)₄—, etc.

The terms "cyclic alkylene" and "cycloalkylene" have the same meaning and are used herein interchangeably. Examples of cyclic alkylene groups include but are not limited to cyclopropylene, cyclobutylene, cyclopentylene, cyclohexylene, cycloheptylene and cyclooctylene, and divalent multicyclic alkyl groups containing fused, spiro or bridged rings. In some embodiments, the cyclic alkylene is a $C_{3-6}$ cyclic alkylene group, particularly $C_{3-4}$ cyclic alkylene group, especially cyclopropyl.

Partially cyclic alkylene groups can include bivalent radicals wherein the two connecting sites which are connected to the rest of the molecule can be both on the one or more linear or branched alkyl moieties, or both on the one or more cyclic alkyl moieties, or respectively on a cyclic alkyl moiety and a linear or branched alkyl moiety. Examples of partially cyclic alkylene groups include but are not limited to: (1) cyclopropylene, cyclobutylene, cyclopentylene, cyclohexylene, cycloheptylene and cyclooctylene, and divalent multicyclic alkyl groups containing fused, spiro or bridged rings, which are each independently substituted by one or more linear or branched alkyl groups; (2) linear or branched alkylene groups, which are each independently substituted by one or more cyclic alkyl groups; and (3) a group formed by combining one or more cyclic alkylene groups and one or more linear or branched alkylene groups, provided that a chemically stable structure is formed. In some embodiments, the partially cyclic alkylene is a $C_{3-9}$ cyclic alkyl-$C_1$ alkylene group, preferably a $C_{3-6}$ cyclic alkyl-$C_{1-2}$ alkylene group, $C_{3-6}$ cyclic alkyl-$C_1$ alkylene group, more preferably $C_{3-4}$ cyclic alkyl-$C_{1-2}$ alkylene group, particularly $C_{3-4}$ cyclic alkyl-$C_1$ alkylene group, especially cyclopropyl-methylene.

As used herein, the expressions "antibody-conjugated drug" and "antibody-drug conjugate" has the same meaning. Compound of Formula (i)

In an aspect, provided is a compound or a pharmaceutically acceptable salt, stereoisomer, solvate, polymorph, tautomer, isotopic compound, metabolite or prodrug thereof, wherein the compound has the structure of formula (i):

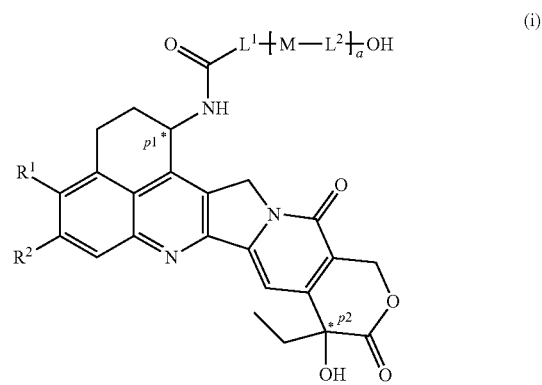

(i)

wherein,
a is 0 or 1;
the carbon atoms marked with p1* and p2* each is asymmetric center, and the asymmetric center is S configured, R configured or racemic;
$L^1$ is selected from $C_{1-6}$ alkylene, which is unsubstituted or substituted with one substituent selected from halogen, —OH and —NH₂;
M is —CH₂—, —NH— or —O—;
$L^2$ is $C_{1-3}$ alkylene;
$R^1$ and $R^2$ are each independently selected from hydrogen, $C_{1-6}$ alkyl, halogen and $C_{1-6}$ alkoxy.

In an embodiment, $L^1$ is selected from $C_{1-6}$ linear alkylene, $C_{1-6}$ branched alkylene, $C_{3-6}$ cyclic alkylene and $C_{3-4}$ cyclic alkyl-$C_{1-2}$ linear alkylene group, which are each independently unsubstituted or substituted with one substituent selected from halogen, —OH and —NH₂. In an embodiment, $L^1$ is selected from $C_{1-4}$ alkylene, which is unsubstituted or substituted with one substituent selected from halogen, —OH and —NH₂. In a preferred embodiment, $L^1$ is selected from —CH₂—, —C₂H₄—,

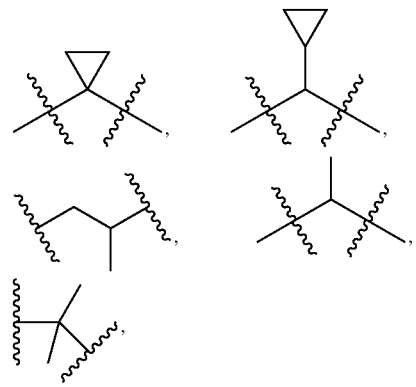

which are each independently unsubstituted or substituted with at least one substituent selected from halogen, —OH and —NH₂. In a preferred embodiment, $L^1$ is selected from —CH₂—,

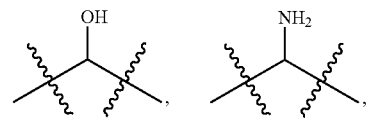

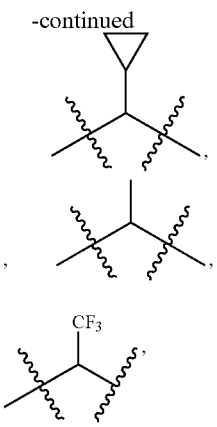

wherein "#" marks the position attached to carbonyl. In a more preferred embodiment, $L^1$ is selected from —CH$_2$—,

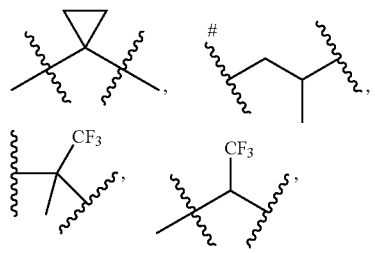

wherein "#" marks the position attached to carbonyl. In a particular embodiment, $L^1$ is selected from —CH$_2$—,

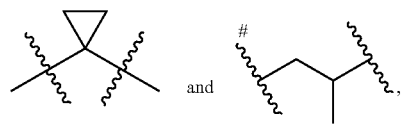 and wherein "#" marks the position attached to carbonyl. In a preferred embodiment, the halogen is selected from F, Cl and Br, especially F.

In an embodiment, a is 1, M is —CH$_2$—, —NH— or —O—; and $L^2$ is —C$_2$H$_4$—. In another embodiment, a is 1, M is —CH$_2$—, and $L^2$ is —CH$_2$—.

In an embodiment, the carbon atom marked with p1* is S configured or racemic, preferably S configured. In another embodiment, the carbon atom marked with p2* is S configured or racemic, preferably S configured.

In an embodiment, $R^1$ and $R^2$ are each independently selected from hydrogen, C$_{1-3}$ alkyl, halogen and C$_{1-3}$ alkoxy. In a preferred embodiment, $R^1$ and $R^2$ are each independently selected from CH$_3$—, F, Cl, Br and CH$_3$O—. In an embodiment, $R^1$ is selected from CH$_3$— and Cl. In another embodiment, $R^2$ is F.

In an embodiment, a is 0, $L^1$ is selected from —CH$_2$—,

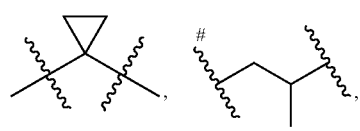

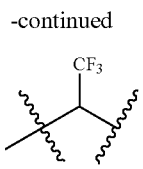

wherein "#" marks the position attached to carbonyl. In an embodiment, a is 1, $L^1$ is

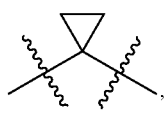 [SMILES: *C1(*)CC1]

M is O, and $L^2$ is —C$_2$H$_4$—.

In an embodiment, a is 0, $R^1$ is Cl, $R^2$ is F, and $L^1$ is selected from —CH$_2$—,

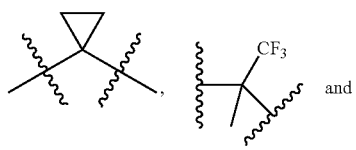 and

In an embodiment, a is 0, $R^1$ is CH$_3$—, $R^2$ is F, and $L^1$ is selected from

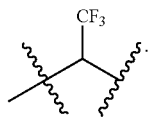

In an embodiment, a is 0, $R^1$ is CH$_3$—, $R^2$ is F, and $L^1$ is selected from

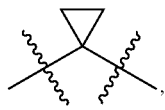 [SMILES: *C1(*)CC1] and wherein "#" marks the position attached to carbonyl.

In an embodiment, a is 1, $R^1$ is CH$_3$—, $R^2$ is F, $L^1$ is

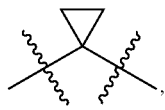 [SMILES: *C1(*)CC1]

M is O, and $L^2$ is —C$_2$H$_4$—.

In an embodiment, the compound is selected from:
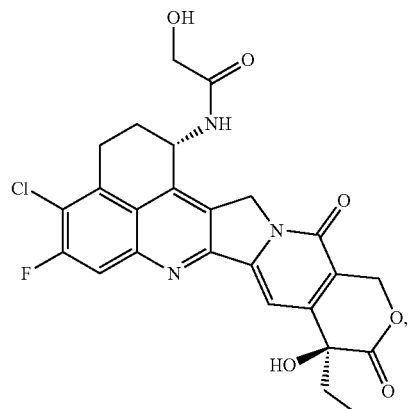
C518
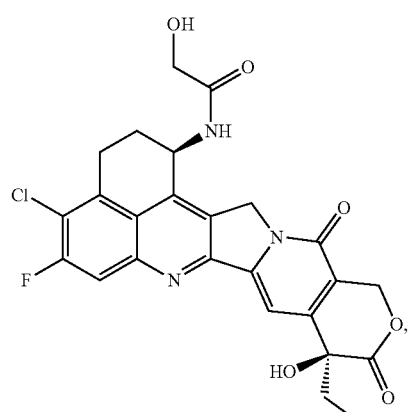
C519
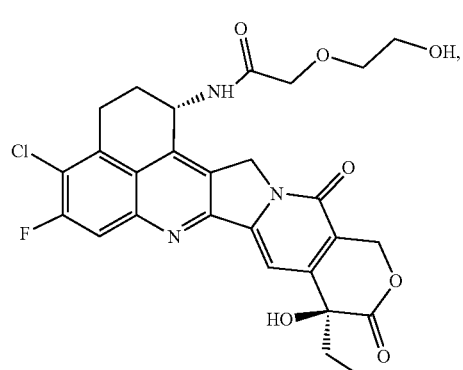
C586
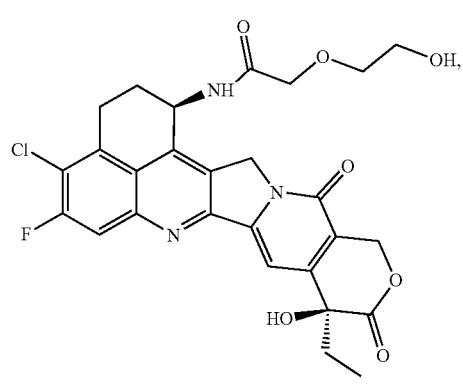
C587
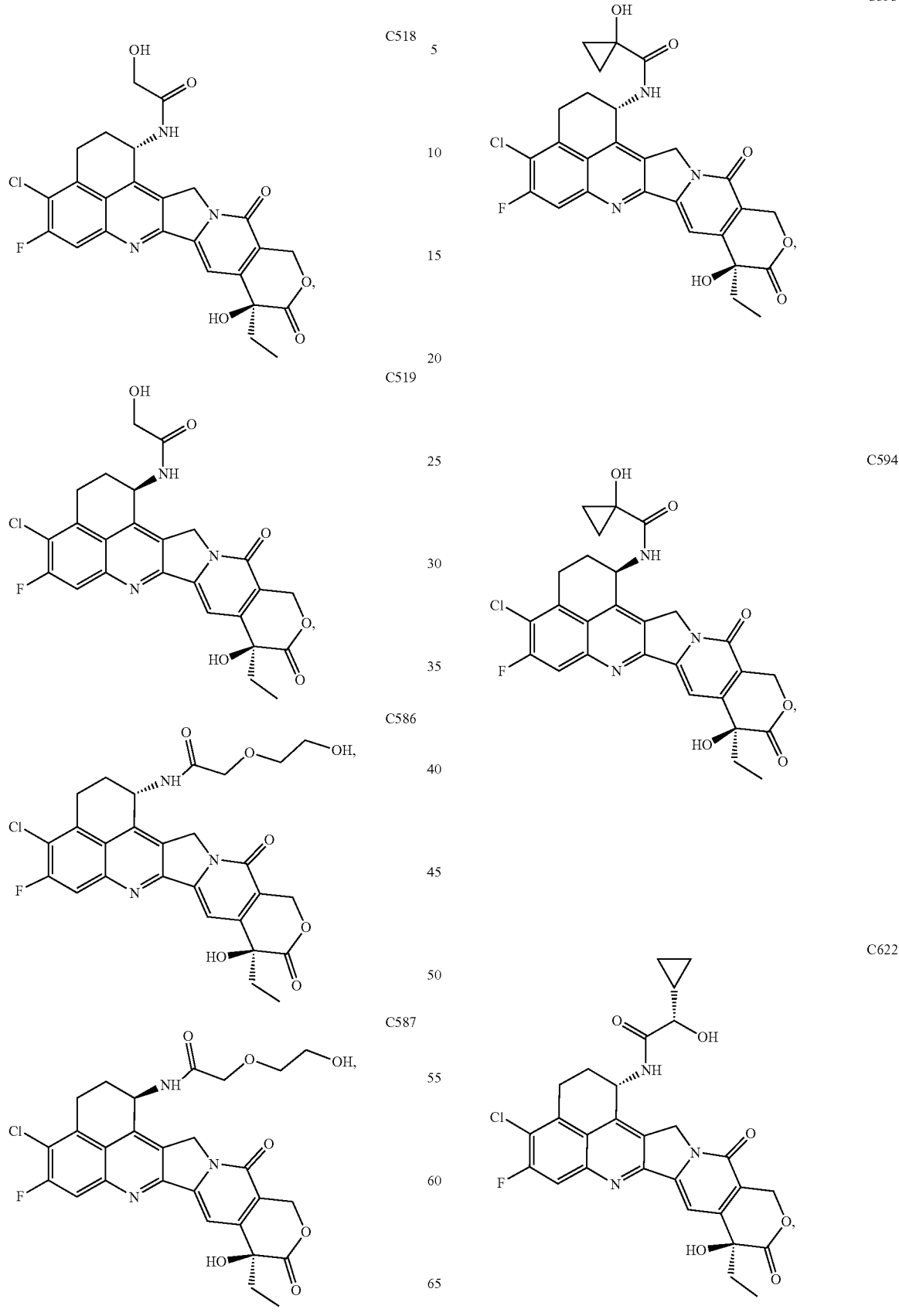

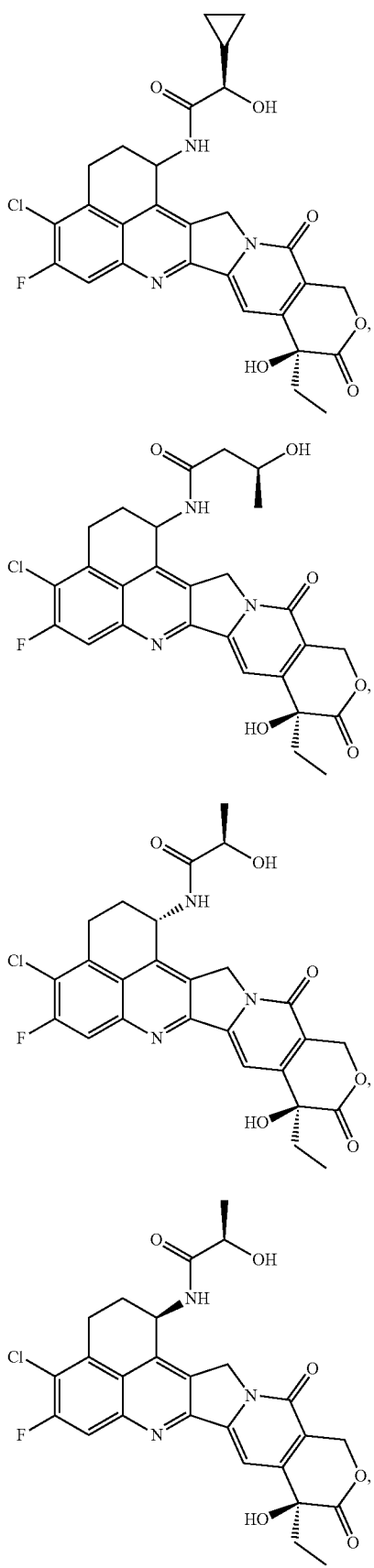
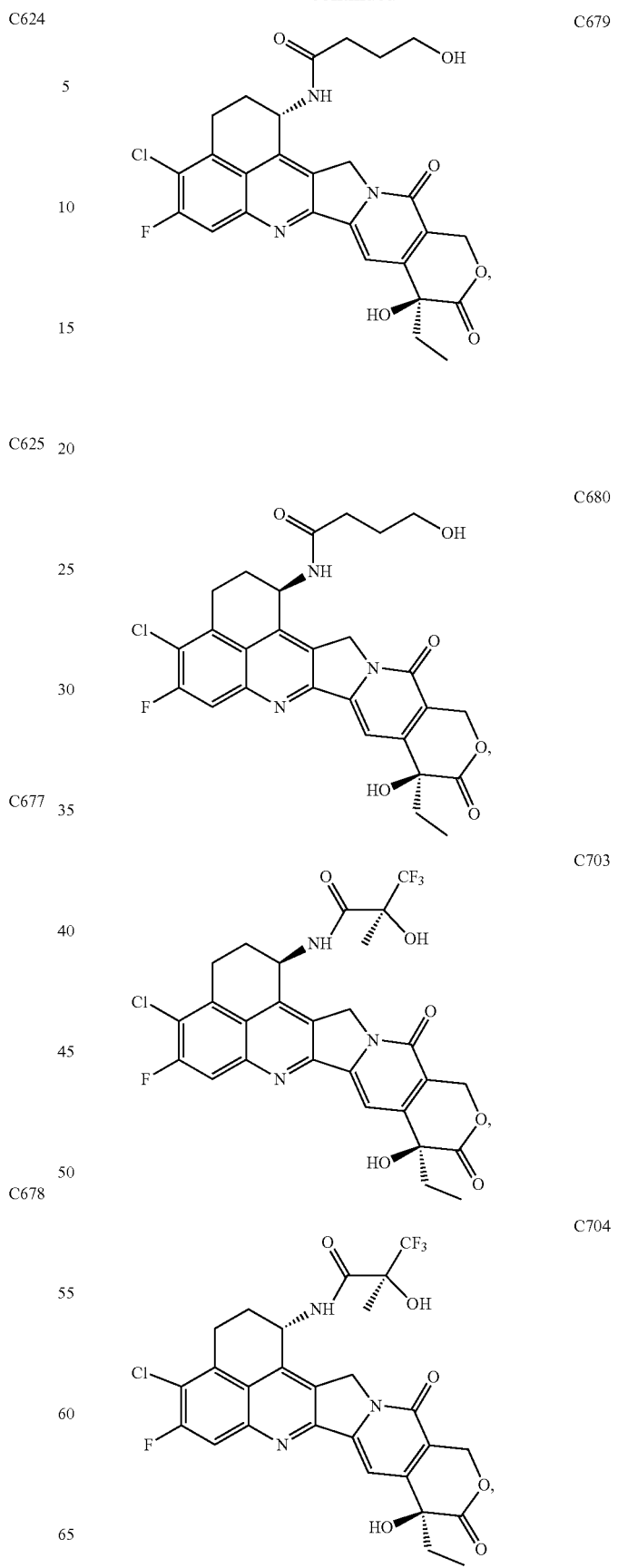

C627 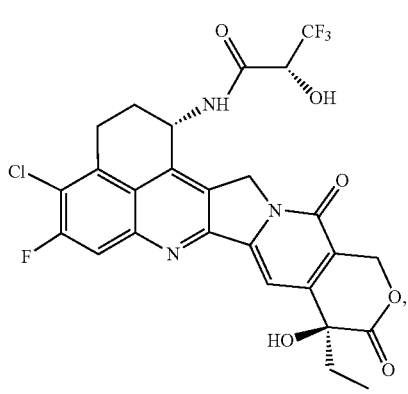
C626 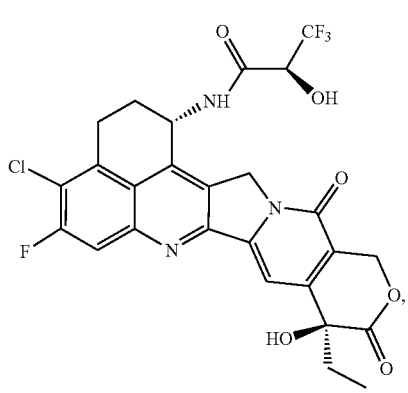
C636 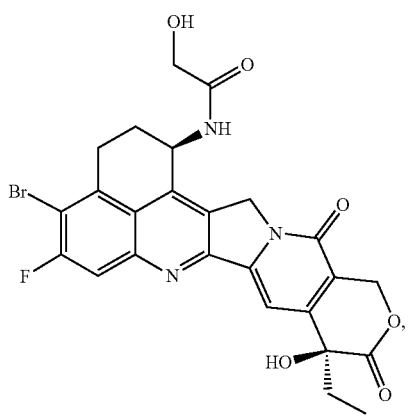
C637 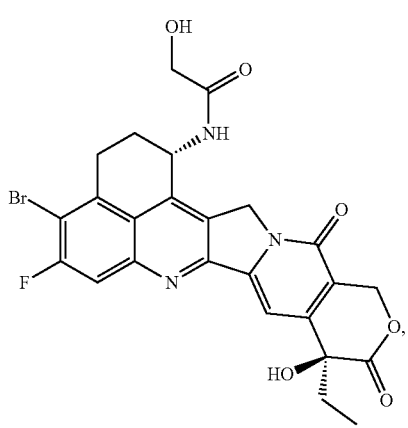
C595 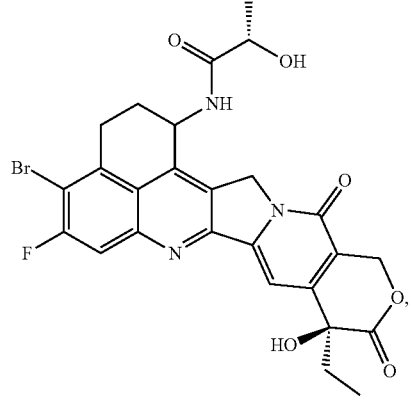
C596 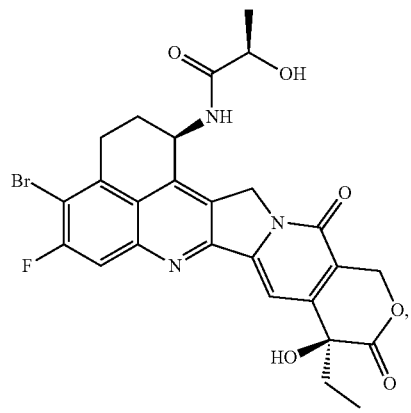
C597 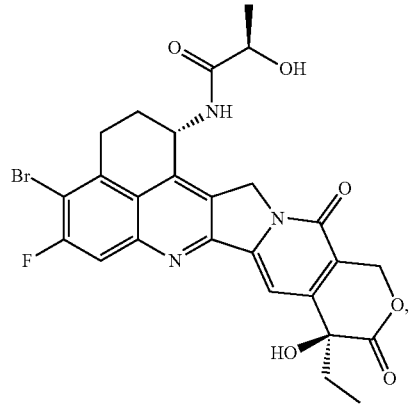
C600 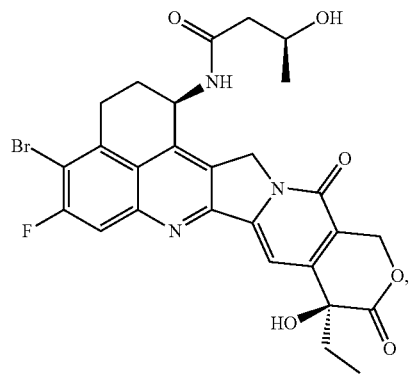

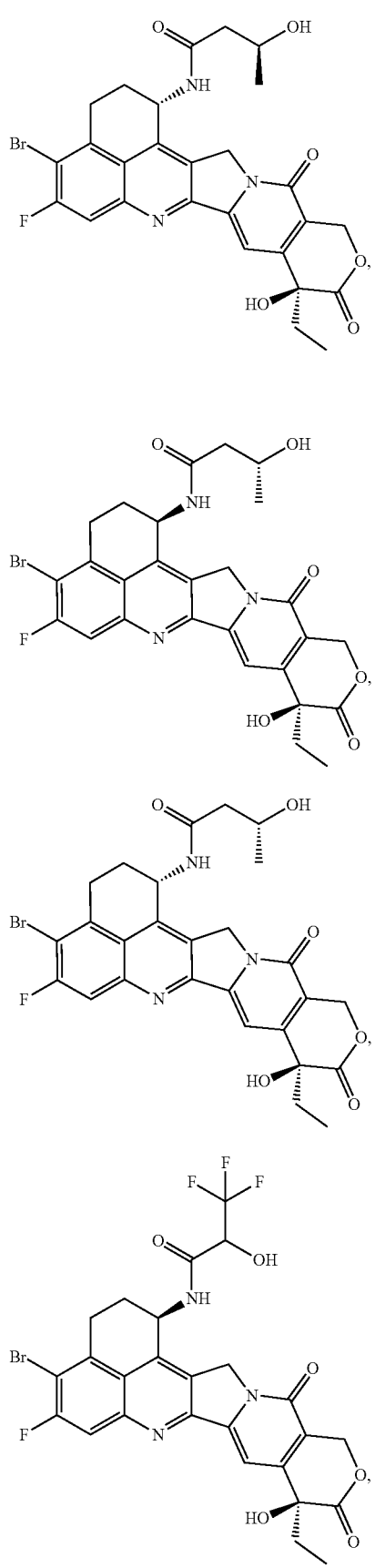
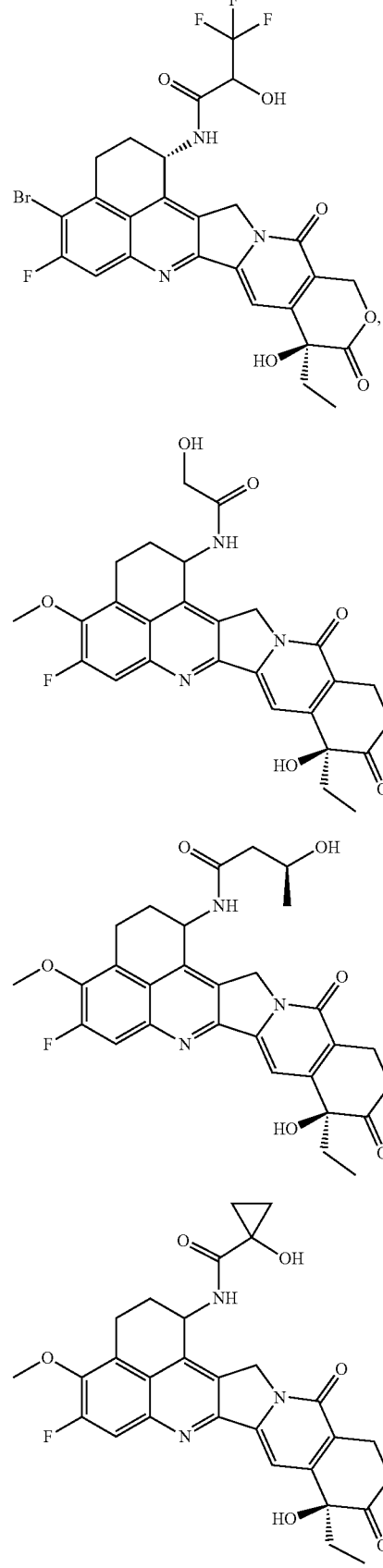

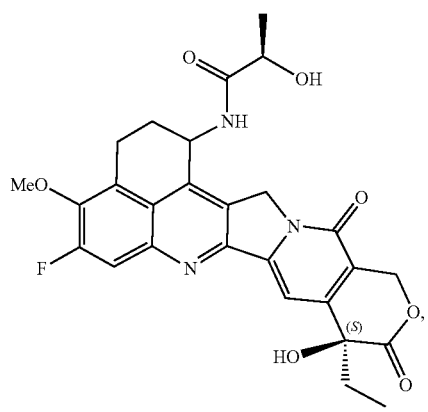
C668
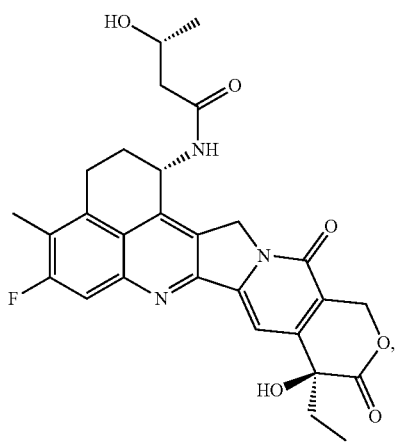
C588
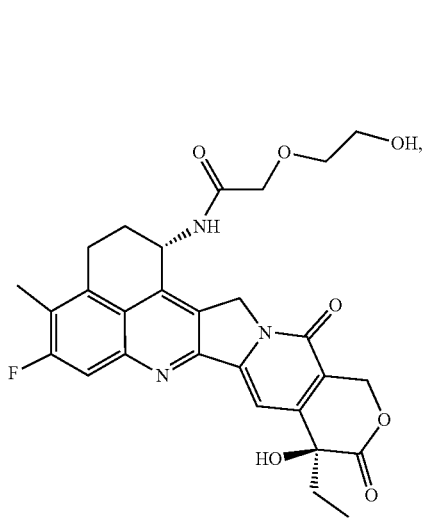
C504
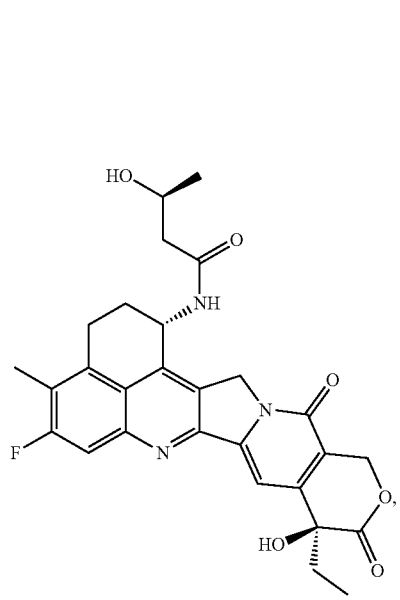
C671
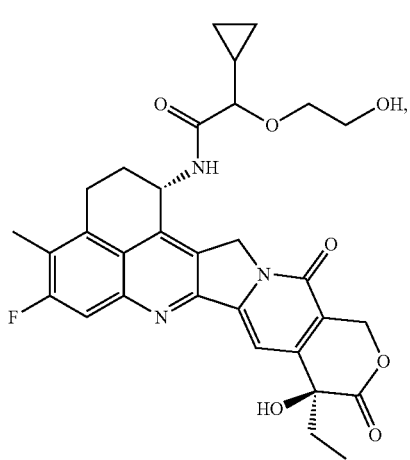
C562
C589

C563
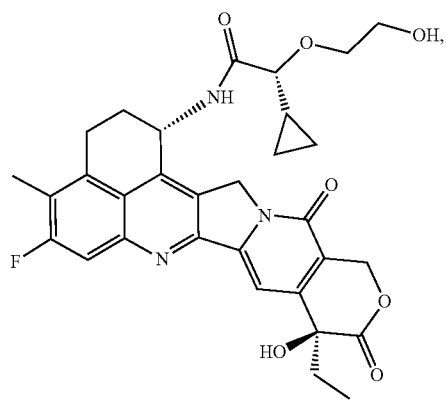
C565
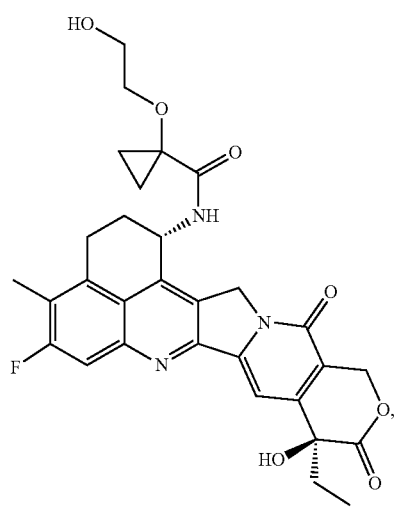
C687
C688
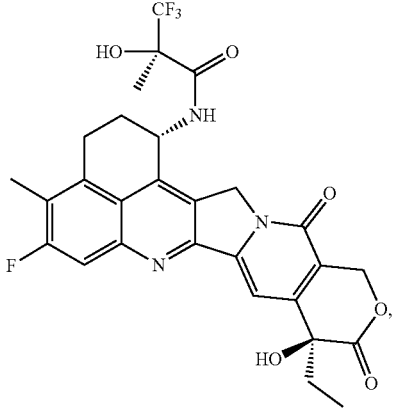
In an embodiment, the compound is selected from:
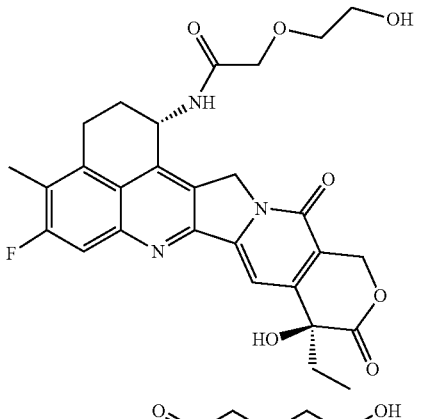
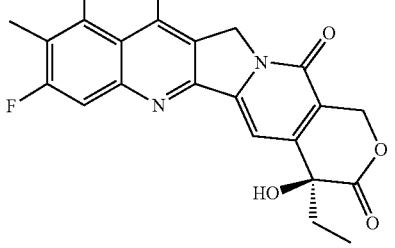
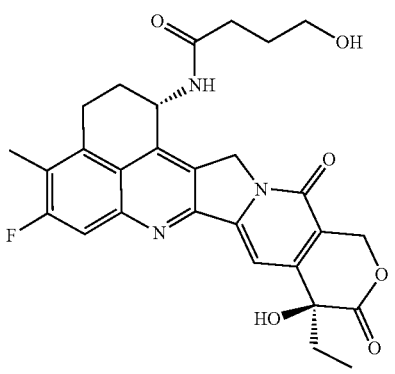

27
-continued
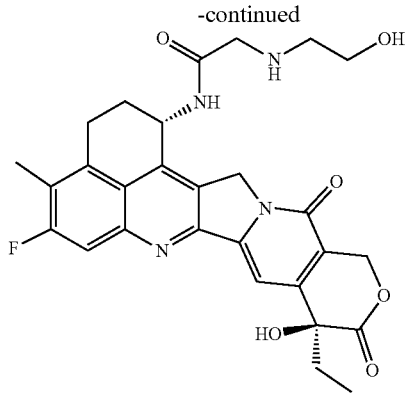
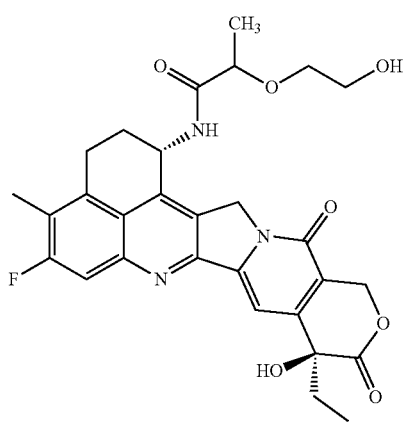
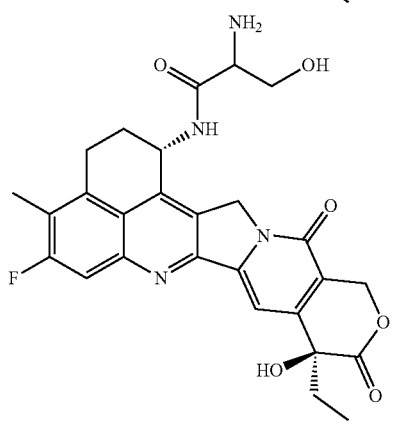
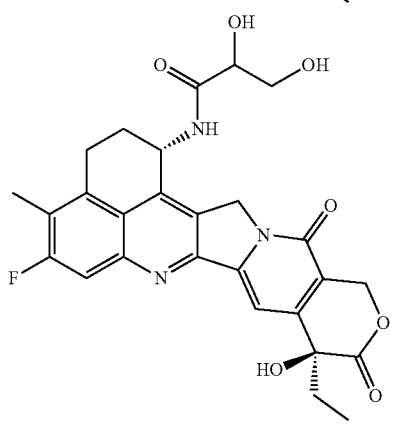
28
-continued
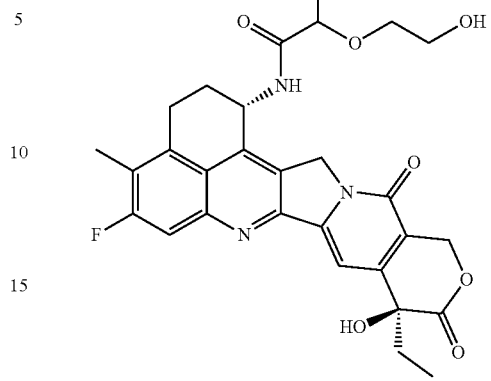
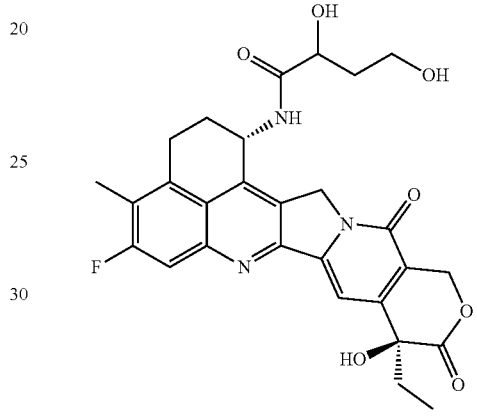
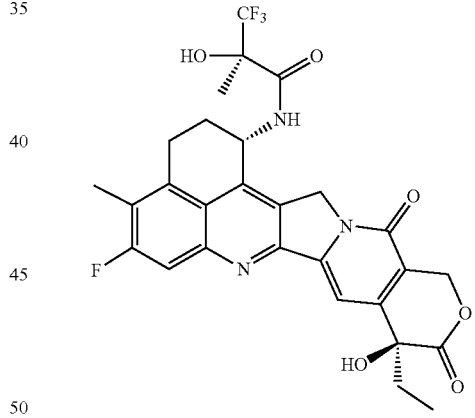
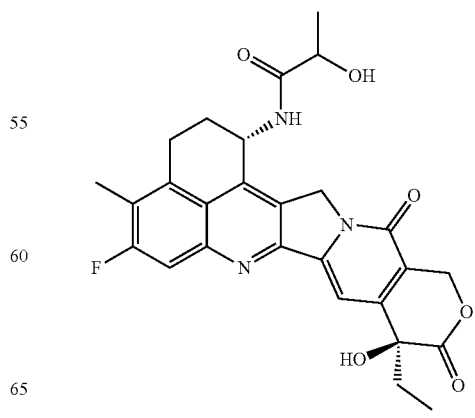

29
-continued
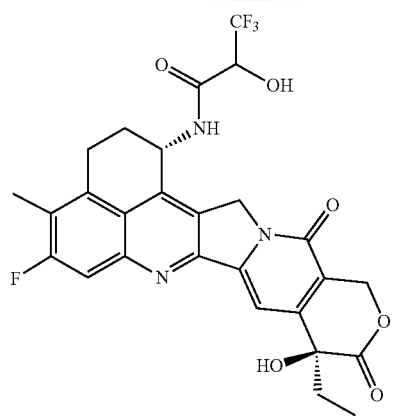
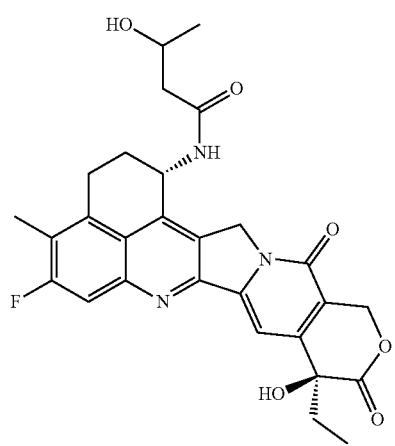
30
-continued
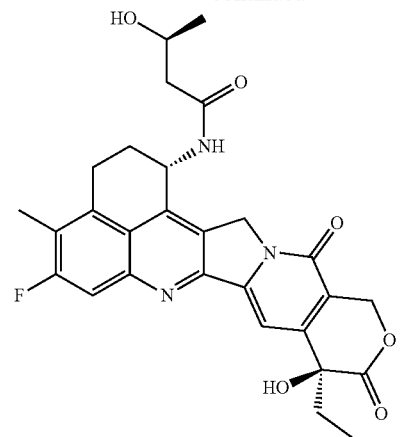
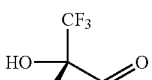
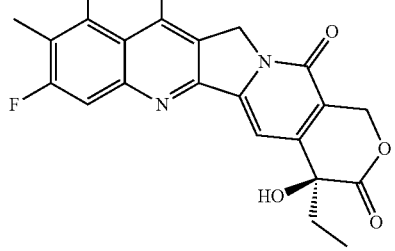
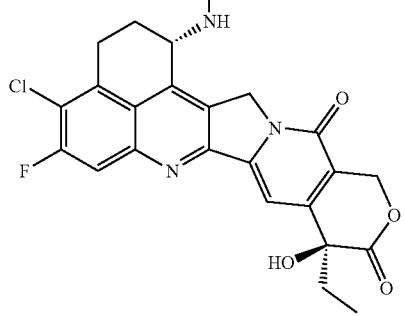
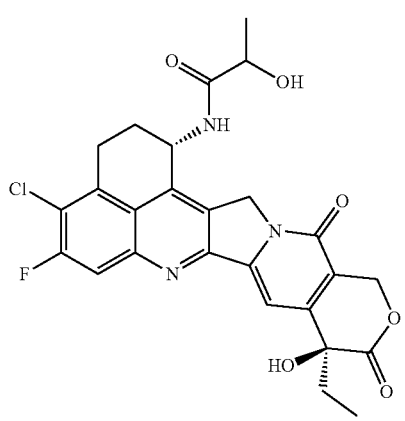

31
-continued
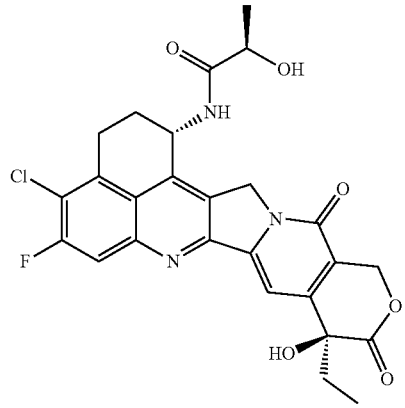
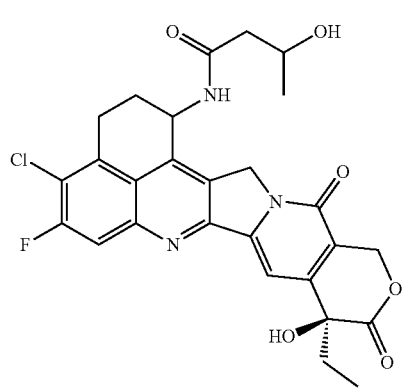
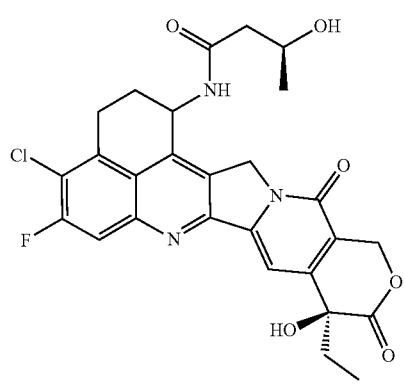
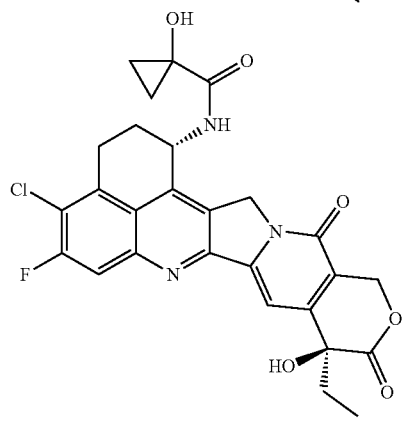
32
-continued
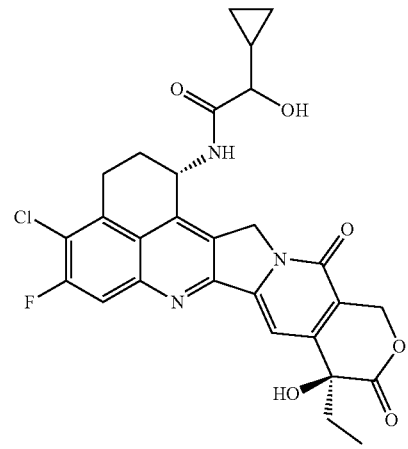
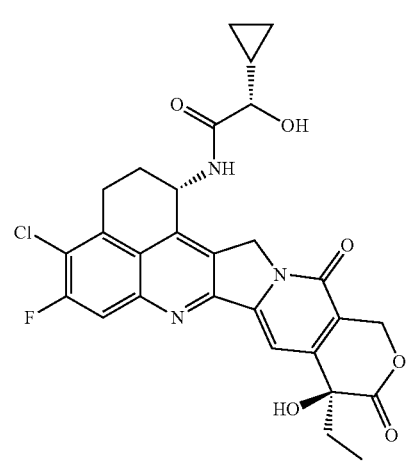
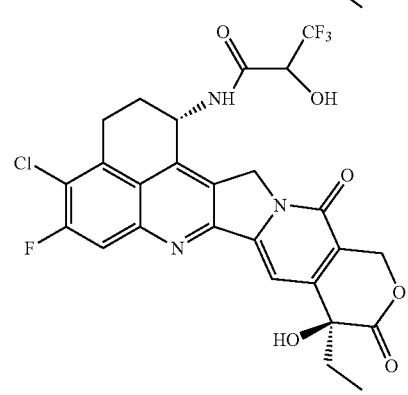
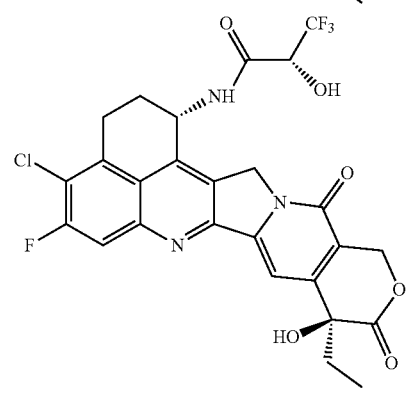

33
-continued
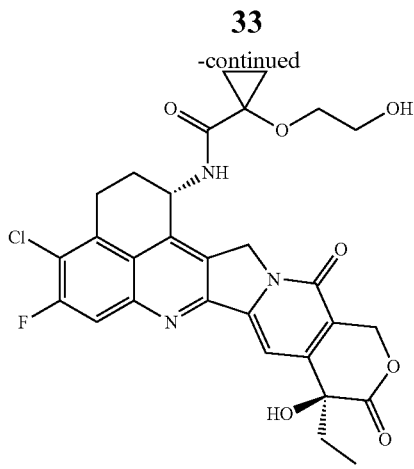
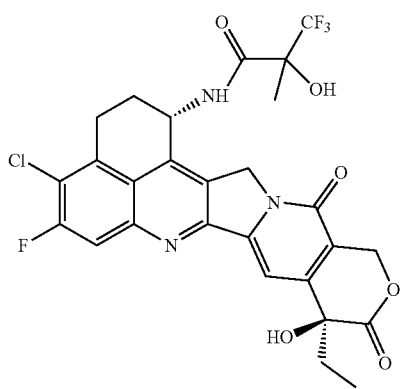
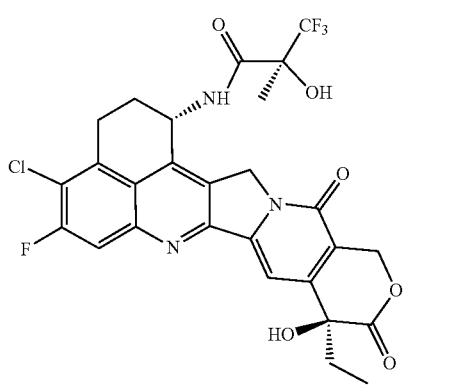
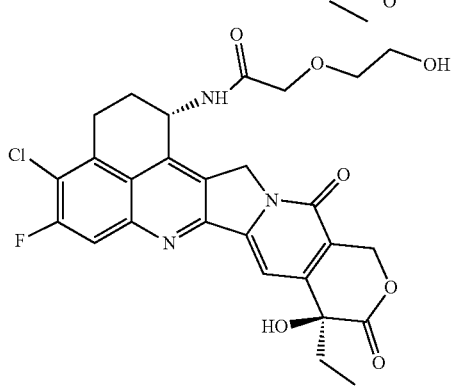
34
-continued
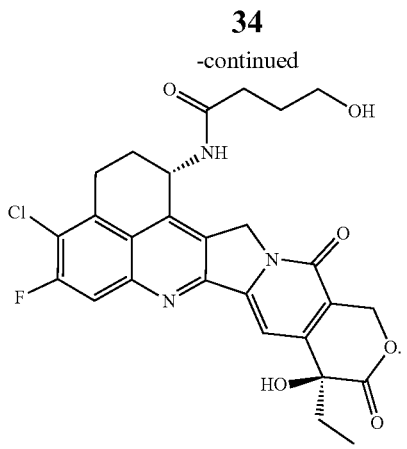
In a preferred embodiment, the compound is selected from:
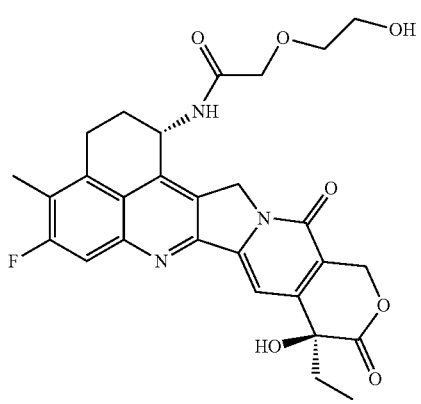
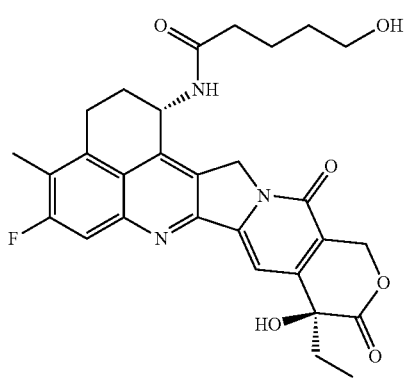
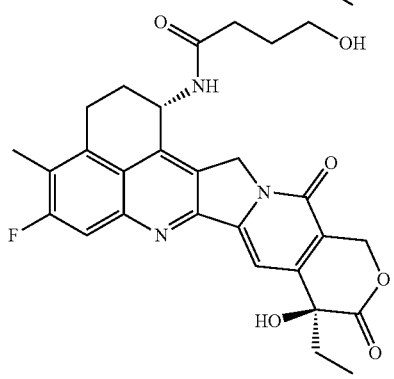

35
-continued
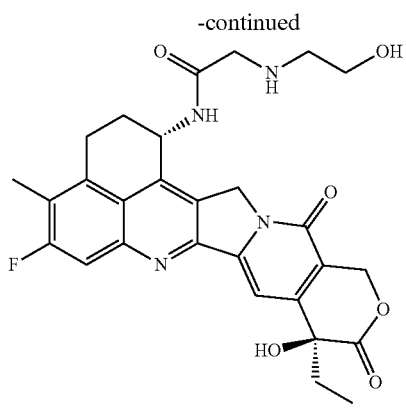
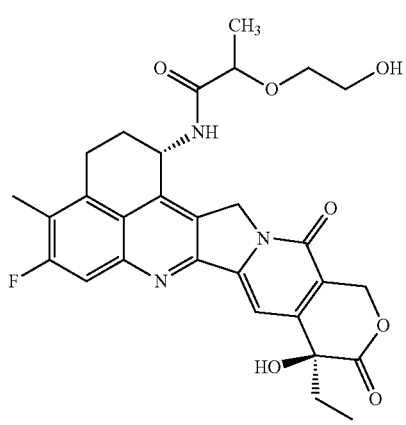
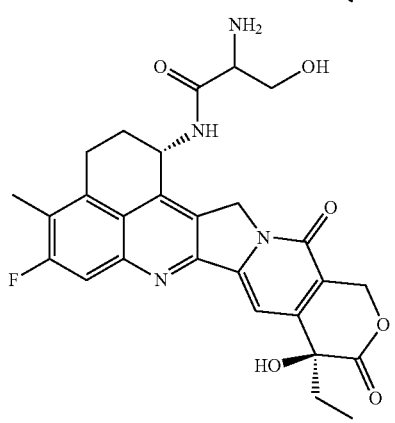
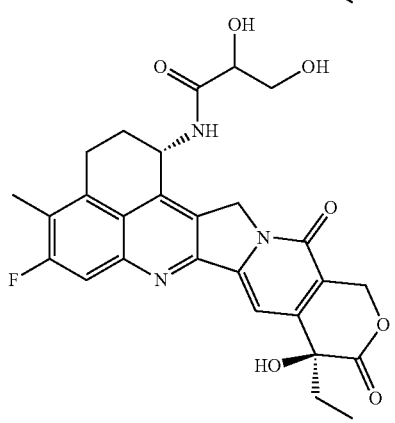
36
-continued
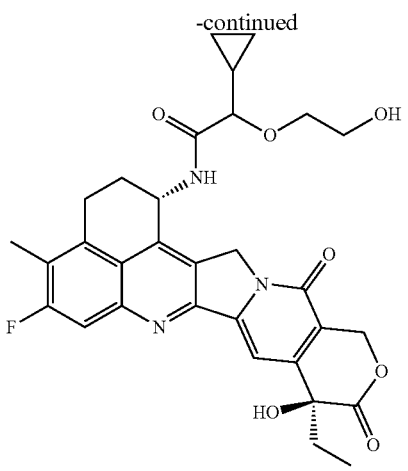
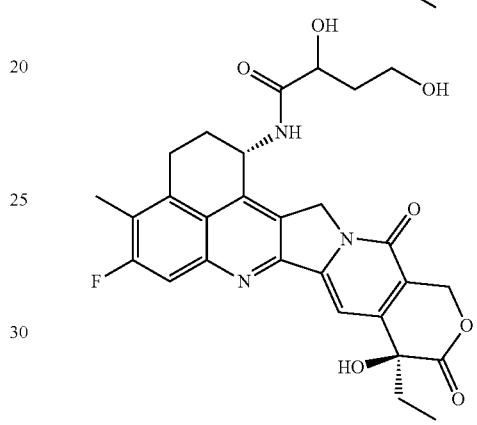
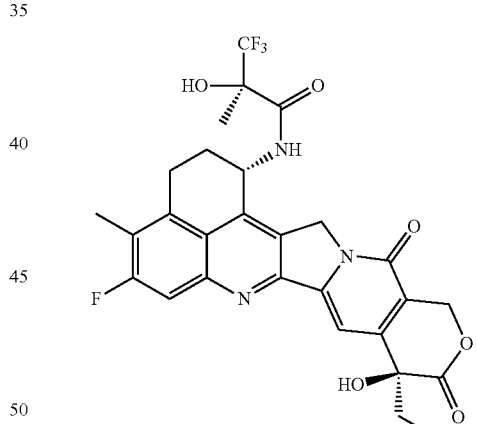
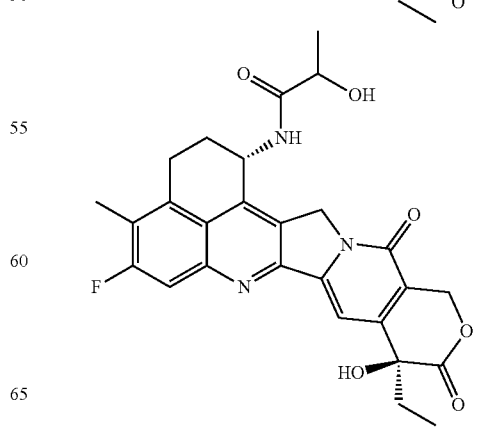

-continued
37
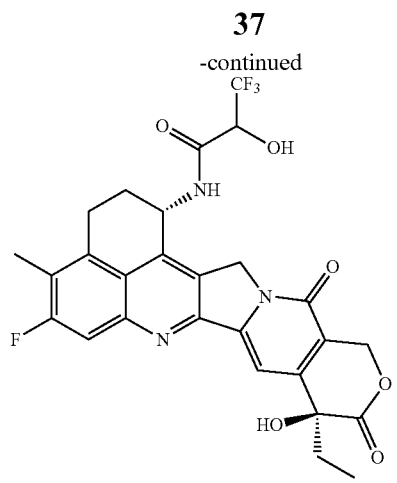
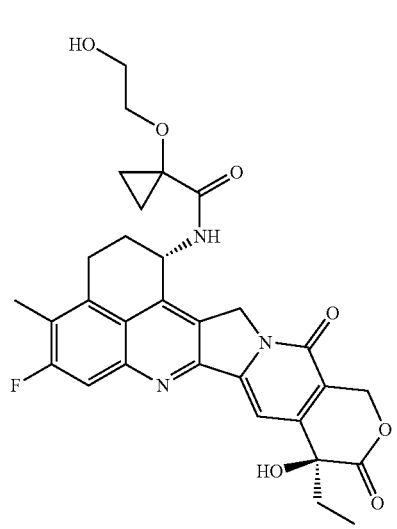
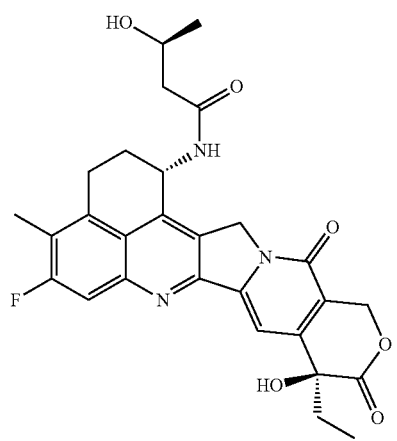
-continued
38
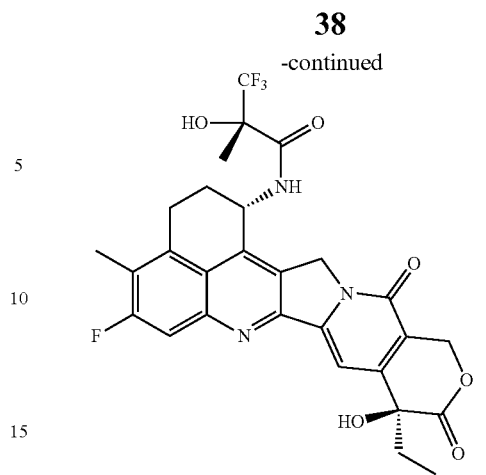
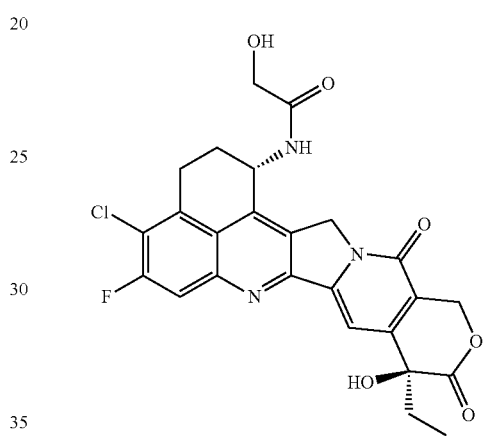
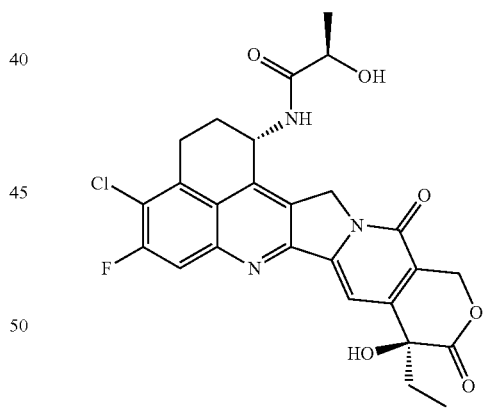
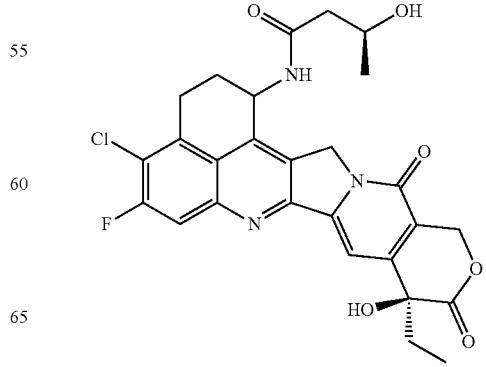

-continued
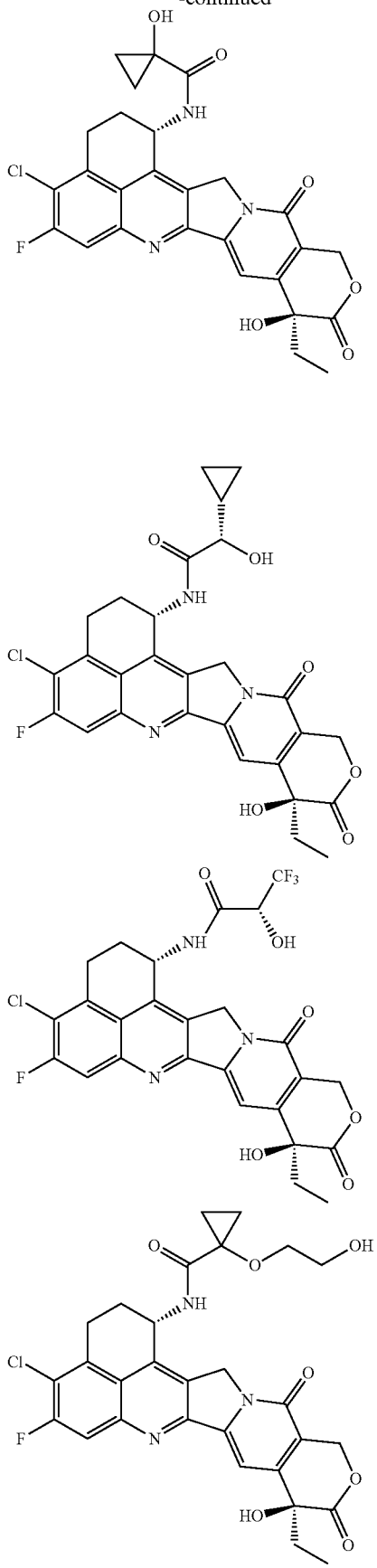
-continued
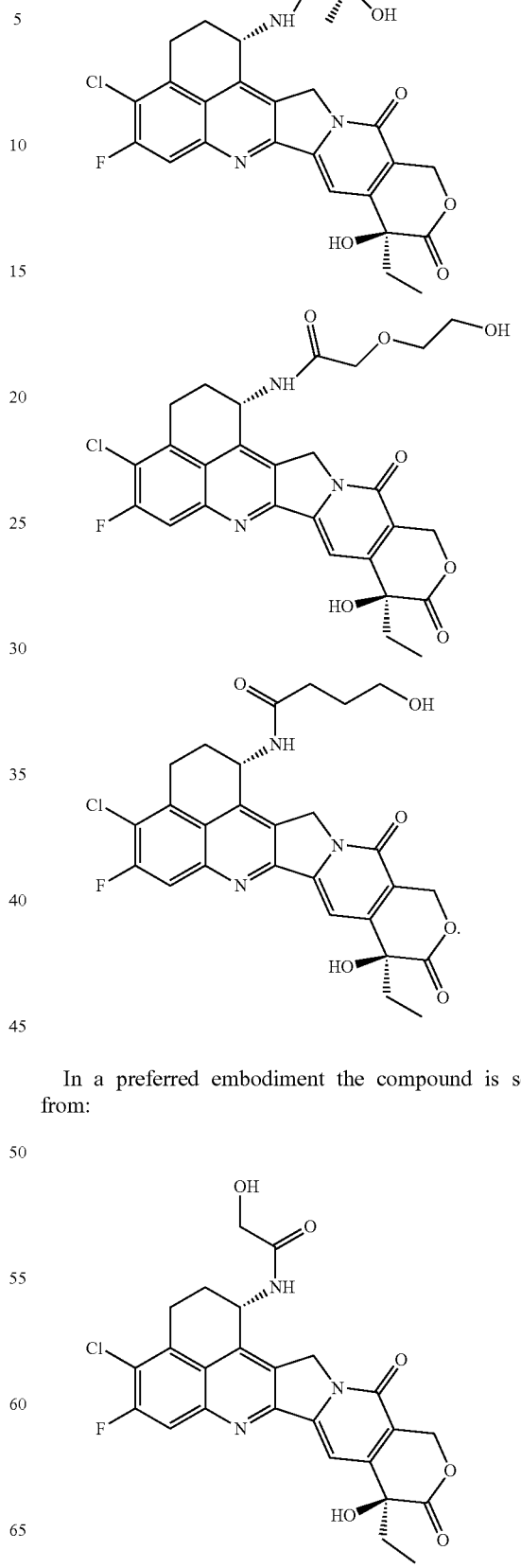
In a preferred embodiment the compound is selected from:

-continued
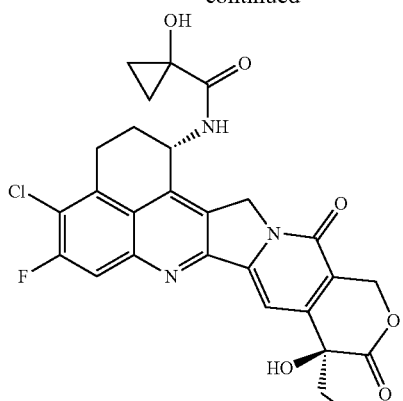
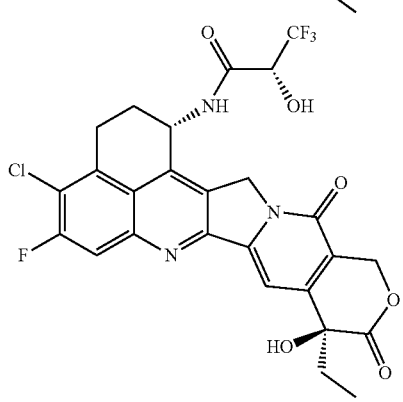
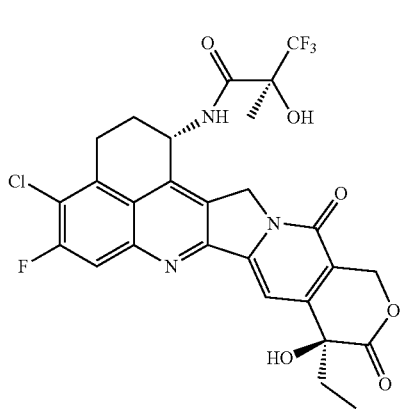 [SMILES: CC[C@@]1(O)C(=O)OCc2c1cc1n(c2=O)Cc2c-1nc1cc(F)c(Cl)c3c1c2[C@@H](NC(=O)[C@@H](O)C(F)(F)F)CC3]
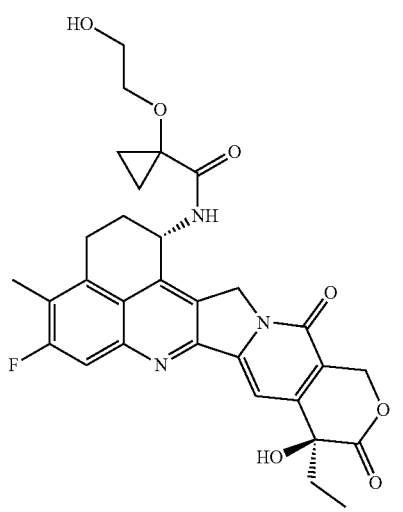
-continued
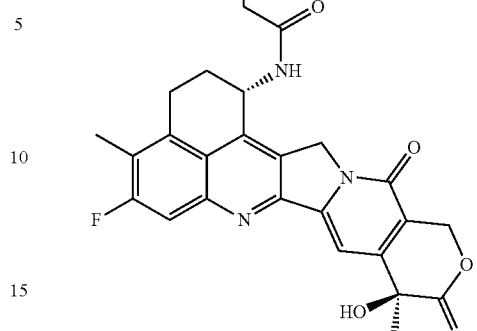
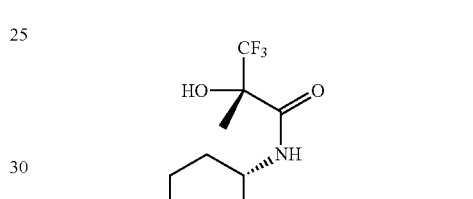
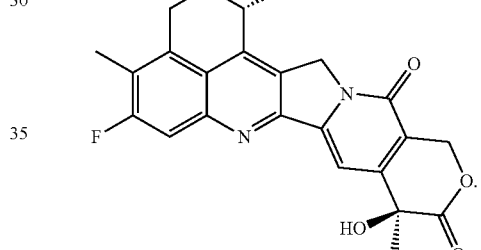
In a more preferred embodiment, the compound is selected from:
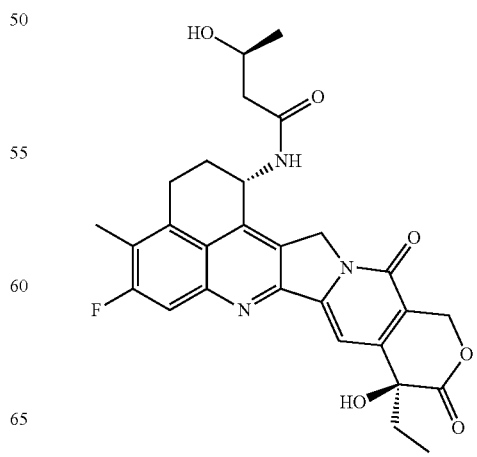

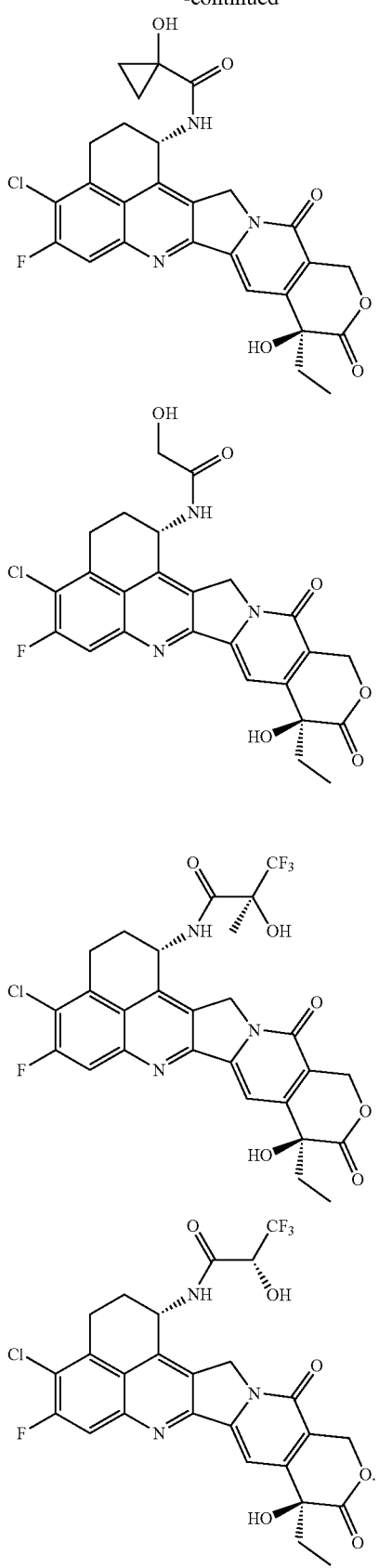
In a particular embodiment the compound is selected from:
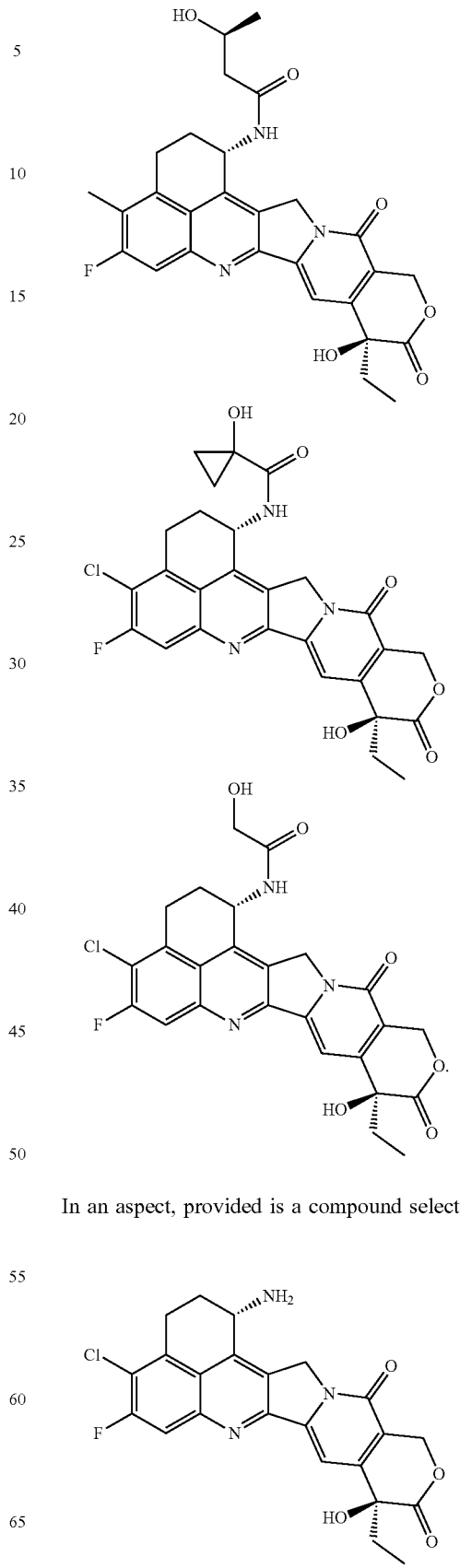
In an aspect, provided is a compound selected from:
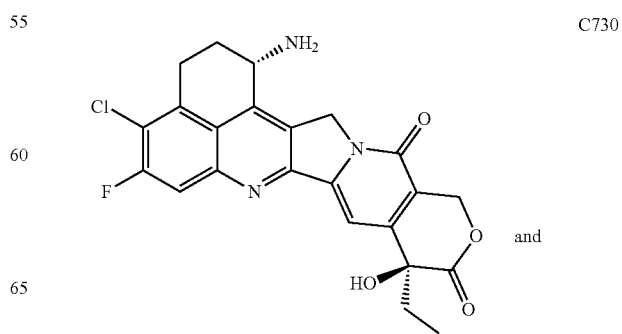
and -continued
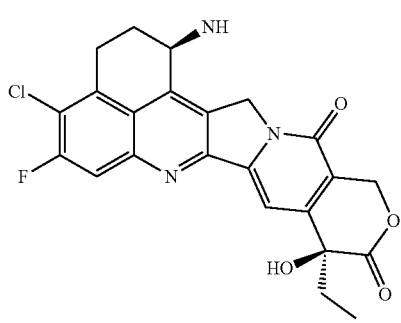
C731
Compound of Formula (I)
In an aspect, provided is a compound having the structure of formula (I):
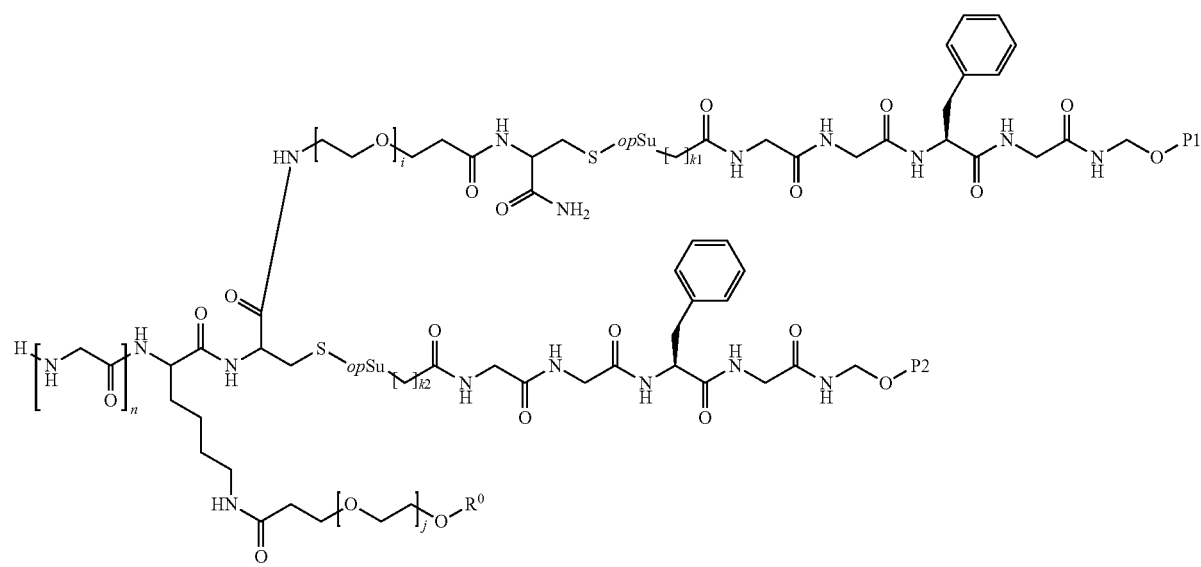
(I)
wherein,
opSu is
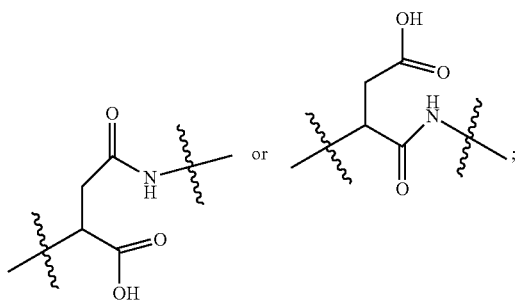 [SMILES: *NC(=O)CC(*)C(=O)O ; *NC(=O)C(*)CC(=O)O]
$R^0$ is $C_{1-10}$ alkyl;
n is any integer of 2 to 20;
k1 and k2 are independently an integer of 1 to 7;
i is an integer of 1-100;
j is an integer of 1-100;
P1 and P2 are independently a payload having the structure of formula (i'):
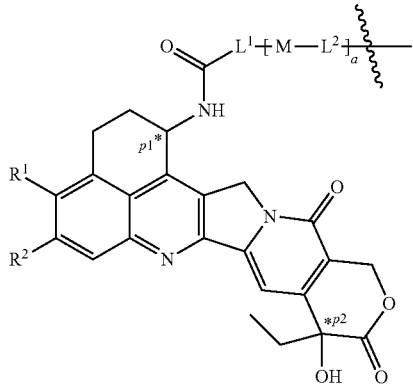
(i')

wherein,
a, the carbon atoms marked with p1* and p2*, $L^1$, M, $L^2$, $R^1$ and $R^2$ are as defined in formula (i).
In an embodiment, the payload is selected from:
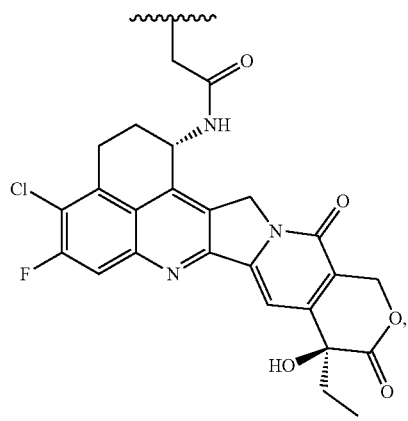
H518
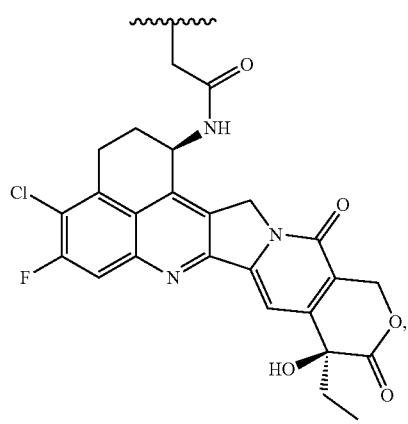
H519
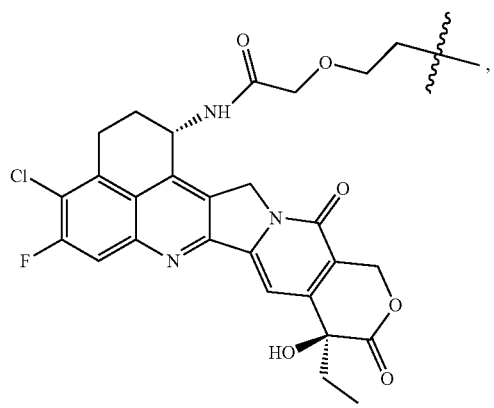
H586
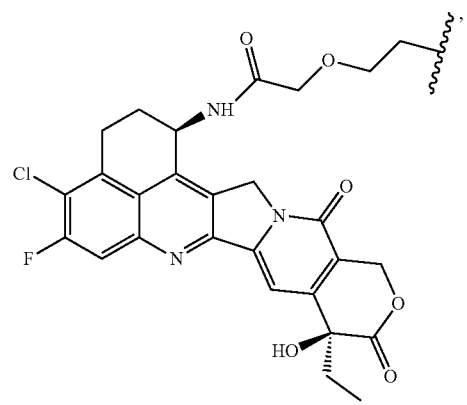
H587
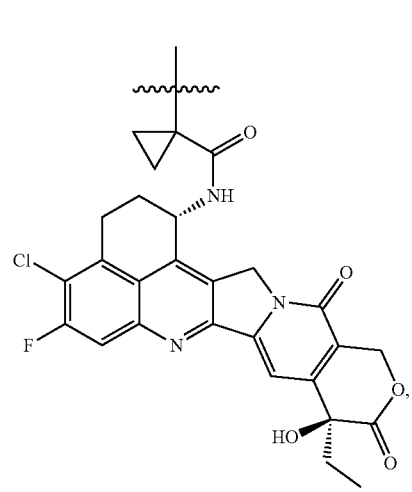
H593
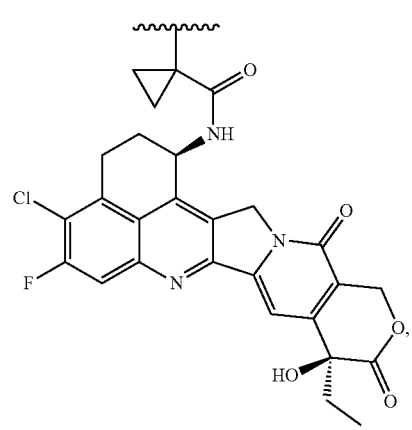
H594

49
-continued
H622
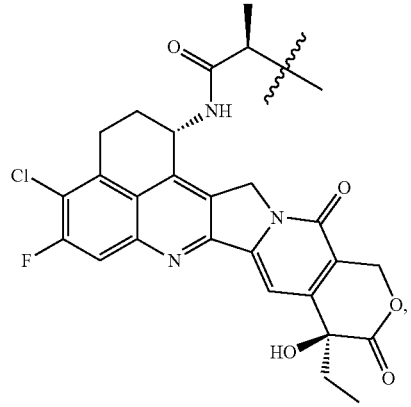
50
-continued
H677
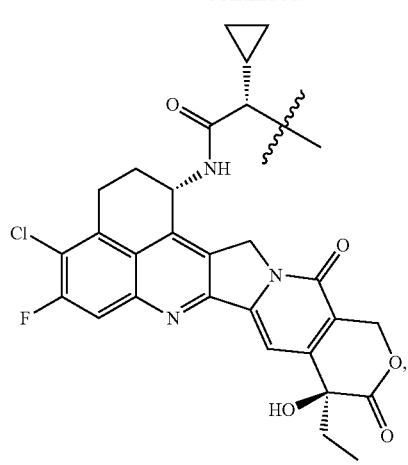
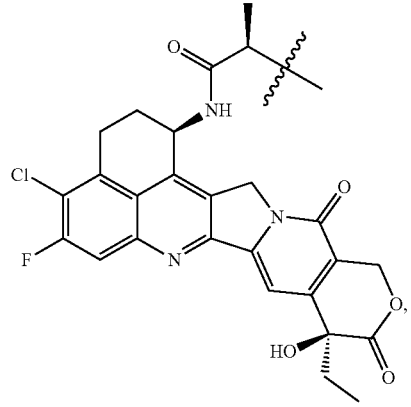
H624
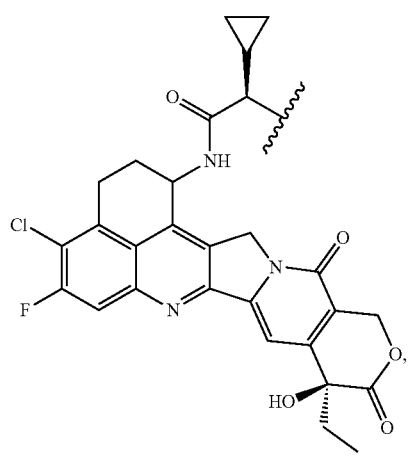
H678
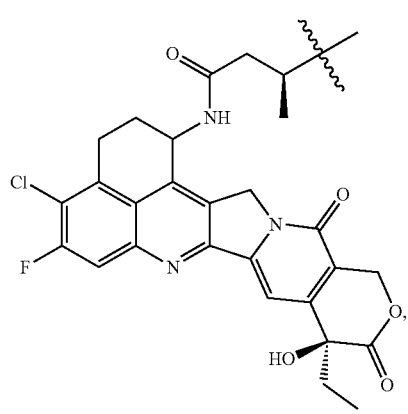
H679
H625
H680

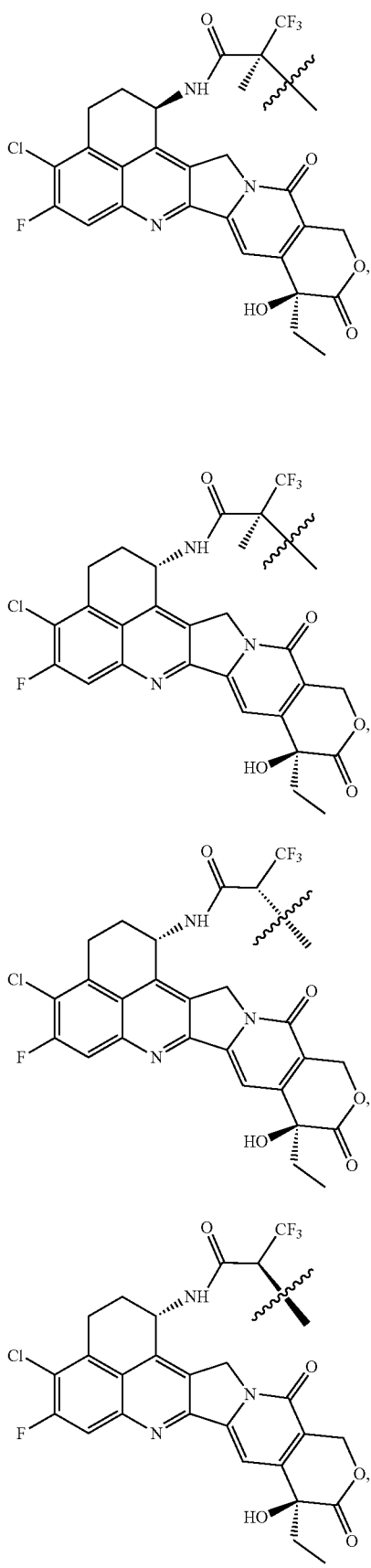
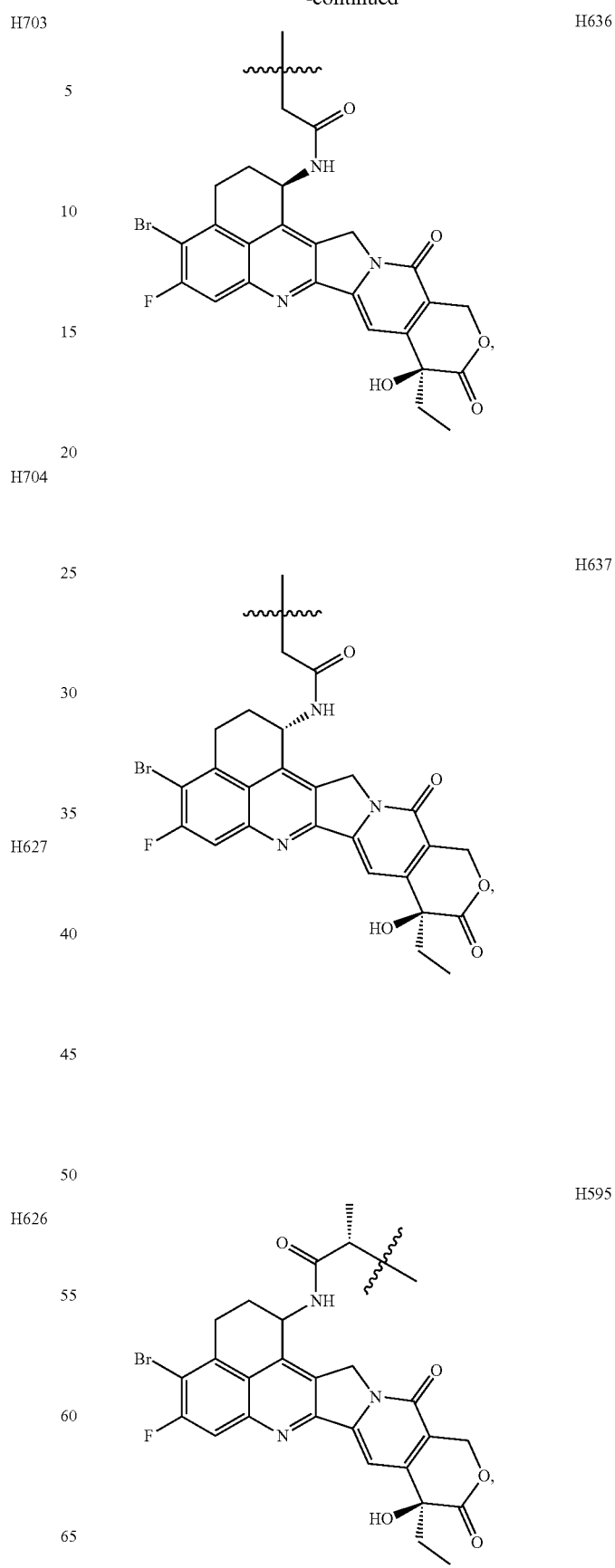

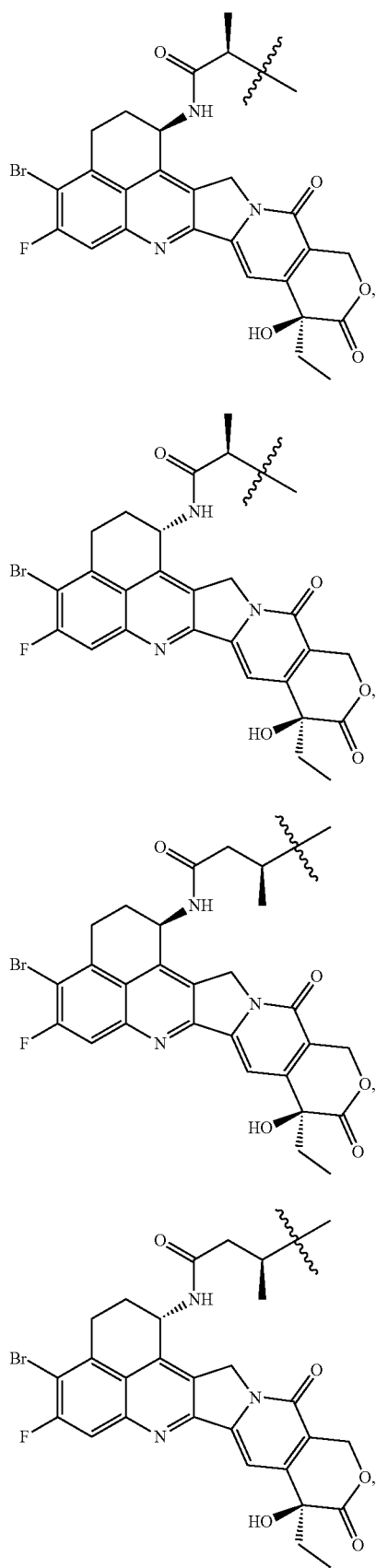
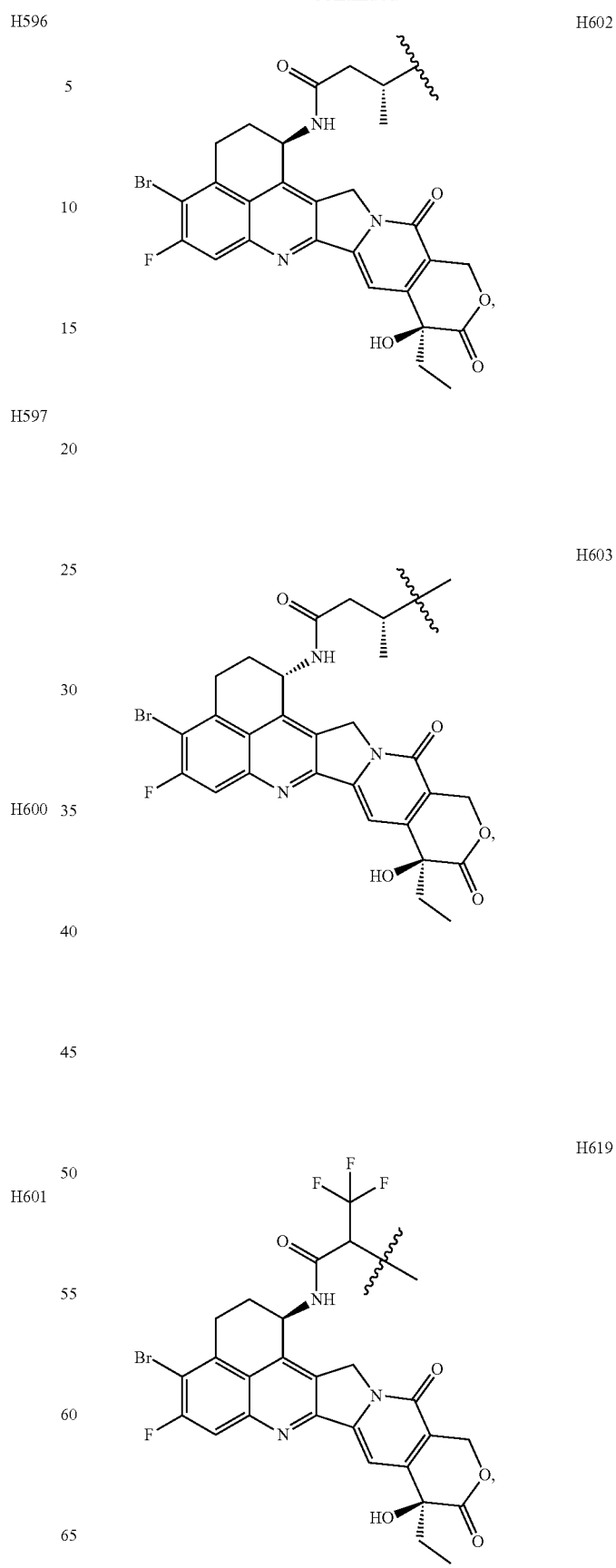

H620
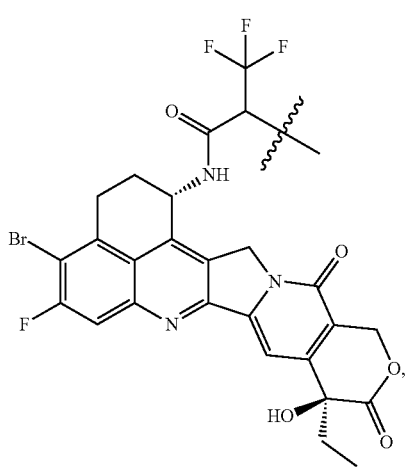
H664
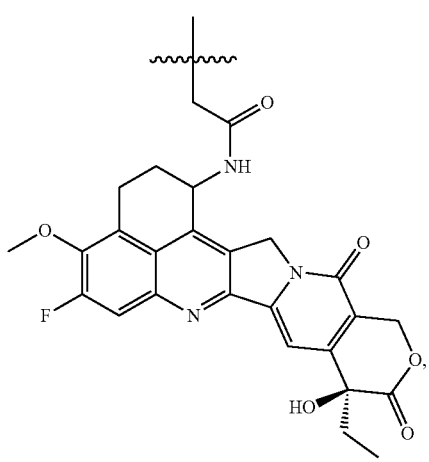
H665
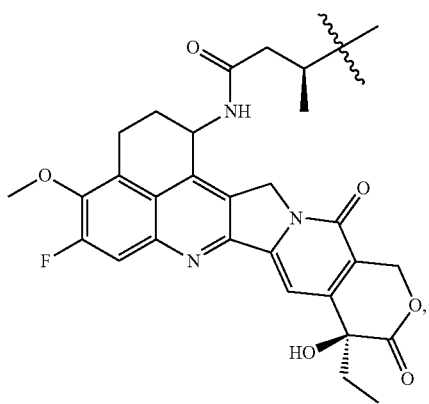
H667
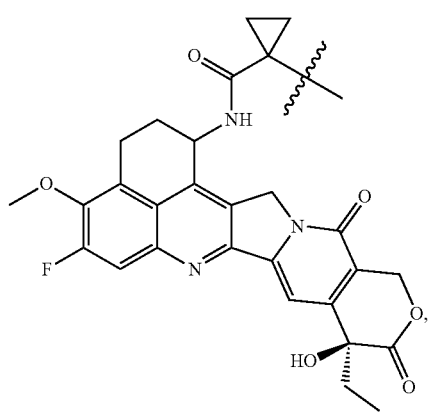
H668
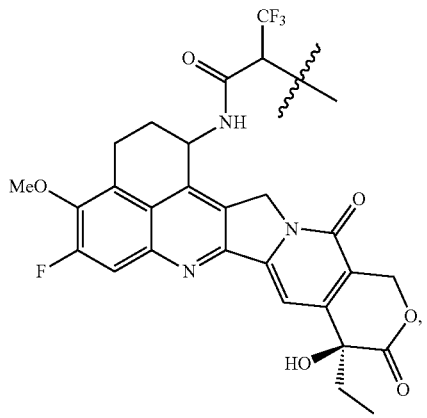
H671

-continued
H589
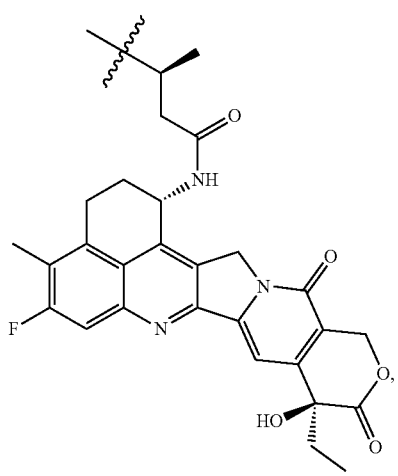
H588
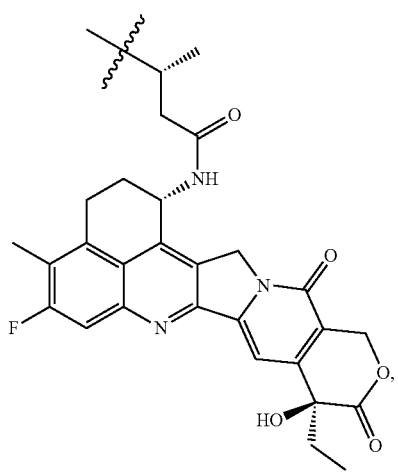
H504
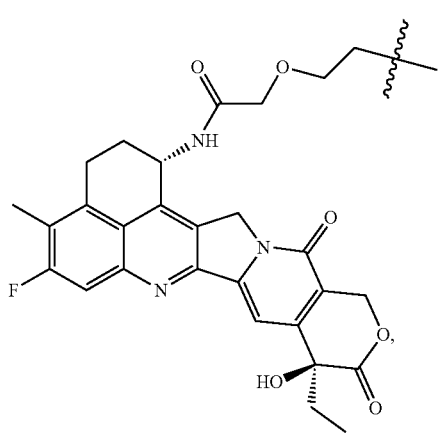
-continued
H562
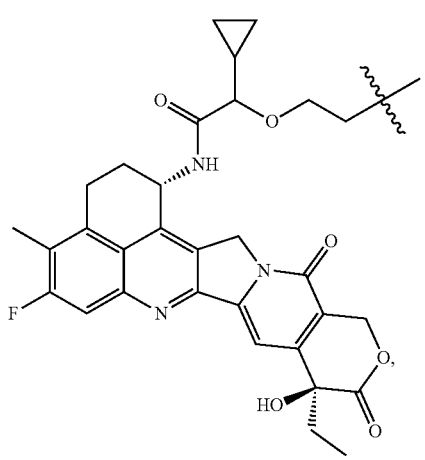
H653
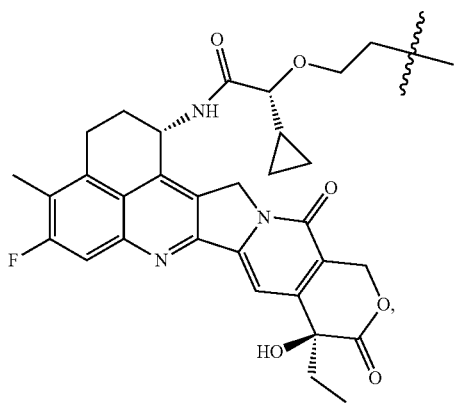
H565
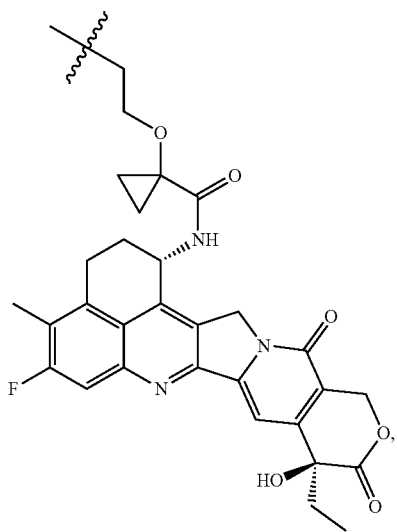

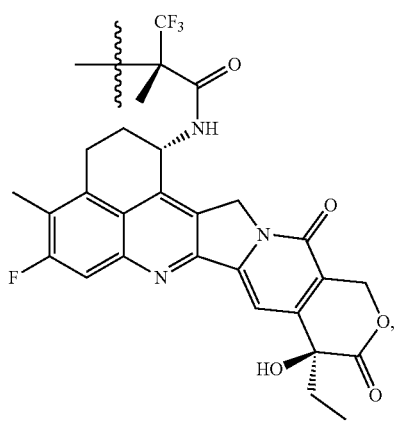
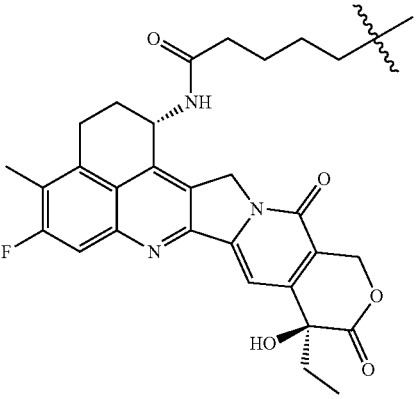
H687
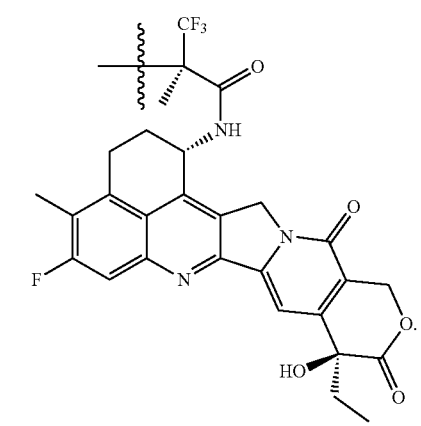
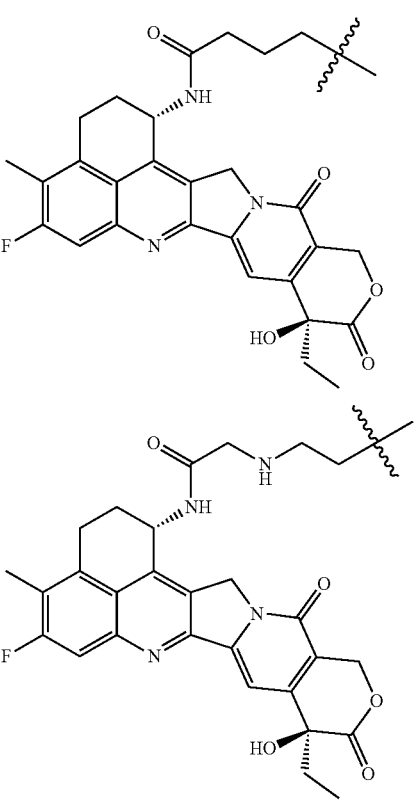
H688
In an embodiment, the payload is selected from:
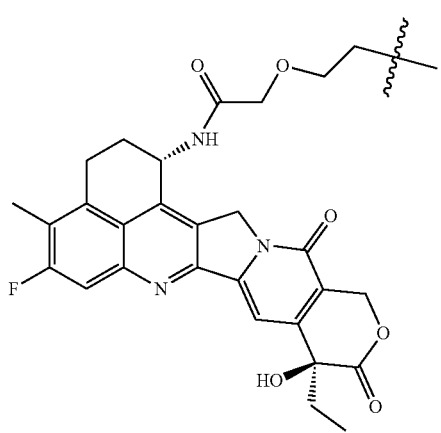
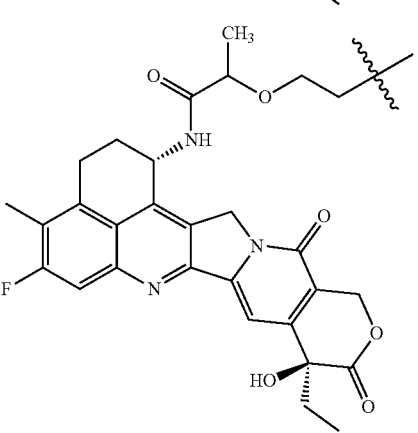

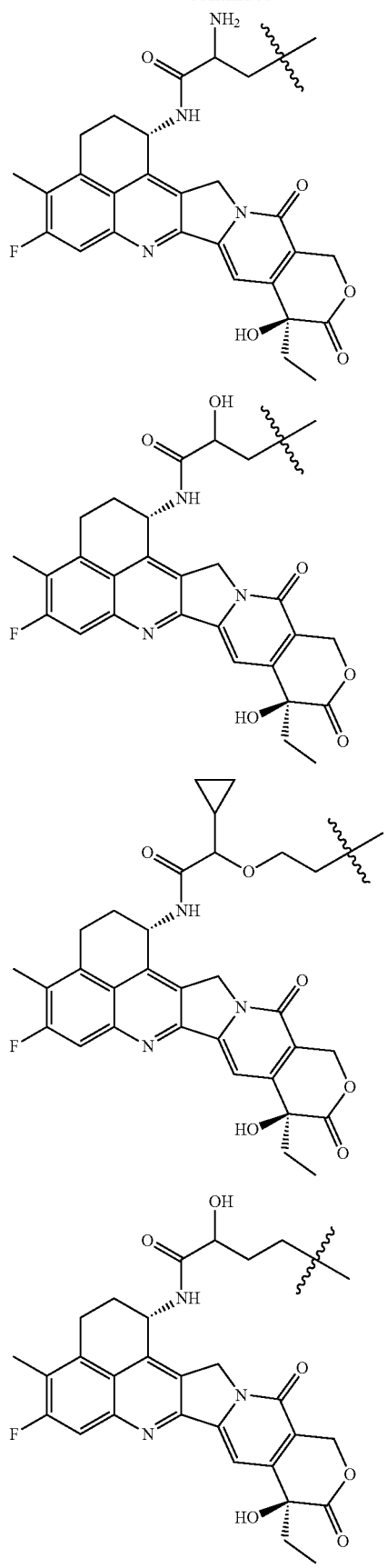
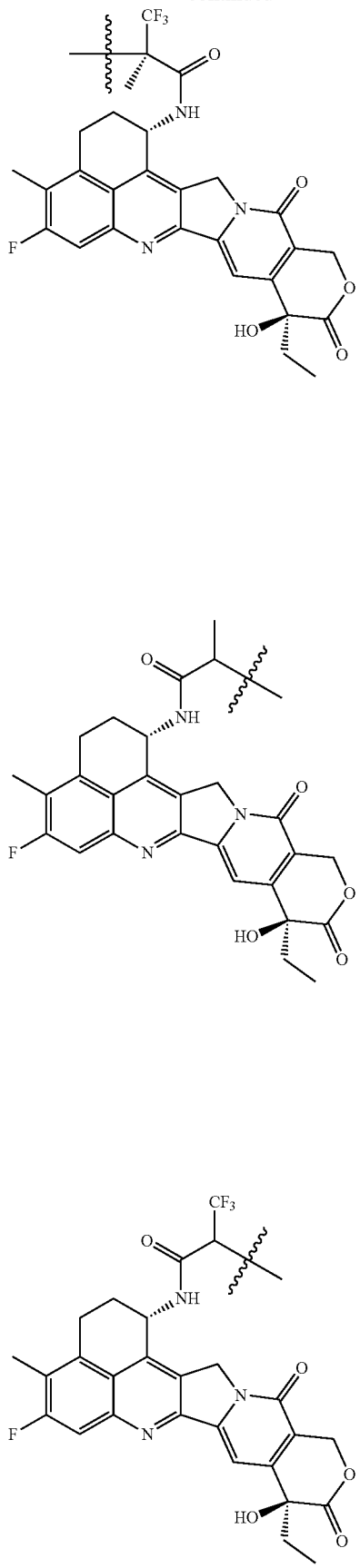

63
-continued
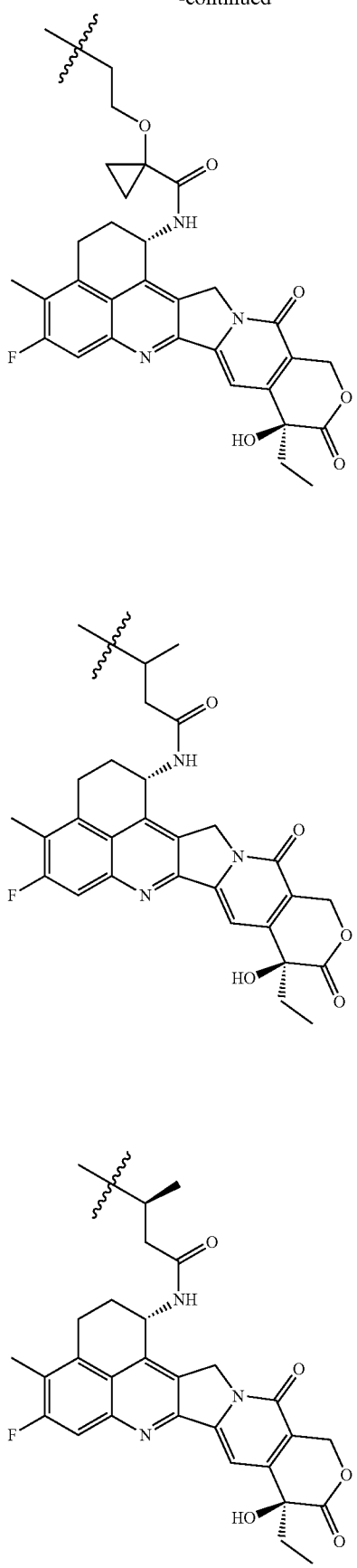
64
-continued
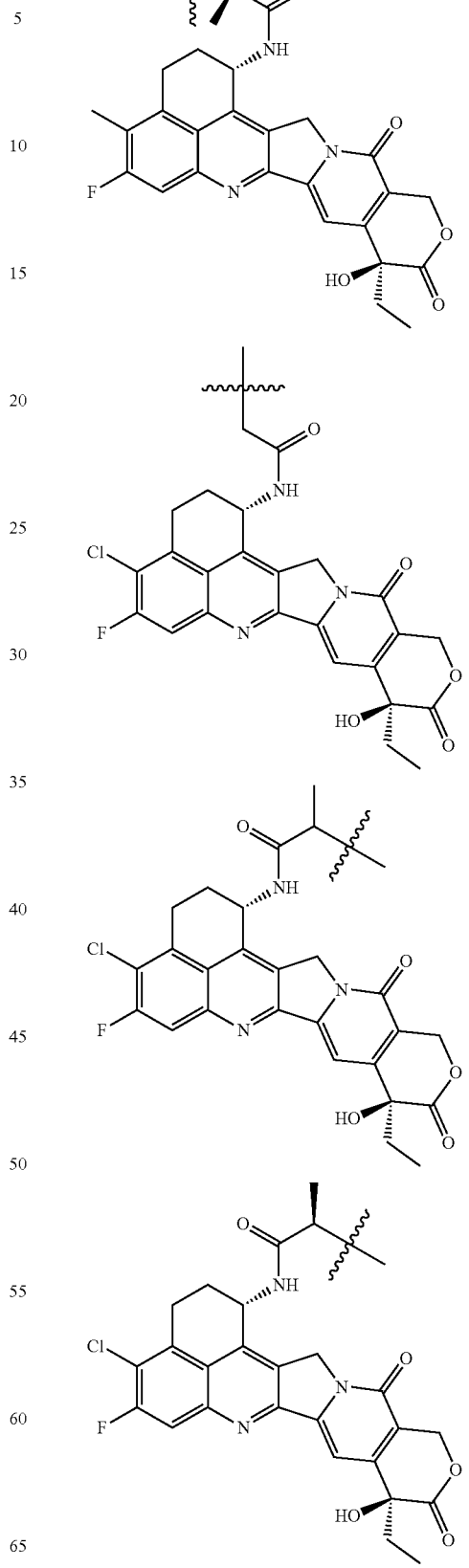

-continued
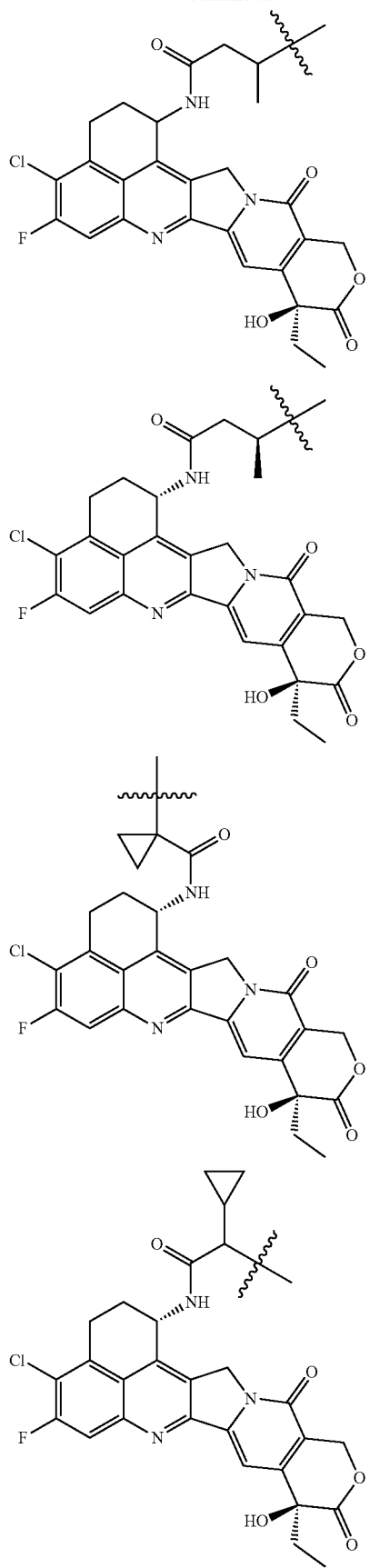
-continued
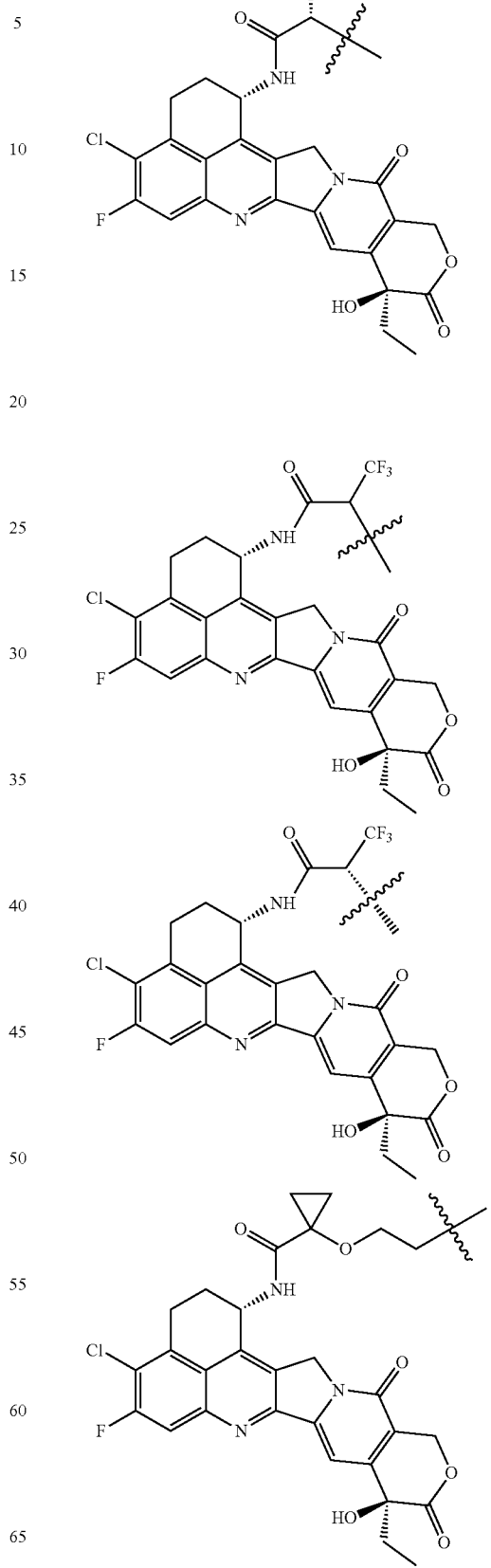

-continued
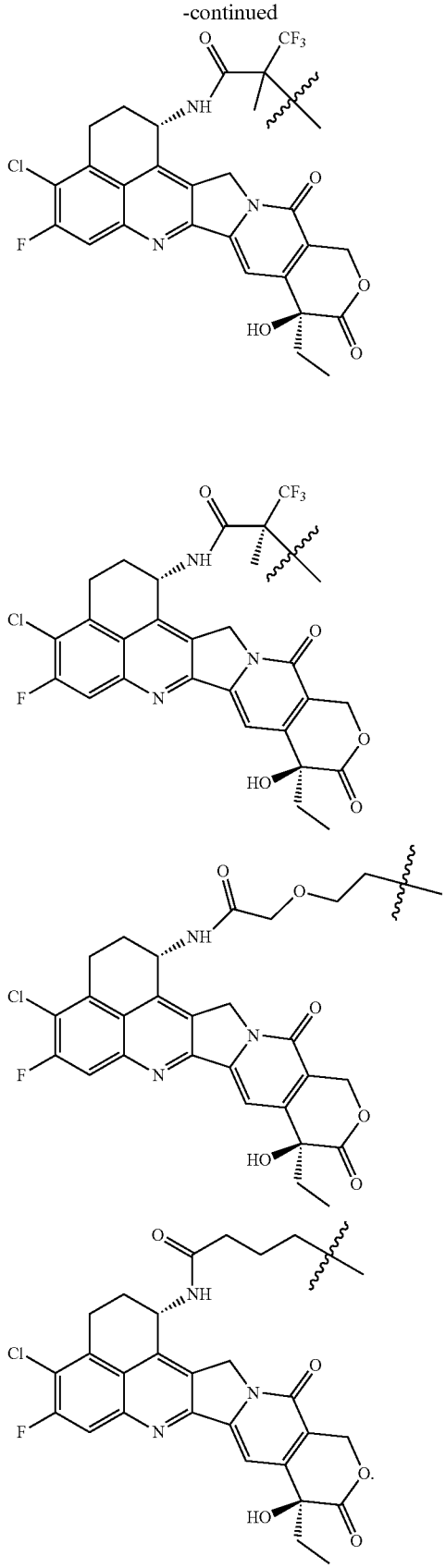
In a preferred embodiment, the payload is selected from:
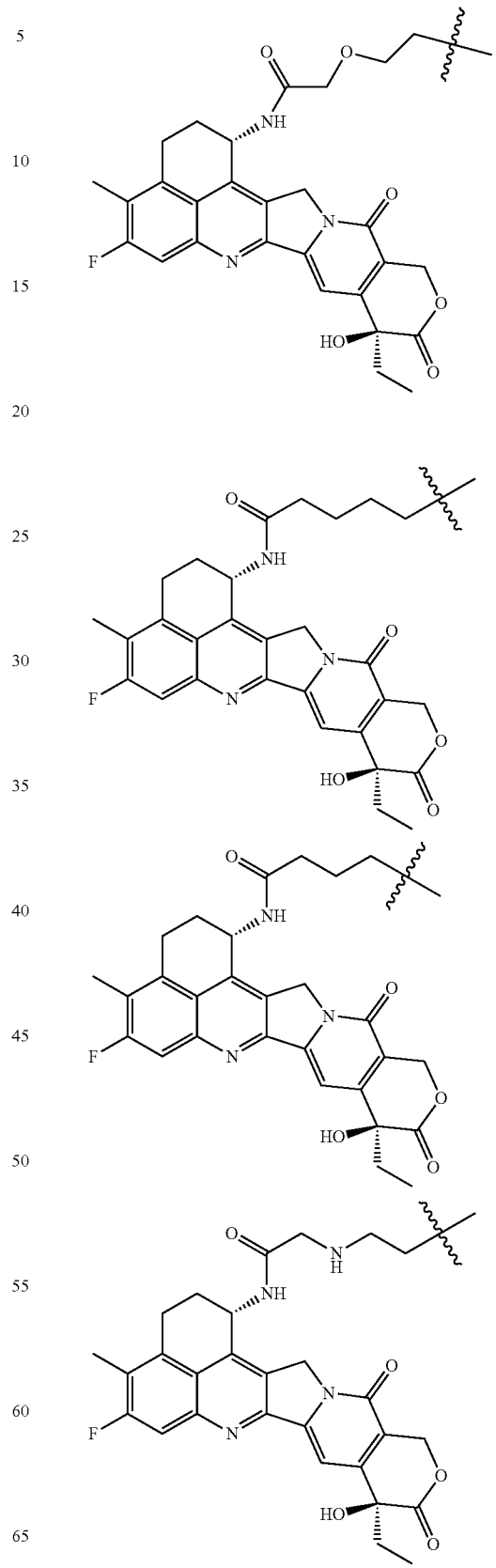

69
-continued
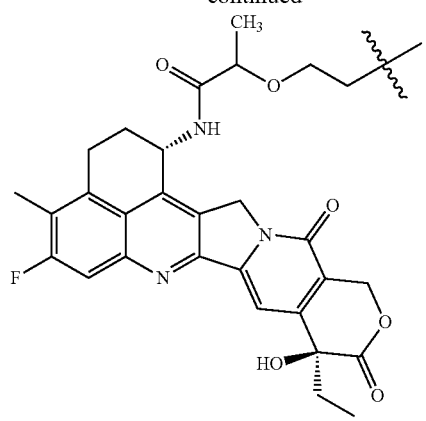
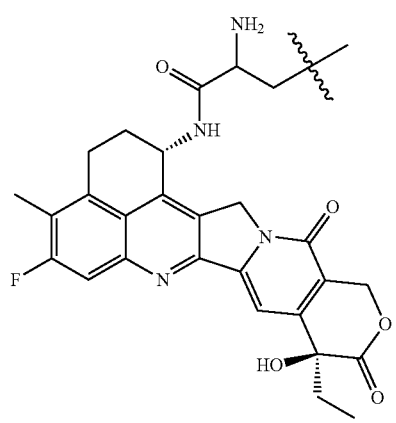
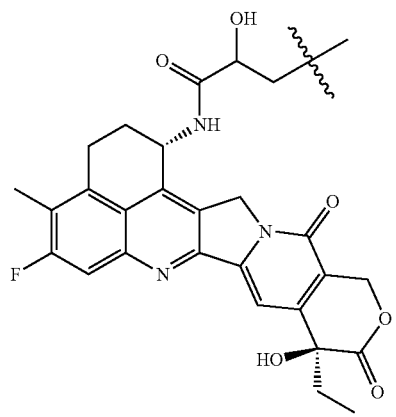
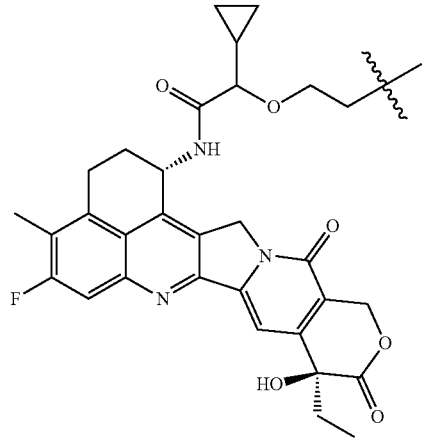
70
-continued
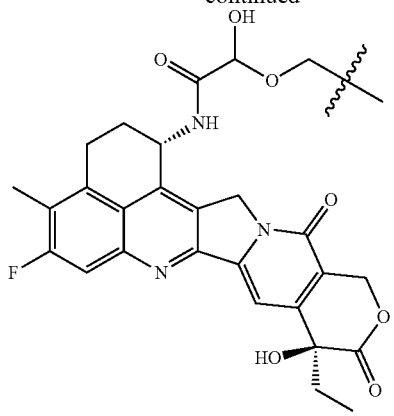
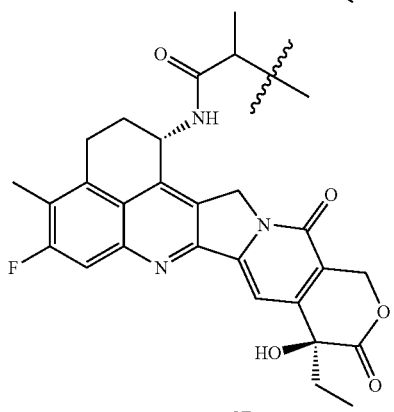
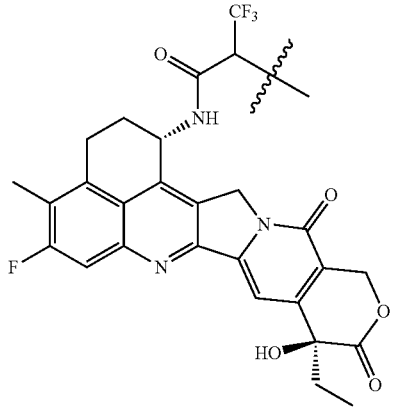

71
-continued
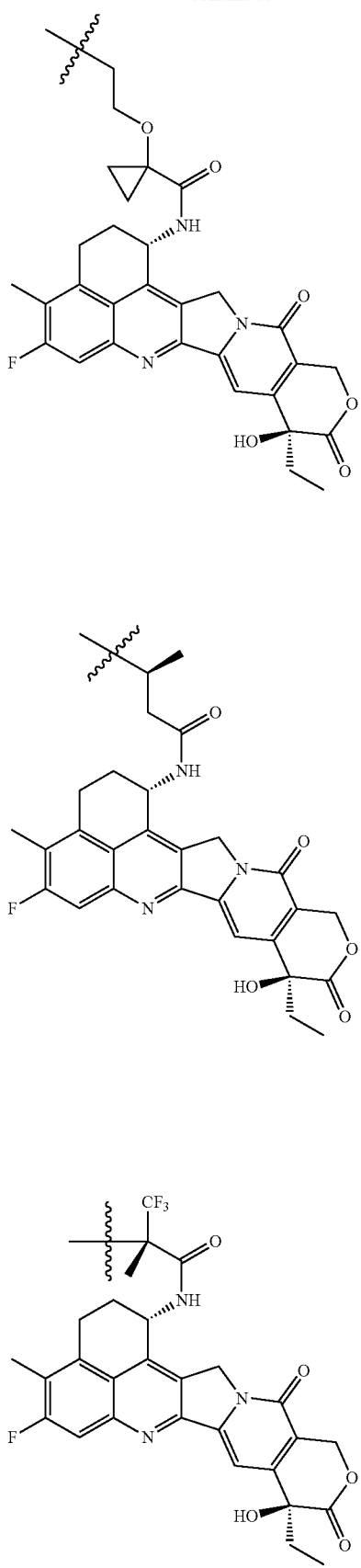
72
-continued
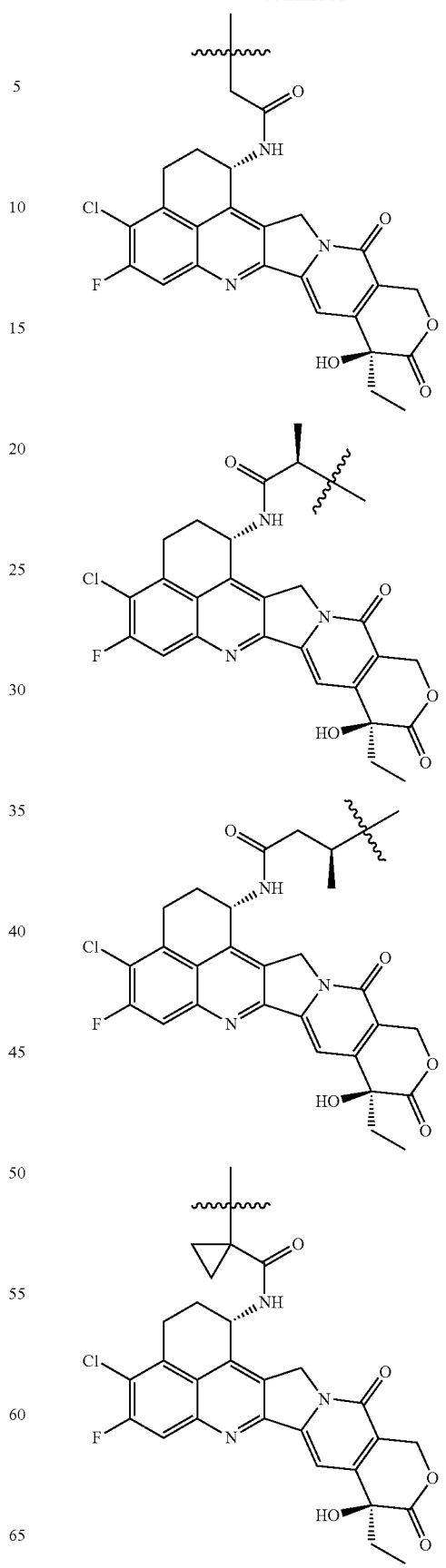

73
-continued
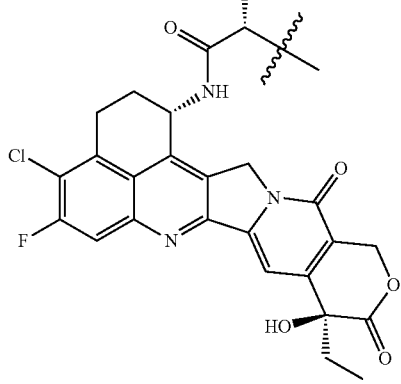
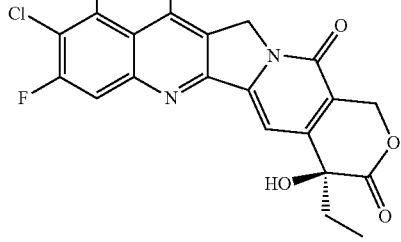
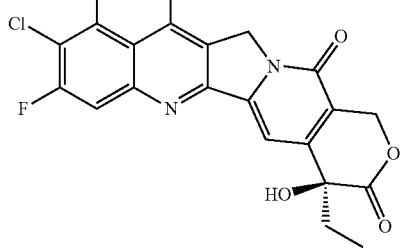
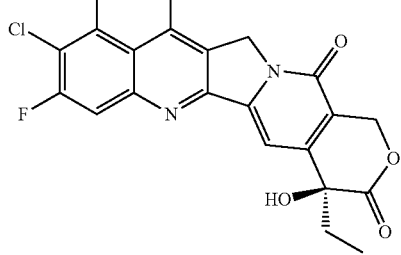
74
-continued
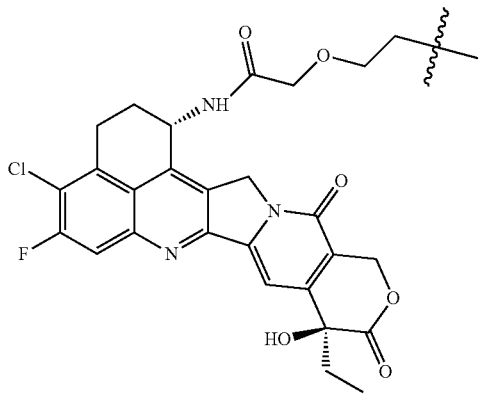
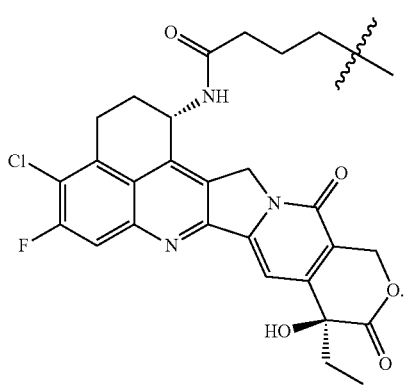
In a preferred embodiment, the payload is selected from:
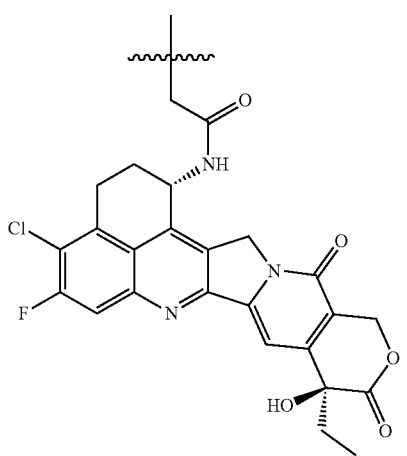

75
-continued
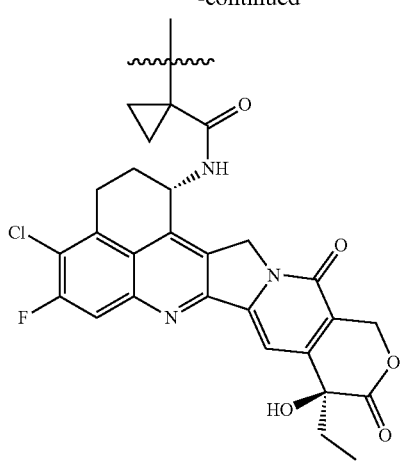
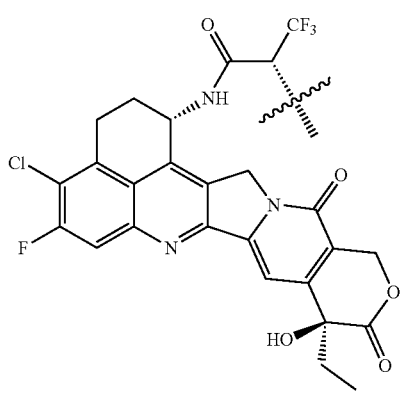
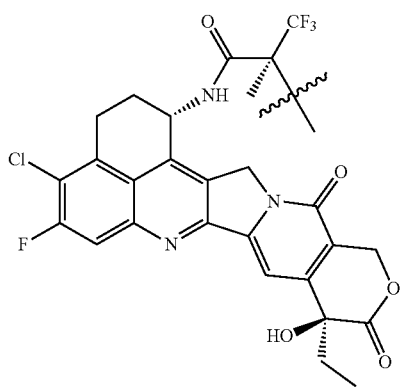
76
-continued
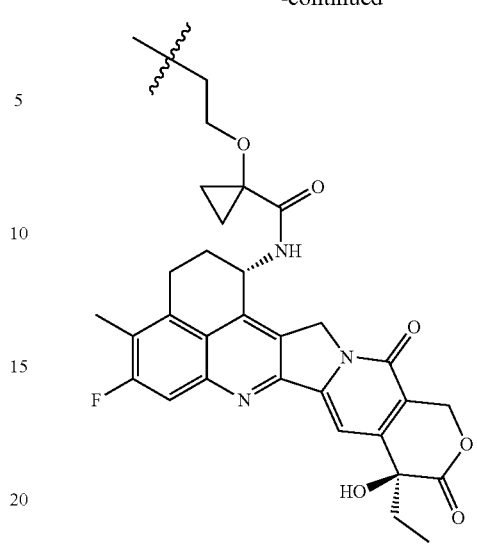
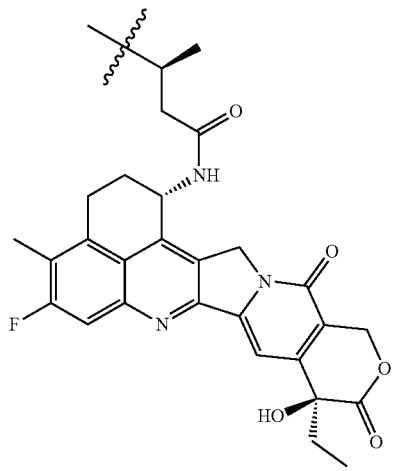
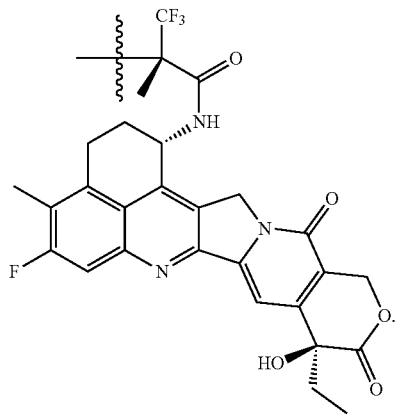

In a more preferred embodiment, the payload is selected from:
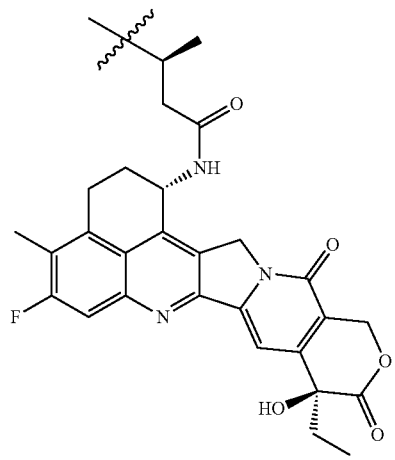
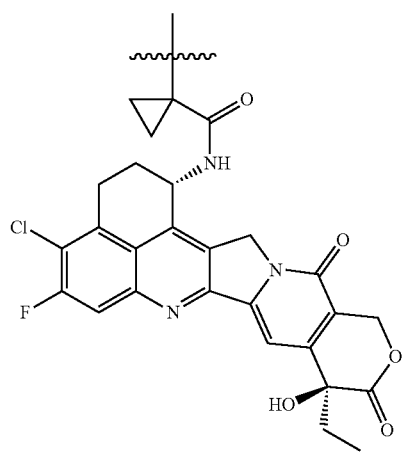
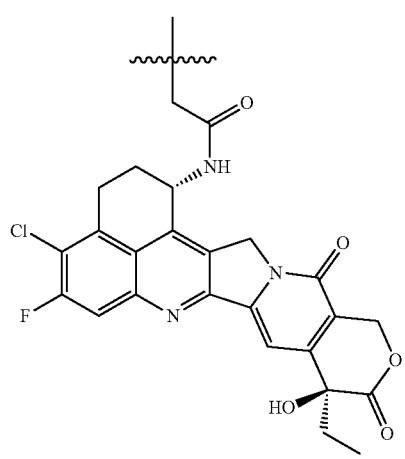
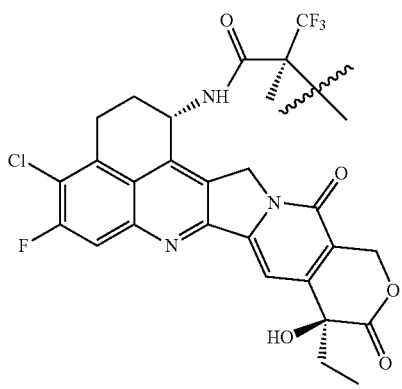
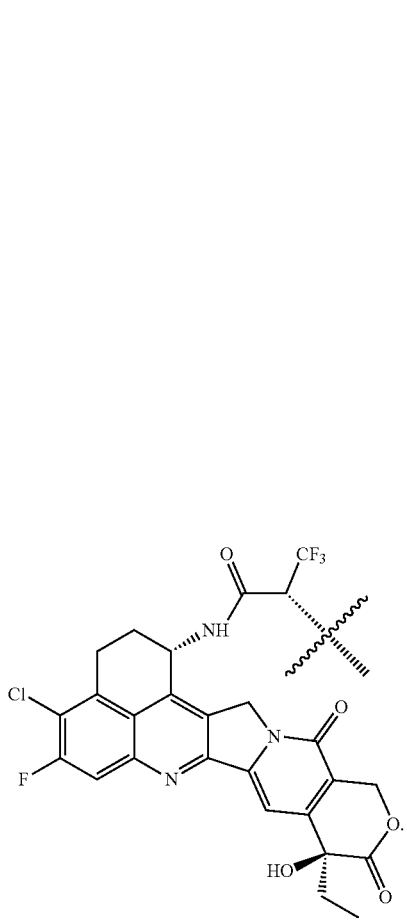

In a particular embodiment, the payload is selected from:

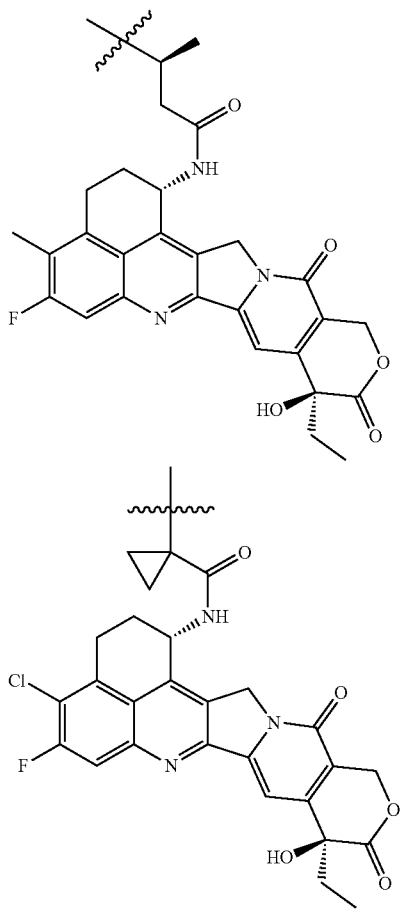

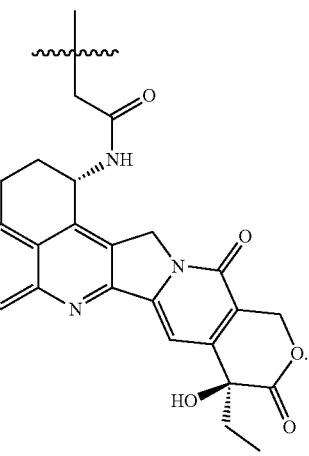

In an embodiment, $R^0$ is $C_{1-6}$ alkyl. In a preferred embodiment, $R^0$ is $C_{1-3}$ alkyl. In a particular embodiment, $R^0$ is methyl.

In an embodiment, n is an integer of 2 to 5. In a particular embodiment, n is 3.

In an embodiment, k1 and k2 are independently 1, or 3 or 5. In a particular embodiment, k1 and k2 are independently 5.

In an embodiment, i is independently an integer of 1 to 20, preferably 1 to 12, more preferably 2 to 8. In a particular embodiment, i is 4.

In an embodiment, j is independently an integer of 1 to 20, preferably 1 to 12, more preferably 8 to 12, especially 8 or 12. In a particular embodiment, j is 12.

In an embodiment, the compound of formula (I) has the structure of formula (I-1)

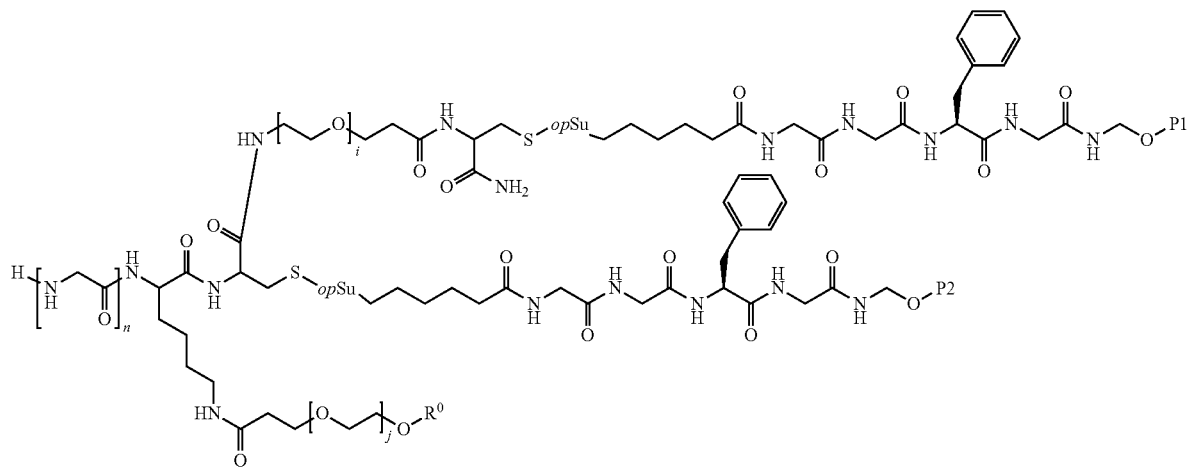

(I-1)

wherein,
P1, P2, R⁰, opSu, n, i and j are as defined in formula (I).
In an embodiment, the compound of formula (I) is selected from the group consisting of:

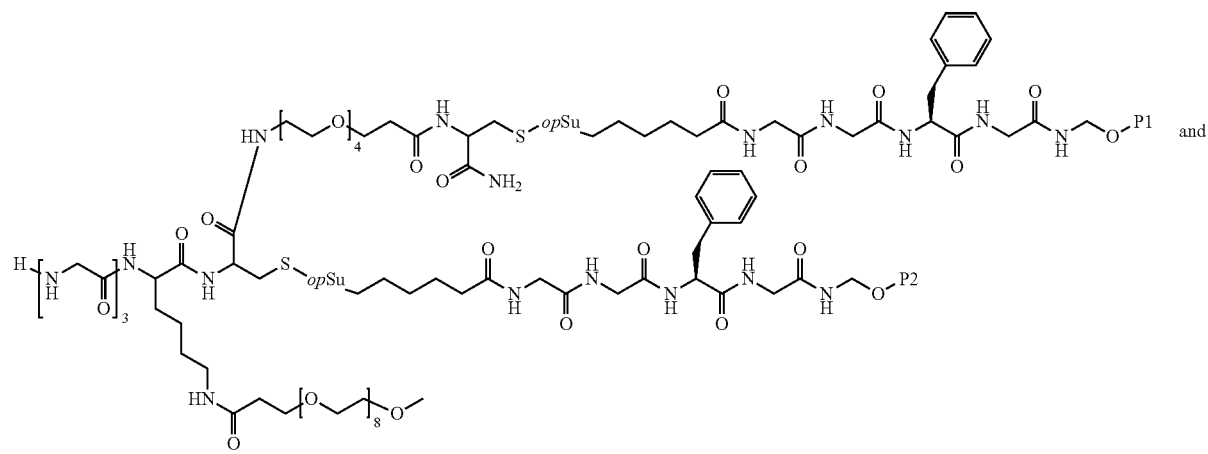

BH-1

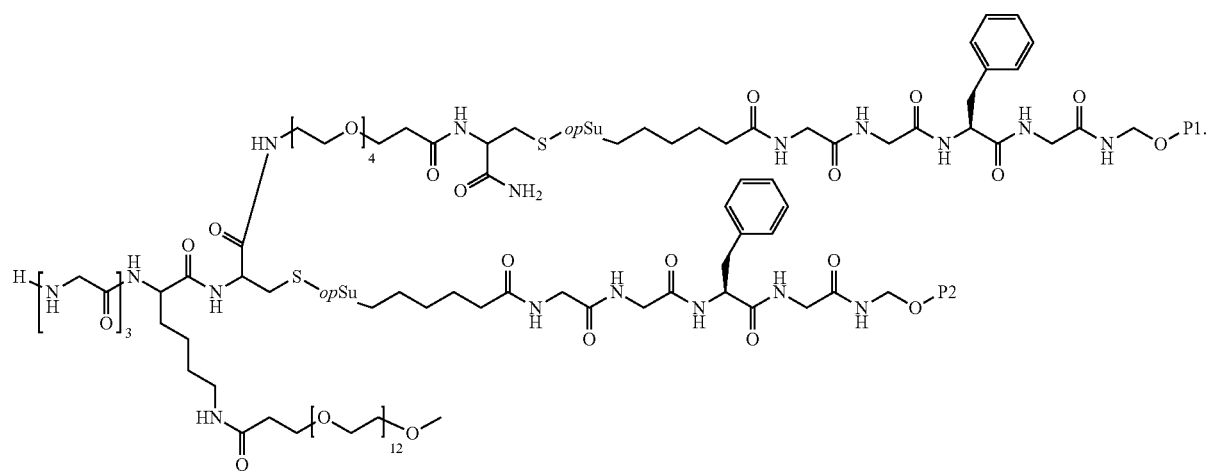

BH-2

Specific Embodiments of Compound of Formula (I)

In an embodiment, the structure of the compound of formula (I) is as shown in the following table.

| Compound of formula (I) | Formula | Payload | Compound of formula (I) | Formula | Payload |
|---|---|---|---|---|---|
| BH-1-730 | BH-1 | P730 | BH-1-731 | BH-1 | P731 |
| BH-1-518 | BH-1 | P518 | BH-1-519 | BH-1 | P519 |
| BH-1-586 | BH-1 | P586 | BH-1-587 | BH-1 | P587 |
| BH-1-593 | BH-1 | P593 | BH-1-594 | BH-1 | P594 |
| BH-1-622 | BH-1 | P622 | BH-1-624 | BH-1 | P624 |
| BH-1-625 | BH-1 | P625 | BH-1-677 | BH-1 | P677 |
| BH-1-678 | BH-1 | P678 | BH-1-679 | BH-1 | P679 |
| BH-1-680 | BH-1 | P680 | BH-1-703 | BH-1 | P703 |
| BH-1-704 | BH-1 | P704 | BH-1-627 | BH-1 | P627 |
| BH-1-626 | BH-1 | P626 | BH-1-636 | BH-1 | P636 |
| BH-1-637 | BH-1 | P637 | BH-1-595 | BH-1 | P595 |
| BH-1-596 | BH-1 | P596 | BH-1-597 | BH-1 | P597 |
| BH-1-600 | BH-1 | P600 | BH-1-601 | BH-1 | P601 |
| BH-1-602 | BH-1 | P602 | BH-1-603 | BH-1 | P603 |
| BH-1-619 | BH-1 | P619 | BH-1-620 | BH-1 | P620 |

-continued

| Compound of formula (I) | Formula | Payload | Compound of formula (I) | Formula | Payload |
|---|---|---|---|---|---|
| BH-1-664 | BH-1 | P664 | BH-1-665 | BH-1 | P665 |
| BH-1-667 | BH-1 | P667 | BH-1-668 | BH-1 | P668 |
| BH-1-671 | BH-1 | P671 | BH-1-589 | BH-1 | P589 |
| BH-1-588 | BH-1 | P588 | BH-1-504 | BH-1 | P504 |
| BH-1-562 | BH-1 | P562 | BH-1-563 | BH-1 | P563 |
| BH-1-565 | BH-1 | P565 | BH-1-687 | BH-1 | P687 |
| BH-1-688 | BH-1 | P688 | LB302-2-1 | BH-1 | Dxd |
| BH-2-730 | BH-2 | P730 | BH-2-731 | BH-2 | P731 |
| BH-2-518 | BH-2 | P518 | BH-2-519 | BH-2 | P519 |
| BH-2-586 | BH-2 | P586 | BH-2-587 | BH-2 | P587 |
| BH-2-593 | BH-2 | P593 | BH-2-594 | BH-2 | P594 |
| BH-2-622 | BH-2 | P622 | BH-2-624 | BH-2 | P624 |
| BH-2-625 | BH-2 | P625 | BH-2-677 | BH-2 | P677 |
| BH-2-678 | BH-2 | P678 | BH-2-679 | BH-2 | P679 |
| BH-2-680 | BH-2 | P680 | BH-2-703 | BH-2 | P703 |
| BH-2-704 | BH-2 | P704 | BH-2-627 | BH-2 | P627 |
| BH-2-626 | BH-2 | P626 | BH-2-636 | BH-2 | P636 |
| BH-2-637 | BH-2 | P637 | BH-2-595 | BH-2 | P595 |
| BH-2-596 | BH-2 | P596 | BH-2-597 | BH-2 | P597 |
| BH-2-600 | BH-2 | P600 | BH-2-601 | BH-2 | P601 |

-continued

| Compound of formula (I) | Formula | Payload | Compound of formula (I) | Formula | Payload |
|---|---|---|---|---|---|
| BH-2-602 | BH-2 | P602 | BH-2-603 | BH-2 | P603 |
| BH-2-619 | BH-2 | P619 | BH-2-620 | BH-2 | P620 |
| BH-2-664 | BH-2 | P664 | BH-2-665 | BH-2 | P665 |
| BH-2-667 | BH-2 | P667 | BH-2-668 | BH-2 | P668 |
| BH-2-671 | BH-2 | P671 | BH-2-589 | BH-2 | P589 |
| BH-2-588 | BH-2 | P588 | BH-2-504 | BH-2 | P504 |
| BH-2-562 | BH-2 | P562 | BH-2-563 | BH-2 | P563 |
| BH-2-565 | BH-2 | P565 | BH-2-687 | BH-2 | P687 |
| BH-2-688 | BH-2 | P688 | LB302-2-4 | BH-2 | Dxd |

*: For all the compounds listed, P1 and P2 are the same, and are described as Payload.

Preparation of the Compound of Formula (I)

In an embodiment, compound of formula (I) can be synthesized by connecting a linker with a payload or by connecting a serial of suitable building blocks. Such building blocks can be easily designed by retrosynthetic analysis, and any reaction known in the art can be used.

In an aspect, provided is a compound having the structure of formula (1):

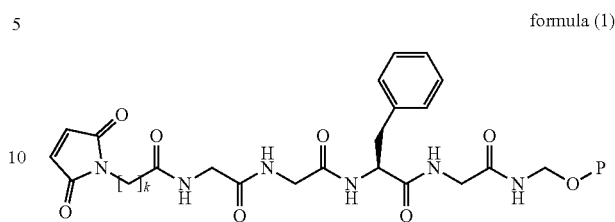

formula (1)

wherein, k is an integer of 1 to 7;

P is a payload having the structure of formula (i'), wherein the structure of formula (i') is as defined above.

In a preferred embodiment, k is 1, or 3 or 5. In a particular embodiment, k is 5.

The compound of formula (1) can be synthesized using the compound of formula (i) and other necessary building blocks, using a method similar to the synthetic method as disclosed in EP2907824A (e.g., synthetic method for formula (2) or (2b) of EP2907824A). Suitable building blocks include but not limited to linking-unit HX20113 and linking-unit HX20111.

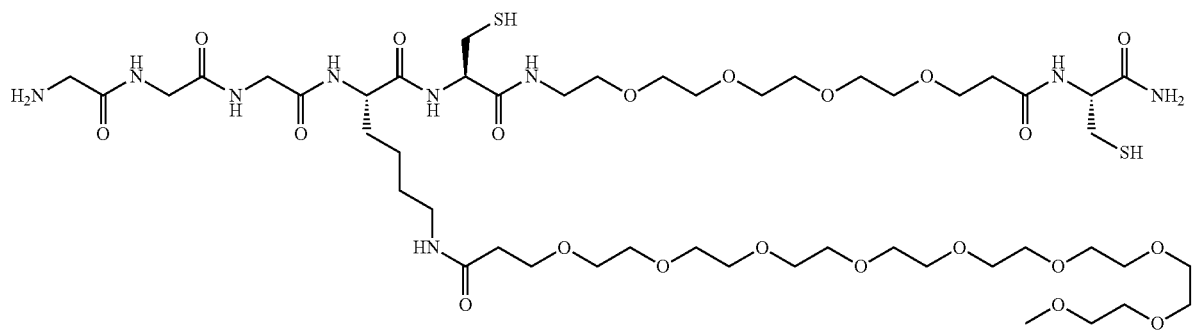

HX20113

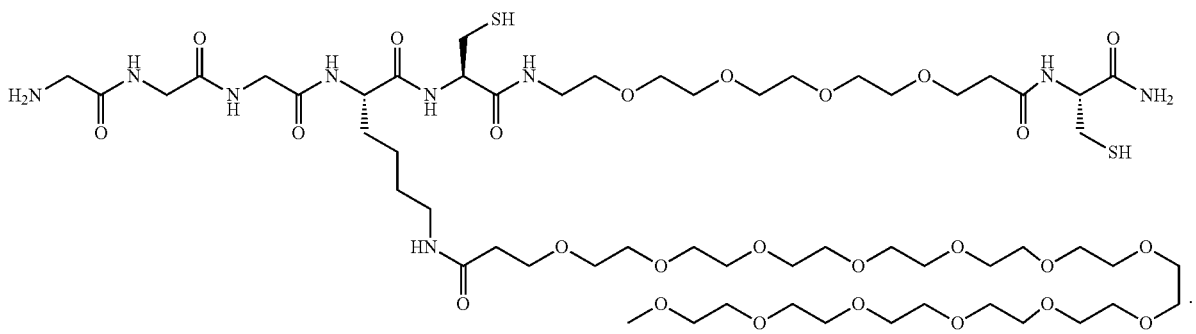

HX20111

Then the maleimide group therein can be reacted to a thiol group on another building block for the compound of formula (I). The resulting thiosuccinimide is unstable under physiological conditions and is liable to reverse Michael addition which leads to cleavage at the connection site. Moreover, when another thiol compound is present in the system, thiosuccinimide may also undergo thiol exchange with the other thiol compound. Both of these reactions cause the fall-off of the payload and result in toxic side effects. The thiosuccinimide is then subjected to ring opening reaction. The compound of formula (I) can then be obtained.

Method of ring opening reaction can be found in WO2015165413A1. The compound comprising ring-opened succinimide moiety can be purified by semi-preparative/preparative HPLC or other suitable separation means to obtain with high purity and defined composition, regardless of the efficiency of the succinimide ring opening reaction.

In the present disclosure, when applied in the linker-payload (linker-small molecule intermediate), the ring-opened succinimide structure no longer undergoes reverse Michael addition or thiol exchange, and thus the product is more stable.

Moiety Comprising Recognition Sequence of the Ligase Acceptor or Donor Substrate In an embodiment, the $(Gly)_n$ moiety of the compound of formula (I) is a recognition sequence of a ligase acceptor or donor substrate, which facilitates enzyme-catalyzed coupling of compound of formula (I) with the an antibody or an antigen binding fragment thereof under the catalysis of the ligase. The antibody or the antigen binding fragment thereof is optionally modified and comprises the corresponding recognition sequence of a ligase acceptor or donor substrate.

In an embodiment, the ligase is a transpeptidase. In an embodiment, the ligase is selected from the group consisting of a natural transpeptidase, an unnatural transpeptidase, variants thereof, and the combination thereof. Unnatural transpeptidase enzymes can be, but are not limited to, those obtained by engineering of natural transpeptidase. In a preferred embodiment, the ligase is selected from the group consisting of a natural Sortase, an unnatural Sortase, and the combination thereof. The species of natural Sortase include Sortase A, Sortase B, Sortase C, Sortase D, Sortase *L. plantarum*, etc. (US20110321183A1). The type of ligase corresponds to the ligase recognition sequence and is thereby used to achieve specific conjugation between different molecules or structural fragments.

In an embodiment, the $(Gly)_n$ moiety of the compound of formula (I) is a recognition sequence of a ligase acceptor substrate; and the antibody or the antigen binding fragment thereof is optionally modified and comprises the corresponding recognition sequence of a ligase donor substrate.

In some embodiments, the ligase is a Sortase selected from Sortase A, Sortase B, Sortase C, Sortase D and Sortase *L. plantarum*.

In a particular embodiment, the ligase is Sortase A from *Staphylococcus aureus*. Accordingly, the ligase recognition sequence of the ligase donor substrate may be the typical recognition sequence LPXTG (SEQ ID NO: 6) of the enzyme. In yet another particular embodiment, the recognition sequence of the ligase donor substrate is LPXTGJ, wherein X can be any single amino acid that is natural or unnatural; J is absent, or is an amino acid fragment comprising 1-10 amino acids, optionally labeled. In an embodiment, J is absent. In yet another embodiment, J is an amino acid fragment comprising 1-10 amino acids, wherein each amino acid is independently any natural or unnatural amino acid. In another embodiment, J is $(Gly)_m$, wherein m is an integer of 1 to 10. In yet another particular embodiment, the recognition sequence of the ligase donor substrate is LPETG (SEQ ID NO: 7). In another particular embodiment, the recognition sequence of the ligase donor substrate is LPETGG (SEQ ID NO: 8).

In an embodiment, the ligase is Sortase B from *Staphylococcus aureus* and the corresponding donor substrate recognition sequence can be NPQTN (SEQ ID NO: 9). In another embodiment, the ligase is Sortase B from *Bacillus anthracis* and the corresponding donor substrate recognition sequence can be NPKTG (SEQ ID NO: 10).

In yet another embodiment, the ligase is Sortase A from *Streptococcus pyogenes* and the corresponding donor substrate recognition sequence can be LPXTGJ, wherein J is as defined above. In another embodiment, the ligase is Sortase subfamily 5 from *Streptomyces coelicolor*, and the corresponding donor substrate recognition sequence can be LAXTG (SEQ ID NO: 11).

In yet another embodiment, the ligase is Sortase A from *Lactobacillus plantarum* and the corresponding donor substrate recognition sequence can be LPQTSEQ (SEQ ID NO: 12).

The ligase recognition sequence can also be other totally new recognition sequence for transpeptidase optimized by manual screening.

Conjugates and Preparation Thereof

Furthermore, the payload-bearing compound (compound of formula (I)) which has the moiety comprising ligase recognition sequence can be conjugated with other molecules comprising a ligase recognition sequence, and can be thereby used in for example, the preparation of a antibody-small molecule Conjugate, such as an antibody-drug conjugate. Accordingly, in yet another aspect, provided is a conjugate which comprises a compound of formula (I), and an antibody or an antigen binding fragment.

In yet another aspect, provided is a conjugate having the structure of formula (II):

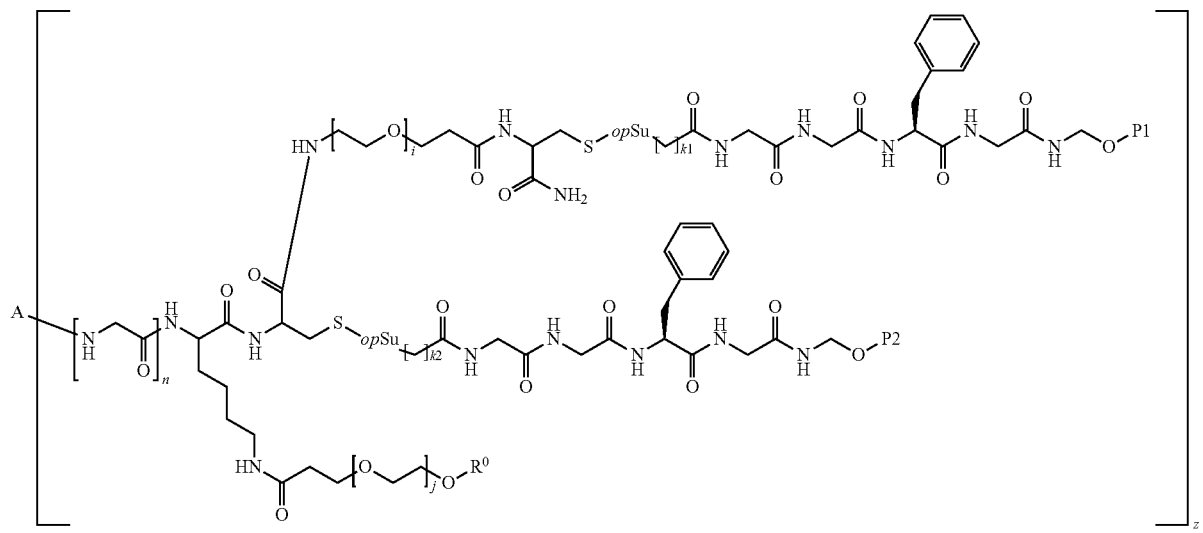

(II)

wherein,
A is an antibody or an antigen binding fragment thereof,
z is an integer of 1 to 20;
P1, P2, $R^0$, opSu, n, k1, k2, i and j are as defined in formula (I).

In a preferred embodiment, the antibody or antigen binding fragment is modified to connect with the $(Gly)_n$ moiety in the compound of formula (I).

In a preferred embodiment, z is 1 to 4. In a particular embodiment, z is 2.

Antibody or the Antigen Binding Fragment Thereof

In an embodiment, the antibody is an anti-human HER2 antibody. Examples of anti-human HER2 antibodies include but are not limited to Pertuzumab and Trastuzumab. Pertuzumab binds to the second extracellular domain (ECD2) of HER2 and is approved for the treatment of HER2-positive breast cancer. Trastuzumab binds to the fourth extracellular domain (ECD4) of HER2 and is approved for the treatment of Her2-positive breast cancer and gastric cancer.

In a preferred embodiment, the anti-human HER2 antibody is one or more selected from engineered anti-HER2 antibodies based on Trastuzumab.

In a preferred embodiment, the anti-human HER2 antibody is a recombinant antibody selected from monoclonal antibody, chimeric antibody, humanized antibody, antibody fragment, and antibody mimic. In an embodiment, the antibody mimic is selected from scFv, minibody, diabody, nanobody. For the conjugation with the compound of formula (I), the antibody or the antigen binding fragment thereof of the present disclosure may comprise a modified moiety to conjugate with the $(Gly)_n$ moiety in the compound of formula (I). The introduction position of such modified moiety is not limited, for example, the introduction position on the antibody or the antigen binding fragment thereof can be, but not limited to, located at the C-terminal or the N-terminal of the heavy chain or light chain of the antibody.

In an alternative embodiment, a modified moiety for the conjugation with the $(Gly)_n$ moiety in the compound of formula (I) can be introduced at a non-terminal position of the heavy chain or light chain of the antibody using, for example, chemical modification methods.

In an embodiment, the antibody or the antigen-binding fragment thereof may comprise terminal modification. A terminal modification refers to a modification at the C-terminal or N-terminal of the heavy chain or light chain of the antibody, which for example comprises a ligase recognition sequence. In another embodiment, the terminal modification may further comprise a spacer Sp comprising 2-100 amino acids, wherein the antibody, Sp and the ligase recognition sequence are sequentially linked. In a preferred embodiment, Sp is a spacer sequence containing 2-20 amino acids. In a particular embodiment, Sp is a spacer sequence selected from GA, GGGGS (SEQ ID NO: 3), GGGGSGGGGS (SEQ ID NO: 4) and GGGGSGGGGSGGGGS (SEQ ID NO: 5), especially GA.

In a preferred embodiment, the light chain of the antibody or antigen-binding fragment thereof includes 3 types: wild-type (LC); the C-terminus modified light chain (LCCT), which is modified by direct introduction of a ligase recognition sequence LPXTG (SEQ ID NO: 6) and C-terminus modified light chain ($LCCT_L$), which is modified by introduction of short peptide spacers plus the ligase donor substrate recognition sequence LPXTG (SEQ ID NO: 6). The heavy chain of the antibody or antigen-binding fragment thereof includes 3 types: wild-type (HC); the C-terminus modified heavy chain (HCCT), which is modified by direct introduction of a ligase recognition sequence LPXTG (SEQ ID NO: 6); and C-terminus modified heavy chain ($HCCT_L$), which is modified by introduction of short peptide spacers plus the ligase donor substrate recognition sequence LPXTG (SEQ ID NO: 6). X can be any natural or non-natural single amino acid. When z in the compound of formula (II) is 1 or 2, the combination of the above heavy and light chains can form 8 preferred antibody molecules, see the amino acid sequence table.

In an embodiment, the compound of formula (II) is selected from the group consisting:

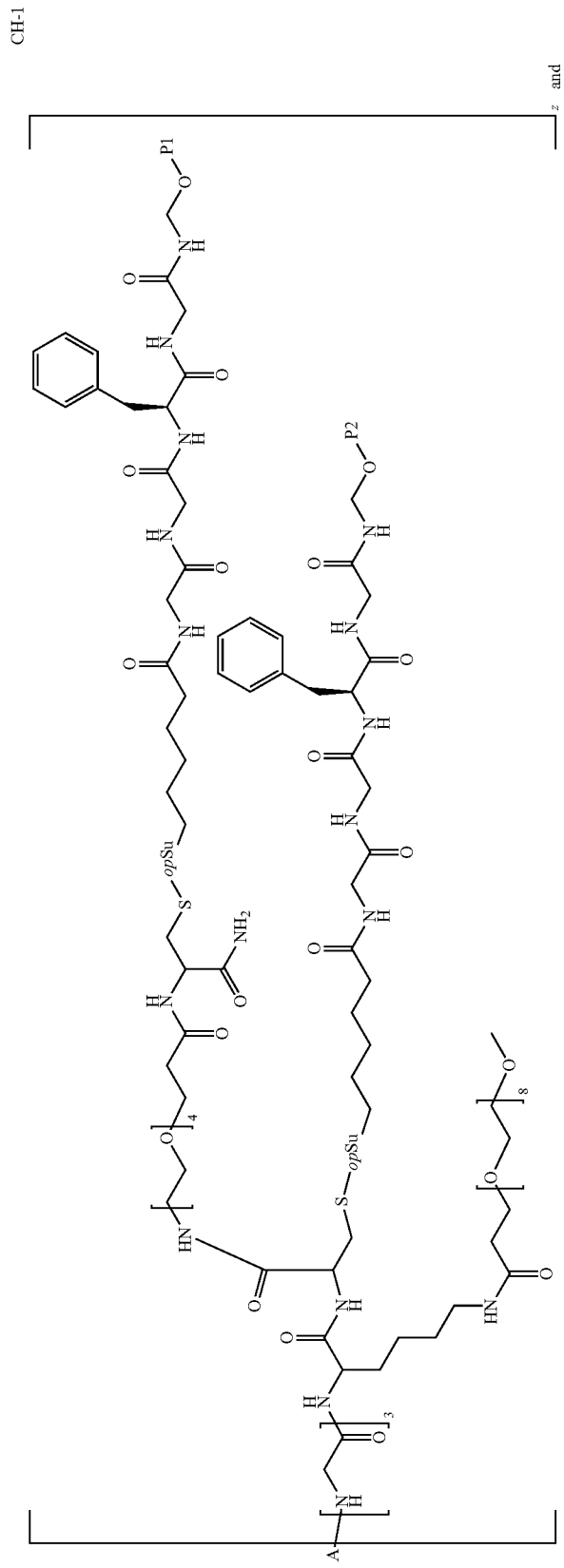

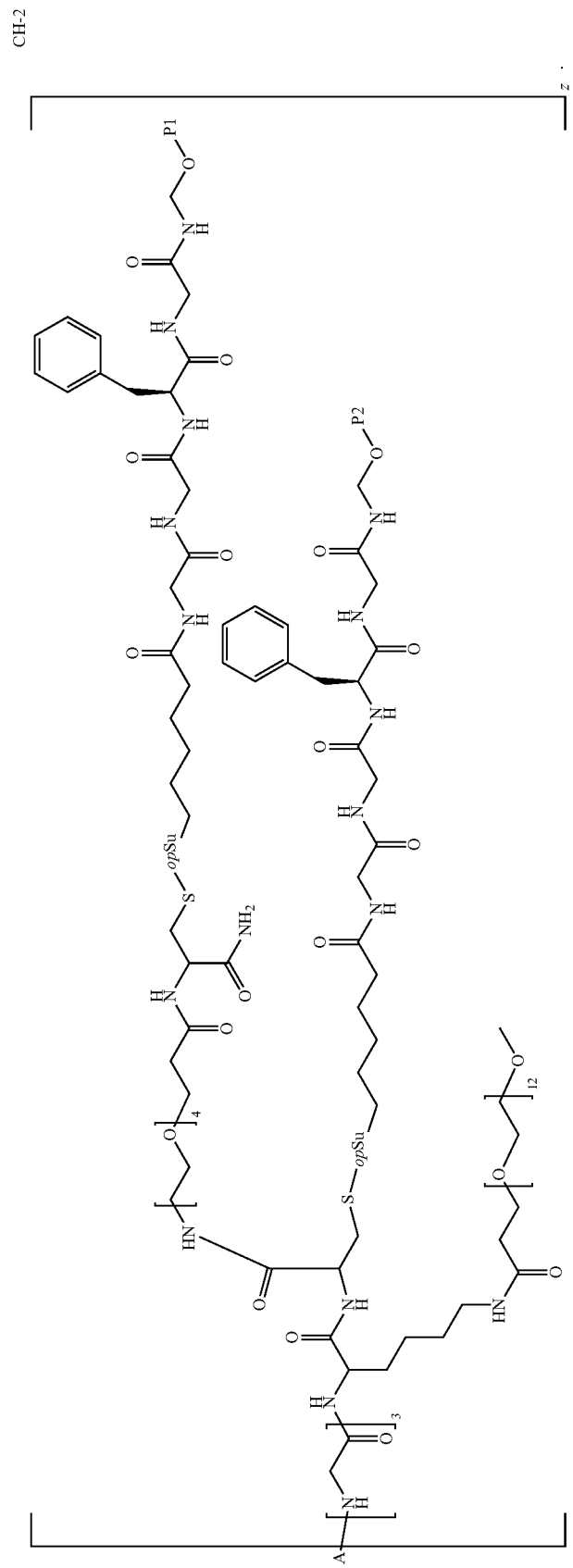

Specific Embodiments of Conjugates

In an embodiment, the payload is a cytotoxin or a fragment thereof. In an embodiment, the antibody is a modified Trastuzumab, preferably Ab0001-LCCT$_L$-HC (light chain SEQ ID NO: 1, heavy chain: SEQ ID NO: 2). The sequence of Ab0001-LCCT$_L$-HC is based on the amino acid sequence of Ab0001 (Trastuzumab), and GALPETGG (SEQ ID NO: 13) was introduced at the C-terminal of the light chain, wherein LPETGG (SEQ ID NO: 8) is the recognition sequence of the ligase donor substrate, and GA is a spacer sequence. In an embodiment, the antibody-drug conjugate is as shown in the following table.

Nomenclature of the ADCs: the number in the parenthesis indicates the number of payload (drug) molecules that is intended to be connected to the antibody.

| ADCs | Compound of formula (I) | ADCs | Compound of formula (I) | ADCs | Compound of formula (I) |
|---|---|---|---|---|---|
| CH-1-730 | BH-1-730 | CH-1-731 | BH-1-731 | CH-1-518 | BH-1-518 |
| CH-1-519 | BH-1-519 | CH-1-586 | BH-1-586 | CH-1-587 | BH-1-587 |
| CH-1-593 | BH-1-593 | CH-1-594 | BH-1-594 | CH-1-622 | BH-1-622 |
| CH-1-624 | BH-1-624 | CH-1-625 | BH-1-625 | CH-1-677 | BH-1-677 |
| CH-1-678 | BH-1-678 | CH-1-679 | BH-1-679 | CH-1-680 | BH-1-680 |
| CH-1-703 | BH-1-703 | CH-1-704 | BH-1-704 | CH-1-627 | BH-1-627 |
| CH-1-626 | BH-1-626 | CH-1-636 | BH-1-636 | CH-1-637 | BH-1-637 |
| CH-1-595 | BH-1-595 | CH-1-596 | BH-1-596 | CH-1-597 | BH-1-597 |
| CH-1-600 | BH-1-600 | CH-1-601 | BH-1-601 | CH-1-602 | BH-1-602 |
| CH-1-603 | BH-1-603 | CH-1-619 | BH-1-619 | CH-1-620 | BH-1-620 |
| CH-1-664 | BH-1-664 | CH-1-665 | BH-1-665 | CH-1-667 | BH-1-667 |
| CH-1-668 | BH-1-668 | CH-1-671 | BH-1-671 | CH-1-589 | BH-1-589 |
| CH-1-588 | BH-1-588 | CH-1-504 | BH-1-504 | CH-1-562 | BH-1-562 |
| CH-1-563 | BH-1-563 | CH-1-565 | BH-1-565 | CH-1-687 | BH-1-687 |
| CH-1-688 | BH-1-688 | LC302-2-1(4) | LB302-2-1 | — | — |
| CH-2-730 | BH-2-730 | CH-2-731 | BH-2-731 | CH-2-518 | BH-2-518 |
| CH-2-519 | BH-2-519 | CH-2-586 | BH-2-586 | CH-2-587 | BH-2-587 |
| CH-2-593 | BH-2-593 | CH-2-594 | BH-2-594 | CH-2-622 | BH-2-622 |
| CH-2-624 | BH-2-624 | CH-2-625 | BH-2-625 | CH-2-677 | BH-2-677 |
| CH-2-678 | BH-2-678 | CH-2-679 | BH-2-679 | CH-2-680 | BH-2-680 |
| CH-2-703 | BH-2-703 | CH-2-704 | BH-2-704 | CH-2-627 | BH-2-627 |
| CH-2-626 | BH-2-626 | CH-2-636 | BH-2-636 | CH-2-637 | BH-2-637 |
| CH-2-595 | BH-2-595 | CH-2-596 | BH-2-596 | CH-2-597 | BH-2-597 |
| CH-2-600 | BH-2-600 | CH-2-601 | BH-2-601 | CH-2-602 | BH-2-602 |
| CH-2-603 | BH-2-603 | CH-2-619 | BH-2-619 | CH-2-620 | BH-2-620 |
| CH-2-664 | BH-2-664 | CH-2-665 | BH-2-665 | CH-2-667 | BH-2-667 |
| CH-2-668 | BH-2-668 | CH-2-671 | BH-2-671 | CH-2-589 | BH-2-589 |
| CH-2-588 | BH-2-588 | CH-2-504 | BH-2-504 | CH-2-562 | BH-2-562 |
| CH-2-563 | BH-2-563 | CH-2-565 | BH-2-565 | CH-2-687 | BH-2-687 |
| CH-2-688 | BH-2-688 | LC302-2-4(4) | LB302-2-4 | — | — |

*: For all the ADCs listed, P1 and P2 are the same, and are described as Payload; z is 2; the antibody is Ab0001-LCCT$_L$-HC (light chain SEQ ID NO: 1, heavy chain: SEQ ID NO: 2).

Preparation of the Conjugate

The conjugates (i.e., the compound of formula (II)) of the present disclosure can be prepared by any method known in the art. In some embodiments, the conjugate is prepared by the ligase-catalyzed site-specific conjugation of an antibody or an antigen binding fragment and a compound of formula (I), wherein the antibody or the antigen binding fragment thereof is modified by a ligase recognition sequence.

The antibody or the antigen binding fragment thereof and the compound of formula (I) are linked to each other via the ligase-specific recognition sequences of the substrates. The recognition sequence depends on the particular ligase employed. In an embodiment, the antibody or the antigen binding fragment thereof is an antibody with recognition sequence-based terminal modifications introduced at the C-terminal of the light chain and/or the heavy chain, and the antibody or the antigen binding fragment thereof is conjugated with the compound of formula (I), under the catalysis of the wild type or optimized engineered ligase or any combination thereof, and under suitable catalytic reaction conditions.

In a specific embodiment, the ligase is Sortase A and the conjugation reaction can be represented by the following scheme:

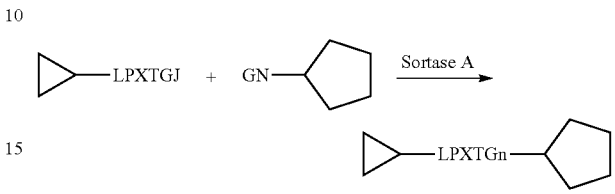

The triangle represents a portion of an antibody; the pentagon represents a portion of a compound of formula (II); and $G_n$ represents the $(Gly)_n$ moiety. n, X and J are respectively as defined above. When conjugated with $G_n$, which is the corresponding recognition sequence of the acceptor substrate, the upstream peptide bond of the glycine in the LPXTGJ sequence is cleaved by Sortase A, and the resulting intermediate is linked to the free N-terminal of $G_n$ to generate a new peptide bond. The resulting amino acid sequence is $LPXTG_n$. The sequences $G_n$ and LPXTGJ are as defined above.

The compound of formula (I) of the present disclosure has defined structure, defined composition and high purity, so that when the conjugation reaction with an antibody is conducted, fewer impurities are introduced or no other impurities are introduced. When such an intermediate is used for the ligase-catalyzed site-specific conjugation with a modified antibody containing a ligase recognition sequence, a homogeneous ADC with highly controllable quality is obtained.

Metabolism of the Conjugate in a Physiological Environment

When a part or whole linker is cleaved in tumor cells, the payload is released. As the linker is cleaved at a connecting position to the antitumor compound, the antitumor compound is released in its intrinsic structure to exhibit its intrinsic antitumor effect.

In an embodiment, the GGFG (Gly-Gly-Phe-Gly) (SEQ ID NO: 14) moiety comprised by the compound of formula (I) can be cleaved by lysosomal enzymes (such as cathepsin B and/or cathepsin L).

In an embodiment, the compound of formula (I) comprises a self-immolative spacer. In an embodiment, the self-immolative spacer is an acetal or a heteroacetal. In an embodiment, the -GGFG-NH—CH$_2$—O— moiety comprised by the compound of formula (I) represents a combination of a restriction enzyme site and a self-immolative spacer, which would cleave in the cell and release the aimed molecule (such as the antitumor compound).

Pharmaceutical Composition and Pharmaceutical Preparation

Another object of the disclosure is to provide a pharmaceutical composition comprising the conjugate of the present disclosure, and at least one pharmaceutically acceptable carrier.

The pharmaceutical composition of the present disclosure may be administered in any manner as long as it achieves the effect of preventing, alleviating, preventing or curing the symptoms of a human or animal. For example, various suitable dosage forms can be prepared according to the administration route, especially injections such as lyophilized powder for injection, injection, or sterile powder for injection.

The term "pharmaceutically acceptable" means that when contacted with tissues of the patient within the scope of normal medical judgment, no undue toxicity, irritation or allergic reaction, etc. shall arise, having reasonable advantage-disadvantage ratios and effective for the intended use.

The term pharmaceutically acceptable carrier refers to those carrier materials which are pharmaceutically acceptable and which do not interfere with the bioactivities and properties of the conjugate. Examples of aqueous carriers include but are not limited to buffered saline, and the like. The pharmaceutically acceptable carrier also includes carrier materials which brings the composition close to physiological conditions, such as pH adjusting agents, buffering agents, toxicity adjusting agents and the like, and sodium acetate, sodium chloride, potassium chloride, calcium chloride, sodium lactate, and the like.

In an embodiment, the pharmaceutical composition of the present disclosure has a drug to antibody ratio (DAR) of an integer or non-integer of about 1 to about 20, such as about 1 to about 10, about 1 to about 8, about 1 to about 6, about 1 to about 4. In a particular embodiment, the conjugate of the present disclosure has a DAR of about 4.

Treatment Method and Use

The conjugates of the present disclosure are useful for the treatment of tumors and/or autoimmune diseases. Tumors susceptible to conjugate treatment include those characterized by specific tumor-associated antigens or cell surface receptors, and those will be recognized by the targeting molecule in the conjugate and can be killed by the payload/cytotoxin in the conjugate.

Accordingly, in yet another aspect, also provided is use of a conjugate of the present disclosure or a pharmaceutical composition of the present disclosure in the manufacture of a medicament for treating a disease, disorder or condition selected from a tumor or an autoimmune disease.

In another aspect, provided is a conjugate of the present disclosure or a pharmaceutical composition of the present disclosure for use in the treatment of a tumor or an autoimmune disease.

In a further aspect, provided is a method of treating a tumor or an autoimmune disease, the method comprising administering to an individual in need thereof an effective amount of a conjugate of the present disclosure or a pharmaceutical composition of the present disclosure In a preferred embodiment, the conjugate of the present disclosure formed by conjugation of the anti-human HER2 antibody and the small molecule cytotoxin can specifically bind to HER2 on the surface of the tumor cell and selectively kill the HER2-expressing tumor cells. In another preferred embodiment, provided is use of a conjugate of the present disclosure or a pharmaceutical composition of the present disclosure in the manufacture of a medicament for treating a disease, disorder or condition selected from HER2-positive tumors. In a more preferred embodiment, the disease, disorder or condition is selected from the group consisting of breast cancer, gastric cancer, lung cancer, ovarian cancer, urothelial cancer, and the like.

The dosage of the conjugate administered to the subject can be adjusted to a considerable extent. The dosage can vary according to the particular route of administration and the needs of the subject, and can be subjected to the judgment of the health care professional.

Beneficial Effects

The novel small molecule topoisomerase I inhibitors provided in the present disclosure, either used alone or as a component of ADCs, could show greater activity, stability, physiochemical properties over the prior art.

The antibody-drug conjugate of the present invention uses specially designed linker-payload, and can achieve great efficacy and bystander killing effects. At the same time, it has a lower DAR, and therefore can reduce side effects and increase the therapeutic index, which is of special importance for bystander killing. The antibody-drug conjugate of the present invention is more stable in its structure such as the ring-opened succinimide structure.

The present disclosure utilizes a linker with unique structure and uses a ligase to catalyze the conjugation of the targeting molecule and the payload. The conjugate of the present disclosure has good homogeneity and high activity. Furthermore, the toxicity of the linker-payload intermediate is much lower than that of the free payload, and thus the manufacture process of the drug is less detrimental, which is advantageous for industrial production.

The conjugate of the present disclosure achieves at least one of the following technical effects:
(1) High inhibitory activity against target cells, or strong killing effect on target cells.
(2) Good physicochemical properties (e.g., solubility, physical and/or chemical stability).
(3) Good pharmacokinetic properties (e.g., good stability in plasma, appropriate half-life and duration of action).
(4) Good safety (low toxicity on non-target normal cells or tissues, and/or fewer side effects, wider treatment window), etc.
(5) Highly modular design, simple assembly of multiple drugs.

EXAMPLES

Preparation Example

In order to more clearly illustrate the objects and technical solutions, the present disclosure is further described below with reference to specific examples. It is to be understood that the examples are not intended to limit the scope of the disclosure. The specific experimental methods which were not mentioned in the following examples were carried out according to conventional experimental method.

Instruments, Materials and Reagents

Unless otherwise stated, the instruments and reagents used in the examples are commercially available. The reagents can be used directly without further purification.

MS: Thermo Fisher Q Exactive Plus, Water2795-Quattro micro triple quadrupole mass spectrometer
HPLC: Waters 2695, Agilent 1100, Agilent 1200
Semi-preparative HPLC: Lisure HP plus 50D
Flow Cytometry: CytoFLEX S
HIC-HPLC: Butyl-HIC; mobile phase A: 25 mM PB, 2M $(NH_4)_2SO_4$, pH 7.0; mobile phase B: 25 mM PB, pH 7.0; flow rate: 0.8 ml/min; acquisition time: 25 min; injection amount: 20 μg; column temperature: 25° C.; detection wavelength: 280 nm; sample chamber temperature: 8° C.
SEC-HPLC: column: TSK-gel G3000 SWXL, TOSOH 7.8 mm ID×300 mm, 5 μm; mobile phase: 0.2 M KH$_2$PO$_4$, 0.25 M KCl, pH 6.2; flow rate: 0.5 ml/min; acquisition time: 30 min; injection volume: 50 μl; column temperature: 25° C.; detection wavelength; 280 nm; sample tray temperature: 8° C.

CHO was obtained from Thermo Fisher Scientific; pcDNA 3.3 was obtained from Life Technology; HEK293F was obtained from Prejin; PEIMAX transfection reagent was obtained from Polyscience; MabSelect Sure ProA was obtained from GE; Capto S ImpAct was obtained from GE; Rink-amide-MBHA-resin and dichloro resin were obtained from Nankai synthesis; HCC1954 was obtained from ATCC CAT #CRL-2338; SK-BR-3 was obtained from ATCC CAT #HTB-30; BT-474 was obtained from ATCC CAT #HTB-20; NCI-N87 cells was obtained from ATCC CAT #CRL-5822; MCF7 was obtained from ATCC CAT #HTB-22; MDA-MB-231 was obtained from ATCC CAT #HTB-26; MDA-MB-468 was obtained from ATCC CAT #HTB-132; CFPAC-1 was obtained from ATCC CAT #CRL-1918; NCI-H2110 was obtained from ATCC CAT #CRL-5924; JIMT-1 was obtained from Wuxi Apptech; Capan-1 was obtained from ATCC CAT #CRL-1573; antibody Trastuzumab is prepared according to the known sequence; optimized recombinant enzyme Sortase A derived from *Staphylococcus aureus* is prepared in *E. coli*.

In some cases, the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Example 1 Preparation of Payload Small Molecules

Intermediate 11

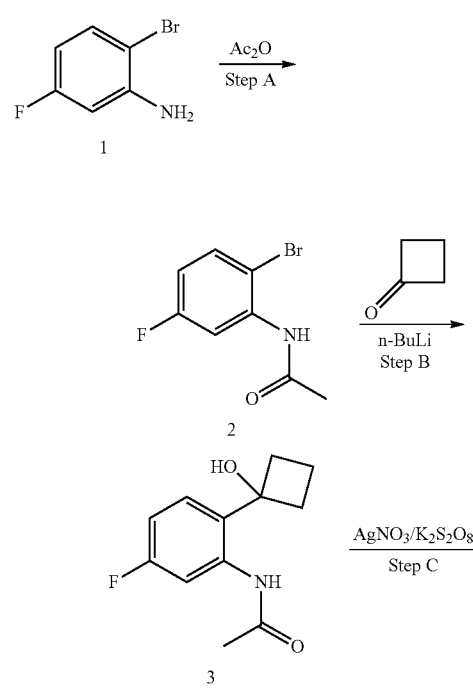

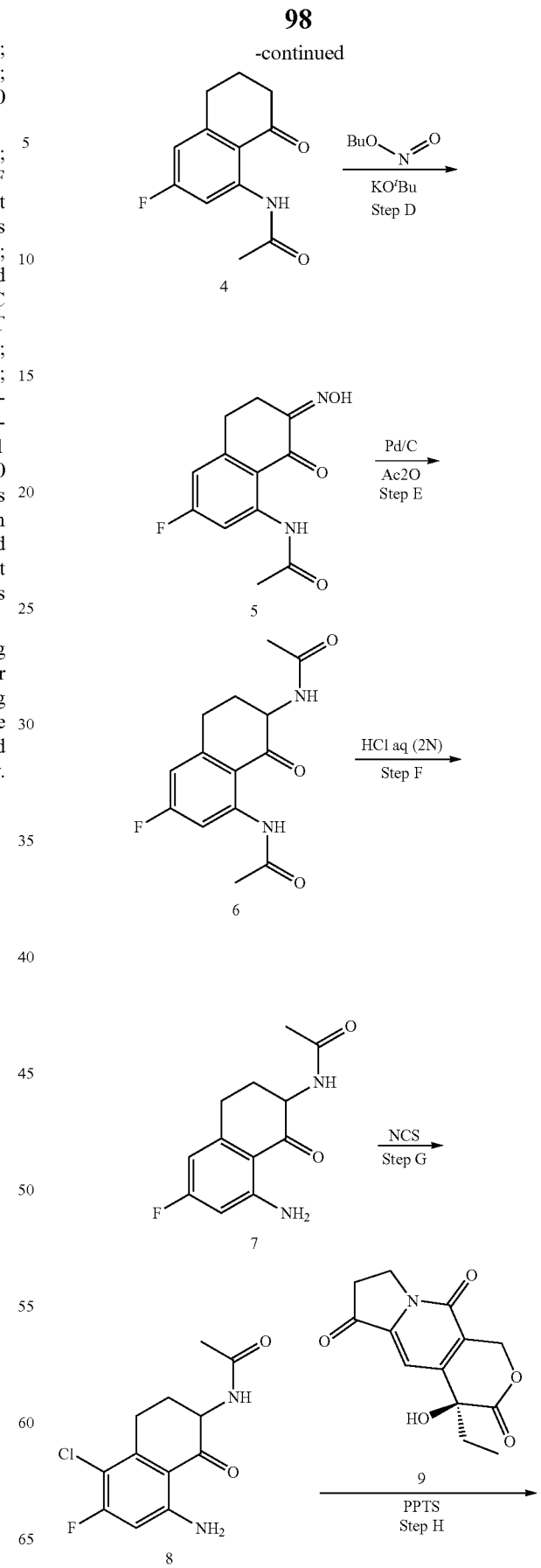

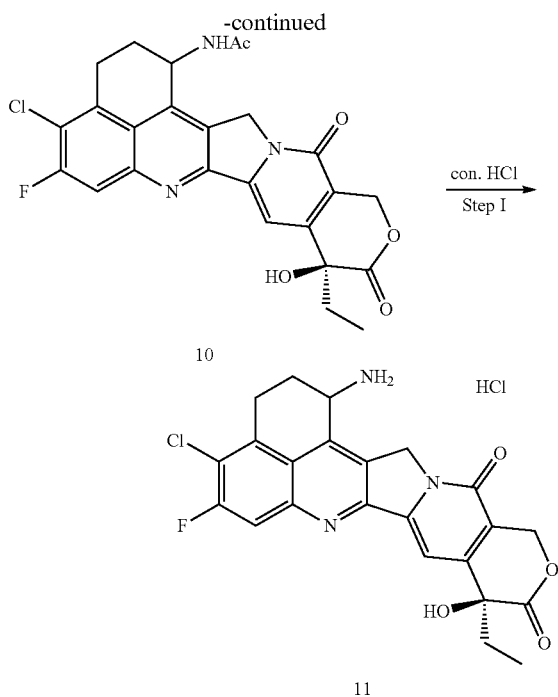

Step A: N-(2-bromo-5-fluorophenyl)acetamide: To a stirred solution of acetic anhydride (214 g, 2.10 mol) in acetic acid (500 mL) was added con. H$_2$SO$_4$ (3 mL), followed with 2-bromo-5-fluoroaniline (100 g, 526.27 mmol) in portions at room temperature. The mixture was stirred for 3 h, then poured into 2000 mL ice-water. A precipitate was formed, which was collected by filtration and dried in vacuo at room temperature to afford N-(2-bromo-5-fluorophenyl)acetamide (105 g) as a yellow solid. $^1$H NMR (400 MHz, DMSO-d$_6$) δ 7.68 (dd, J=8.9, 6.0 Hz, 1H), 7.61 (ddd, J=10.7, 5.3, 3.1 Hz, 1H), 7.02 (ddd, J=8.9, 8.0, 3.1 Hz, 1H), 2.11 (s, 3H). LCMS m/z 232.0 (M+H).

Step B: N-(5-fluoro-2-(1-hydroxycyclobutyl)phenyl)acetamide: To a stirred solution of N-(2-bromo-5-fluorophenyl)acetamide (105 g, 452.48 mmol) in THF (1000 mL) was added n-BuLi (594 mL, 1.6 M in n-hexane, 950.22 mmol) dropwise over 1 h at −78° C. After completion, the mixture was stirred for 0.5 h under N$_2$. Then a solution of cyclobutanone (38.06 g, 542.98 mmol) in THF (50 mL) was added dropwise at −78° C. over 0.5 h, the mixture was stirred at −78° C. to room temperature for 6 h. The mixture was poured into 500 mL saturated NH$_4$Cl aq at 0° C. Extracted with ethyl acetate (500 mL×3), washed with brine (250 mL×2), dried over Na$_2$SO$_4$ and concentrated. The mixture was triturated with (PE/EA=1:1, 100 mL) for 10 mins, filtered and the cake was collected and dried in vacuo to afford N-(5-fluoro-2-(1-hydroxycyclobutyl)phenyl)acetamide (24 g) as a yellow solid. LCMS m/z 206.1 (M−18+H), 246.1 (M+Na).

Step C: N-(3-fluoro-8-oxo-5,6,7,8-tetrahydronaphthalen-1-yl)acetamide: To a stirred mixture of N-(5-fluoro-2-(1-hydroxycyclobutyl)phenyl)acetamide (24 g, 107.50 mmol) in CH$_2$Cl$_2$ (170 mL) and water (170 mL) was added silver nitrate (AgNO$_3$) (5.48 g, 32.25 mmol) and potassium persulfate (K$_2$S$_2$O$_8$) (58.12 g, 215.01 mmol), the mixture was stirred at 30° C. for 6 h. The mixture was filtered on Celite and washed with CH$_2$Cl$_2$ (100 mL), the filtrate was concentrated and purified by FCC (EA/PE=0-40%) to afford N-(3-fluoro-8-oxo-5,6,7,8-tetrahydronaphthalen-1-yl)acetamide (14 g) as a light yellow solid. LCMS m/z 222.1 (M+H).

Step D: N-(3-fluoro-7-(hydroxyimino)-8-oxo-5,6,7,8-tetrahydronaphthalen-1-yl)acetamide: To a stirring mixture of N-(3-fluoro-8-oxo-5,6,7,8-tetrahydronaphthalen-1-yl)acetamide (14 g, 63.28 mmol) in THF (500 mL) at 0° C. was added 1-butyl nitrite (8.48 g, 63.28 mmol), followed with t-BuOK (8.52 g, 75.94 mmol). The mixture was stirred at 0° C. for 2 h. After completion, the mixture was acidified by HCl (2 N) to adjust pH=3. The mixture was extracted by ethyl acetate (200 mL×3), washed by brine (100 mL×2), dried over Na$_2$SO$_4$ and concentrated under reduced pressure. The crude mixture was triturated with tert-butyl methyl ether (200 mL) for 10 mins, filtered and the cake was collected and dried in vacuo to afford N-(3-fluoro-7-(hydroxyimino)-8-oxo-5,6,7,8-tetrahydronaphthalen-1-yl)acetamide (12 g) as a yellow solid. LCMS m/z 251.1 (M+H).

Step E: N,N'-(3-fluoro-8-oxo-5,6,7,8-tetrahydronaphthalene-1,7-diyl)diacetamide: To a solution of N-(3-fluoro-7-(hydroxyimino)-8-oxo-5,6,7,8-tetrahydronaphthalen-1-yl)acetamide (12 g, 47.96 mmol) in acetic anhydride (90 mL) and THF (90 mL) was added 10% Pd/C (1 g), the mixture was stirred at 25° C. under H$_2$ atmosphere for 16 h. After cooling to 0° C., Et$_3$N (20 mL) was added dropwise, the mixture was stirred at 0° C. for 1 h. Filtered on Celite, the filtrate was poured into ice-water (500 mL). Extracted with ethyl acetate (500 mL×3), washed with brine (250 mL×2), dried over Na$_2$SO$_4$ and concentrated. The residue was triturated with tert-butyl methyl ether (120 mL) for 10 mins, filtered and the cake was collected and dried in vacuo to give N,N'-(3-fluoro-8-oxo-5,6,7,8-tetrahydronaphthalene-1,7-diyl)diacetamide (7.9 g) as a yellow solid. LCMS m/z 279.1 (M+H).

Step F: N,N'-(3-fluoro-8-oxo-5,6,7,8-tetrahydronaphthalene-1,7-diyl)diacetamide: To a solution of N,N'-(3-fluoro-8-oxo-5,6,7,8-tetrahydronaphthalene-1,7-diyl)diacetamide (7.9 g, 28.39 mmol) in MeOH (150 mL) was added HCl aq (2 N, 150 mL), the mixture was stirred at 50° C. for 7 h. After cooling to 0° C., Sat. NaHCO$_3$ aq was added dropwise to adjust pH=8. Extracted with ethyl acetate (200 mL×3), washed with brine (200 mL×2), dried over Na$_2$SO$_4$ and concentrated under reduced pressure to give N,N'-(3-fluoro-8-oxo-5,6,7,8-tetrahydronaphthalene-1,7-diyl)diacetamide (6.0 g) as a yellow solid. $^1$H NMR (400 MHz, Chloroform-d) δ 6.57 (s, 3H), 6.18 (td, J=11.1, 2.4 Hz, 2H), 4.52 (dt, J=13.3, 5.0 Hz, 1H), 3.13 (ddd, J=17.5, 13.0, 4.6 Hz, 1H), 3.00-2.81 (m, 1H), 2.69 (dtd, J=9.4, 4.6, 2.5 Hz, 1H), 2.09 (s, 3H), 1.79 (qd, J=13.0, 4.3 Hz, 1H). LCMS m/z 237.1 (M+H).

Step G: N-(8-amino-5-chloro-6-fluoro-1-oxo-1,2,3,4-tetrahydronaphthalen-2-yl)acetamide: To a solution of N,N'-(3-fluoro-8-oxo-5,6,7,8-tetrahydronaphthalene-1,7-diyl)diacetamide (4.0 g, 16.93 mmol) in DMF (80 mL) was added NCS (2.26 g, 16.93 mmol) in portions at 0° C., the mixture was stirred at room temperature for 16 h. The mixture was poured into 200 mL ice-water. A precipitate was formed, which was collected by filtration and dried in vacuo at room temperature to afford N-(8-amino-5-chloro-6-fluoro-1-oxo-1,2,3,4-tetrahydronaphthalen-2-yl)acetamide (4.0 g) as a yellow solid. $^1$H NMR (400 MHz, DMSO-d$_6$) δ 8.11 (d, J=8.0 Hz, 1H), 7.71 (s, 2H), 6.62 (d, J=11.9 Hz, 1H), 4.53 (ddd, J=13.0, 8.0, 4.7 Hz, 1H), 3.18-3.04 (m, 1H), 2.91 (ddd, J=17.5, 12.4, 4.8 Hz, 1H), 2.21-2.08 (m, 1H), 1.99-1.83 (m, 4H). LCMS m/z 271.0 (M+H).

Step H: N-((9S)-4-chloro-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl)acetamide: To a mixture of N-(8-amino-5-chloro-6-fluoro-1-oxo-1,2,3,4-tetrahydronaphthalen-2-yl)acetamide (4.0 g, 14.78 mmol) in toluene (400 mL) was added (S)-4-ethyl-4-hydroxy-7,8-dihydro-1H-pyrano[3,4-f]indolizine-3,6,10(4H)-trione (4.28 g, 16.25 mmol), pyridinium p-Toluenesulfonate (1.11 g, 4.43 mmol) and o-cresol (10 mL), the mixture was heated to reflux under N₂ for 24 h. The solvent was removed by reduced pressure and the mixture was purified by FCC (THF/CH₂Cl₂=0-60%) to afford N-((9S)-4-chloro-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl)acetamide (4.1 g) as a brown solid. LCMS m/z 498.1 (M+H).

Step I: (9S)-1-amino-4-chloro-9-ethyl-5-fluoro-9-hydroxy-1,2,3,9,12,15-hexahydro-10H,13H-benzo[de]pyrano[3',4':6,7]indolizino[1,2-b]quinoline-10,13-dione: A mixture of N-((9S)-4-chloro-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl)acetamide (2.0 g, 4.02 mmol) in 20 mL con. HCl aq was stirred at 70° C. under N₂ for 36 h. The mixture was concentrated under reduced pressure to give crude (9S)-1-amino-4-chloro-9-ethyl-5-fluoro-9-hydroxy-1,2,3,9,12,15-hexahydro-10H,13H-benzo[de]pyrano[3',4':6,7]indolizino[1,2-b]quinoline-10,13-dione hydrochloride (2 g) as a brown solid. LCMS (ESI) m/z 456.1 (M+H).

Intermediate 12

Intermediate 13

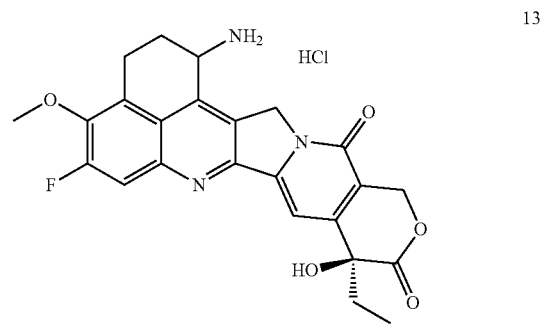 [SMILES: CC[C@@]1(O)C(=O)OCc2c1cc1n(c2=O)Cc2c-1nc1cc(F)c(OC)c3c1c2C(N)CC3 ; Cl]

Intermediate 13: (9S)-1-amino-9-ethyl-5-fluoro-9-hydroxy-4-methoxy-1,2,3,9,12,15-hexahydro-10H,13H-benzo[de]pyrano[3',4':6,7]indolizino[1,2-b]quinoline-10,13-dione hydrochloride was synthesized from 2-bromo-5-fluoro-4-methoxyaniline using a similar procedure as above for intermediate 11. LCMS (ESI) m/z 452.1 (M+H).

Procedure of C730 and C731

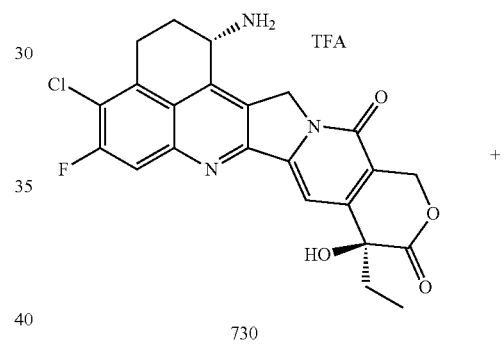

730

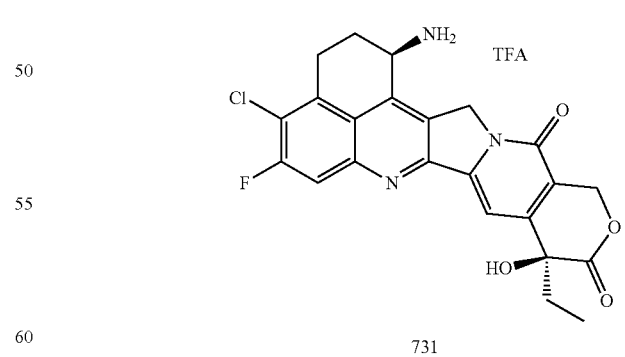

12

Intermediate 12: (9S)-1-amino-4-bromo-9-ethyl-5-fluoro-9-hydroxy-1,2,3,9,12,15-hexahydro-10H,13H-benzo[de]pyrano[3',4':6,7]indolizino[1,2-b]quinoline-10,13-dione hydrobromide was synthesized from 2-bromo-5-fluoroaniline using a similar procedure as above for intermediate 11. LCMS (ESI) m/z 500.0 (M+H).

731

C730 and C731 was prepared by prep-HPLC from (9S)-1-amino-4-chloro-9-ethyl-5-fluoro-9-hydroxy-1,2,3,9,12,15-hexahydro-10H,13H-benzo[de]pyrano[3',4':6,7]indolizino[1,2-b]quinoline-10,13-dione hydrochloride (intermediate 11) as TFA salt.

TABLE I

| Number | Structure | ¹HNMR | MS (M + H) | Retention time on HPLC (min) |
|---|---|---|---|---|
| C730 | 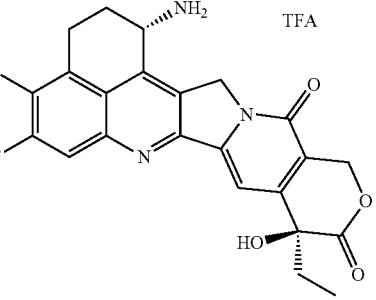 | ¹H NMR (400 MHz, DMSO-d6) δ 8.51 (d, J = 4.8 Hz, 3H), 8.17 (d, J = 10.2 Hz, 1H), 7.38 (s, 1H), 6.56 (s, 1H), 5.74 (d, J = 19.4 Hz, 1H), 5.52-5.40 (m, 3H), 5.16 (s, 1H), 3.44 (dd, J = 16.3, 4.1 Hz, 1H), 3.19 (t, J = 13.9 Hz, 1H), 2.57 (d, J = 14.0 Hz, 1H), 2.26 (t, J = 14.3 Hz, 1H), 1.89 (hept, J = 7.0 Hz, 2H), 0.89 (t, J = 7.3 Hz, 3H). | 456.0 | 1.395 |
| C731 | 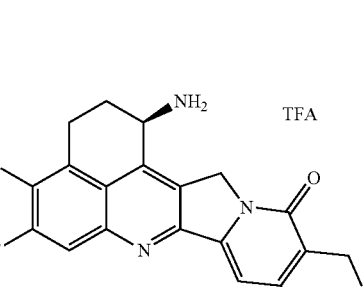 | ¹H NMR (400 MHz, DMSO-d6) δ 8.56 (s, 2H), 8.17 (d, J = 10.1 Hz, 1H), 7.38 (s, 1H), 6.57 (s, 1H), 5.74 (d, J = 19.4 Hz, 1H), 5.53-5.28 (m, 3H), 5.16 (s, 1H), 3.59-3.01 (m, 2H), 2.35-2.19 (m, 2H), 2.00-1.78 (m, 2H), 0.88 (t, J = 7.3 Hz, 3H). | 456.0 | 1.541 |

Conditions of HPLC above: Equipment: Agilent 1200; Chromatographic column: Waters XBridge C18 4.6*50 mm, 3.5 um; Flow: 2.0 mL/min; Gradient elute: 5.0%-95.0%-95.0%-5.0%-5.0%, 0.00 min-1.50 min-2.50 min-2.52 min-3.00 min; Temperature: 40° C.; Phase: A: Acetonitrile, B: H2O (0.05% TFA); Wavelength: 214 nm/254 nm.

Procedure of C518

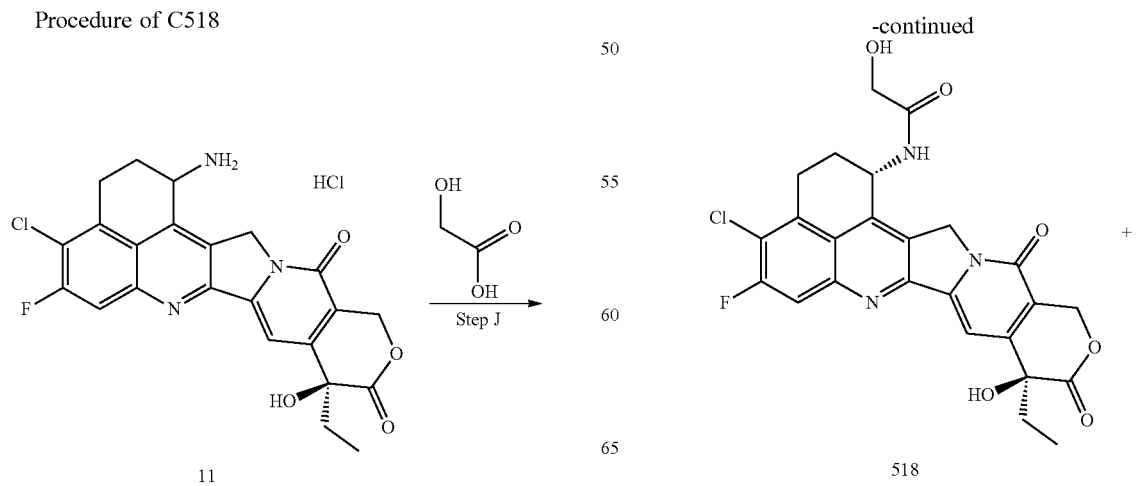

-continued

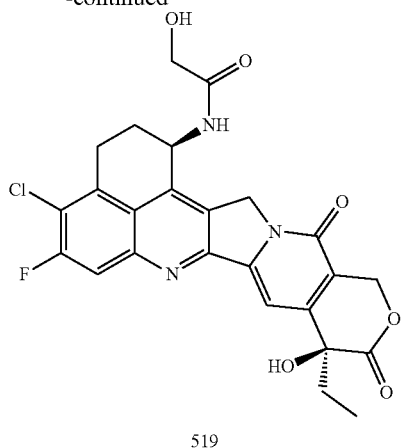

519

Step J: N-((1S,9S)-4-chloro-9-ethyl-5-fluoro-9-hydroxy-10,13-dioxo-2,3,9,10,13,15-hexahydro-1H,12H-benzo[de] pyrano[3',4':6,7]indolizino[1,2-b]quinolin-1-yl)-2-hydroxy-acetamide: To a solution of crude (9S)-1-amino-4-chloro-9-ethyl-5-fluoro-9-hydroxy-1,2,3,9,12,15-hexahydro-10H,13H-benzo[de]pyrano[3',4':6,7]indolizino[1,2-b]quinoline-10,13-dione hydrochloride (50 mg, 0.10 mmol) in 2 mL DMF was added 2-hydroxyacetic acid (11.6 mg, 0.15 mmol), HATU (57.9 mg, 0.15 mmol) and followed with $Et_3N$ (20.5 mg, 0.20 mmol) dropwise at 0° C., the mixture was stirred at 0° C. to room temperature for 2 h. The mixture was poured into 10 mL ice-water, extracted with ethyl acetate (20 mL×3), washed with brine (20 mL×2), dried over $Na_2SO_4$ and concentrated. The residue was purified by prep-HPLC to give N-((1S,9S)-4-chloro-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl)-2-hydroxyacetamide (6 mg) as a yellow solid and N-((1R,9S)-4-chloro-9-ethyl-5-fluoro-9-hydroxy-10,13-dioxo-2,3,9,10,13,15-hexahydro-1H,12H-benzo[de]pyrano[3,4':6,7]indolizino[1,2-b]quinolin-1-yl)-2-hydroxyacetamide (5 mg) as a yellow solid.

The compounds prepared in the table II below was reacted and post-treated in the same manner as in Example C518.

TABLE II

| Number | Structure | $^1$HNMR | MS (M + H) | Retention time on HPLC (min) |
|---|---|---|---|---|
| C518 | 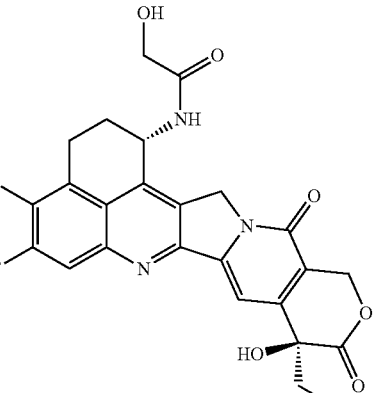 | $^1$H NMR (400 MHz, DMSO-$d_6$) δ 8.50 (d, J = 8.9 Hz, 1H), 8.04 (d, J = 10.3 Hz, 1H), 7.33 (s, 1H), 6.54 (s, 1H), 5.80-5.48 (m, 2H), 5.42 (s, 2H), 5.21 (s, 2H), 3.96 (d, J = 5.8 Hz, 2H), 3.26 (d, J = 20.3 Hz, 2H), 2.22 (dd, J = 18.8, 9.7 Hz, 2H), 1.86 (p, J = 7.5 Hz, 2H), 0.88 (d, J = 7.3 Hz, 3H). | 514.0 | 1.548 |
| C519 | 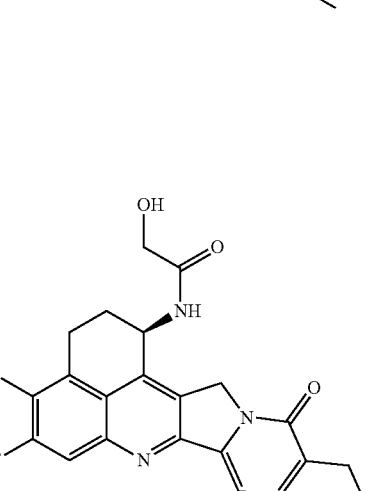 | $^1$H NMR (400 MHz, Methanol-$d_4$) δ 7.86 (d, J = 9.9 Hz, 1H), 7.66 (s, 1H), 5.74 (s, 1H), 5.61 (d, J = 16.4 Hz, 1H), 5.42 (dd, J = 17.4, 8.4 Hz, 2H), 5.22 (d, J = 18.9 Hz, 1H), 4.34-4.12 (m, 2H), 3.53 (d, J = 18.8 Hz, 2H), 2.35 (d, J = 30.7 Hz, 2H), 1.98 (s, 2H), 1.02 (t, J = 7.4 Hz, 3H). | 514.0 | 1.602 |

TABLE II-continued

| Number | Structure | ¹HNMR | MS (M + H) | Retention time on HPLC (min) |
|---|---|---|---|---|
| C586 | 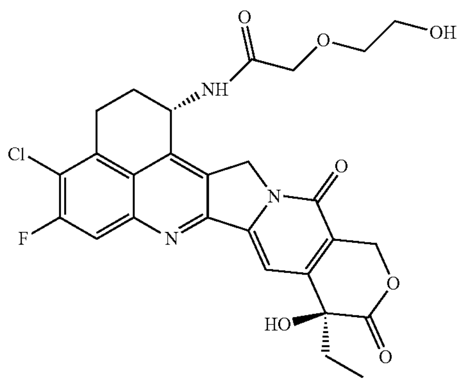 [SMILES: CC[C@@]1(O)C(=O)OCc2c1cc1n(c2=O)Cc2c-1nc1cc(F)c(Cl)c3c1c2[C@@H](NC(=O)COCCO)CC3] | ¹H NMR (400 MHz, DMSO-d₆) δ 8.56 (d, J = 8.9 Hz, 1H), 8.07 (d, J = 10.2 Hz, 1H), 7.34 (s, 1H), 6.55 (s, 1H), 5.74-5.61 (m, 1H), 5.44 (s, 2H), 5.24 (s, 2H), 4.69 (s, 1H), 4.05 (s, 2H), 3.62-3.42 (m, 4H), 3.41-3.21 (m, 2H), 2.33-2.15 (m, 2H), 1.97-1.78 (m, 2H), 0.88 (t, J = 7.2 Hz, 3H). | 558.0 | 1.621 |
| C587 | 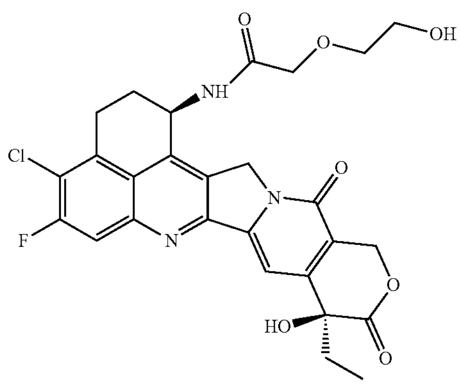 [SMILES: CC[C@@]1(O)C(=O)OCc2c1cc1n(c2=O)Cc2c-1nc1cc(F)c(Cl)c3c1c2[C@H](NC(=O)COCCO)CC3] | ¹H NMR (400 MHz, DMSO-d₆) δ 8.56 (d, J = 8.9 Hz, 1H), 8.07 (d, J = 10.2 Hz, 1H), 7.35 (s, 1H), 6.54 (s, 1H), 5.76-5.61 (m, 1H), 5.44 (s, 2H), 5.23 (s, 2H), 4.68 (s, 1H), 4.05 (s, 2H), 3.60-3.45 (m, 4H), 3.34-3.23 (m, 2H), 2.26-2.16 (m, 2H), 2.04-1.81 (m, 2H), 0.88 (t, J = 7.3 Hz, 3H). | 558.0 | 1.675 |
| C593 | 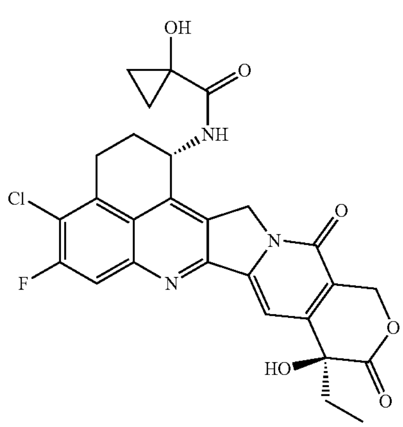 [SMILES: CC[C@@]1(O)C(=O)OCc2c1cc1n(c2=O)Cc2c-1nc1cc(F)c(Cl)c3c1c2[C@@H](NC(=O)C1(O)CC1)CC3] | ¹H NMR (400 MHz, DMSO-d₆) δ 8.66 (d, J = 9.2 Hz, 1H), 8.05 (d, J = 10.7 Hz, 1H), 7.34 (s, 1H), 6.54 (s, 1H), 6.29 (s, 1H), 5.71-5.48 (m, 1H), 5.44 (s, 2H), 5.32-5.04 (m, 2H), 3.33-3.06 (m, 2H), 2.37-2.13 (m, 2H), 2.04-1.69 (m, 2H), 1.30-1.09 (m, 2H), 1.00-0.64 (m, 5H). | 540.0 | 1.746 |

TABLE II-continued
| Number | Structure | ¹HNMR | MS (M + H) | Retention time on HPLC (min) |
|---|---|---|---|---|
| C594 | 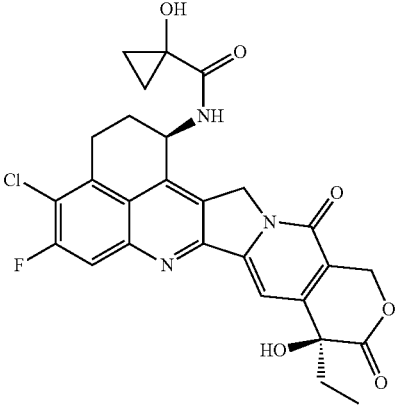 [SMILES: CC[C@@]1(O)C(=O)OCc2c1cc1n(c2=O)Cc2c-1nc1cc(F)c(Cl)c3c1c2[C@H](NC(=O)C1(O)CC1)CC3] | ¹H NMR (400 MHz, DMSO-d₆) δ 8.69 (d, J = 9.4 Hz, 1H), 8.05 (d, J = 10.2 Hz, 1H), 7.34 (s, 1H), 6.54 (s, 1H), 6.31 (s, 1H), 5.67-5.55 (m, 1H), 5.44 (s, 2H), 5.36-5.06 (m, 2H), 3.33-3.07 (m, 2H), 2.38-2.15 (m, 2H), 1.96-1.79 (m, 2H), 1.28-1.13 (m, 2H), 1.05-0.92 (m, 2H), 0.88 (t, J = 7.2 Hz, 3H). | 540.0 | 1.783 |
| C622 | 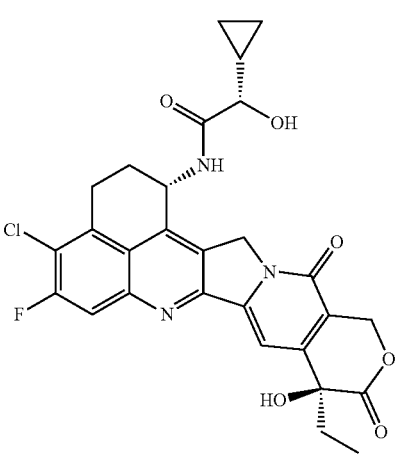 [SMILES: CC[C@@]1(O)C(=O)OCc2c1cc1n(c2=O)Cc2c-1nc1cc(F)c(Cl)c3c1c2[C@@H](NC(=O)[C@@H](O)C1CC1)CC3] | ¹H NMR (400 MHz, DMSO-d₆) δ 8.43 (d, J = 8.9 Hz, 1H), 8.06 (d, J = 10.2 Hz, 1H), 7.34 (s, 1H), 6.53 (s, 1H), 5.62 (d, J = 8.0 Hz, 1H), 5.51 (d, J = 5.2 Hz, 1H), 5.43 (s, 2H), 5.37-5.15 (m, 2H), 3.61 (t, J = 5.8 Hz, 1H), 3.34-3.12 (m, 2H), 2.25-2.15 (m, 2H), 1.96-1.80 (m, 2H), 1.29-1.15 (m, 1H), 0.88 (t, J = 7.3 Hz, 3H), 0.58-0.27 (m, 4H). | 554.0 | 1.694 |
| C624 | 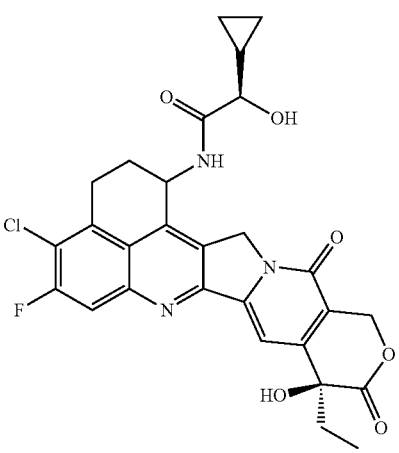(mixture) | ¹H NMR (400 MHz, DMSO-d₆) δ 8.43 (dd, J = 8.7, 5.3 Hz, 1H), 8.05 (d, J = 10.2 Hz, 1H), 7.34 (d, J = 1.6 Hz, 1H), 6.54 (d, J = 2.0 Hz, 1H), 5.68-5.52 (m, 1H), 5.49-5.35 (m, 2H), 5.34-5.11 (m, 2H), 3.81-3.57 (m, 1H), 3.35-3.22 (m, 2H), 2.29-2.07 (m, 2H), 1.96-1.71 (m, 2H), 1.19-1.06 (m, 1H), 0.88 (t, J = 7.3 Hz, 3H), 0.46-0.24 (m, 4H). | 554.0 | 1.753 |

TABLE II-continued
| Number | Structure | ¹HNMR | MS (M + H) | Retention time on HPLC (min) |
|---|---|---|---|---|
| C625 | 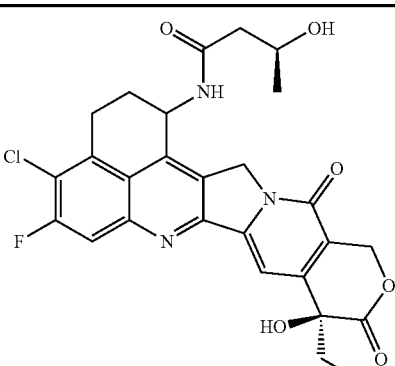 (mixture) | ¹H NMR (400 MHz, DMSO-d₆) δ 8.44 (t, J = 7.7 Hz, 1H), 8.08 (d, J = 10.2 Hz, 1H), 7.34 (s, 1H), 6.54 (s, 1H), 5.70-5.54 (m, 1H), 5.44 (s, 2H), 5.37-5.16 (m, 2H), 4.16-3.93 (m, 1H), 3.38-2.84 (m, 2H), 2.35-2.21 (m, 2H), 2.22-2.09 (m, 2H), 1.96-1.74 (m, 2H), 1.09 (d, J = 6.2 Hz, 3H), 0.88 (t, J = 7.4 Hz, 3H). | 542.0 | 1.646 |
| C677 | 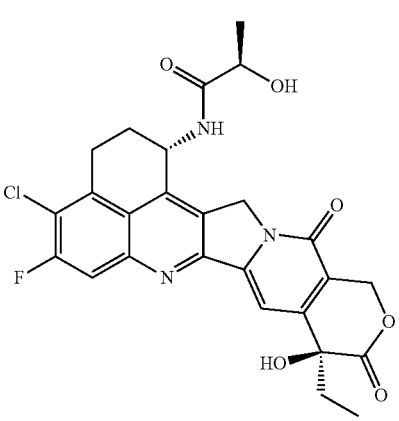 [SMILES: CC[C@@]1(O)C(=O)OCc2c1cc1n(c2=O)Cc2c-1nc1cc(F)c(Cl)c3c1c2[C@@H](NC(=O)[C@@H](C)O)CC3] | ¹H NMR (400 MHz, DMSO-d₆) δ 8.50 (d, J = 9.2 Hz, 1H), 8.04 (d, J = 10.2 Hz, 1H), 7.33 (s, 1H), 6.53 (s, 1H), 5.87-5.53 (m, 1H), 5.42 (s, 2H), 5.33-5.04 (m, 2H), 4.26-4.06 (m, 1H), 3.34-3.15 (m, 2H), 2.27-2.12 (m, 2H), 2.02-1.75 (m, 2H), 1.40 (d, J = 6.8 Hz, 3H), 0.87 (t, J = 7.3 Hz, 3H). | 528.0 | 1.658 |
| C678 | 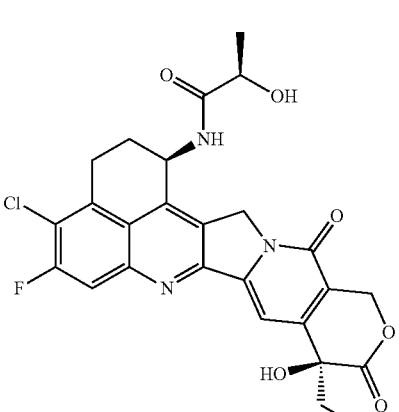 | ¹H NMR (400 MHz, DMSO-d₆) δ 8.46 (d, J = 8.9 Hz, 1H), 8.05 (d, J = 10.2 Hz, 1H), 7.34 (s, 1H), 6.53 (s, 1H), 5.71-5.52 (m, 1H), 5.43 (s, 2H), 5.34-5.02 (m, 2H), 4.47-3.80 (m, 1H), 3.34-3.13 (m, 2H), 2.31-2.10 (m, 2H), 2.02-1.76 (m, 2H), 1.30 (d, J = 6.7 Hz, 3H), 0.87 (t, J = 7.3 Hz, 3H). | 528.0 | 1.717 |

TABLE II-continued

| Number | Structure | ¹HNMR | MS (M + H) | Retention time on HPLC (min) |
|---|---|---|---|---|
| C679 | 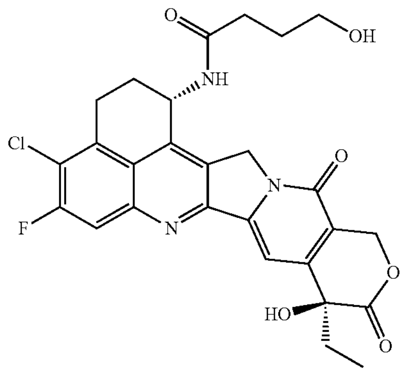 [SMILES: CC[C@@]1(O)C(=O)OCc2c1cc1n(c2=O)Cc2c-1nc1cc(F)c(Cl)c3c1c2[C@@H](NC(=O)CCCO)CC3] | ¹H NMR (400 MHz, DMSO-d₆) δ 8.47 (d, J = 8.8 Hz, 1H), 8.06 (d, J = 10.3 Hz, 1H), 7.34 (s, 1H), 6.54 (s, 1H), 5.77-5.51 (m, 1H), 5.44 (s, 2H), 5.34-5.10 (m, 2H), 3.50-3.35 (m, 2H), 3.33-3.14 (m, 2H), 2.28-2.19 (m, 2H), 2.19-2.09 (m, 2H), 1.92-1.80 (m, 2H), 1.79-1.62 (m, 2H), 0.87 (t, J = 7.3 Hz, 3H) | 542.0 | 1.603 |
| C680 | 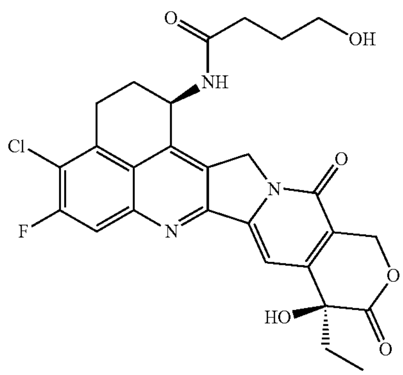 [SMILES: CC[C@@]1(O)C(=O)OCc2c1cc1n(c2=O)Cc2c-1nc1cc(F)c(Cl)c3c1c2[C@H](NC(=O)CCCO)CC3] | ¹H NMR (400 MHz, DMSO-d₆) δ 8.45 (d, J = 8.8 Hz, 1H), 8.06 (d, J = 10.2 Hz, 1H), 7.33 (s, 1H), 6.54 (s, 1H), 5.69-5.54 (m, 1H), 5.43 (s, 2H), 5.36-5.10 (m, 2H), 3.42-3.37 (m, 2H), 3.33-3.26 (m, 2H), 2.27-2.07 (m, 4H), 1.99-1.79 (m, 2H), 1.77-1.67 (m, 2H), 0.87 (t, J = 7.3 Hz, 3H). | 542.0 | 1.645 |
| C703 | 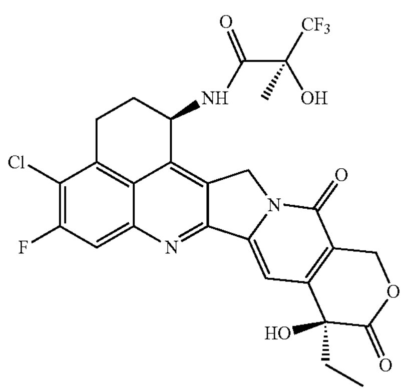 [SMILES: CC[C@@]1(O)C(=O)OCc2c1cc1n(c2=O)Cc2c-1nc1cc(F)c(Cl)c3c1c2[C@H](NC(=O)[C@](C)(O)C(F)(F)F)CC3] | ¹H NMR (400 MHz, DMSO-d6) δ 8.96 (d, J = 8.7 Hz, 1H), 8.07 (d, J = 10.2 Hz, 1H), 7.34 (s, 1H), 7.13 (s, 1H), 6.55 (s, 1H), 5.63-5.53 (m, 1H), 5.43 (s, 2H), 5.31-5.03 (m, 2H), 3.31-3.24 (m, 2H), 2.31-2.11 (m, 2H), 1.95-1.75 (m, 2H), 1.55 (s, 3H), 0.88 (t, J = 7.3 Hz, 3H). | 596.0 | 1.792 |
| C704 | 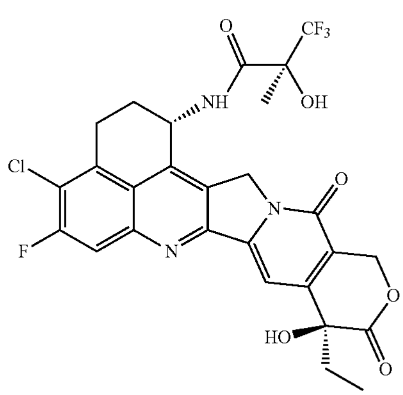 [SMILES: CC[C@@]1(O)C(=O)OCc2c1cc1n(c2=O)Cc2c-1nc1cc(F)c(Cl)c3c1c2[C@@H](NC(=O)[C@](C)(O)C(F)(F)F)CC3] | ¹H NMR (400 MHz, DMSO-d6) δ 9.06 (d, J = 9.2 Hz, 1H), 8.06 (d, J = 10.3 Hz, 1H), 7.35 (s, 1H), 7.33 (s, 1H), 6.56 (s, 1H), 5.67-5.59 (m, 1H), 5.44 (s, 2H), 5.31-5.02 (m, 2H), 3.32-3.19 (m, 2H), 2.30-2.10 (m, 2H), 1.96-1.80 (m, 2H), 1.71 (s, 3H), 0.88 (t, J = 7.3 Hz, 3H). | 596.0 | 1.896 |

TABLE II-continued

| Number | Structure | ¹HNMR | MS (M + H) | Retention time on HPLC (min) |
|---|---|---|---|---|
| C627 | 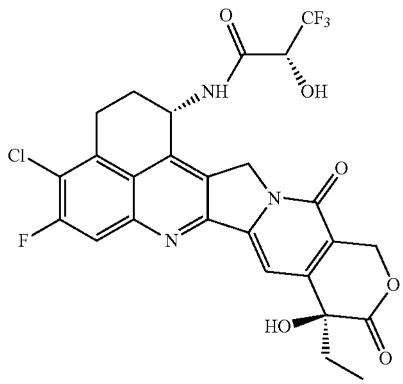 [SMILES: CC[C@@]1(O)C(=O)OCc2c1cc1n(c2=O)Cc2c-1nc1cc(F)c(Cl)c3c1c2[C@@H](NC(=O)[C@@H](O)C(F)(F)F)CC3] | ¹H NMR (400 MHz, DMSO-d6) δ 9.00 (d, J = 8.5 Hz, 1H), 8.07 (d, J = 10.3 Hz, 1H), 7.34 (s, 1H), 6.55 (s, 1H), 5.70-5.47 (m, 1H), 5.43 (s, 2H), 5.34-5.06 (m, 2H), 4.72-4.52 (m, 1H), 3.34-3.16 (m, 2H), 2.29-2.09 (m, 2H), 1.99-1.75 (m, 2H), 0.87 (t, J = 7.3 Hz, 3H). | 582.0 | 1.835 |
| C626 | 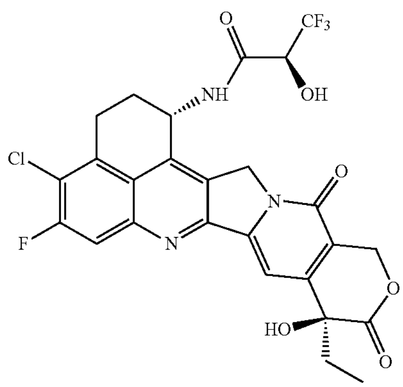 [SMILES: CC[C@@]1(O)C(=O)OCc2c1cc1n(c2=O)Cc2c-1nc1cc(F)c(Cl)c3c1c2[C@@H](NC(=O)[C@H](O)C(F)(F)F)CC3] | ¹H NMR (400 MHz, DMSO-d$_6$) δ 9.02 (d, J = 8.6 Hz, 1H), 8.07 (d, J = 10.2 Hz, 1H), 7.34 (s, 1H), 7.21 (d, J = 6.9 Hz, 1H), 6.55 (s, 1H), 5.73-5.58 (m, 1H), 5.43 (s, 2H), 5.29 (d, J = 19.2 Hz, 1H), 5.13 (d, J = 19.2 Hz, 1H), 4.63 (d, J = 8.2 Hz, 1H), 3.26 (d, J = 7.7 Hz, 2H), 2.20 (p, J = 6.8 Hz, 2H), 1.86 (dt, J = 15.5, 7.2 Hz, 2H), 0.87 (t, J = 7.3 Hz, 3H). | 582.0 | 1.820 |

Conditions of HPLC above: Equipment: Agilent 1200; Chromatographic column: Waters XBridge C18 4.6*50 mm, 3.5 um; Flow: 2.0 mL/min; Gradient elute: 5.0%-95.0%-95.0%-5.0%-5.0%, 0.00 min-1.50 min-2.50 min-2.52 min-3.00 min; Temperature: 40° C.; Phase: A: Acetonitrile, B: H2O (0.05% TFA); Wavelength: 214 nm/254 nm.

The compounds prepared in the table III below was synthesized from intermediate 12 or intermediate 13 using a similar procedure as above for C518.

TABLE III

| Number | Structure | ¹HNMR | MS (M + H) | Retention time on HPLC (min) |
|---|---|---|---|---|
| C636 | 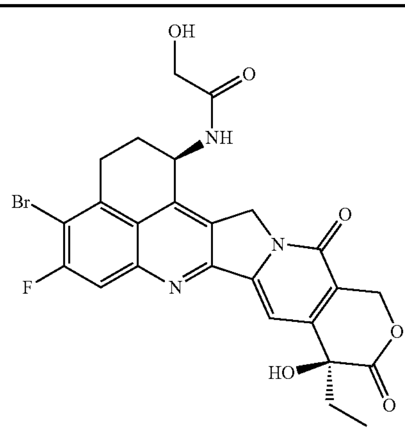 | ¹H NMR (400 MHz, DMSO-d$_6$) δ 8.49 (d, J = 9.1 Hz, 1H), 8.01 (d, J = 9.8 Hz, 1H), 7.34 (s, 1H), 6.54 (s, 1H), 5.71-5.56 (m, 1H), 5.58-5.45 (m, 1H), 5.43 (s, 2H), 5.22 (s, 2H), 3.96 (d, J = 5.7 Hz, 2H), 3.35-3.23 (m, 2H), 2.30-2.10 (m, 2H), 1.96-1.79 (m, 2H), 0.87 (t, J = 8.3, 5.9 Hz, 3H). | 558.0 | 1.612 |

| Number | Structure | ¹HNMR | MS (M + H) | Retention time on HPLC (min) |
|---|---|---|---|---|
| C637 | 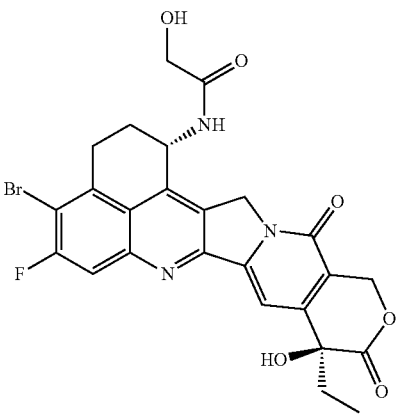 | ¹H NMR (400 MHz, DMSO-d₆) δ 8.51 (d, J = 8.9 Hz, 1H), 8.01 (d, J = 9.8 Hz, 1H), 7.35 (s, 1H), 6.54 (s, 1H), 5.74-5.58 (m, 1H), 5.52 (t, J = 5.8 Hz, 1H), 5.43 (s, 2H), 5.29-5.16 (m, 2H), 3.97 (d, J = 5.5 Hz, 2H), 3.36-3.14 (m, 2H), 2.26-2.14 (m, 2H), 1.96-1.78 (m, 2H), 0.88 (t, J = 7.3 Hz, 3H). | 558.0 | 1.642 |
| C595 | 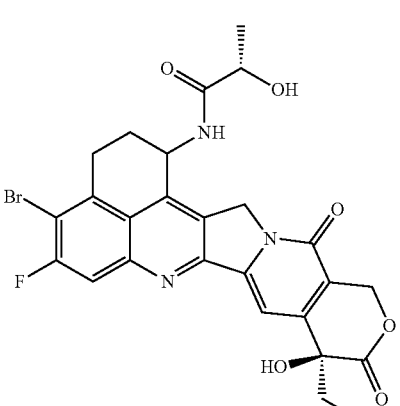<br>(mixture) | ¹H NMR (400 MHz, DMSO-d₆) δ 8.62-8.36 (m, 1H), 8.01 (d, J = 10.2 Hz, 1H), 7.34 (s, 1H), 6.68-6.45 (m, 2H), 5.73-5.49 (m, 1H), 5.43 (s, 2H), 5.36-5.04 (m, 2H), 4.13 (s, 1H), 3.22-2.99 (m, 2H), 2.36-2.03 (m, 2H), 1.97-1.69 (m, 2H), 1.48-1.10 (m, 3H), 0.87 (t, 3H). | 572.0 | 1.747 |
| C596 | 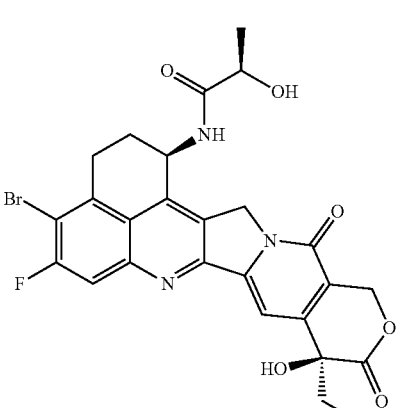 | ¹H NMR (400 MHz, DMSO-d₆) δ 8.52 (d, 1H), 8.02 (d, J = 14.2 Hz, 1H), 7.33 (s, 1H), 6.56 (d, J = 17.9 Hz, 2H), 5.71-5.54 (m, 1H), 5.42 (s, 2H), 5.34-5.06 (m, 2H), 4.13 (s, 1H), 3.25-2.94 (m, 2H), 2.27-2.07 (m, 2H), 2.03-1.72 (m, 2H), 1.53-1.10 (m, 3H), 0.86 (t, 3H). | 572.0 | 1.720 |

TABLE III-continued

| Number | Structure | ¹HNMR | MS (M + H) | Retention time on HPLC (min) |
|---|---|---|---|---|
| C597 | 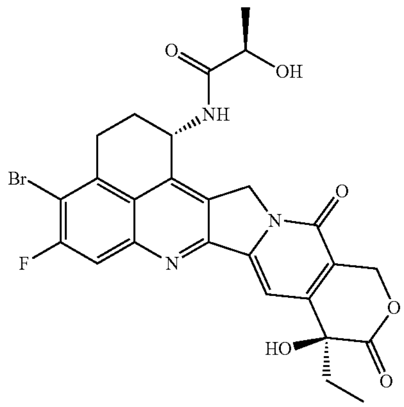 | ¹H NMR (400 MHz, DMSO-d₆) δ 8.47 (d, J = 8.9 Hz, 1H), 8.02 (d, J = 9.7 Hz, 1H), 7.35 (s, 1H), 6.54 (s, 2H), 5.64-5.50 (m, 1H), 5.44 (s, 2H), 5.31-5.08 (m, 2H), 4.17-4.08 (m, 1H), 3.33-3.00 (m, 2H), 2.26-2.12 (m, 2H), 1.96-1.74 (m, 2H), 1.30 (d, J = 6.7 Hz, 3H), 0.88 (t, J = 7.3 Hz, 3H). | 572.0 | 1.773 |
| C600 | 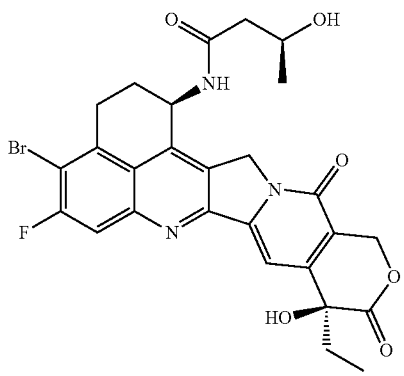 [SMILES: CC[C@@]1(O)C(=O)OCc2c1cc1n(c2=O)Cc2c-1nc1cc(F)c(Br)c3c1c2[C@H](NC(=O)C[C@H](C)O)CC3] | | 586.0 | 1.792 |
| C601 | 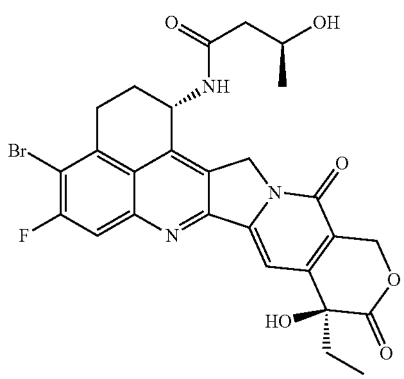 [SMILES: CC[C@@]1(O)C(=O)OCc2c1cc1n(c2=O)Cc2c-1nc1cc(F)c(Br)c3c1c2[C@@H](NC(=O)C[C@H](C)O)CC3] | | 586.0 | 1.712 |
| C602 | 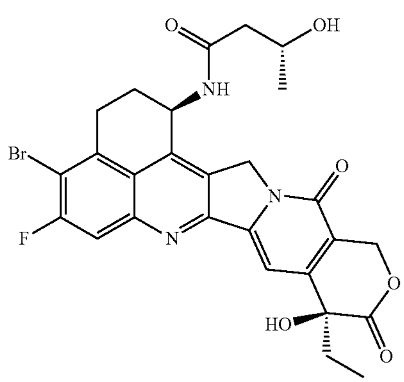 [SMILES: CC[C@@]1(O)C(=O)OCc2c1cc1n(c2=O)Cc2c-1nc1cc(F)c(Br)c3c1c2[C@H](NC(=O)C[C@@H](C)O)CC3] | | 586.0 | 1.741 |

TABLE III-continued

| Number | Structure | ¹HNMR | MS (M + H) | Retention time on HPLC (min) |
|---|---|---|---|---|
| C603 | 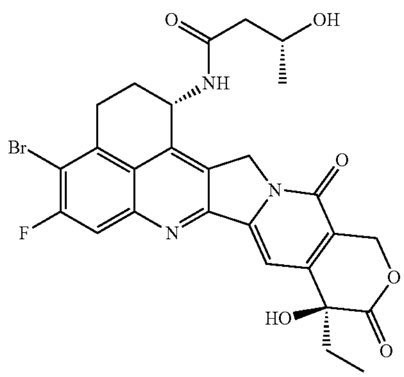 [SMILES: CC[C@@]1(O)C(=O)OCc2c1cc1n(c2=O)Cc2c-1nc1cc(F)c(Br)c3c1c2[C@@H](NC(=O)C[C@@H](C)O)CC3] | | 586.0 | 1.682 |
| C619 | (mixture) | ¹H NMR (400 MHz, DMSO-d$_6$) δ 9.06 (d, J = 8.1 Hz, 1H), 8.03 (d, J = 9.7 Hz, 1H), 7.38 (s, 1H), 6.55 (s, 1H), 5.74-5.54 (m, 1H), 5.43 (s, 2H), 5.36-5.05 (m, 2H), 4.77-4.56 (m, 1H), 3.13-3.00 (m, 2H), 2.27-2.12 (m, 2H), 1.95-1.78 (m, 2H), 0.87 (t, J = 7.2 Hz, 3H). | 625.9 | 1.785 |
| C620 | (mixture) | ¹H NMR (400 MHz, DMSO-d$_6$) δ 9.06 (d, J = 8.1 Hz, 1H), 8.03 (d, J = 9.7 Hz, 1H), 7.38 (s, 1H), 6.55 (s, 1H), 5.74-5.54 (m, 1H), 5.43 (s, 2H), 5.36-5.05 (m, 2H), 4.77-4.56 (m, 1H), 3.13-3.00 (m, 2H), 2.27-2.12 (m, 2H), 1.95-1.78 (m, 2H), 0.87 (t, J = 7.2 Hz, 3H). | 626.0 | 1.847 |

TABLE III-continued

| Number | Structure | ¹HNMR | MS (M + H) | Retention time on HPLC (min) |
|---|---|---|---|---|
| C664 | 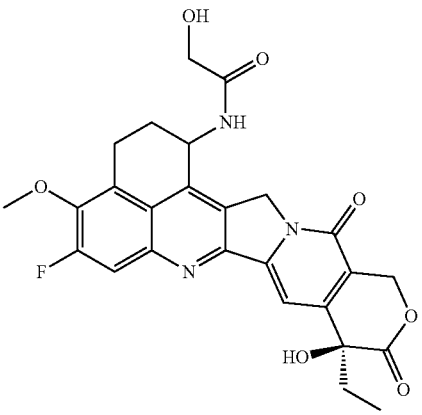<br>(mixture) | ¹H NMR (400 MHz, DMSO-d$_6$) δ 8.46 (d, J = 8.9 Hz, 1H), 7.91 (d, J = 12.4 Hz, 1H), 7.31 (s, 1H), 6.53 (s, 1H), 5.59 (s, 1H), 5.42 (s, 2H), 5.19 (d, J = 2.8 Hz, 2H), 3.97 (s, 3H), 3.20 (dt, J = 13.7, 6.8 Hz, 3H), 2.23-2.07 (m, 2H), 1.86 (s, 2H), 1.24 (s, 2H), 0.87 (t, J = 7.2 Hz, 3H). | 510.1 | 1.510 |
| C665 | 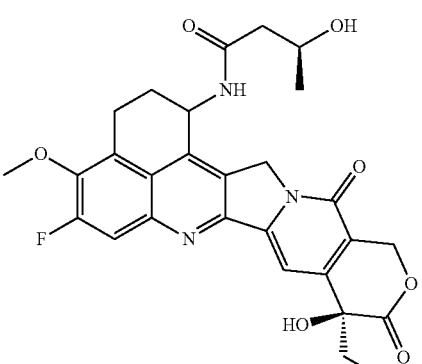<br>(mixture) | ¹H NMR (400 MHz, DMSO-d$_6$) δ 8.42 (d, J = 8.7 Hz, 1H), 7.93 (d, J = 12.4 Hz, 1H), 7.30 (s, 1H), 6.52 (s, 1H), 5.57 (s, 1H), 5.43 (s, 2H), 5.24 (d, J = 6.7 Hz, 2H), 4.04 (d, J = 6.5 Hz, 1H), 3.97 (s, 3H), 3.18 (d, J = 25.1 Hz, 2H), 2.26 (d, J = 7.5 Hz, 2H), 2.20 (d, J = 5.8 Hz, 1H), 2.09 (s, 2H), 1.93-1.79 (m, 2H), 1.09 (d, J = 6.2 Hz, 3H), 0.87 (s, 3H). | 538.2 | 1.521 |
| C667 | 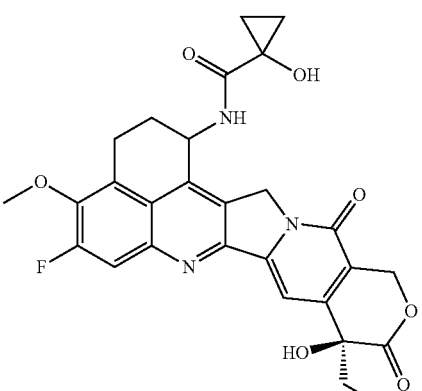<br>(mixture) | ¹H NMR (400 MHz, DMSO-d$_6$) δ 8.60 (d, J = 9.0 Hz, 1H), 7.88 (d, J = 12.4 Hz, 1H), 7.30 (s, 1H), 6.52 (s, 1H), 6.30 (s, 1H), 5.56 (d, J = 7.0 Hz, 1H), 5.42 (s, 2H), 5.34-5.01 (m, 2H), 3.96 (s, 3H), 3.13 (dd, J = 16.9, 7.7 Hz, 2H), 2.18 (t, J = 6.2 Hz, 2H), 1.96-1.77 (m, 2H), 1.26-1.14 (m, 2H), 0.94 (d, J = 3.5 Hz, 2H), 0.87 (t, J = 7.3 Hz, 3H). | 536.1 | 1.578 |

TABLE III-continued

| Number | Structure | ¹HNMR | MS (M + H) | Retention time on HPLC (min) |
|---|---|---|---|---|
| C668 | 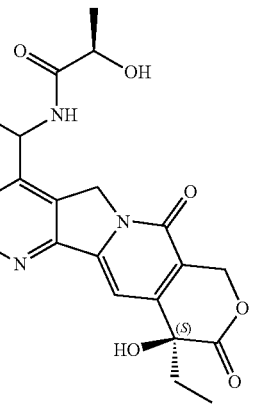 (mixture) | ¹H NMR (400 MHz, DMSO-d₆) δ 8.48 (d, J = 9.2 Hz, 1H), 7.92 (s, 1H), 7.30 (s, 1H), 6.53 (s, 1H), 5.61 (dd, J = 21.7, 6.1 Hz, 2H), 5.42 (s, 2H), 5.23 (d, J = 19.1 Hz, 2H), 5.10 (d, J = 19.0 Hz, 1H), 4.12 (d, J = 6.8 Hz, 1H), 3.96 (d, J = 1.1 Hz, 3H), 3.25-3.04 (m, 2H), 2.13 (d, J = 6.4 Hz, 2H), 1.86 (s, 2H), 1.40 (d, J = 6.8 Hz, 3H), 0.87 (s, 3H). | 524.2 | 1.740 |
| C671 | 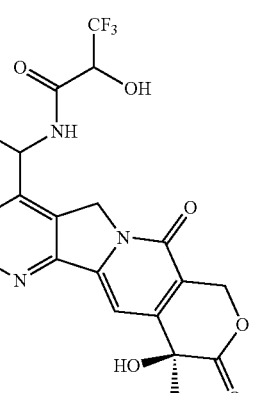 (mixture) | ¹H NMR (400 MHz, DMSO-d₆) δ 9.01 (d, J = 8.5 Hz, 1H), 7.94 (d, J = 12.4 Hz, 1H), 7.31 (s, 1H), 7.24 (d, J = 6.8 Hz, 1H), 6.55 (s, 1H), 5.59 (d, J = 6.3 Hz, 1H), 5.43 (s, 2H), 5.32 (dd, J = 5.5, 4.2 Hz, 1H), 4.64 (t, J = 7.3 Hz, 1H), 3.97 (d, J = 1.1 Hz, 3H), 3.19 (d, J = 6.2 Hz, 3H), 2.05-1.96 (m, 2H), 1.94-1.78 (m, 2H), 1.46 (d, J = 7.7 Hz, 1H), 0.86 (d, J = 8.2 Hz, 3H). | 578.1 | 1.736 |

Conditions of HPLC above: Equipment: Agilent 1200; Chromatographic column: Waters XBridge C18 4.6*50 mm, 3.5 um; Flow: 2.0 mL/min; Gradient elute: 5.0%-95.0%-95.0%-5.0%-5.0%, 0.00 min-1.50 min-2.50 min-2.52 min-3.00 min; Temperature: 40° C.; Phase: A: Acetonitrile, B: H2O (0.05% TFA); Wavelength: 214 nm/254 nm.

Procedure of C589

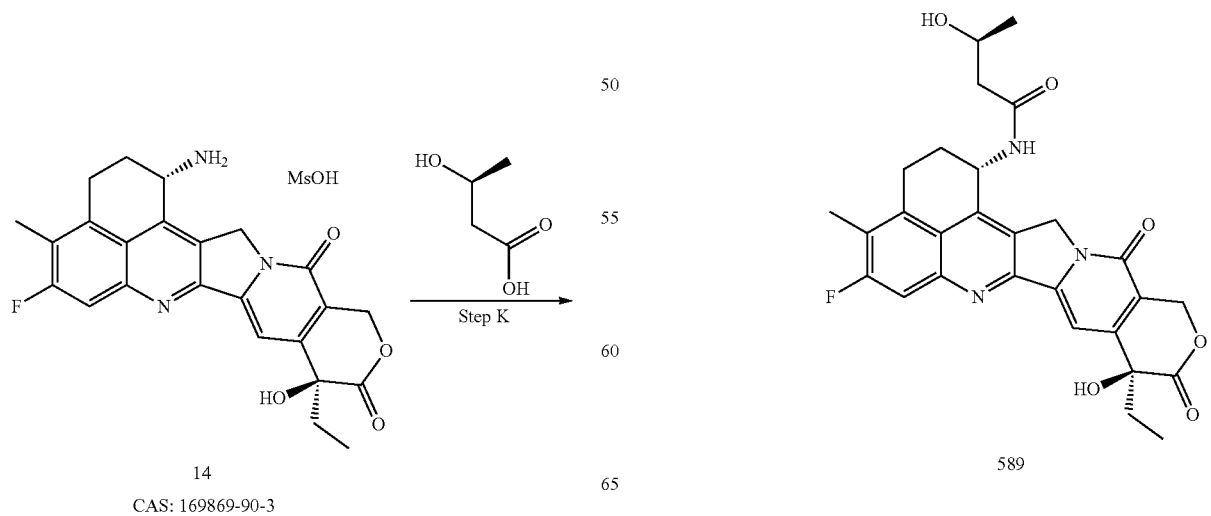

Step K: (S)—N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3-hydroxybutanamide: To a solution of (1S,9S)-1-amino-9-ethyl-5-fluoro-9-hydroxy-4-methyl-1,2,3,9,12,15-hexahydro-10H,13H-benzo[de]pyrano[3',4':6,7]indolizino[1,2-b]quinoline-10,13-dione mesylate (50 mg, 0.10 mmol, CAS: 169869-90-3) in 2 mL DMF was added (S)-3-hydroxybutanoic acid (15.6 mg, 0.15 mmol), HATU (57.9 mg, 0.15 mmol) and followed with Et$_3$N (20.5 mg, 0.20 mmol) dropwise at 0° C., the mixture was stirred at 0° C. to room temperature for 2 h. The mixture was poured into 10 mL ice-water, extracted with ethyl acetate (20 mL×3), washed with brine (20 mL×2), dried over Na$_2$SO$_4$ and concentrated. The residue was purified by prep-HPLC to give (S)—N-((1S,9S)-9-ethyl-5-fluoro-9-hydroxy-4-methyl-10,13-dioxo-2,3,9,10,13,15-hexahydro-1H,12H-benzo[de]pyrano[3,4':6,7]indolizino[1,2-b]quinolin-1-yl)-3-hydroxybutanamide (9.4 mg) as a yellow solid.

The compounds prepared in the table IV below was reacted and post-treated in the same manner as in Example C589.

TABLE IV

| Number | Structure | $^1$HNMR | MS (M + H) | Retention time on HPLC (min) |
|---|---|---|---|---|
| C589 | 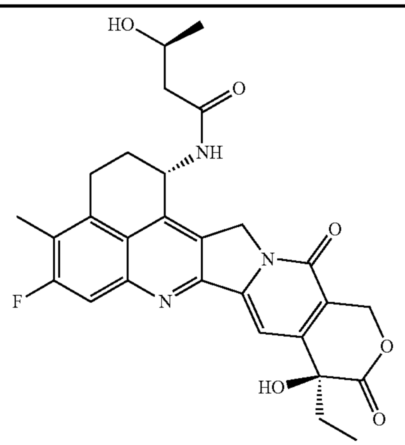 | $^1$H NMR (400 MHz, DMSO-d$_6$) δ 8.44 (d, J = 8.8 Hz, 1H), 7.80 (d, J = 11.0 Hz, 1H), 7.31 (s, 1H), 6.53 (s, 1H), 5.71-5.51 (m, 1H), 5.43 (s, 2H), 5.31-5.11 (m, 2H), 4.67 (s, 1H), 4.05 (dd, J = 12.5, 6.3 Hz, 1H), 3.23-3.09 (m, 2H), 2.41 (s, 3H), 2.36-2.26 (m, 1H), 2.26-2.18 (m, 1H), 2.20-2.08 (m, 2H), 1.96-1.77 (m, 2H), 1.09 (d, J = 6.2 Hz, 3H), 0.88 (t, J = 7.3 Hz, 3H). | 522.1 | 1.643 |
| C588 | 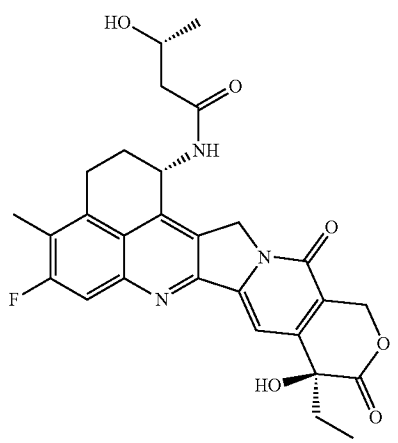 [SMILES: CC[C@@]1(O)C(=O)OCc2c1cc1n(c2=O)Cc2c-1nc1cc(F)c(C)c3c1c2[C@@H](NC(=O)C[C@@H](C)O)CC3] | $^1$H NMR (400 MHz, DMSO-d$_6$) δ 8.43 (d, J = 8.7 Hz, 1H), 7.80 (d, J = 11.0 Hz, 1H), 7.31 (s, 1H), 6.53 (s, 1H), 5.83-5.49 (m, 1H), 5.43 (s, 2H), 5.32-5.12 (m, 2H), 4.64 (s, 1H), 4.05 (dd, J = 12.6, 6.1 Hz, 1H), 3.18 (t, J = 6.2 Hz, 2H), 2.41 (s, 3H), 2.33-2.24 (m, 1H), 2.23-2.05 (m, 3H), 1.96-1.75 (m, 2H), 1.09 (d, J = 6.2 Hz, 3H), 0.88 (t, J = 7.3 Hz, 3H). | 522.1 | 1.629 |
| C504 | 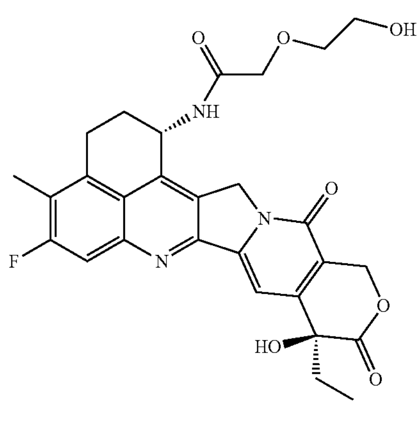 [SMILES: CC[C@@]1(O)C(=O)OCc2c1cc1n(c2=O)Cc2c-1nc1cc(F)c(C)c3c1c2[C@@H](NC(=O)COCCO)CC3] | $^1$H NMR (400 MHz, DMSO-d$_6$) δ 8.51 (d, J = 8.9 Hz, 1H), 7.79 (d, J = 10.9 Hz, 1H), 7.31 (s, 1H), 6.52 (s, 1H), 5.68-5.58 (m, 1H), 5.43 (s, 2H), 5.27-5.15 (m, 2H), 4.05 (s, 2H), 3.64-3.52 (m, 2H), 3.49-3.47 (m, 2H), 3.28-3.10 (m, 2H), 2.40 (s, 3H), 2.22-2.11 (m, 2H), 1.94-1.80 (m, 2H), 0.88 (t, J = 7.3 Hz, 3H). | 538.5 | 1.429 |

TABLE IV-continued

| Number | Structure | ¹HNMR | MS (M + H) | Retention time on HPLC (min) |
|---|---|---|---|---|
| C562 | 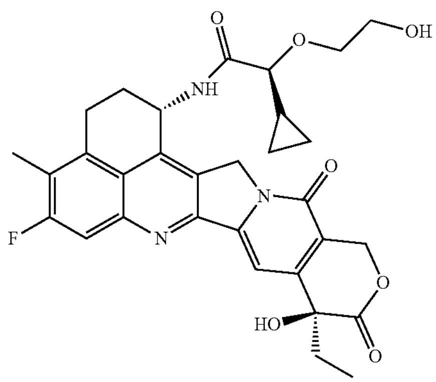 [SMILES: CC[C@@]1(O)C(=O)OCc2c1cc1n(c2=O)Cc2c-1nc1cc(F)c(C)c3c1c2[C@@H](NC(=O)[C@@H](OCCO)C1CC1)CC3] | ¹H NMR (400 MHz, DMSO-d₆) δ 8.49 (d, J = 9.0 Hz, 1H), 7.79 (d, J = 10.9 Hz, 1H), 7.31 (s, 1H), 6.52 (s, 1H), 5.82-5.54 (m, 1H), 5.42 (s, 2H), 5.31-5.09 (m, 2H), 4.67 (s, 1H), 3.59-3.45 (m, 2H), 3.43-3.33 (m, 2H), 3.25-3.09 (m, 2H), 2.40 (s, 3H), 2.23-2.07 (m, 2H), 2.03-1.62 (m, 2H), 1.39-1.07 (m, 1H), 0.88 (t, J = 7.3 Hz, 3H), 0.72-0.31 (m, 4H). | 578.2 | 1.581 |
| C563 | 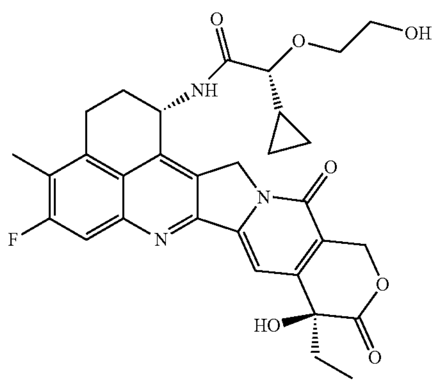 [SMILES: CC[C@@]1(O)C(=O)OCc2c1cc1n(c2=O)Cc2c-1nc1cc(F)c(C)c3c1c2[C@@H](NC(=O)[C@H](OCCO)C1CC1)CC3] | ¹H NMR (400 MHz, DMSO-d₆) δ 8.50 (d, J = 8.5 Hz, 1H), 7.80 (d, J = 10.9 Hz, 1H), 7.32 (s, 1H), 6.52 (s, 1H), 5.56 (d, J = 6.7 Hz, 1H), 5.43 (s, 2H), 5.35-5.12 (m, 2H), 4.55 (s, 1H), 3.56-3.42 (m, 2H), 3.42-3.35 (m, 2H), 3.24-3.11 (m, 2H), 2.40 (s, 3H), 2.27-2.08 (m, 2H), 1.98-1.82 (m, 2H), 1.20-1.05 (m, 1H), 0.89 (t, J = 7.3 Hz, 3H), 0.58-0.46 (m, 2H), 0.47-0.35 (m, 2H). | 578.2 | 1.628 |
| C565 | 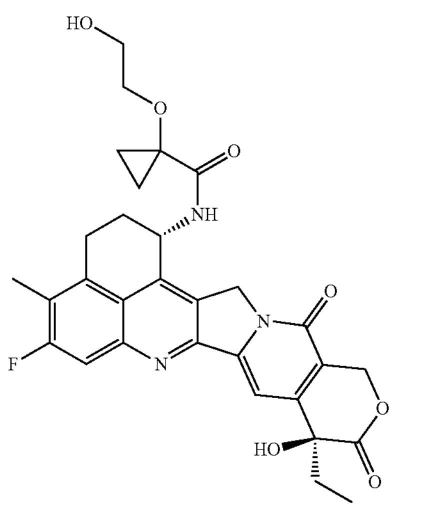 [SMILES: CC[C@@]1(O)C(=O)OCc2c1cc1n(c2=O)Cc2c-1nc1cc(F)c(C)c3c1c2[C@@H](NC(=O)C1(OCCO)CC1)CC3] | ¹H NMR (400 MHz, DMSO-d₆) δ 8.82 (d, J = 8.8 Hz, 1H), 7.78 (d, J = 10.9 Hz, 1H), 7.31 (s, 1H), 6.52 (s, 1H), 5.67-5.52 (m, 1H), 5.43 (s, 2H), 5.28-5.10 (m, 2H), 4.95 (s, 1H), 3.59-3.48 (m, 2H), 3.50-3.41 (m, 2H), 3.29-3.03 (m, 2H), 2.40 (s, 3H), 2.28-2.17 (m, 2H), 2.02-1.73 (m, 2H), 1.30-1.19 (m, 2H), 1.19-1.02 (m, 2H), 0.88 (t, J = 7.3 Hz, 3H). | 564.1 | 1.624 |

TABLE IV-continued

| Number | Structure | ¹HNMR | MS (M + H) | Retention time on HPLC (min) |
|---|---|---|---|---|
| C687 | 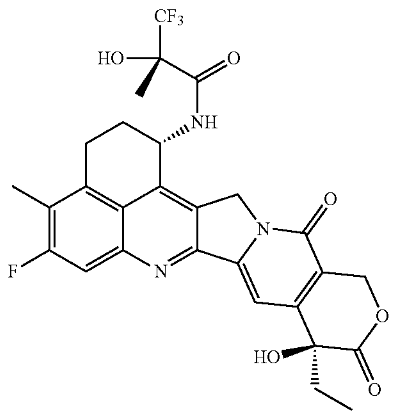 [SMILES: CC[C@@]1(O)C(=O)OCc2c1cc1n(c2=O)Cc2c-1nc1cc(F)c(C)c3c1c2[C@@H](NC(=O)[C@](C)(O)C(F)(F)F)CC3] | ¹H NMR (400 MHz, DMSO-d$_6$) δ 8.85 (d, J = 8.7 Hz, 1H), 7.78 (d, J = 10.9 Hz, 1H), 7.30 (s, 1H), 5.66-5.49 (m, 1H), 5.41 (s, 2H), 5.31-4.91 (m, 2H), 3.23-3.06 (m, 2H), 2.39 (s, 3H), 2.26-2.07 (m, 2H), 1.95-1.75 (m, 2H), 1.54 (s, 3H), 0.87 (t, J = 7.3 Hz, 3H). | 576.1 | 1.719 |
| C688 | 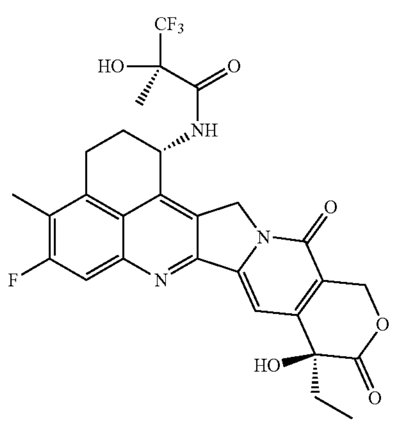 [SMILES: CC[C@@]1(O)C(=O)OCc2c1cc1n(c2=O)Cc2c-1nc1cc(F)c(C)c3c1c2[C@@H](NC(=O)[C@@](C)(O)C(F)(F)F)CC3] | ¹H NMR (400 MHz, DMSO-d$_6$) δ 8.95 (d, J = 9.1 Hz, 1H), 7.77 (d, J = 10.9 Hz, 1H), 7.31 (s, 1H), 6.52 (s, 1H), 5.68-5.51 (m, 1H), 5.42 (s, 2H), 5.29-4.93 (m, 2H), 3.28-3.06 (m, 2H), 2.38 (s, 3H), 2.24-2.08 (m, 2H), 1.97-1.79 (m, 2H), 1.71 (s, 3H), 0.87 (t, J = 7.3 Hz, 3H). | 576.1 | 1.806 |

Conditions of HPLC above: Equipment: Agilent 1200; Chromatographic column: Waters XBridge C18 4.6*50 mm, 3.5 um; Flow: 2.0 mL/min; Gradient elute: 5.0%-95.0%-95.0%-5.0%-5.0%, 0.00 min-1.50 min-2.50 min-2.52 min-3.00 min; Temperature: 40° C.; Phase: A: Acetonitrile, B: H2O (0.05% TFA); Wavelength: 214 nm/254 nm.

Example 2 Preparation of Linkers 2.1 Preparation of Linker HX20113

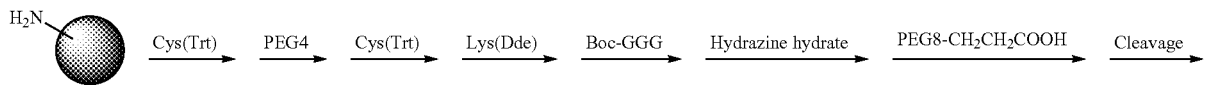

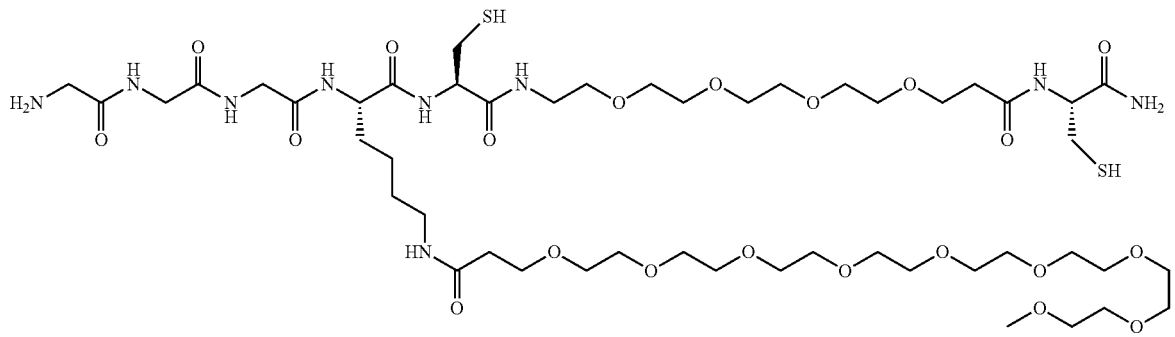

HX20113

HX20113 synthesized by a conventional solid phase polypeptide synthesis using Rink-amide-MBHA-resin. Fmoc was used to protect the amino acid in the linking unit. The conjugation reagent was selected from HOBT, HOAt/DIC, DCC, EDCI or HATU. After synthesis, the resin was cleaved using trifluoroacetic acid. The product was purified by HPLC, lyophilized and stored for use. Theoretical Mass: 1207.59, measured: $[M-H]^-=1206.7$.

Preparation of Linker HX20111

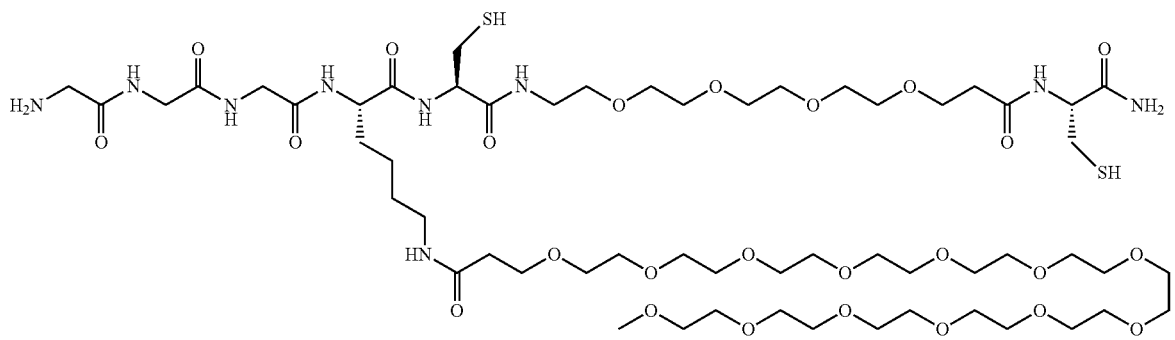

HX20111

HX20111 synthesized by a conventional solid phase polypeptide synthesis using Rink-amide-MBHA-resin. Fmoc was used to protect the amino acid in the linking unit. The conjugation reagent was selected from HOBT, HOAt/DIC, DCC, EDCI or HATU. After synthesis, the resin was cleaved using trifluoroacetic acid. The product was purified by HPLC, lyophilized and stored for use. Theoretical Mass: 1383.70, measured: $[M-H]^- = 1382.6$.

Example 3 Preparation of Linker-Payload Intermediates 3.1 Preparation of Intermediate Mc-GGFG-Dxd The intermediate Mc-GGFG-Dxd is commercial available or prepared following the procedures as described in EP2907824. This compound is used to prepare the Linker-Payload intermediate (formula (I) compound), and is also used to directly connect to the (optionally modified) antibody to prepare reference ADCs LC1184(8) and LC1184(4).

3.2 Preparation of H0019

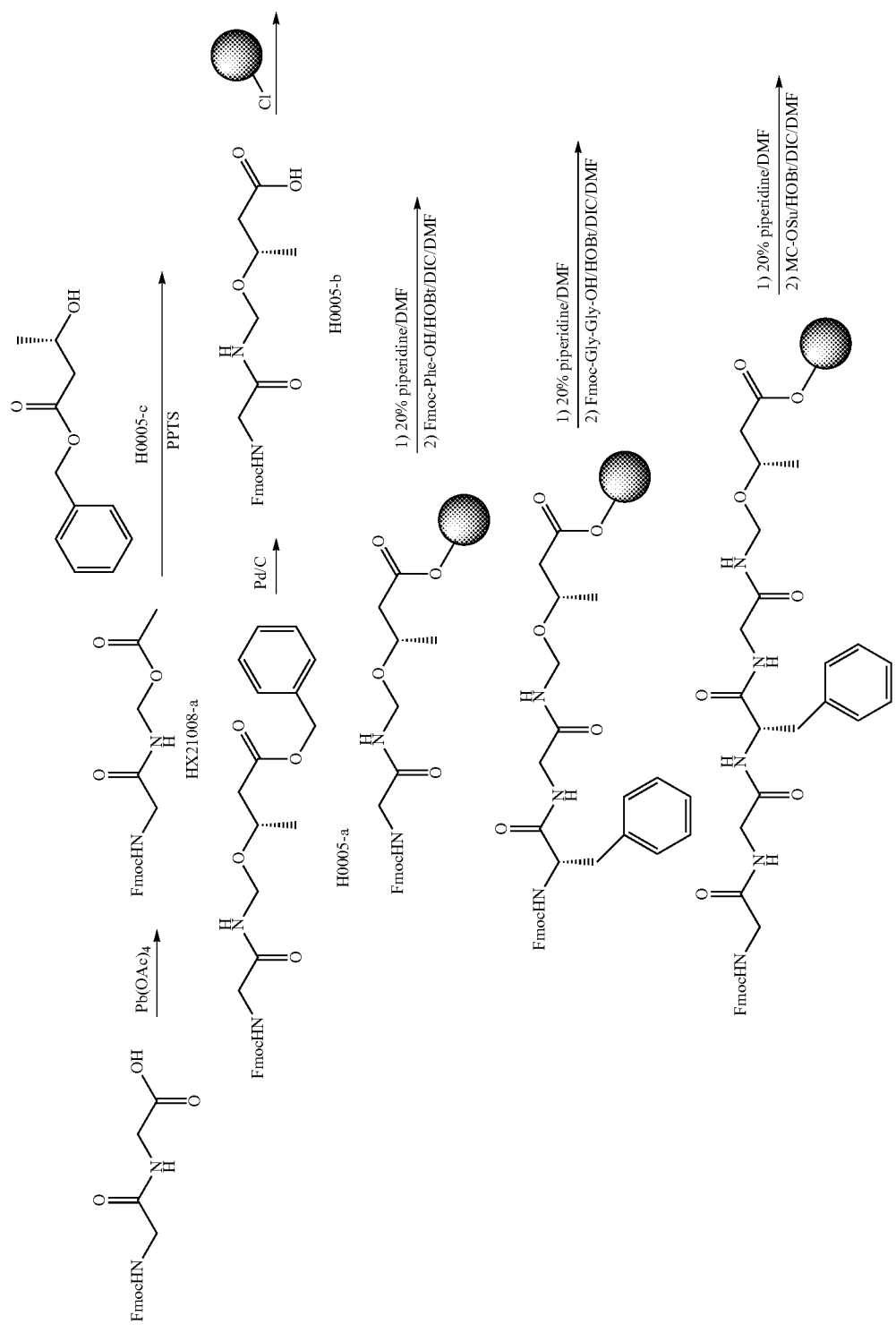

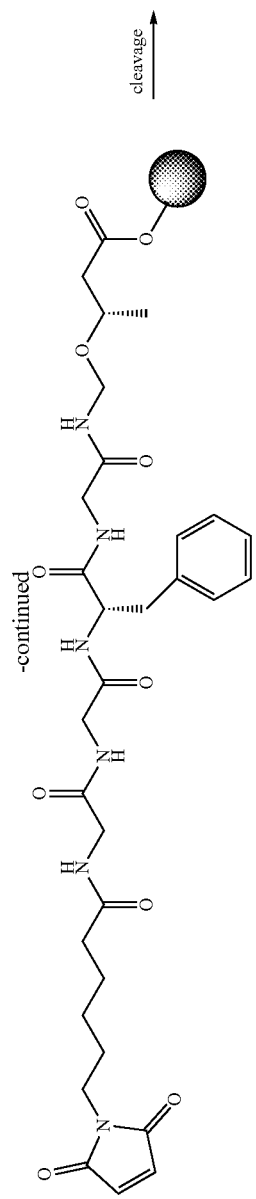
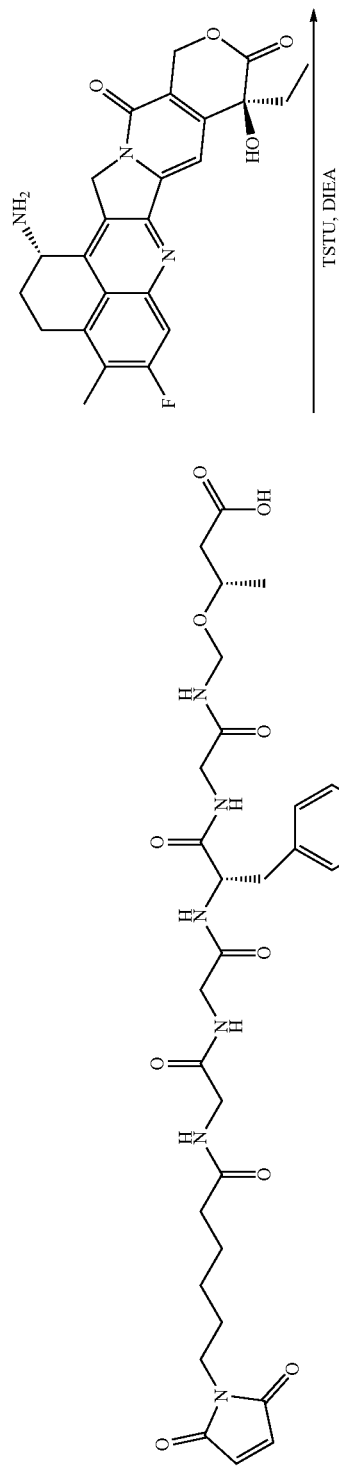

-continued
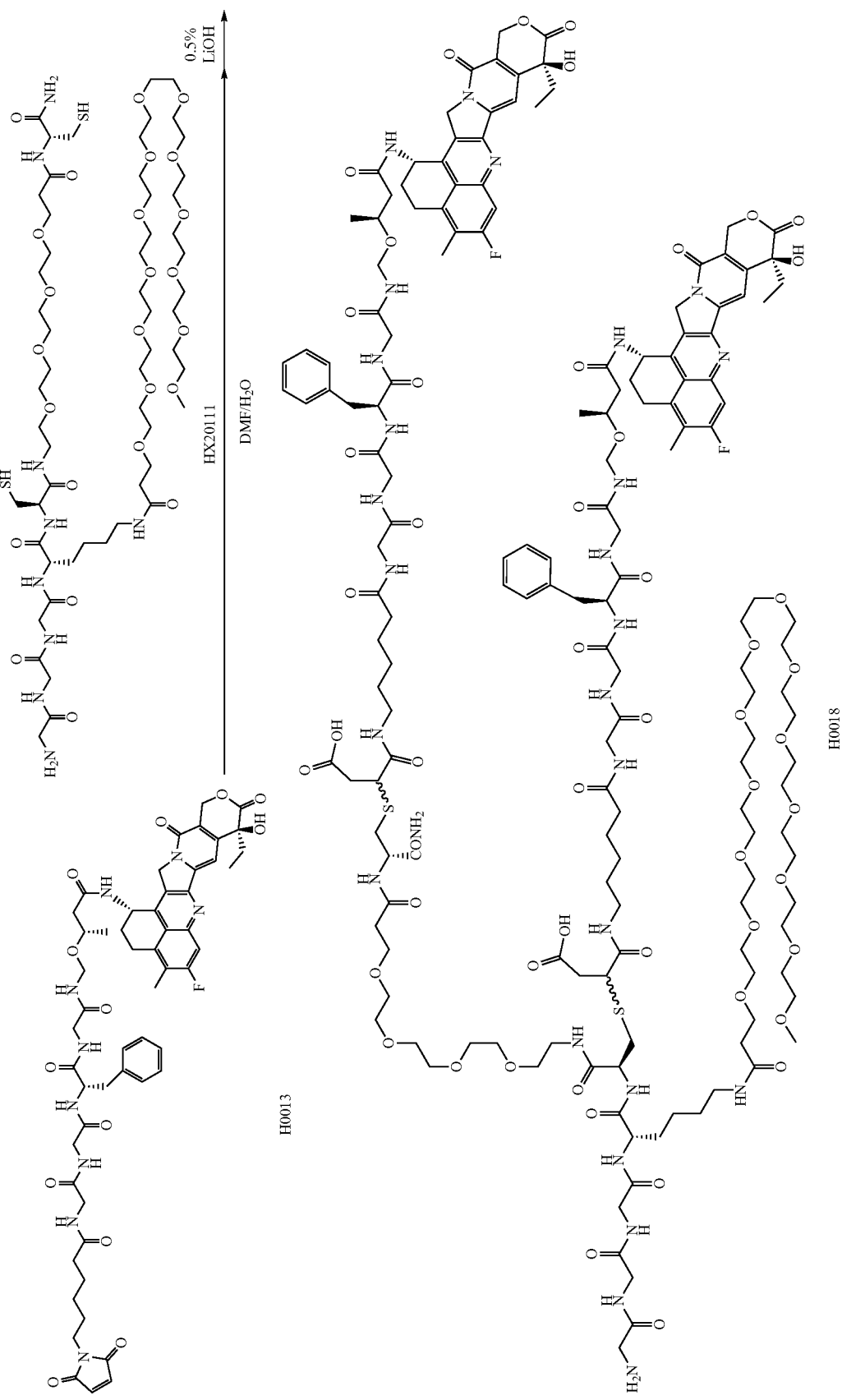

Synthesis of HX21008-a 4.33 g Fmoc-Gly-Gly-OH and 6.84 g Pb(OAc)$_4$ were weighed and added into a 500 ml single-neck round bottom flask. Anhydrous THF/Toluene (120/40 ml) was added under nitrogen atmosphere and stirred for dissolving. Then 1.16 mL of pyridine was added to the reaction system. The reaction system was heated to 80° C. and refluxed for 5 hr under nitrogen atmosphere. Samples were taken and detected by HPLC to monitor the reaction.

The reaction system was cooled to room temperature, filtered, and the filter cake was washed with EA for 3 times. The filtrates were combined and concentrated to dryness. Column chromatography was performed (PE:EA=100:0-50:100) to give about 2000 mg of the target product in white solid with a yield of 44%.

Synthesis of H0005-a 200 mg HX21008-a was weighed and added into a 100 ml single-neck round bottom flask. Then 15 ml THF was added and stirred for dissolving. Then H0005 (316 mg, 3.0 eq) and TsOH·H$_2$O (15 mg, 0.15 eq) were added to the reaction system. The reaction system was reacted overnight at room temperature. Samples were taken and detected by TLC (PE/EA=1:1) to monitor the reaction. The raw material basically disappeared, and a new point was detected.

Saturated sodium bicarbonate solution was added to quench reaction. Extraction was conducted with EA for 3 times. The organic phase was combined and washed with saline, dried with anhydrous magnesium sulfate and concentrated. The crude product was purified by column chromatography (PE:EA=5:1~1:1) to give about 165 mg of the target product in colorless oil with a yield of 60%. MS: [M+H]$^+$=503.4.

Synthesis of H0005-b 200 mg of H0005-a was weighed and added into a 100 ml single-neck round bottom flask. Then 10 ml of EtOH and 5 ml of EA were added with complete dissolution. Then 40 mg of palladium carbon was added to the reaction system under nitrogen atmosphere, and the reaction system was purged with hydrogen gas for three times. The reaction system was kept under hydrogen atmosphere and stirred for 0.5 hr at room temperature. Samples were taken and detected by TLC (DCM/MeOH=10:1) to monitor the reaction. The raw material basically disappeared, and a new point was detected.

The reaction system was filtered, and the filter cake was washed with EA for 3 times. The filtrates were combined and concentrated to dryness to give 200 mg product in white solid with 100% yield. The product can be directly used in the next reaction without purification. [M+H]$^+$=413.3.

Synthesis of H0005

2.0 g of dichlororesin was weighed and placed in a polypeptide synthesis tube. DCM (10 ml) was added and swelled at room temperature for 30 minutes. The solvent was removed by vacuum suction. The resin was washed twice with DCM, with a volume of 7 mL and a time length of 1 minute for each wash. The solvent was removed by vacuum suction. Then H0005-b (200 mg) was weighed and added into a 50 ml centrifuge tube. DCM (about 10 ml) was added. the solid was dissolved by shaking. Added to the above resin. Stirring was conducted to soak all the resin in the solution (if there was resin attached to the tube wall, a small amount of DCM was used to wash the tube wall). Stirring was conducted for 4-5 hours. After the reaction was complete, an appropriate amount of methanol was added. Stirring was conducted for 30 min. The solvent was removed by vacuum suction. The resin was washed with DMF once, methanol once, DMF once, methanol once and DMF twice in sequence, with a volume of 10 mL and a time length of 1 minute for each wash. The solvent was removed by vacuum suction. A small amount of dry resin was taken for ninhydrin detection. The resin was colorless and transparent, and the solution was yellowish, indicating qualified for the next coupling step.

The deprotection was conducted twice by adding 10 mL readymade 20% piperidine/DMF solution and reacting for 10 minutes for each time. After the reaction was complete, the solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. Both the resin and solution were dark blue.

To a 50 mL centrifuge tube was added 563 mg Fmoc-Phe-OH, 197 mg HOBt. Then about 7 mL DMF was added. The solid was dissolved by shaking. Then 0.24 mL DIC was added. Activated for 10-30 minutes to give the activated reaction solution.

3 molar equivalent of activated reaction solution added to the resin. Stirring was conducted to soak the resin completely in the solution (if there was resin attached to the tube wall, a small amount of DCM was used to wash the tube wall). Stirring was conducted for 2-3 hours. After the reaction was complete, the solvent was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. The resin was colorless and transparent, and the solution was yellowish, indicating qualified for the next coupling step.

The deprotection was conducted twice by adding 10 mL readymade 20% piperidine/DMF solution and reacting for 10 minutes for each time. After the reaction was complete, the solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. Both the resin and solution were dark blue.

To a 50 mL centrifuge tube was added 531 mg Fmoc-GG-OH, 197 mg HOBt. Then about 10 mL DMF was added. The solid was dissolved by shaking. Then 0.24 mL DIC was added. Activated for 10-30 minutes to give the activated reaction solution.

3 molar equivalent of activated reaction solution was added to the resin. Stirring was conducted to soak the resin completely in the solution (if there was resin attached to the tube wall, a small amount of DCM was used to wash the tube wall). Stirring was conducted for 2-3 hours. After the reaction was complete, the reaction solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. The resin was colorless and transparent, and the solution was yellowish, indicating qualified for the next coupling step.

The deprotection was conducted twice by adding 10 mL readymade 20% piperidine/DMF solution and reacting for 10 minutes for each time. After the reaction was complete, the solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. Both the resin and solution were dark blue. Then, 462 mg MC-OSu was placed in a 50 mL centrifuge tube, about 10 mL DMF was added. The solid was dissolved by shaking. Then 0.24 mL DIEA was added to the resin. Stirring was conducted to soak the resin completely in the solution (if there was resin attached to the tube wall, a small amount of DCM was used to wash the tube wall). Stirring was conducted for 2-3 hours. After the reaction was complete, the reaction solution was removed by vacuum suction. The resin was washed with DMF twice, methanol once, DMF once, methanol once and DMF twice in sequence, with a volume of 10 mL and a time length of 1 minute for each wash. The solvent was removed by vacuum suction. A small amount of dry resin was taken for ninhydrin detection. The resin was colorless and transparent, and the solution was yellowish, indicating qualified for the next coupling step.

The resin was washed twice with 10 mL of methanol. Then the solvent was removed thoroughly by vacuum suction. The resin was poured out and weighed. The lysis buffer was prepared in a 250 mL conical flask, wherein: the ratio of TFE/DCM was 80%/20%, and the volume was 7-8 times of the weight of peptide resin. The lysis buffer was added into the peptide resin, shaken well. The resin was fully soaked in the lysis buffer, and lysis was carried out at room temperature for 2-3 hours. The lysis buffer was then filtered out using a simple filter made of a syringe, and the resin was washed with 1-2 ml DCM and discarded. Then 150 mL precooled anhydrous ether was added to the lysis buffer, shaken well and then stood for 20-30 minutes. Using a 50 mL centrifuge tube, the above system was centrifuged in a centrifuge at 3500 rpm for 3 minutes, and the supernatant was poured out and discarded. The solid was shaken with precooled anhydrous ether, washed once under ultrasound, centrifuged at 3500 rpm for 3 minutes, and the supernatant was poured out and discarded. The solid was placed in a centrifuge tube and allowed to air dry overnight, and then subjected to preparative purification to give 125 mg of product in white solid with a yield of 40%. $[M+H]^+=645.4$.

Synthesis of H0013

150 mg of raw material H0005 and 55 mg of TSTU were weighed and added into a 10 mL single-neck round bottom flask, and anhydrous DMF (3 mL) was added under nitrogen atmosphere and stirred for 20 min. Then 18 mg TSN00643 and 20 μl DIEA were added in sequence to the reaction system. Stirring was conducted at room temperature for 2 hr under nitrogen atmosphere. Samples were taken and detected by HPLC to monitor the reaction. The raw material peak completely disappeared, and new peaks were detected.

The reaction system was subjected to preparative purification, and the target product was collected and lyophilized to give about 22 mg of product in yellowish solid. $[M+H]^+=1062.7$.

Synthesis of H0019

H0013 (30 mg) was weighed and added into a 10 ml single-neck round bottom flask, purified water (2 ml) was added. Stirring was conducted for dissolving. DMF solution (2 ml) containing HX20111 (19.5 mg) was added to the reaction system and stirred. After reacting overnight, HPLC was used to monitor the reaction until all of the raw material had converted into intermediates. Then the reaction system was cooled to 0~10° C., and 0.5% LiOH solution was added to the reaction system under controlled temperature until the pH of the reaction system was about 12. The reaction was stirred for 20 min, and the reaction was monitored by HPLC until all the intermediates were consumed and then 30% acetic acid (1.5 mL) was added to the reaction system to quench the reaction.

The reaction system was subjected to preparative purification, and the target product was collected and lyophilized to give about 25 mg of product in yellowish solid. $[⅓ M+H]^+=1182.3$.

3.3 H0020, H0021, H0034 and H0035

The following linker-payload intermediates H0020, H0021, H0034 and H0035 can be prepared using similar synthetic routes and reagents. The intermediates H0014, H0015, H0026 and H0032 are synthesized using similar method for H0013, and then used for synthesizing H0020, H0021, H0034 and H0035, respectively.

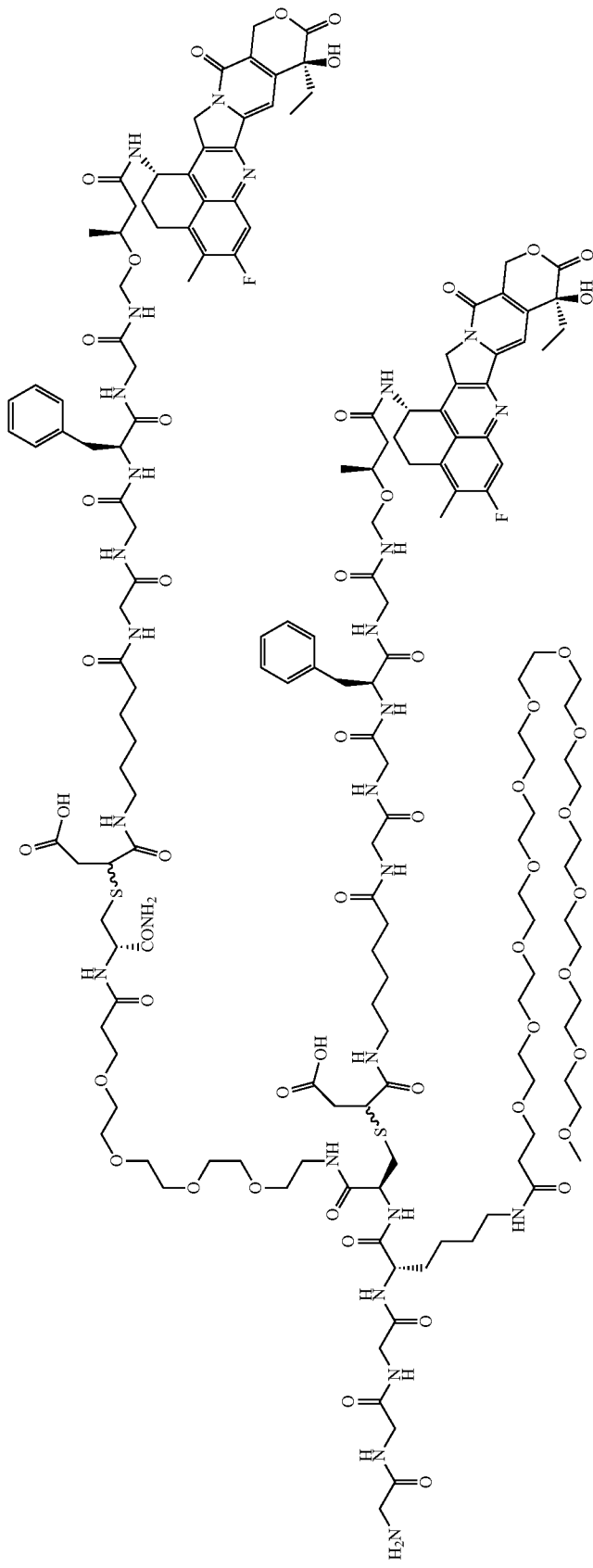

H0020
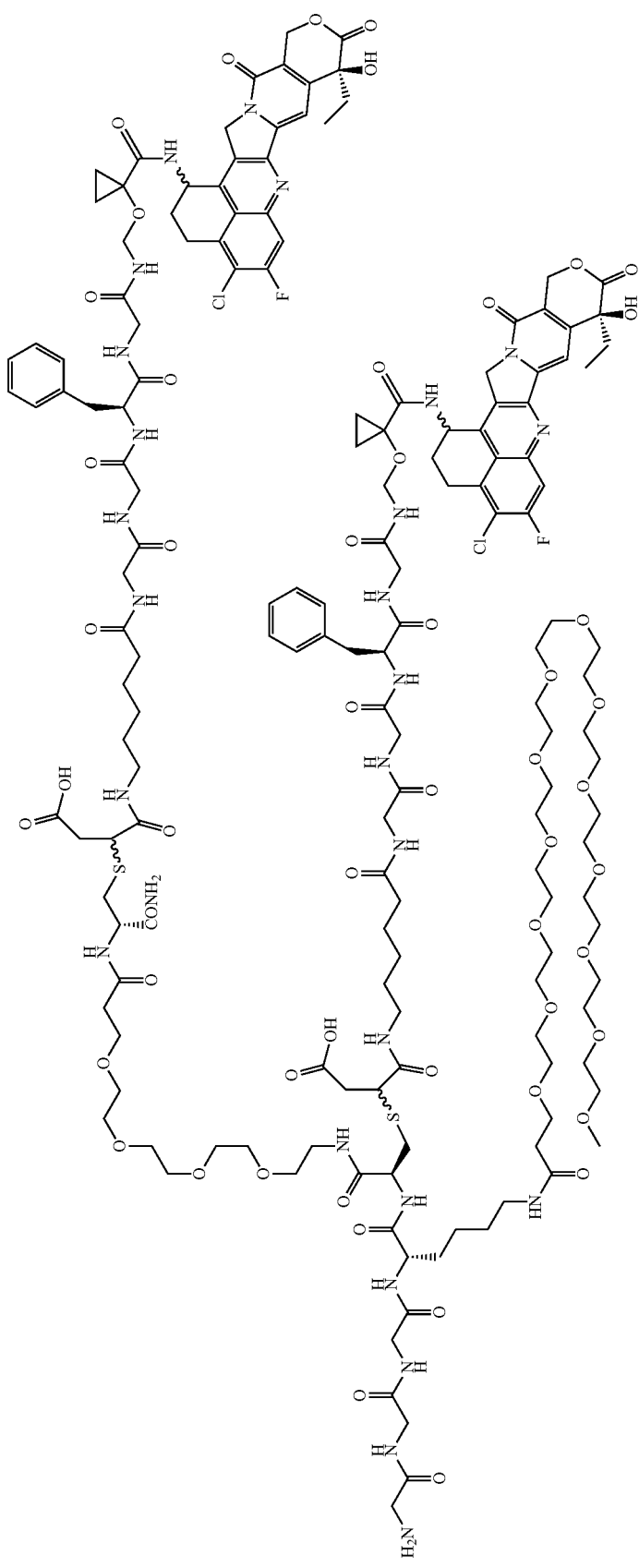

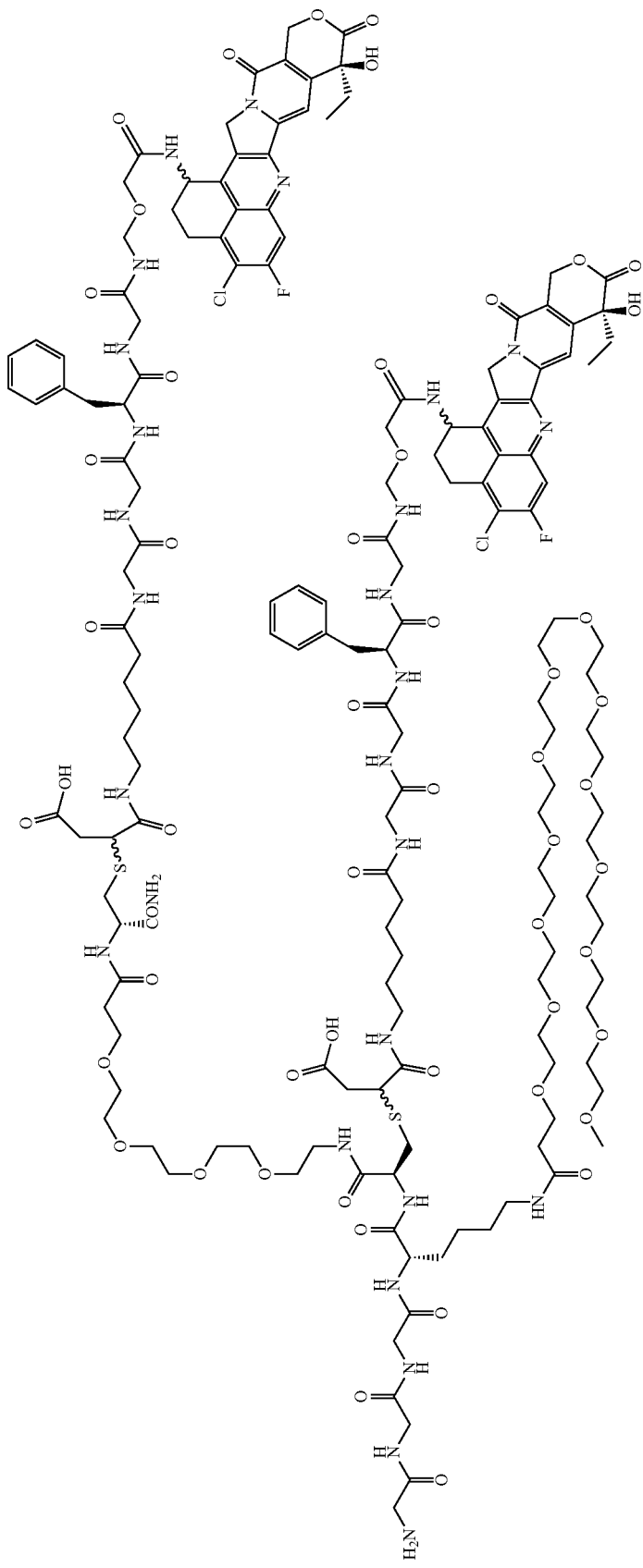

H0034
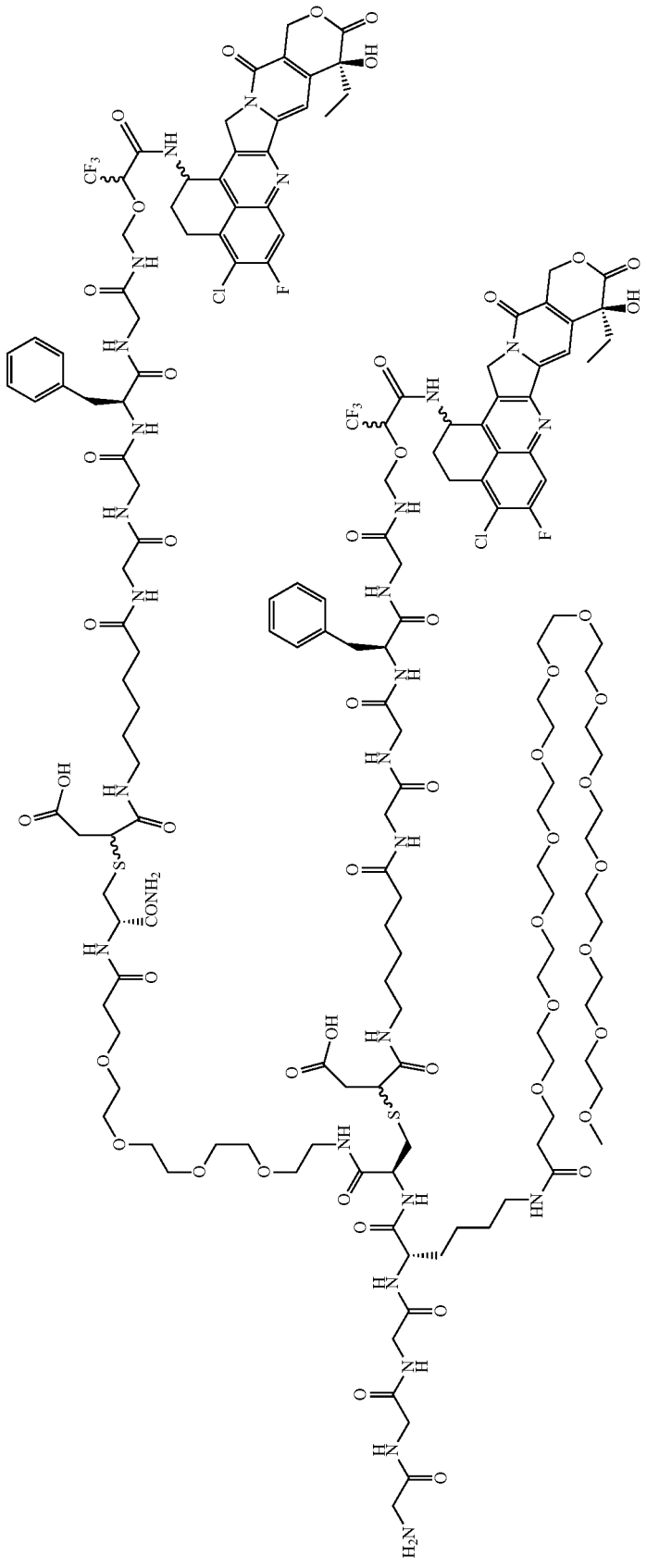

155 156
-continued
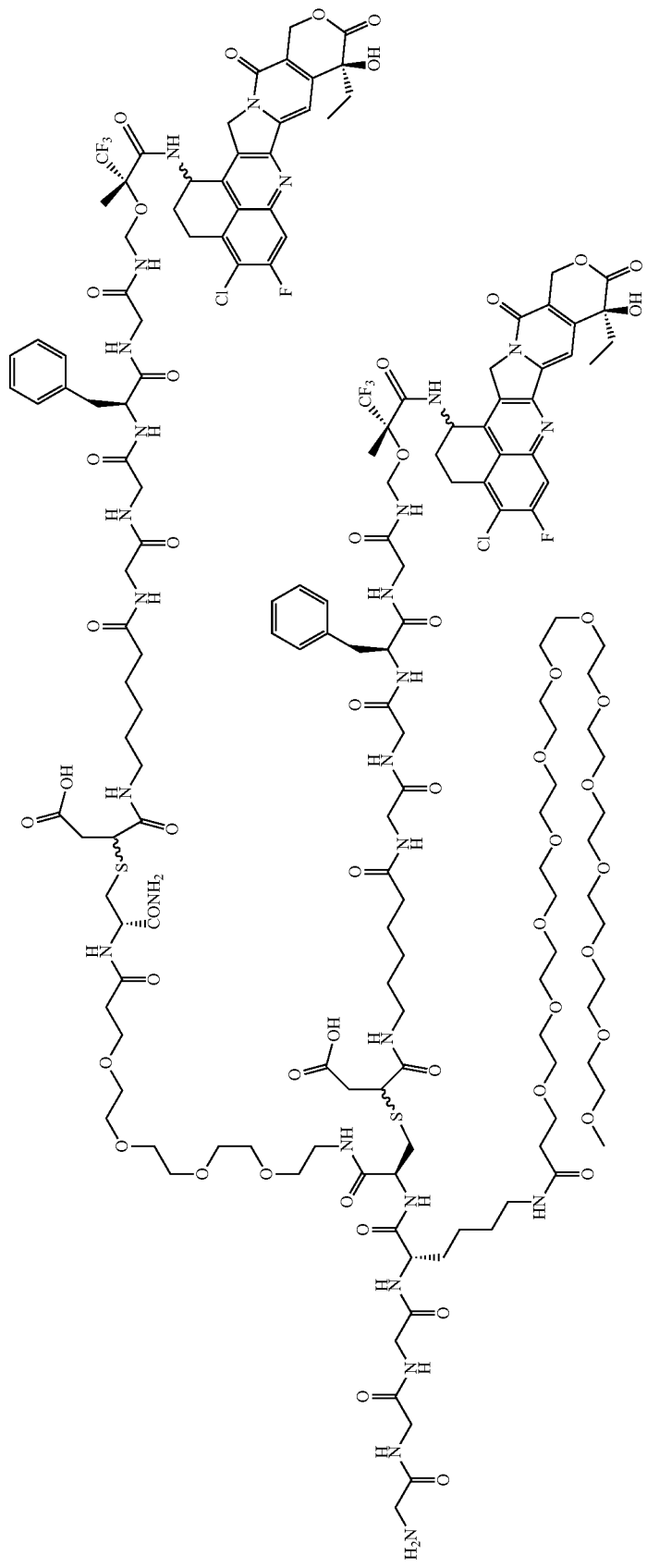
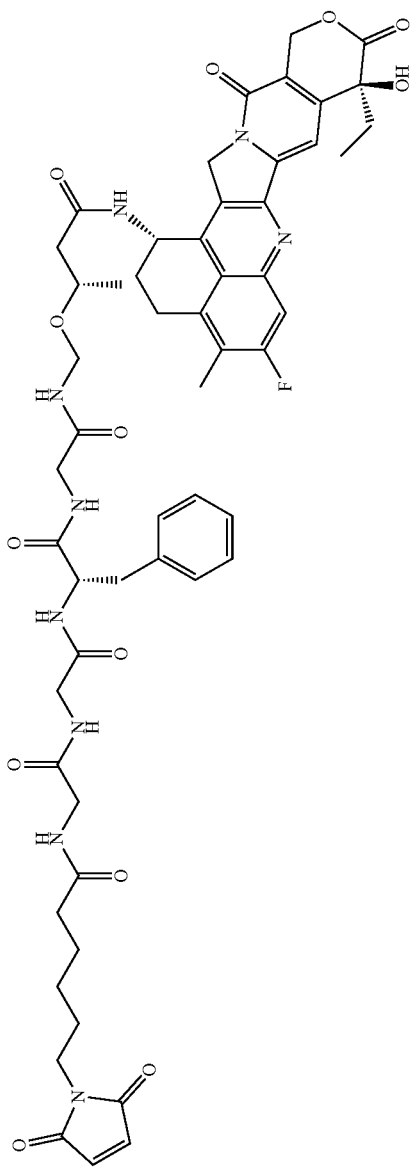

H0014
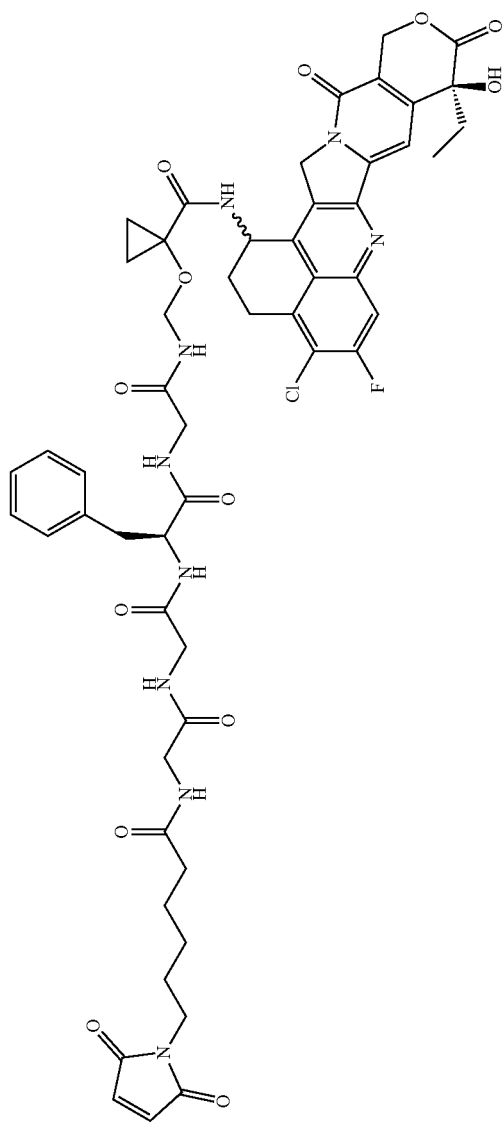
H0015
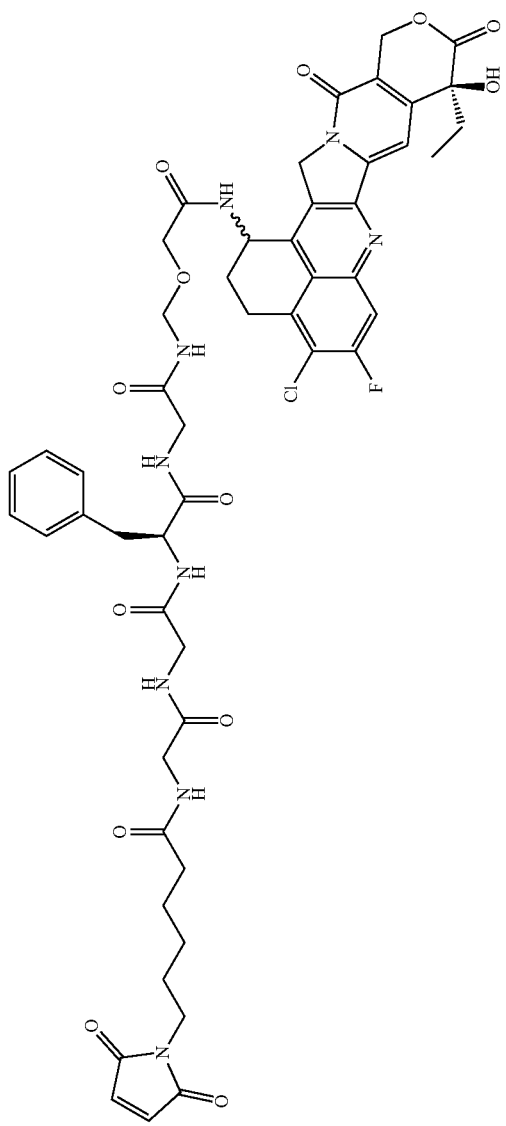

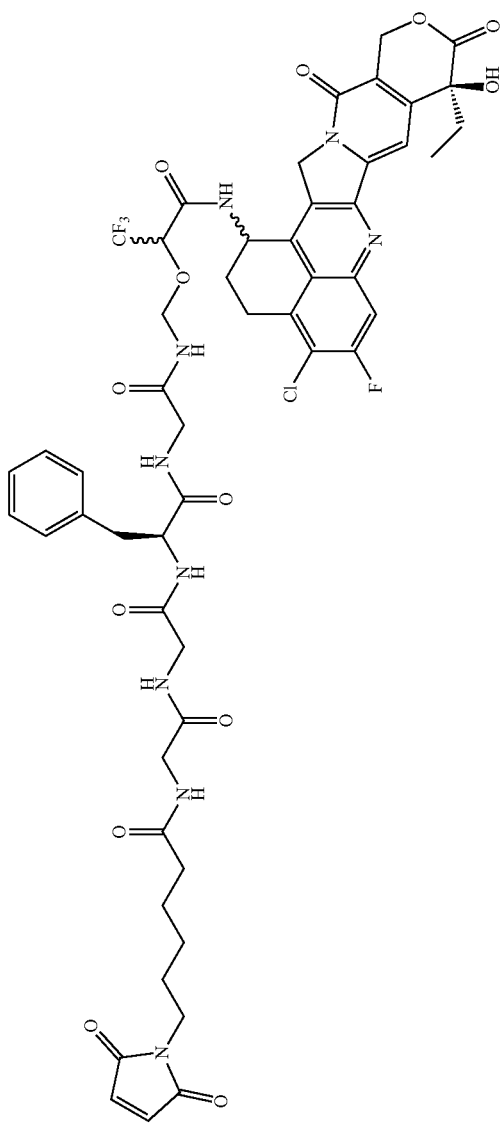

-continued
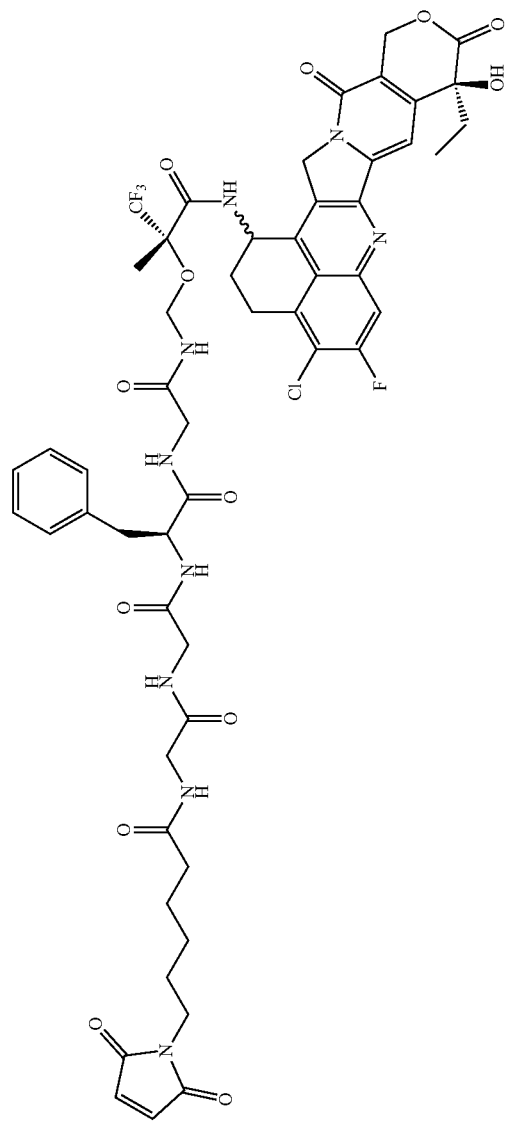
H0032

The LC-Ms data is shown in the following table:

| | MS data |
|---|---|
| H0020 | $[1/3\ M + H]^+ = 1193.9$ |
| H0021 | $[1/3\ M + H]^+ = 1177.9$ |

3.4 Preparation of LB302-2-4

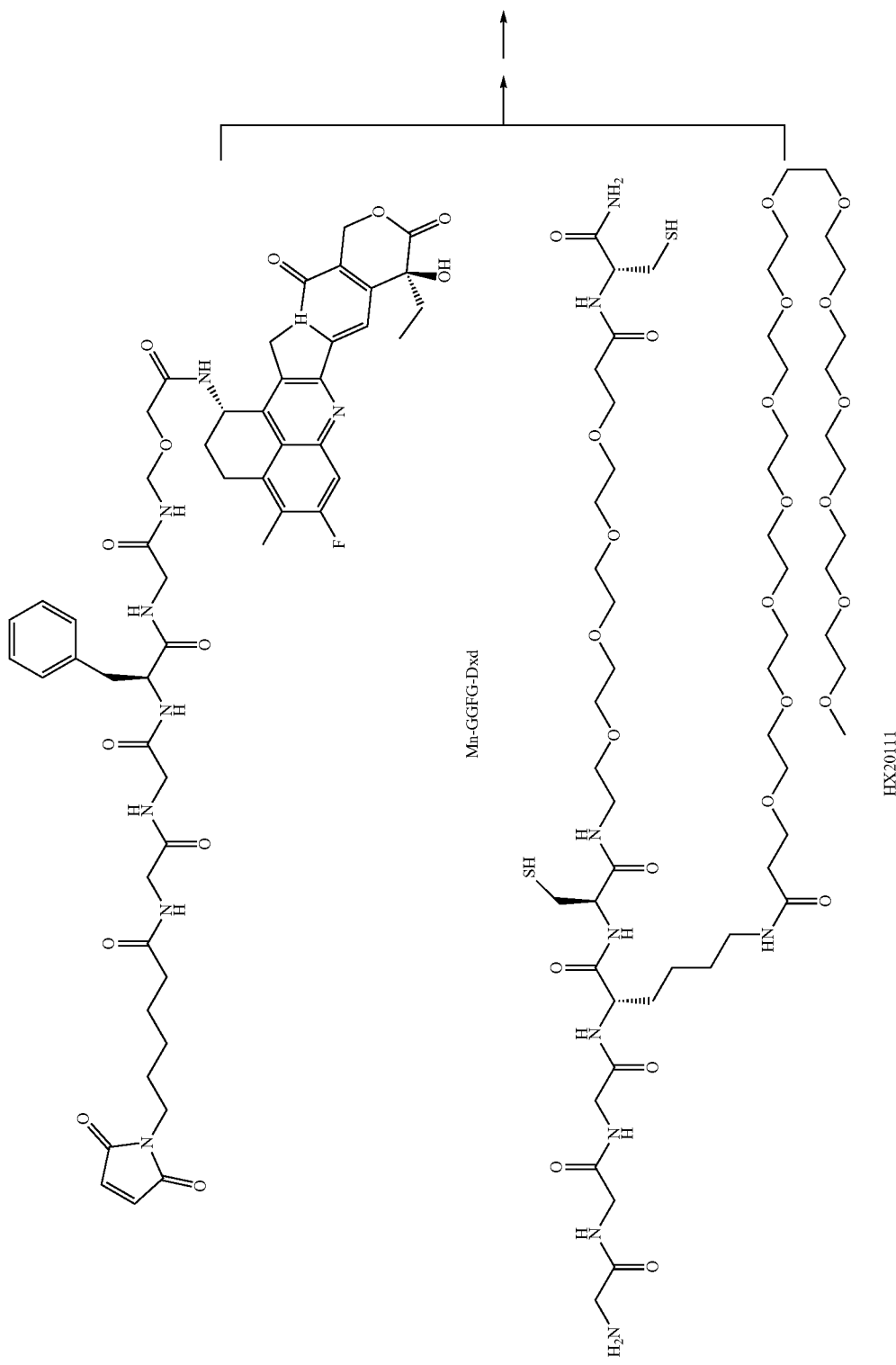

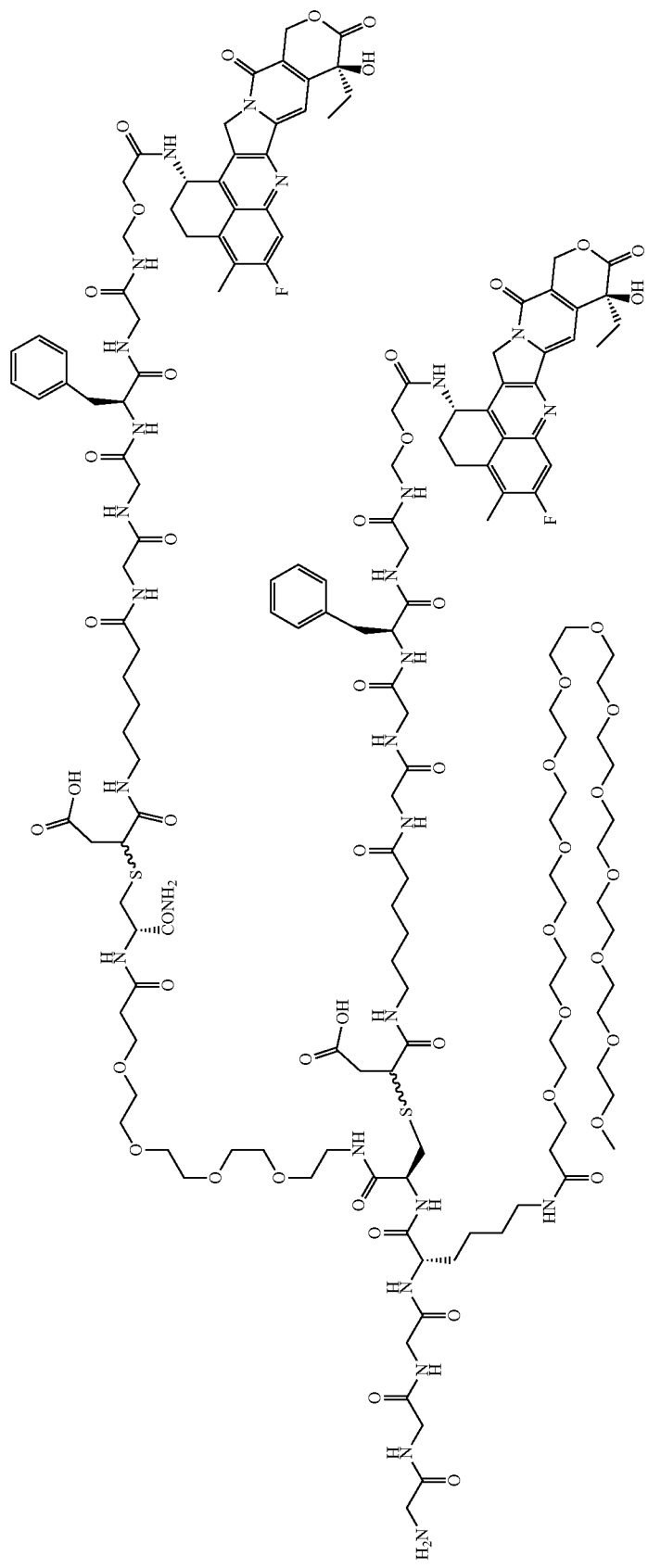

HX20111 and intermediate MC-GGFG-Dxd (molar ratio ~1:2) were weighed and dissolved in water and DMF, respectively, and then thoroughly mixed to give a mixture, which was reacted at 0-40° C. for 0.5-30 h. Once the reaction was completed, the reaction mixture was directly added with an appropriate amount of Tris Base solution or other solution that promotes the ring-opening reaction, and the reaction was performed at 0-40° C. for another 0.2-20 h. After the reaction was completed, the product was purified by semi-preparative/preparative HPLC and lyophilized to obtain linker-payload intermediate LB302-2-4. Theoretical Mass: 3486.52, measured: $[(M+3H)/3]^+=1163.3$.

3.5 Preparation of LB302-2-1

LB302-2-1 can be prepared using similar synthetic routes and reagents.

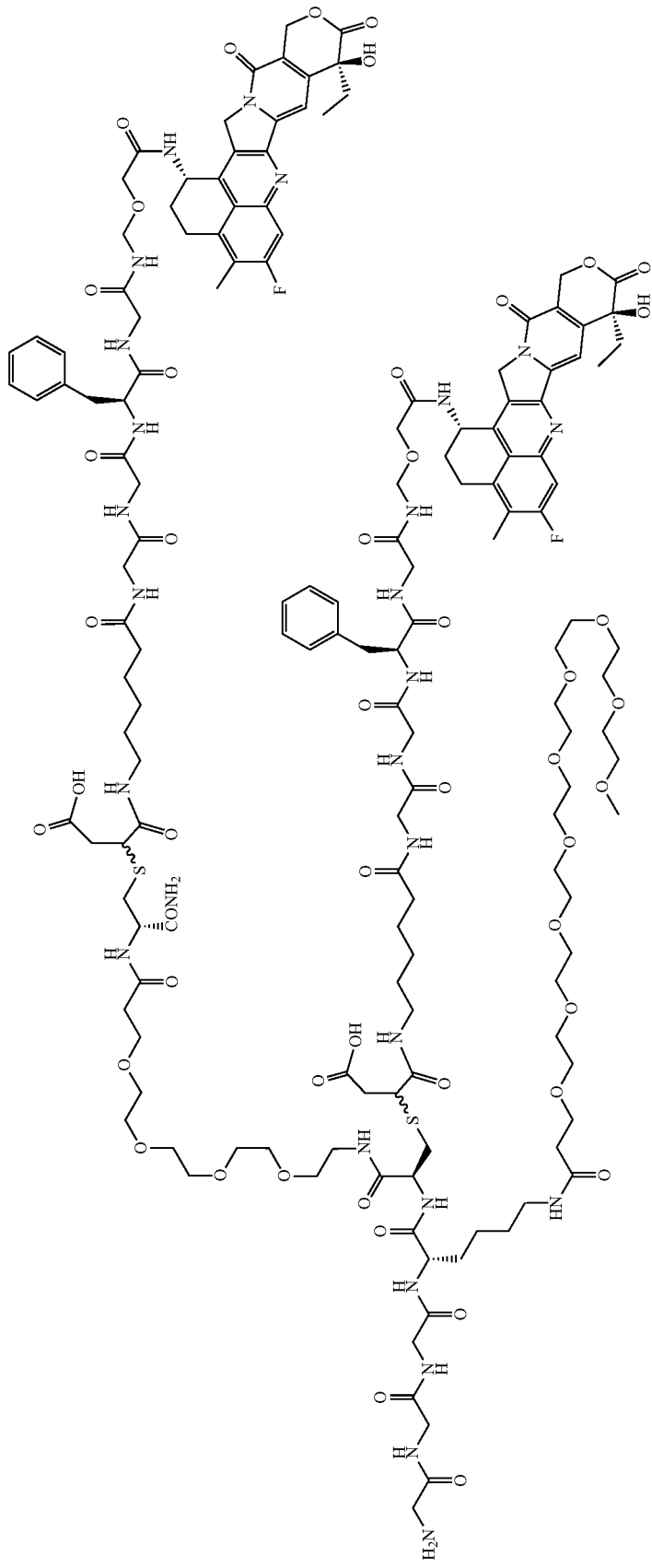

Example 4 Construction of Antibody Expression Vector, Antibody Expression, Purification and Identification 1.1 Production of the Modified Anti-Human HER2 Antibody Ab0001-LCCT$_L$-HC The expression plasmids for antibody Ab0001-LCCT$_L$-HC (light chain SEQ ID NO: 1, heavy chain: SEQ ID NO: 2) were constructed as follows. The sequence of the antibody Ab0001-LCCT$_L$-HC: based on the amino acid sequence of Trastuzumab, and GALPETGG was introduced at the C-terminal of the light chain, wherein LPETGG (SEQ ID NO: 8) is the recognition sequence of the ligase donor substrate, and GA is a spacer sequence. The plasmids were transfected into CHO cells and the cell population was established and screened for a highly expressed cell population, which was cultured with reference to the culture process of Trastuzumab in a 5-10 L reactor, and supernatant was collected.

1.2 The Purification of Antibody Ab0001-LCCT$_L$-HC

The purification of Ab0001-LCCT$_L$-HC was carried out in a standard process using the combination of MabSelect affinity chromatography and Sepharose S cation exchange chromatography, the purified products were dissolved in the original Trastuzumab drug buffer (5 mM histidine-HCl, 2% Trehalose, 0.009% Polysorbate 20, PH 6.0), and frozen in small aliquots.

1.3 The Quality Control of Antibody Ab0001-LCCT$_L$-HC

The purity of the above purified antibody Ab0001-LCCT$_L$-HC is 98.5% by SDS-PAGE; the content of high molecular weight polymer of the sample is less than 0.4% by SEC-HPLC; endotoxin content is less than 0.098 EU/mg.

1.4 Preparation of Other Modified Anti-Human Antibodies

According to a similar method, a terminal modification based on the ligase recognition sequence was introduced at the C-terminal of the light and/or heavy chain of the Trastuzumab, respectively, giving a modified antibody.

The modified anti-human HER2 antibodies based on Ab0001 (Trastuzumab) are listed in the following table. LPETGG in the terminal modification sequence is a recognition sequence of the ligase donor substrate, and GA is a spacer sequence.

| Modified anti-human HER2 antibodies | | |
|---|---|---|
| | Sequence | Sequence introduced at the terminal |
| Ab0001-LCCT$_L$-HC light chain | SEQ ID NO: 1 | GALPETGG |
| Ab0001-LCCT$_L$-HC heavy chain | SEQ ID NO: 2 | -* |

*"-" indicates no terminal modification

Example 5 Preparation of Antibody-Small Molecule Conjugates 3.1 The Linker-payload intermediates were respectively conjugated to an antibody in a site-specific manner by a ligase to form an ADC. The method for conjugation reaction can be found in WO2015165413A1. The resulting ADCs are as listed in the following table:

| Name of ADC | Linker-Payload | Antibody | DAR |
|---|---|---|---|
| CH-2-589 | BH-2-589 | Ab0001-LCCT$_L$-HC | 3.44 |
| CH-2-593 | BH-2-593 | Ab0001-LCCT$_L$-HC | 3.49 |
| CH-2-518 | BH-2-518 | Ab0001-LCCT$_L$-HC | 3.61 |
| LC302-2-1 | LB302-2-1 | Ab0001-LCCT$_L$-HC | 3.42 |
| LC302-2-4(4) | LB302-2-4 | Ab0001-LCCT$_L$-HC | 3.41 |

3.2 The reference ADCs LC1184(8) and LC1184(4) are prepared respectively by directly connecting the intermediate Mc-GGFG-Dxd to Ab0001-LCCT$_L$-HC (Cys conjugation, i.e. conjugation through connections formed by maleimide structure(s) with thiol group(s) of Cys). The method for conjugation reaction is known in the art. LC1184(8) has eight Mc-GGFG-Dxd introduced to the reduced inter-chain cysteines. LC1184(4) has four Mc-GGFG-Dxd introduced to the reduced inter-chain cysteines.

Effect Example 1 Effect of Small Molecules on Cell Proliferation

Study Purpose: In this experiment, cell viability was detected using CellTiter-Glo to evaluate the effects of the small molecule compounds on the proliferation of a high HER2 tumor cell line SK-BR-3, and to analyze the effects of the small molecule compounds on the proliferation of tumor cells.

Materials and Equipment

PBS: Gibco, Cat #10010-023); Trypsin: Gibco, Cat #25200056); FBS: Gibco, Cat #10270-106); CellTiter-Glo® Luminescent Cell Viability Assay: Promega, Cat #G7573); McCoy'5A: Gibco, Cat #16600-082); L15: Hyclone, Cat #SH30525.01); DMEM: Gibco, Cat #11995-065). 96-well plate: Corning/3603; 96-well deep-well Plate: Thermo/278743; 15 ml EP tube: Thermo/339650; 1.5 ml EP tube: Beaver.

Cell plating—Day 1
 (1) Microscopic examination of cells
 (2) Digestion: digested using 2 mL 0.25% trypsin for 3 minutes;
 (3) Centrifuge: 1000 rpm for 5 min;
 (4) Cell counting
 A. Cell dilution:
 B. Cell plating: in 100 µl/well
 C. Incubation: 37° C., 5% $CO_2$, overnight
Cell Test
 (1) Microscopic examination
 (2) Drug preparation:
 A. Preparation of Buffer for preparation of samples: the desired amount of Buffer for preparation of samples was prepared using the culture medium (10% FBS) for the testing cells;
 B. Sample preparation: the sample was diluted from the first concentration to the desired concentration in a 96-well deep-well Plate.

Test compounds: Ten final concentrations are prepared from dilution with the cell medium: 1000, 200, 40, 8, 1.6, 0.32, 0.064, 0.0128, 0.00256 and 0.000512 nM.

Positive control Puromycin: A stock solution of 2.5 mg/ml was used, and diluted with the cell medium. A dilution of 250-fold was preformed, and then a dilution of 2-fold was preformed when applying the compounds to reach the testing concentration 5 µg/ml for puromycin.
 (3) Application of the compounds: for each concentration of the diluted series, the compound was applied in triplicate. In 100 µl/well.

(4) After the drug was added, the cells were incubated in the incubator for 120 h.

Cell Viability Test (1) Preparation of detection reagents: CellTiter-Glo Luminescent Cell Viability Assay detection reagent was allowed to warm to room temperature with protection from light (2) Cell preparation: The cells to be tested were taken out from the incubator and equilibrated at room temperature (25° C.) 30 min.

(3) ATP detection: Discard the culture medium and 100 μl/well DMEM was added, 50 μl/hole CTG was added into 96-well plate, protected from light using aluminum foil and oscillated using a vortex oscillator at room temperature of 200 rpm for 10 min.

(4) Detection procedure: After setting up the procedure, the black-wall clear-bottom plate was placed in the instrument without its cover.

(5) Data acquisition.

5. Data Processing and Analysis

GraphPad software was used to process the data. The cell proliferation inhibition rate was plotted against the concentration of the control sample or the test sample using four-parameter curve model for data-fitting, and the $R^2$ (rounded to 4 significant digits) and $IC_{50}$ (rounded to 4 significant digits), or $EC_{50}$ of the control sample and the test sample were obtained respectively. If necessary, the relative biological activity of sample A, i.e., ratio activity was calculated. Dxd was used as the control sample for the ratio activity calculation.

Cell proliferation inhibition rate (%)=(luminescence value of drug-treated group−luminescence value of puro group)/(luminescence value of blank control group−luminescence value of puro group)×100

Ratio activity of sample (%)=($IC_{50}$ value of the control sample/$IC_{50}$ value of the test sample)×100

Ratio activity of control sample (%)=($IC_{50}$ value of the control sample/$IC_{50}$ value of the previous control sample)×100

6. Result Verification $R^2$ Value ≥0.950; CV % between parallel pores ≤30%.

Results:

The results are listed in the following table.

| Test compound | Ratio activity (%) | Test compound | Ratio activity (%) | Test compound | Ratio activity (%) |
|---|---|---|---|---|---|
| C730 | 1.35 | C703 | 0.846 | C667 | 0.658 |
| C731 | 0.82 | C704 | 2.271 | C668 | 0.231 |
| C518 | 2.272 | C636 | 0.682 | C671 | 0.365 |
| C519 | 1.059 | C637 | 1.585 | C588 | 1.019 |
| C586 | 0.259 | C595 | 0.832 | C589 | 1.325 |
| C587 | 0.285 | C596 | 0.911 | C504 | 0.703 |
| C593 | 2.514 | C597 | 0.684 | C562 | 1.029 |
| C594 | 0.568 | C600 | 0.62 | C563 | 1.284 |
| C622 | 0.669 | C601 | 1.826 | C565 | 1.381 |
| C624 | 0.916 | C602 | 0.29 | C687 | 1.835 |
| C625 | 0.783 | C603 | 1.439 | C688 | 0.744 |
| C677 | 1.008 | C619 | 0.434 | C716 | 2.305 |
| C678 | 0.277 | C620 | 0.384 | C626 | 0.54 |
| C679 | 0.49 | C664 | 0.269 | C627 | 5.054 |
| C680 | 0.546 | C665 | 0.495 | Dxd | 1 |

Effect Example 2 Effect of Conjugates Targeting HER2 on Cell Proliferation

Study Purpose: Cell viability was detected by CellTiter-Glo assay to evaluate the effects of the ADCs on the proliferation of two high HER2 tumor cell lines SK-BR-3, NCI-N87 and a HER2-negative tumor cell line MDA-MB-468, and to analyze the effects of the ADCs on the proliferation of tumor cells.

Materials and Equipment

PBS: Gibco, Cat #10010-023); Trypsin: Gibco, Cat #25200056); FBS: Gibco, Cat #10270-106); CellTiter-Glo® Luminescent Cell Viability Assay: Promega, Cat #G7573); McCoy'5A: Gibco, Cat #16600-082); L15: Hyclone, Cat #SH30525.01); DMEM: Gibco, Cat #11995-065). 96-well plate: Corning/3603; 96-well deep-well Plate: Thermo/278743; 15 ml EP tube: Thermo/339650; 1.5 ml EP tube: Beaver.

Cell plating—Day 1

(1) Microscopic examination of cells (2) Digestion: digested using 2 mL 0.25% trypsin for 3 minutes;

(3) Centrifuge: 1000 rpm for 5 min;

(4) Cell counting

A. Cell dilution:

B. Cell plating: in 100 μl/well

C. Incubation: 37° C., 5% $CO_2$, overnight

Cell Test (1) Microscopic examination (2) Drug preparation:

A. Preparation of Buffer for preparation of samples: the desired amount of Buffer for preparation of samples was prepared using the culture medium (10% FBS) for the testing cells;

B. Sample preparation: the sample was diluted from the first concentration to the desired concentration in a 96-well deep-well Plate.

Test samples: Ten final concentrations are prepared from dilution with the cell medium: 200, 40, 8, 1.6, 0.32, 0.064, 0.0128, 0.00256, 0.000512 and 0.0001024 nM.

Positive control Puromycin: A stock solution of 10 mg/ml was used, and diluted with the cell medium. A dilution of 100-fold was preformed, and then a dilution of 10-fold was preformed when applying the compounds to reach the testing concentration 5 μg/ml for puromycin.

(4) Application of the compounds: for each concentration of the diluted series, the compound was applied in triplicate. In 100 μl/well.

(5) After the drug was added, the cells were incubated in the incubator for 120 h.

Cell Viability Detection (1) Preparation of detection reagents: CellTiter-Glo Luminescent Cell Viability Assay detection reagent was allowed to warm to room temperature with protection from light (2) Cell preparation: The cells to be tested were taken out from the incubator and equilibrated at room temperature (25° C.) 30 min.

(3) ATP detection: Discard the culture medium and 100 μl/well DMEM was added, 50 μl/hole CTG was added into 96-well plate, protected from light using aluminum foil and oscillated using a vortex oscillator at room temperature of 200 rpm for 10 min.

(4) Detection procedure: After setting up the procedure, the black-wall clear-bottom plate was placed in the instrument without its cover.

(5) Data acquisition.

5. Data Processing and Analysis

GraphPad software was used to process the data. The cell proliferation inhibition rate was plotted against the concentration of the control sample or the test sample using four-parameter curve model for data-fitting, and the $R^2$ (rounded to 4 significant digits) and IC50 (rounded to 4 significant digits), or EC50 of the control sample and the test sample were obtained respectively.

Cell proliferation inhibition rate (%)=(luminescence value of drug-treated group−luminescence value of puro group)/(luminescence value of blank control group−luminescence value of puro group)×100

6. Result Verification $R^2$ Value ≥0.950; CV % between parallel pores ≤30%.

Figure 2:
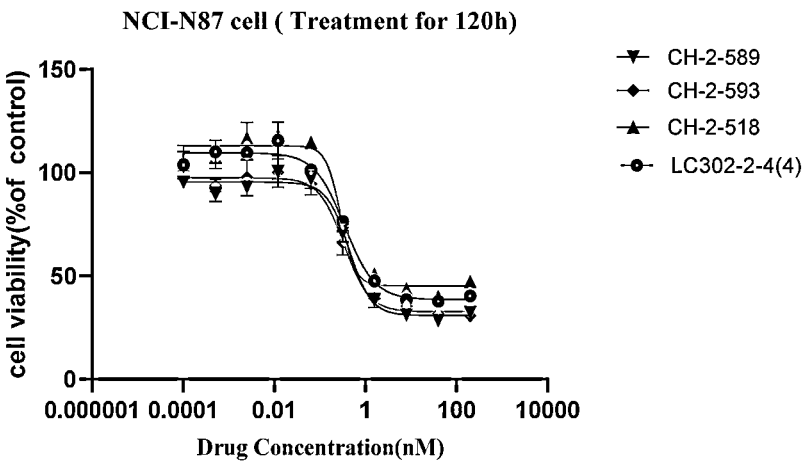
FIG. 2 shows the efficacy of conjugates in the NCI-N87 HER2-high cell line.
Figure 3:
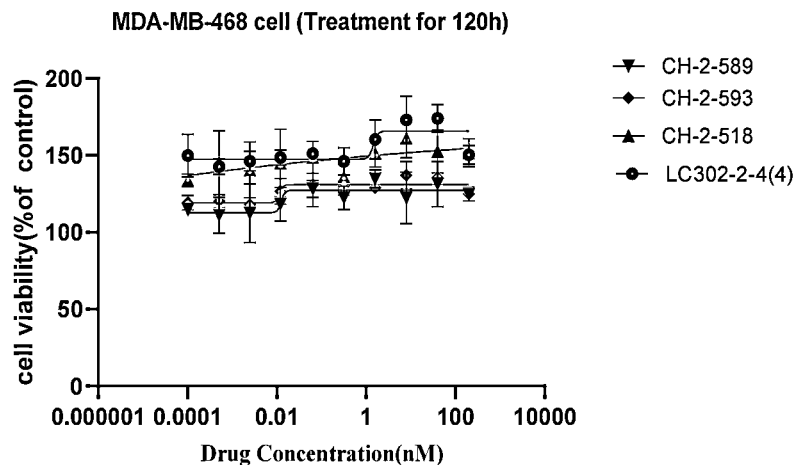
FIG. 3 shows the efficacy of conjugates in the MDA-MB-468 HER2-negative cell line.

Results:

The results are shown in the following table and FIG. 1, FIG. 2 and FIG. 3.

| Samples | $IC_{50}$ (nM) | | |
|---|---|---|---|
| | SK-BR-3 | N87 | MDA-MB-468 |
| CH-2-589 | 0.1737 | 0.4363 | N/A |
| CH-2-593 | ~0.2679 | 0.3431 | N/A |
| CH-2-518 | 0.1621 | 0.2888 | N/A |
| LC302-2-1(4) | 0.1926 | 0.6353 | N/A |
| LC302-2-4(4) | 0.2208 | 0.7226 | N/A |
| Dxd | 1.472 | 4.682 | N/A |

In HER2 high-expressing SK-BR-3 and NCI-N87, the conjugates (CH-2-589, CH-2-593, CH-2-518, LC302-2-1(4) and LC302-2-4(4)) exhibited outstanding efficacy. The $IC_{50}$ values of the conjugates are lower than the small molecule payload Dxd. In HER2 negative cells, the conjugates exhibited minimal efficacy.

Effect Example 3 Assessment of Bystander Killing Effect

Purpose of experiment The Bystander killing activities of ADCs (CH-2-589, CH-2-593, CH-2-518 and LC302-2-4(4)) on MDA-MB-468 cells were tested in a co-culture system of a HER2-positive tumor cell line SK-BR-3 and a HER2-negative tumor cell line MDA-MB-468, and compared the bystander killing effect with a reference ADC (LC1184 (8)) with a structure similar to DS8201a.

Materials and Equipment

L15: Hyclone, SH30525.01; McCoy's 5A: Gibco, 16600-082; FBS: Gibco, 10099-141; Firefly luciferase reporter gene assay kit: Beyotime, RG006; 50 ml Centrifugal tube: corning, 430829; 15 ml Centrifugal tube: corning, 430791; 96-well plate: corning, 3599; $CO_2$ Cell incubator: Thermo; Centrifuge: Thermos, L550; Microscope: Nikon, ISZ; Cell counter: Countstar, IC1000; Cytation3 Plate reader: BioTek, Cytation3; HTX Multi-mode microplate reader: BioTek, Synergy HTX; SK-BR-3: ATCC, HTB-30; MDA-MB-468-Lucia-GFP: prepared in-house using lentivirus infection.

Experimental Method

1) Cell collection and counting.
2) The cell density was adjusted to $1*10^5$ cells/ml
3) The cell mixture was prepared, wherein SKBR3: MDA-MB-468-Lucia-GFP=4:1, 5 ml.

Cell plating: $1*10^4$ cells/well, 100 μl/well

Test samples: Three final concentrations are prepared from dilution with the cell medium: 50, 10 and 1 nM.

4) The drug was administered the next day, 100 μl/well.
5) Incubate in a 5% $CO_2$ incubator at 37° C. for 120 h.
① washed by PBS to remove dead cells, and detected by Cytation3 plate reader;
② Biyuntian luciferase reporter gene assay kit: lysed in 37° C. incubator for 10 min using 100 μl lysis buffer. Centrifuged at 2000 rpm for 5 minutes. 100 μl supernatant was taken. 100 μl substrate was added. The chemiluminescence was detected by microplate reader (gain: 200).

Figure 4A:
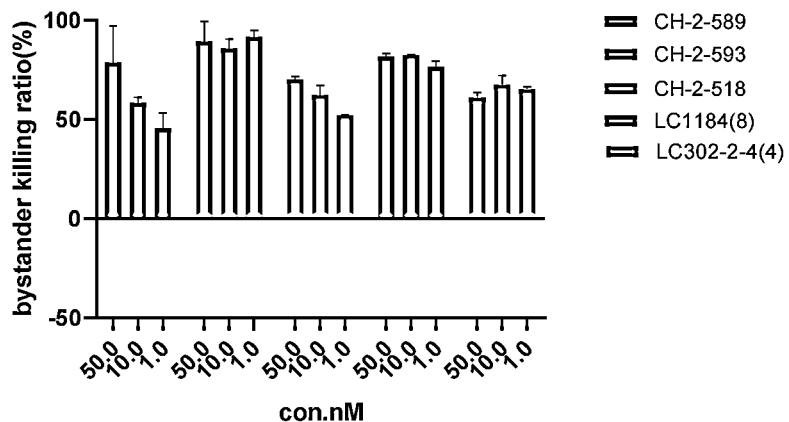
FIG. 4a and FIG. 4b show the efficacy of conjugates in the co-culture system of SK-BR-3 and MDA-MB-468.
Figure 4B:
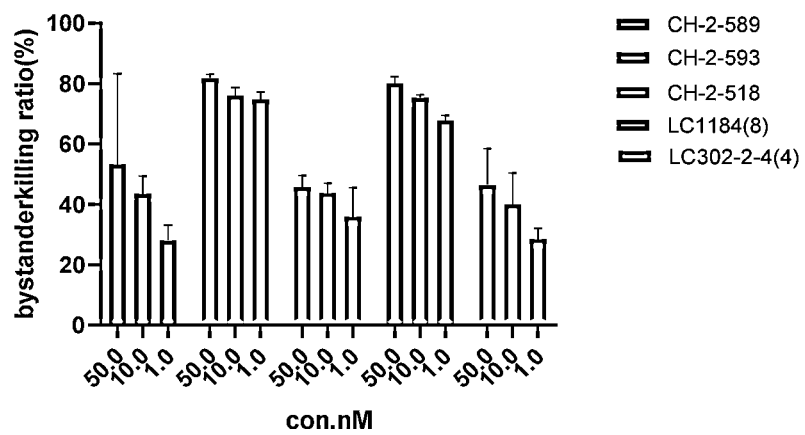
Figure 5:
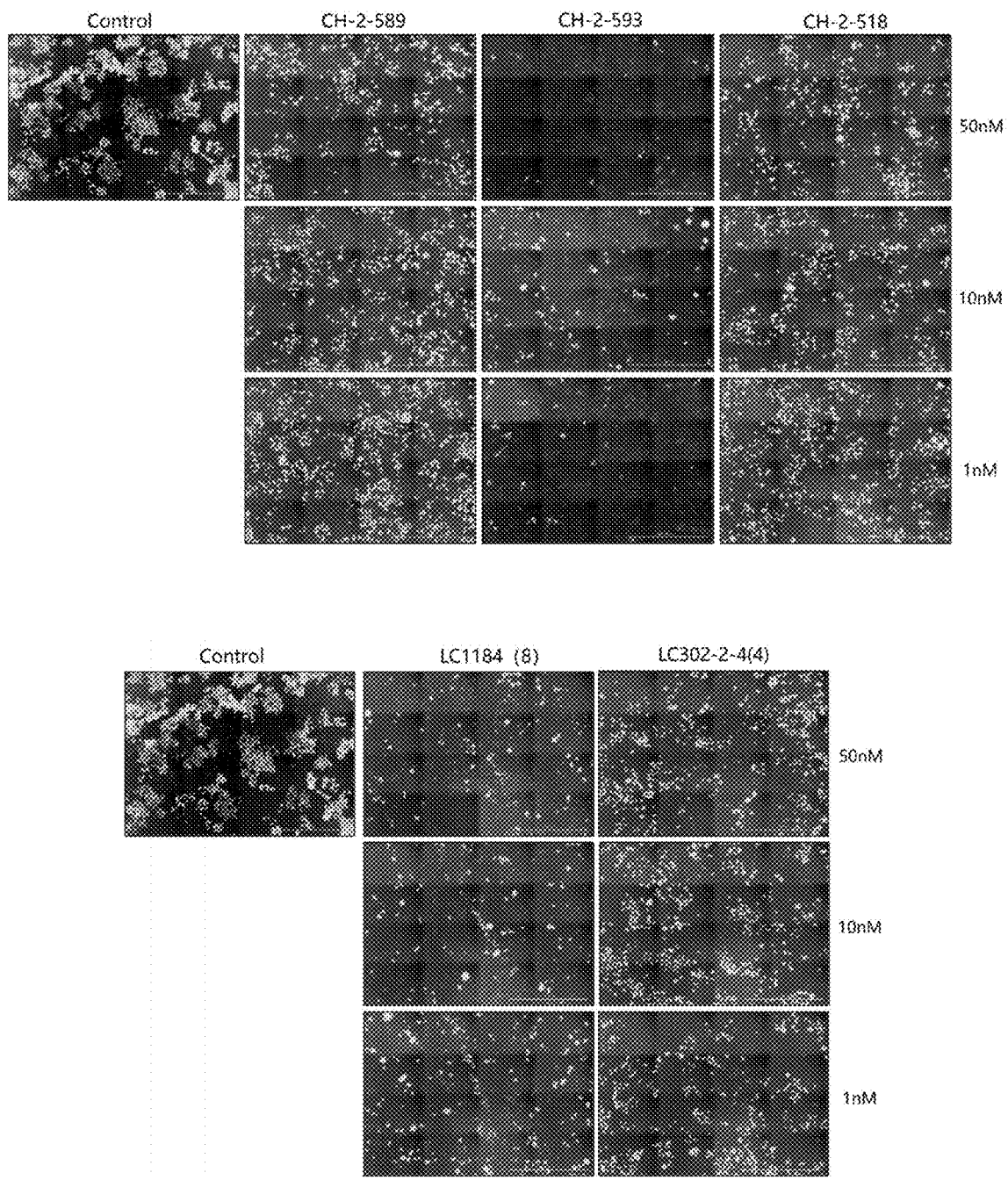
FIG. 5 shows the efficacy of conjugates in the co-culture system of SK-BR-3 and MDA-MB-468 detected by GFP fluorescence.

Result:

Two methods (GFP fluorescence counting and luciferase substrate luminescence method) were used for determination of bystander killing effects (FIG. 4a, 4b and FIG. 5).

The conjugates (CH-2-593, CH-2-589, CH-2-518 and LC302-2-4(4)) all show outstanding bystander killing effects in the detections using both of the two methods. CH-2-593 shows a bystander killing effect comparable to or stronger than LC1184(8).

Figure 6:
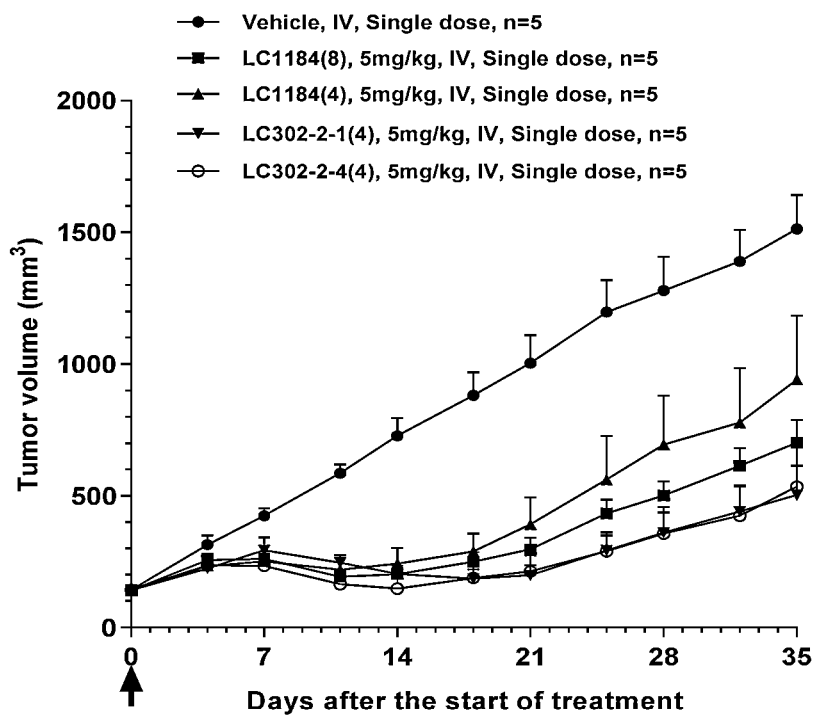
FIG. 6 shows the mean tumor volume change over time in SCID Beige mice with JIMT1 CDX model dosed with 5 mg/kg of conjugates.

Effect Example 4 Assessment of Conjugates In Vivo 4.1 On JIMT-1 Human Breast Cancer Xenograft Model $5×10^6$ JIMT-1 human breast cancer cells (HER2 medium) were inoculated subcutaneously in the right flank in SCID Beige mice. After 7 days, when tumor volume reached 142 $mm^3$ on average, the tumor bearing mice were assigned and administrated intravenously of LC1184(8) and other five different conjugates at 5 mg/kg. The tumor volume was measured twice weekly with calipers. LC1184(8) showed better efficacy than LC1184(4), suggesting that with same payload, higher DAR would result in better efficacy. LC302-2-1(4) and LC302-2-4(4) showed better efficacy than LC1184(8) (FIG. 6). The conjugate of the present invention achieves great efficacy in lower DAR.

4.2 On Capan-1 Human Pancreatic Cancer Xenograft Model (1)

Figure 7:
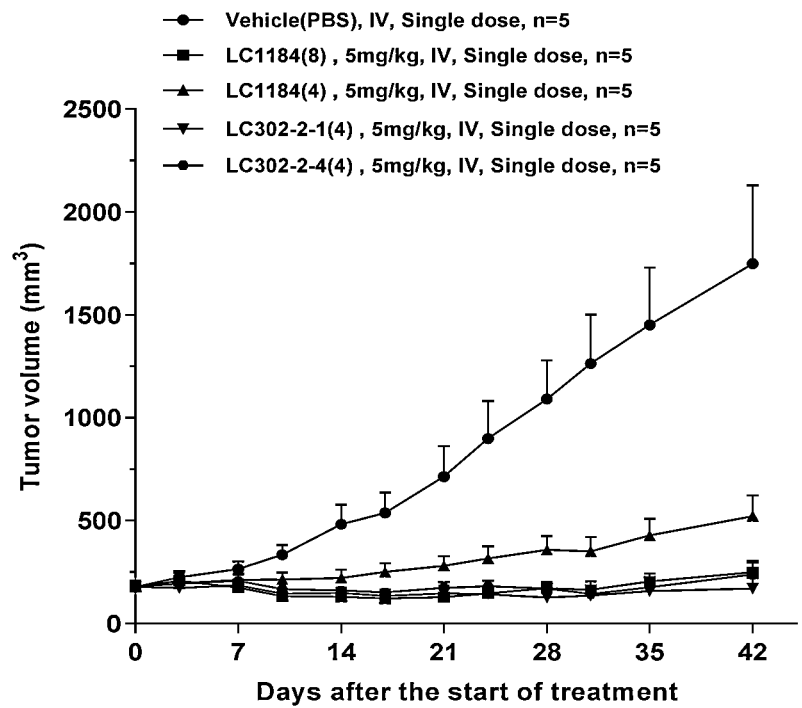
FIG. 7 shows the mean tumor volume change over time in BALB/c nude mice with Capan-1 CDX model dosed with 5 mg/kg of conjugates.

$5×10^6$ Capan-1 human pancreatic cancer cells (HER2 low) were inoculated subcutaneously in the right flank in BALB/c nude mice to generate xenograft model. After 8 days, when tumor volume reached 178 $mm^3$ on average, the tumor bearing mice were administrated intravenously of LC1184(8) and other five different conjugates at 5 mg/kg. The tumor volume was measured twice weekly with calipers. LC1184(8) showed better efficacy than LC1184(4). LC302-2-1(4) and LC302-2-4(4) showed comparable efficacy to LC1184(8) (FIG. 7).

4.3 On Capan-1 Human Pancreatic Cancer Xenograft Model (2)

Study Purpose: The objective of the research is to evaluate the in vivo anti-tumor efficacy of CH-2-589, CH-2-593, CH-2-518 and LC302-2-4(4) in the treatment of the subcutaneous Capan-1 human pancreatic cancer xenograft model in female BALB/c Nude mice.

Study Design:

Cell Culture: The Capan-1 tumor cells (ATCC-HTB-79) will be maintained in vitro as a monolayer culture in IMDM supplemented with 20% fetal bovine serum, 1% Antibiotic-Antimycotic at 37° C. in an atmosphere of 5% $CO_2$ in air. The tumor cells will be routinely subcultured twice weekly by trypsin-EDTA treatment. The cells growing in an exponential growth phase will be harvested and counted for tumor inoculation.

Animals: BALB/c Nude, female, 6-8 weeks, weighing approximately 18-20 g. A total of 48 (30 plus 60%) will be needed for the study, which will be purchased from Shanghai Lingchang Laboratory Animal Co., LTD. or other certified vendors.

Tumor Inoculation: Each mouse will be inoculated subcutaneously at the right flank with Capan-1 tumor cells ($5×10^6$) in 0.2 mL of PBS with Matrigel (1:1) for tumor development. The animals will be randomized and treatment will be started when the average tumor volume reaches approximately 150-200 $mm^3$ for the efficacy study. The test article administration and the animal numbers in each group are shown in the following experimental design table.

Groups and Treatments

| Group | N[1] | Treatment | Dose (mg/kg) | Dosing Volume (mL/kg)[2] | Dosing Route | Schedule[3] |
|---|---|---|---|---|---|---|
| 1 | 6 | Vehicle | — | 10 | IV | Single dose |
| 2 | 6 | CH-2-589 | 5 | 10 | IV | Single dose |
| 3 | 6 | CH-2-593 | 5 | 10 | IV | Single dose |
| 4 | 6 | CH-2-518 | 5 | 10 | IV | Single dose |
| 5 | 6 | LC302-2-4(4) | 5 | 10 | IV | Single dose |

N: animal number;
Dosing volume: adjust dosing volume based on body weight 10 mL/kg.
The experiment duration will be adjusted according to tumor volume.

Animal Housing: An acclimation period of approximately one week will be allowed between animal arrival and tumor inoculation in order to accustom the animals to the laboratory environment. The mice will be maintained in a special pathogen-free environment and in individual ventilation cages (3 mice per cage). All cages, bedding, and water will be sterilized before use. When working in the mouse room, the investigators will wear lab coat and latex or vinyl gloves. Each cage will be clearly labeled with a cage card indicating number of animals, sex, strain, date received, treatment, study number, group number, and the starting date of the treatment. The cages with food and water will be changed twice a week. The targeted conditions for animal room environment and photoperiod will be as follows:

Temperature 20~26° C.

Humidity 40~70%

Light cycle 12 hours light and 12 hours dark

Dietary Materials: All animals will have free access to a standard certified commercial laboratory diet. Maximum allowable concentrations of contaminants in the diet are controlled and routinely analyzed by the manufacturers. Autoclaved municipal tap water, suitable for human consumption will be available to the animals ad libitum. It is considered that there are no known contaminants in the dietary materials that could influence the tumor growth.

Assignment to Groups: Before commencement of treatment, all animals will be weighed and the tumor volumes will be measured. Since the tumor volume can affect the effectiveness of any given treatment, mice will be assigned into groups using an Excel-based randomization software performing stratified randomization based upon their tumor volumes. This ensures that all the groups are comparable at the baseline.

Observations: The protocol and any amendment(s) or procedures involving the care and use of animals in this study will be reviewed and approved by the Institutional Animal Care and Use Committee (IACUC) of WuXi AppTec prior to conduct. During the study, the care and use of animals will be conducted in accordance with the regulations of the Association for Assessment and Accreditation of Laboratory Animal Care (AAALAC). After inoculation, the animals will be checked daily for morbidity and mortality. At the time of routine monitoring, the animals will be checked for any effects of tumor growth and treatments on normal behavior such as mobility, food and water consumption, body weight gain/loss (body weights will be measured twice weekly), eye/hair matting and any other abnormal effect. Death and observed clinical signs will be recorded on the basis of the numbers of animals within each subset.

Endpoints: The major endpoint is to see if the tumor growth can be delayed or mice can be cured. Tumor sizes will be measured twice weekly in two dimensions using a caliper, and the volume will be expressed in mm$^3$ using the formula: V=0.5 a×b$^2$ where a and b are the long and short diameters of the tumor, respectively. The tumor sizes are then used for the calculations of both TGI (%) and the relative tumor proliferation rate T/C (%) values. TGI is calculated for each group using the formula: TGI (%)=[1−(Ti−T0)/(Vi−V0)]×100; Ti is the average tumor volume of a treatment group on a given day, T0 is the average tumor volume of the treatment group on the first day of treatment, Vi is the average tumor volume of the vehicle control group on the same day with Ti, and V0 is the average tumor volume of the vehicle group on the first day of treatment.

The T/C (%) value is calculated for each group using the formula: T/C %=$T_{RTV}/C_{RTV}$×100% ($T_{RTV}$: relative average tumor volume (RTV) of the treatment group; $C_{RTV}$: relative average tumor volume (RTV) of the vehicle control group on the same day with $T_{RTV}$). The relative tumor volume (RTV) is calculated for each group using the formula: RTV=$V_t/V_0$; $V_0$ is the tumor volume on the first day of treatment, $V_t$ is the tumor volume on a given day.

Termination:

1) Bodyweight loss: Any animal exhibiting 20% bodyweight loss at any one day will be humanely killed or the veterinary staff will be contacted.

2) Tumor burden: Tumor burden should not exceed 3,000 mm$^3$. Individual animal will be sacrificed immediately when its tumor volume reaches 3,000 mm$^3$.

Ulceration: If Tumor Ulceration Occurs, the Following Procedures Will Apply:

Animals with ulcerated tumors will be monitored at least 3 times per week with increasing frequency, up to daily, depending upon clinical signs.

Ulcerated tumors, which have not scabbed over, should be cleaned with an appropriate wound cleansing solution (e.g., Novalsan). Antibiotic cream is to be applied to the ulceration/lesion only if directed by the Veterinary staff.

Criteria for Euthanasia Include if the Lesion (Meet One or More):

Does not heal or form a scab within 1 week.

Is greater than 5 mm diameter.

Becomes cavitated.

Develops signs of infection (such as presence of pus) or bleeding, or if the animal shows signs of discomfort (e.g. excessive licking and biting directed at the site) or systemic signs of illness (lethargy, decreased activity, decreased food consumption, decreased body condition or weight loss). Contact the veterinary staff to discuss any possible exceptions.

3) Clinical signs: Animals must be euthanized if they found to be moribund (unless special permission is granted by the IACUC based on adequate justification, which must be included in the protocol and increased supportive care provided such as warm SQ fluids, Diet Gel food cup next to animal so they can reach food, cage on a warming pad for supplemental heat, etc. Note: a moribund condition indicates an animal is unlikely to survive.) For questions regarding these endpoints, please contact the Veterinary Staff.

Clinical Examples of Morbidity May Include:

Hunched.

Persistent recumbency and lack of response to handling or other stimuli.

Signs of severe organ or system failure.

Emaciation.

Hypothermia.

CNS deficits: convulsions.

Respiratory: rapid respiratory rate, labored breathing, coughing, rales.

GI: diarrhea lasting >2 days, jaundice.

Any animal that exhibits the above clinical issues will be humanely sacrificed by $CO_2$.

Necropsy will not be performed in the event of an unexpected death.

Statistical Analysis: For comparison between two groups, an independent sample t-test will be used. For comparison among three or more groups, a one-way ANOVA will be performed. If a significant F-statistics (a ratio of treatment variance to the error variance) is obtained, multiple comparison procedures will be applied after ANOVA. All data will be analyzed using SPSS 17.0. $p<0.05$ is considered to be statistically significant.

Figure 8A:
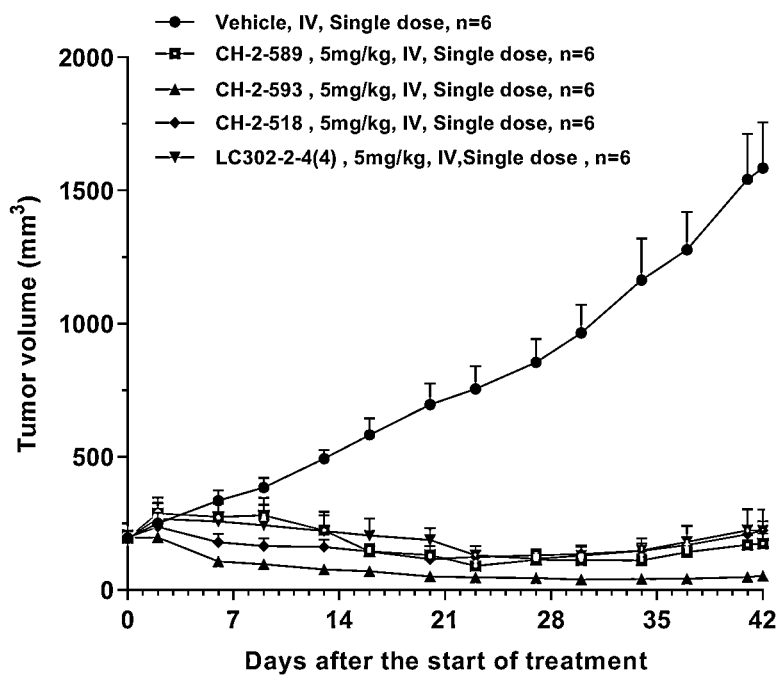
FIG. 8a and FIG. 8b show the mean tumor volume change and body weight change over time in BALB/c nude mice with Capan-1 CDX model dosed with 5 mg/kg of conjugates.
Figure 8B:
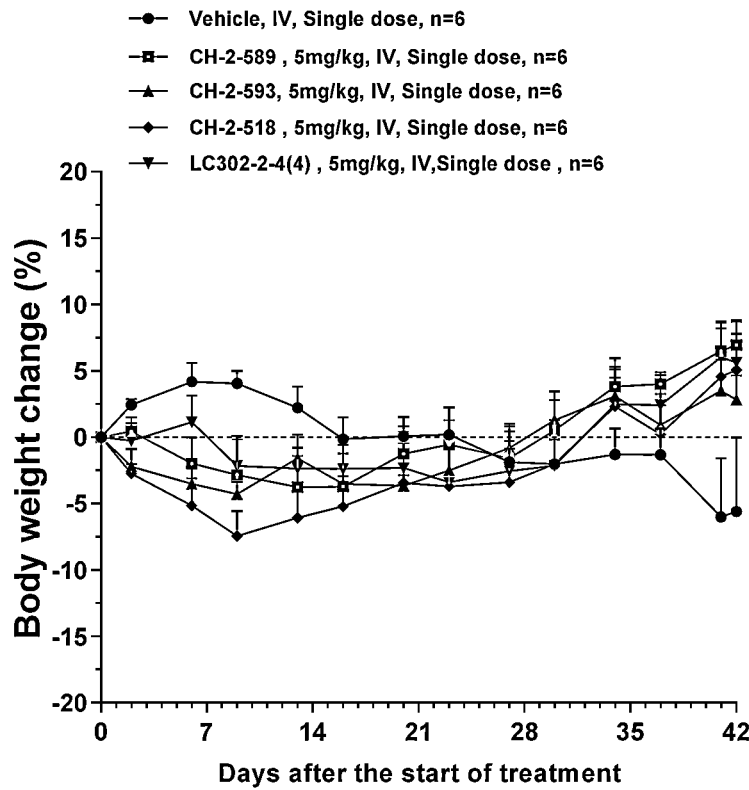

Results:

All the conjugates show outstanding tumor inhibitory effects ((FIG. 8a and FIG. 8b).

4.4 On NCI-N87 Human Gastric Cancer Xenograft Model

Study Purpose: The objective of the research is to evaluate the in vivo anti-tumor efficacy of CH-2-589, CH-2-593, CH-2-518 and LC302-2-4(4) in the treatment of the subcutaneous NCI-N87 human gastric cancer xenograft model in female BALB/c Nude mice.

Study Design:

Cell Culture: The NCI-N87 tumor cells (ATCC, Manassas, VA, cat #CRL-5822) will be maintained in vitro as a monolayer culture in RPMI 1640 medium supplemented with 10% fetal bovine serum, 1% Antibiotic-Antimycotic, at 37° C. in an atmosphere of 5% $CO_2$ in air. The tumor cells will be routinely subcultured twice weekly by trypsin-EDTA treatment. The cells growing in an exponential growth phase will be harvested and counted for tumor inoculation.

Animals: BALB/c Nude, female, 6-8 weeks, weighing approximately 18-22 g. A total of 36 (30 plus 20%) will be needed for the study, which will be purchased from Shanghai Lingchang Laboratory Animal Co., LTD. or other certified vendors.

Tumor Inoculation: Each mouse will be inoculated subcutaneously at the right flank with NCI-N87 tumor cells ($10\times10^6$) in 0.2 mL of PBS with Matrigel (1:1) for tumor development. The animals will be randomized and treatment will be started when the average tumor volume reaches approximately 150-200 mm³ for the efficacy study. The test article administration and the animal numbers in each group are shown in the following experimental design table.

Groups and Treatments

| Group | N[1] | Treatment | Dose (mg/kg) | Dosing Volume (mL/kg)[2] | Dosing Route | Schedule[3] |
|---|---|---|---|---|---|---|
| 1 | 6 | Vehicle | — | 10 | IV | Single dose |
| 2 | 6 | CH-2-589 | 5 | 10 | IV | Single dose |
| 3 | 6 | CH-2-593 | 5 | 10 | IV | Single dose |
| 4 | 6 | CH-2-518 | 5 | 10 | IV | Single dose |
| 5 | 6 | LC302-2-4(4) | 5 | 10 | IV | Single dose |

N: animal number;
Dosing volume: adjust dosing volume based on body weight 10 mL/kg.
The experiment duration will be adjusted according to tumor volume.

Figure 9A:
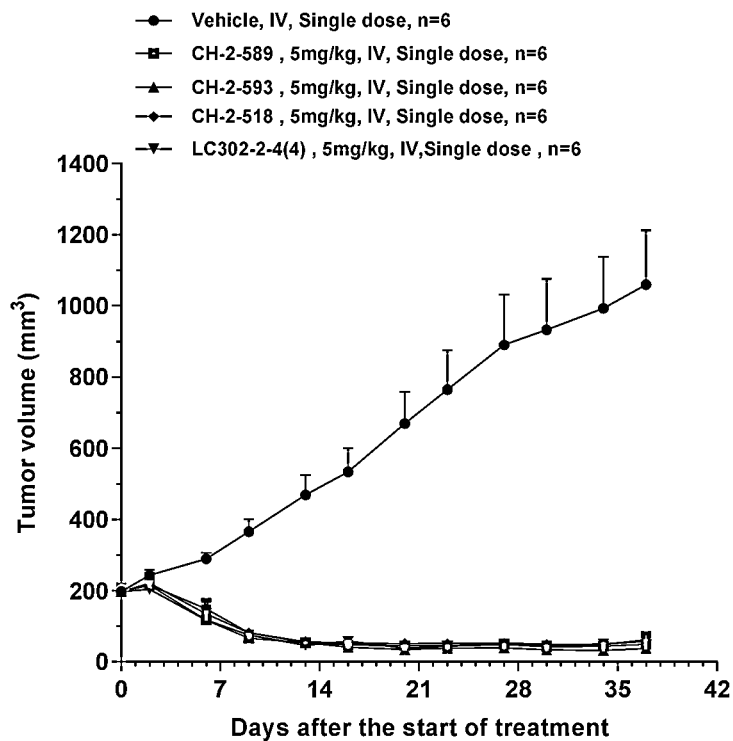
FIG. 9a and FIG. 9b shows the mean tumor volume change and body weight change over time in BALB/c Nude mice with NCI-N87 CDX model dosed with 5 mg/kg of conjugates.
Figure 9B:
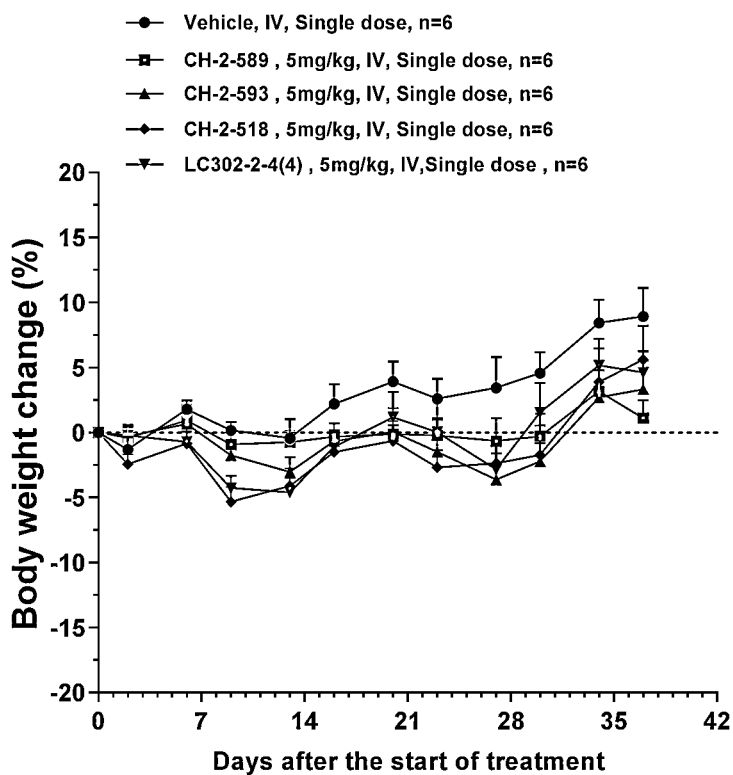

Results:

All the conjugates show outstanding tumor inhibitory effects (FIG. 9a and FIG. 9b).

Effect Example 5 Ex-Vivo Serum Stability of the Conjugates

For ex-vivo serum stability study, the conjugates LC302-2-1(4), LC302-2-4(4) and LC1184(8) were inoculated in pooled human serum at 37° C., respectively. At 0, 24, 48 and 96 h, the conjugates were captured by antigen, then deglycosylated by glycosidase and dissociated by acid. Supernatant were collected and centrifuged, and then detected by high resolution LC-MS to determine DAR.

Figure 10:
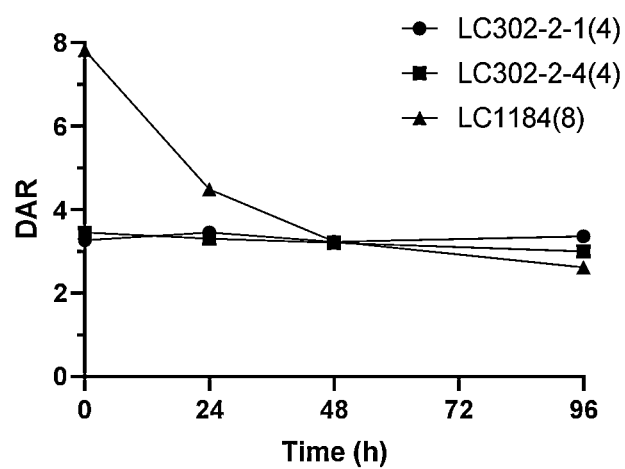
FIG. 10 shows the ex-vivo serum stability of the conjugates after 0, 24, 48 and 96 h of incubation in pooled human serum.

LC302-2-1(4) and LC302-2-4(4) are quite stable after incubated in serum for 96 hours. There is no observable decrease in the DARs of LC302-2-1(4) and LC302-2-4(4) after incubation for 96 h. However, the DAR of LC1184(8) dropped from 7.8 to 2.6 after incubation for 96 h (FIG. 10). Stability of the linker indicates the delivery of more payloads to target tumour and decrease of off-target free payload release, and thus increases therapeutic index.

Sequence Listing

SEQ ID No. 1: Ab0001-LCCT$_L$-HC Light chain:
DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGECGALPETGG

SEQ ID No. 2: Ab0001-LCCT$_L$-HC Heavy chain:
EVQLVESGGGLVQPGGSLRLSCAASGFNIKDTYIHWVRQAPGKGLEWVA

RIYPTNGYTRYADSVKGRFTISADTSKNTAYLQMNSLRAEDTAVYYCSR

WGGDGFYAMDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK

SEQUENCE LISTING

```
Sequence total quantity: 14
SEQ ID NO: 1              moltype = AA   length = 222
FEATURE                   Location/Qualifiers
REGION                    1..222
                          note = Ab0001-LCCTL-HC Light chain
source                    1..222
                          mol_type = protein
                          organism = synthetic construct
SEQUENCE: 1
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGALPET GG                      222

SEQ ID NO: 2              moltype = AA   length = 450
FEATURE                   Location/Qualifiers
REGION                    1..450
                          note = Ab0001-LCCTL-HC Heavy chain
source                    1..450
                          mol_type = protein
                          organism = synthetic construct
SEQUENCE: 2
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 3              moltype = AA   length = 5
FEATURE                   Location/Qualifiers
source                    1..5
                          mol_type = protein
                          organism = synthetic construct
SEQUENCE: 3
GGGGS                                                                 5

SEQ ID NO: 4              moltype = AA   length = 10
FEATURE                   Location/Qualifiers
source                    1..10
                          mol_type = protein
                          organism = synthetic construct
SEQUENCE: 4
GGGGSGGGGS                                                           10

SEQ ID NO: 5              moltype = AA   length = 15
FEATURE                   Location/Qualifiers
source                    1..15
                          mol_type = protein
                          organism = synthetic construct
SEQUENCE: 5
GGGGSGGGGS GGGGS                                                     15

SEQ ID NO: 6              moltype = AA   length = 5
FEATURE                   Location/Qualifiers
source                    1..5
                          mol_type = protein
                          organism = synthetic construct
SEQUENCE: 6
LPXTG                                                                 5

SEQ ID NO: 7              moltype = AA   length = 5
FEATURE                   Location/Qualifiers
source                    1..5
                          mol_type = protein
                          organism = synthetic construct
SEQUENCE: 7
LPETG                                                                 5

SEQ ID NO: 8              moltype = AA   length = 6
FEATURE                   Location/Qualifiers
source                    1..6
                          mol_type = protein
                          organism = synthetic construct
SEQUENCE: 8
LPETGG                                                                6
```

```
SEQ ID NO: 9              moltype = AA  length = 5
FEATURE                   Location/Qualifiers
source                    1..5
                          mol_type = protein
                          organism = synthetic construct
SEQUENCE: 9
NPQTN                                                                    5

SEQ ID NO: 10             moltype = AA  length = 5
FEATURE                   Location/Qualifiers
source                    1..5
                          mol_type = protein
                          organism = synthetic construct
SEQUENCE: 10
NPKTG                                                                    5

SEQ ID NO: 11             moltype = AA  length = 5
FEATURE                   Location/Qualifiers
source                    1..5
                          mol_type = protein
                          organism = synthetic construct
SEQUENCE: 11
LAXTG                                                                    5

SEQ ID NO: 12             moltype = AA  length = 7
FEATURE                   Location/Qualifiers
source                    1..7
                          mol_type = protein
                          organism = synthetic construct
SEQUENCE: 12
LPQTSEQ                                                                  7

SEQ ID NO: 13             moltype = AA  length = 8
FEATURE                   Location/Qualifiers
source                    1..8
                          mol_type = protein
                          organism = synthetic construct
SEQUENCE: 13
GALPETGG                                                                 8

SEQ ID NO: 14             moltype = AA  length = 4
FEATURE                   Location/Qualifiers
source                    1..4
                          mol_type = protein
                          organism = synthetic construct
SEQUENCE: 14
GGFG                                                                     4
```

The invention claimed is:

1. A compound or a pharmaceutically acceptable salt thereof, wherein the compound has the structure of formula (i):

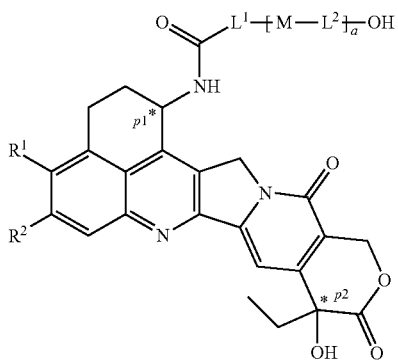

wherein, a is 0 or 1;

the carbon atoms marked with p1* and p2* each is asymmetric center, and the asymmetric center is S configured, R configured or racemic;

$L^1$ is selected from $C_{1-6}$ alkylene, which is unsubstituted or substituted with one substituent selected from halogen, —OH and —NH$_2$;

M is —CH$_2$—, —NH— or —O—;

$L^2$ is $C_{1-3}$ alkylene;

$R^1$ is Cl; and $R^2$ is F.

2. The compound of claim 1, which is selected from:

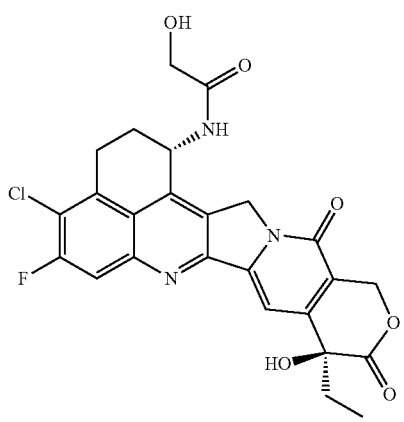

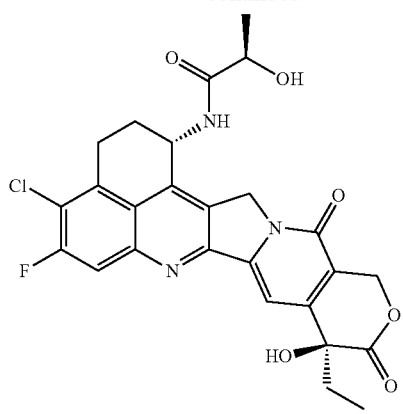

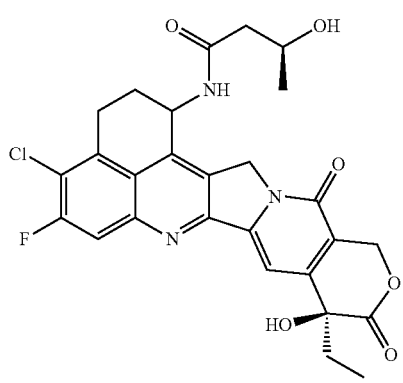

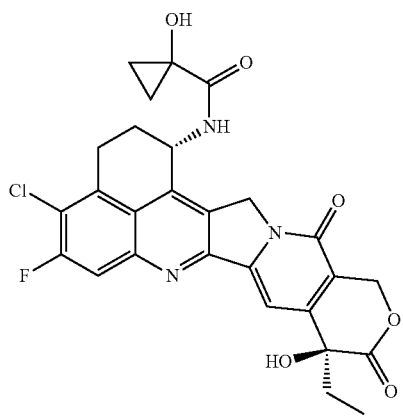

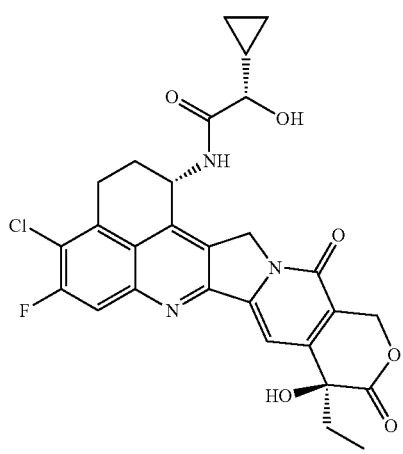

189
-continued

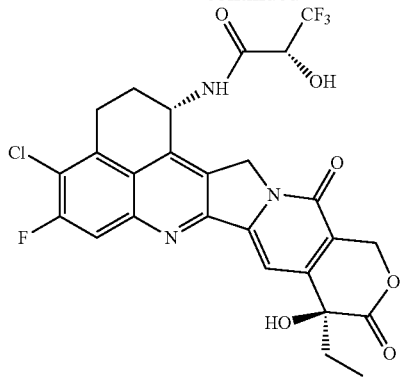

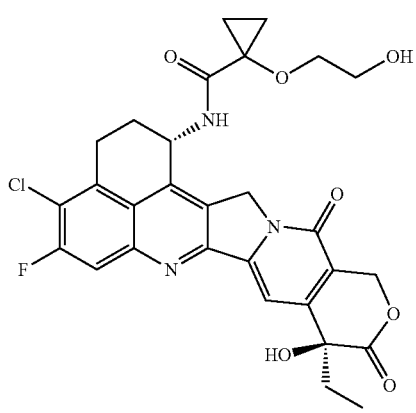

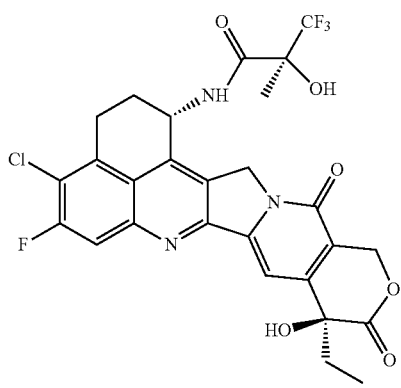

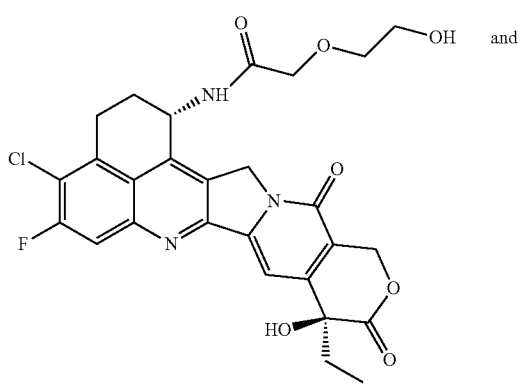 and

190
-continued

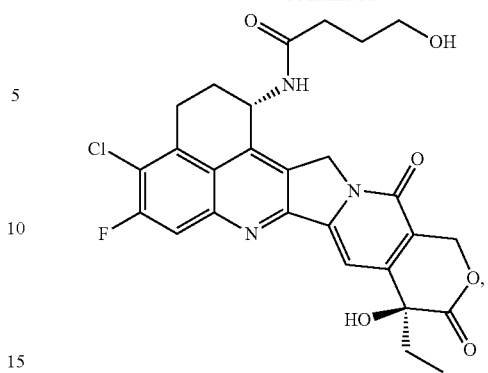

or a pharmaceutically acceptable salt thereof.

3. The compound of claim 1, wherein $L^1$ is selected from $C_{1-6}$ linear alkylene, $C_{1-6}$ branched alkylene, $C_{3-6}$ cyclic alkylene and $C_{3-4}$ cyclic alkyl-$C_{1-2}$ linear alkylene group, which are each independently unsubstituted or substituted with one substituent selected from halogen, —OH and —NH$_2$.

4. The compound of claim 1, wherein $L^1$ is selected from $C_{1-4}$ linear alkylene, $C_{1-4}$ branched alkylene, $C_{3-4}$ cyclic alkylene and cyclopropyl-methylene, which are each independently unsubstituted or substituted with one substituent selected from halogen, —OH and —NH$_2$.

5. The compound of claim 1, wherein $L^1$ is selected from —CH$_2$—, —C$_2$H$_4$—,

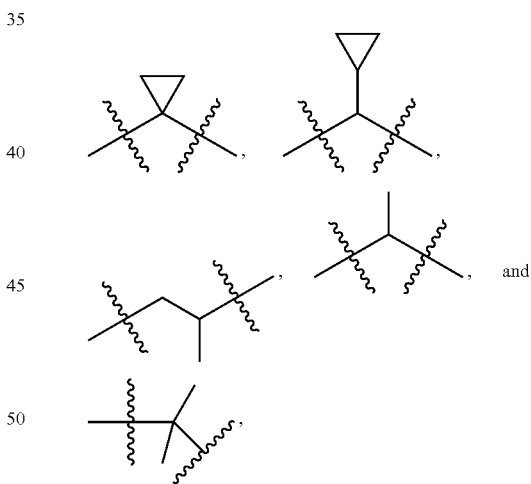

which are each independently unsubstituted or substituted with at least one substituent selected from halogen, —OH and —NH$_2$.

6. The compound of claim 1, wherein $L^1$ is selected from —CH$_2$—,

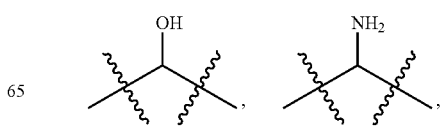

-continued

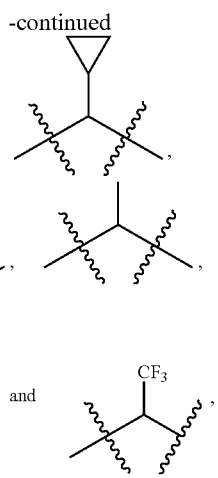

wherein "#" marks the position attached to carbonyl.

7. The compound of claim 1, wherein $L^1$ is selected from —CH$_2$—,

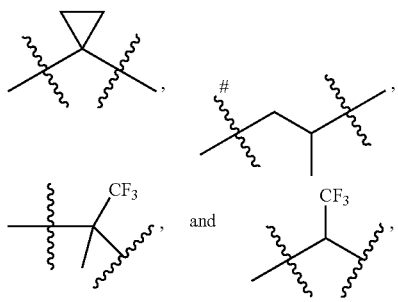

wherein "#" marks the position attached to carbonyl.

8. The compound of claim 1, wherein $L^1$ is selected from —CH$_2$—,

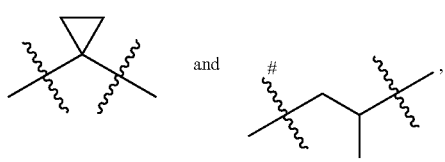

wherein "#" marks the position attached to carbonyl.

9. The compound of claim 1, wherein the halogen is selected from F, Cl and Br.

10. The compound of claim 1, wherein M is —CH$_2$—, —NH— or —O—; and $L^2$ is —C$_2$H$_4$—; or M is —CH$_2$—, and $L^2$ is —CH$_2$—.

11. The compound of claim 1, wherein the carbon atom marked with p1* is S configured or racemic; and/or the carbon atom marked with p2* is S configured or racemic.

12. The compound of claim 1, wherein
a is 0, $R^1$ is Cl, $R^2$ is F, and $L^1$ is selected from —CH$_2$—,

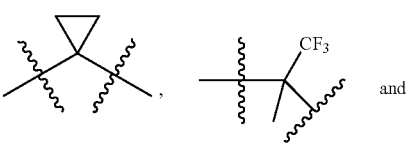

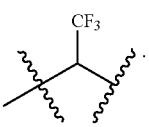

13. The compound of claim 1, wherein the carbon atom marked with p1* is S configured; and/or the carbon atom marked with p2* is S configured.

14. A method of inhibiting the proliferation of a tumor and/or cancel cell, comprising contacting the tumor and/or cancer cell with the compound of claim 1.

15. The method of claim 14, wherein the compound of claim 1 is delivered to the tumor and/or cancer cell using an ADC (antibody-drug conjugate) comprising the compound of claim 1.

16. A method of inhibiting the proliferation of a tumor and/or cancer cell, comprising contacting the tumor and/or cancer cell with the compound of claim 2.

17. The method of claim 16, wherein the compound of claim 2 is delivered to the tumor and/or cancer cell using an ADC (antibody-drug conjugate) comprising the compound of claim 2.

* * * * *